(12) United States Patent
Blanc et al.

(10) Patent No.: US 8,163,781 B2
(45) Date of Patent: Apr. 24, 2012

(54) BI-ARYL AMINOTETRALINES

(75) Inventors: Jean-Baptiste Blanc, Westfield, NJ (US); Li Chen, Shanghai (CN); Fariborz Firooznia, Florham Park, NJ (US); Paul Gillespie, Westfield, NJ (US); Robert Alan Goodnow, Jr., Gillette, NJ (US); Yun He, Shanghai (CN); Tai-An Lin, Pequannock, NJ (US); Sung-Sau So, Verona, NJ (US); HongYing Yun, Shanghai (CN); Zhenshan Zhang, Shanghai (CN)

(73) Assignee: Hoffman-La Roche Inc., Nutley, NJ (US)

( * ) Notice: Subject to any disclaimer, the term of this patent is extended or adjusted under 35 U.S.C. 154(b) by 450 days.

(21) Appl. No.: 12/540,804

(22) Filed: Aug. 13, 2009

(65) Prior Publication Data

US 2010/0041714 A1   Feb. 18, 2010

Related U.S. Application Data

(60) Provisional application No. 61/089,155, filed on Aug. 15, 2008.

(51) Int. Cl.
*C07D 213/62* (2006.01)
*A61K 31/4412* (2006.01)
(52) U.S. Cl. ......... 514/348; 514/562; 546/293; 562/427
(58) Field of Classification Search .................... None
See application file for complete search history.

(56) References Cited

U.S. PATENT DOCUMENTS

| | | | |
|---|---|---|---|
| 3,899,529 | A | 8/1975 | Witzel |
| 4,868,331 | A | 9/1989 | Niewöhner et al. |
| 4,921,998 | A | 5/1990 | Niewöhner et al. |
| 2006/0154965 | A1 | 7/2006 | Harris et al. |

FOREIGN PATENT DOCUMENTS

| | | |
|---|---|---|
| DE | 4411856 | 1/1994 |
| EP | 0 253 257 | 1/1988 |
| EP | 0 405 602 | 1/1991 |
| EP | 0657422 A2 | 6/1995 |
| WO | WO 92/01675 | 2/1992 |
| WO | WO 00/16798 | 3/2000 |
| WO | WO 2005/040114 | 5/2005 |
| WO | WO 2005/054232 | 6/2005 |
| WO | WO 2006/034418 | 3/2006 |
| WO | WO 2006/091674 | 8/2006 |

OTHER PUBLICATIONS

U.S. Appl. No. 12/497,807, filed Jul. 6, 2009, Chen et al.
U.S. Appl. No. 12/540,804, filed Aug. 13, 2009, Blanc et al.
U.S. Appl. No. 12/540,839, filed Aug. 13, 2009, Firooznia et al.
U.S. Appl. No. 12/540,780, filed Aug. 13, 2009, Blanc et al.
U.S. Appl. No. 61/222,235, filed Jul. 1, 2009, Firooznia et al.
U.S. Appl. No. 61/222,182, filed Jul. 1, 2009, Chen et al.
U.S. Appl. No. 61/222,262, filed Jul. 1, 2009, Firooznia et al.
Anderson et al., J.Am. Chem. Soc., 128, pp. 10694-10695 (2006).
Walsh, D.A., J. Medicinal Chem., 21, pp. 582-585 (1978).
Feixas et al., Bioorg. Med. Chem. Lett., 11, pp. 2687-2690 (2001).
Llauger et al., Tetrahedron Lett., 45, pp. 9549-9552 (2004).
Kropp et al., J. Am. Chem. Soc., 122, pp. 4280-4285 (2000).
Fuji et al., Am. Chem. Soc., 118, pp. 2521-2522 (1996).
Wagner et al., Agnew. Chem. Internat. Edit., 9, pp. 50-54 (1970).
Lee et al., Bioorg. Med. Chem. Lett., 15, pp. 2998-3001 (2005).
Ulven Trond et al: "Targeting the prostaglandin D2 receptors DP and CRTH2 for treatment of inflammation" Current Topics in Medical Chemistry 6:13 (2006) 1427-1444 xp008104082.

*Primary Examiner* — Zinna Northington Davis
(74) *Attorney, Agent, or Firm* — George W. Johnston; Dennis P. Tramaloni; Brian C. Remy

(57) ABSTRACT

The invention is concerned with the compounds of formula I:

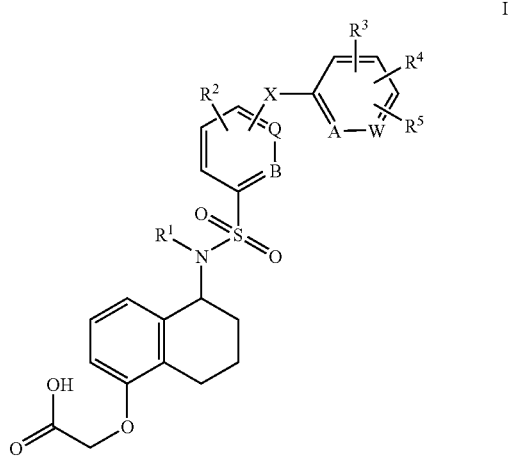

and pharmaceutically acceptable salts and esters thereof, wherein $R^1$-$R^5$, A, B, Q, W, and X are defined in the detailed description and claims. In addition, the present invention relates to methods of manufacturing and using the compounds of formula I as well as pharmaceutical compositions containing such compounds. The compounds of formula I are antagonists at the CRTH2 receptor and may be useful in treating diseases and disorders associated with that receptor such as asthma.

25 Claims, No Drawings

BI-ARYL AMINOTETRALINES

PRIORITY TO RELATED APPLICATIONS

This application claims the benefit of U.S. Provisional Application No. 61/089,155, filed Aug. 15, 2008, which is hereby incorporated by reference in its entirety.

BACKGROUND OF THE INVENTION

The present invention relates to novel 5-amino-5,6,7,8-tetrahydro-naphthalen-1-yloxy)-acetic acids, their manufacture, pharmaceutical compositions containing them and their use as CRTH2 antagonists.

Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Allergy* 34:1283-1290). Sequence variants of the gene encoding CRTH2, which differentially influence its mRNA stability, are shown to be associated with asthma (Huang et al., *Hum Mol Genet.* 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists of CRTH2 are believed to be useful for treating disorders such as asthma, allergic inflammation, COPD, allergic rhinitis, and atopic dermatitis.

SUMMARY OF THE INVENTION

The invention is concerned with the compounds of formula I:

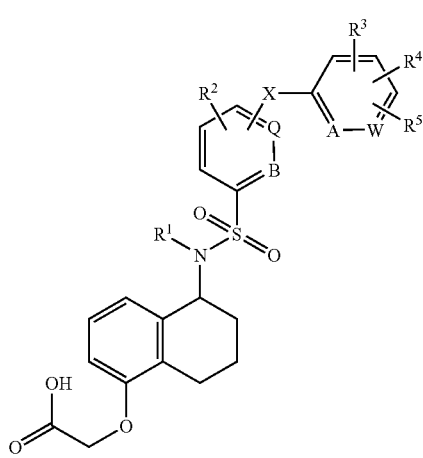

and pharmaceutically acceptable salts and esters thereof, wherein $R^1$-$R^5$, A, B, Q, W, and X are defined in the detailed description and claims. In addition, the present invention relates to methods of manufacturing and using the compounds of formula I as well as pharmaceutical compositions containing such compounds. The compounds of formula I are antagonists at the CRTH2 receptor and may be useful in treating diseases and disorders associated with that receptor such as asthma.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$-$R^5$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen or hydroxyl" refers to the fact that one or more hydrogen atoms of a lower alkyl (as defined below) is replaced by one or more halogen or hydroxyl moieties (i.e, trifluoromethyl, difluoromethyl, fluoromethyl, chloromethyl, hydroxymethyl, etc.). Similarly, the term "lower cycloalkyl substituted by lower alkyl" refers to the fact that one or more hydrogen atoms of a lower cycloalkyl (as defined below) is replaced by one or more lower alkyls (i.e, 1-methyl-cyclopropyl, 1-ethyl-cyclopropyl, etc.).

The term "optionally substituted" refers to the fact that one or more hydrogen atoms of a moiety (with one or more hydrogen atoms) can be, but does not necessarily have to be, substituted with another substituent.

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "lower cycloalkyl" refers to a saturated or partly unsaturated non-aromatic hydrocarbon ring moiety having 3 to 7 carbon atoms bonded together to form a ring structure. Examples of cycloalkyls include cyclopropyl, cyclobutyl, cyclopentyl, cyclohexyl and cycloheptyl.

The term "lower alkoxy" refers to the moiety —O—R, wherein R is lower alkyl as defined previously. Examples of lower alkoxy moieties include methoxy, ethoxy, n-propoxy, isopropoxy, n-butoxy, isobutoxy, sec-butoxy and tert-butoxy.

The term "lower alkanoyl" refers to the moiety —C(O)—R, wherein R is lower alkyl as defined previously. An example of a lower alkanoyl is acetyl.

The term "lower alkylsulfanyl" refers to the moiety —S—R, wherein R is lower alkyl as defined previously. Examples of lower alkylsulfanyls include methylsulfanyl and ethylsulfanyl.

The term "lower cycloalkylsulfanyl" refers to the moiety —S—R, wherein R is lower cycloalkyl as defined previously. Examples of lower cycloalkylsulfanyls include cyclopropylsulfanyl, cyclobutylsulfanyl and cyclopentylsulfanyl.

The term "lower alkylsulfinyl" refers to the moiety —S(O)—R, wherein R is lower alkyl as defined previously. Examples of lower alkylsulfinyls include methylsulfinyl and ethylsulfinyl.

The term "lower cycloalkylsulfinyl" refers to the moiety —S(O)—R, wherein R is lower cycloalkyl as defined previously. Examples of lower cycloalkylsulfinyls include cyclopropylsulfinyl, cyclobutylsulfinyl and cyclopentylsulfinyl.

The term "lower alkylsulfonyl" refers to the moiety —S(O)$_2$—R, wherein R is lower alkyl as defined previously. Examples of lower alkylsulfonyls include methylsulfonyl and ethylsulfonyl.

The term "lower cycloalkylsulfonyl" refers to the moiety —S(O)$_2$—R, wherein R is lower cycloalkyl as defined previously. Examples of lower cycloalkylsulfonyls include cyclopropylsulfonyl, cyclobutylsulfonyl and cyclopentylsulfonyl.

The term "lower alkylamino" refers to the moiety —N(R)(H), wherein R is lower alkyl as defined previously. An example of a lower alkylamino is methylamino.

The term "lower dialkylamino" refers to the moiety —N(R)(R'), wherein R and R' are lower alkyl as defined previously. An example of a lower dialkylamino is dimethylamino.

The term "carbamoyl" refers to the moiety —C(O)—NH$_2$.

The term "lower alkylaminocarbonyl" refers to the moiety —C(O)—N(H)(R), wherein R is lower alkyl as defined previously. An example of a lower alkylaminocarbonyl is methylaminocarbonyl.

The term "lower dialkylaminocarbonyl" refers to the moiety —C(O)—N(R)(R'), wherein R and R' are lower alkyl as defined previously. An example of a lower dialkylaminocarbonyl is dimethylaminocarbonyl.

The term "lower alkylcarbonylamino" refers to the moiety —N(H)—C(O)—R, wherein R is lower alkyl as defined previously. An example of a lower alkylcarbonylamino is methylcarbonylamino.

The term "lower trialkylsilyl" refers to the moiety —Si(R)(R')(R'') wherein R, R' and R'' are lower alkyl as defined previously. An example of a lower trialkylsilyl is trimethylsilyl.

The term "halogen" refers to a moiety of fluoro, chloro, bromo or iodo.

Unless otherwise indicated, the term "hydrogen" or "hydro" refers to the moiety of a hydrogen atom (—H) and not H$_2$.

Unless otherwise indicated, the term "a compound of the formula" or "a compound of formula" or "compounds of the formula" or "compounds of formula" refers to any compound selected from the genus of compounds as defined by the formula (Including any pharmaceutically acceptable salt or ester of any such compound).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention relates to the compounds of formula I:

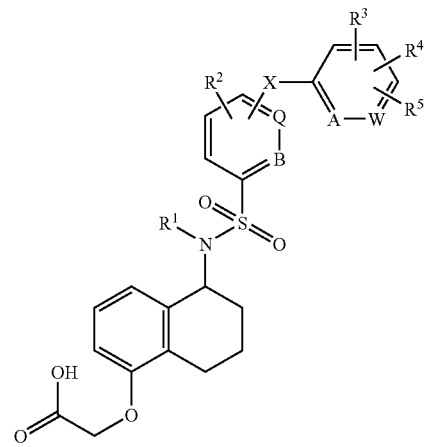

and pharmaceutically acceptable salts and esters thereof, wherein:

X is a direct bond, oxygen, $-S(O)_2-$, $-NHCO-$ or $-NHSO_2-$; and wherein X is bonded to the ring containing Q and B by substitution of a hydrogen atom of a ring carbon atom;

A, B, Q, and W, independently of each other, are carbon or nitrogen with the proviso that: (1) B and Q are not both nitrogen, (2) W and A are not both nitrogen, and (3) when A, B, Q or W is nitrogen, the nitrogen is unsubstituted;

$R^1$ is hydrogen or methyl;

$R^2$ is selected from the group consisting of:
(1) hydrogen;
(2) halogen;
(3) lower alkyl optionally substituted by halogen; and
(4) lower cycloalkyl optionally substituted by lower alkyl;

$R^3$, $R^4$ and $R^5$ are bonded to the ring containing A and W by substitution of a hydrogen atom of a ring carbon atom; and $R^3$, $R^4$ and $R^5$, independently of each other, are selected from the group consisting of:
(1) hydrogen;
(2) hydroxyl;
(3) halogen;
(4) nitro;
(5) cyano;
(6) lower alkyl optionally substituted by halogen or hydroxyl;
(7) lower alkoxy optionally substituted by halogen;
(8) lower alkanoyl;
(9) carbamoyl, lower alkylaminocarbonyl, or lower dialkylaminocarbonyl;
(10) lower alkylcarbonylamino;
(11) lower alkylsulfanyl or lower cycloalkylsulfanyl
(12) lower alkylsulfinyl or lower cycloalkylsulfinyl;
(13) lower alkylsulfonyl or lower cycloalkylsulfonyl; and
(14) trimethylsilyl;

or alternatively, one of $R^3$, $R^4$ or $R^5$ is hydrogen and the remaining two of $R^3$, $R^4$ or $R^5$ are bound together with the carbon atom to which they are attached to form a ring of 5 or 6 carbon atoms.

Unless indicated otherwise, the term "A, B, Q, and W, independently of each other, are carbon or nitrogen" (or similar references to A, B, Q, or W in relation to carbon or nitrogen) indicates that: (1) when A, B, Q, or W is carbon as depicted in formula I, the carbon is either unsubstituted by being bonded to a hydrogen (C—H) or substituted by being bonded to another moiety as indicated in formula I (for example, A or W may be bonded to $R^3$, $R^4$, or $R^5$; and B and Q may be bonded to $R^2$ or X (if X is oxygen or —$SO_2$—) or to the ring containing A and W (if X is a direct bond); and (2) when A, B, Q, or W is nitrogen, the nitrogen is not bonded to either a hydrogen or $R^2$, $R^3$, $R^4$, $R^5$ or X (if X is oxygen or —$SO_2$—) or to the ring containing A and W (if X is a direct bond).

Unless indicated otherwise, the term "X is bonded to the ring containing Q and B by substitution of a hydrogen atom of a ring carbon atom" refers to the fact that: (1) when X is oxygen or —$SO_2$—, the oxygen or —$SO_2$— is bonded to one of the ring carbon atoms (of the aromatic ring in formula I containing Q and B) in place of a hydrogen atom that would otherwise be bonded to that carbon atom absent being substituted by X; and (2) when X is a direct bond, the ring containing A and W is bonded to one of the ring carbon atoms (of the aromatic ring in formula I containing Q and B) in place of a hydrogen atom that would otherwise be bonded to that carbon atom absent being substituted by the ring containing A and W.

Similarly, unless indicated otherwise, the term "$R^3$, $R^4$ and $R^5$ are bonded to the ring containing A and W by substitution of a hydrogen atom of a ring carbon atom" refers to the fact that $R^3$, $R^4$ and $R^5$ as depicted in formula I (independently of each other) are bonded to one of the ring carbon atoms (of the aromatic ring in formula I containing A and W) in place of a hydrogen atom that would otherwise be bonded to that carbon atom absent being substituted by $R^3$, $R^4$ or $R^5$; with the understanding that $R^3$, $R^4$ and $R^5$ are not simultaneously bonded to the same carbon atom.

Unless indicated otherwise, the genus of formula I and any subgenera thereof encompass all possible stereoisomers (i.e., (R)-enantiomers and (S)-enantiomers) as well as racemic and scalemic mixtures thereof. In one embodiment of the invention, the compounds of formula I are (R)-enantiomers or pharmaceutically acceptable salts or esters thereof as depicted in the following subgeneric structural formula IA for the (R)-enantiomers of formula I:

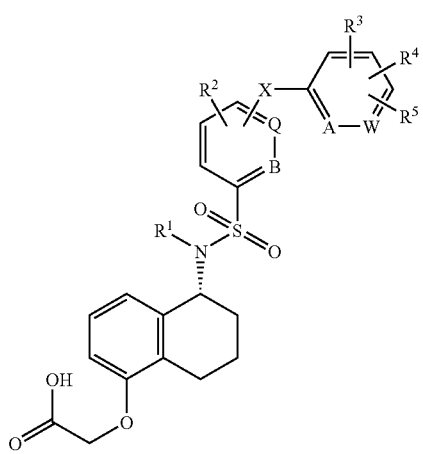

IA wherein $R^1$-$R^5$, A, B, Q, W, and X are as defined previously.

In another embodiment, the compounds of formula I are (S)-enantiomers or pharmaceutically acceptable salts or esters thereof as depicted in the following subgeneric structural formula IB for the (S)-enantiomers of formula I:

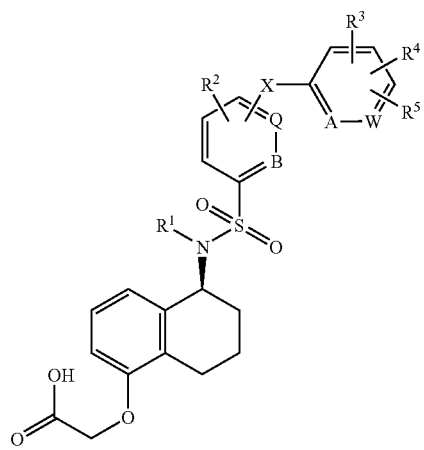

IB wherein $R^1$-$R^5$, A, B, Q, W, and X are as defined previously.

In another embodiment the present invention is directed to a composition comprising a mixture (racemic or otherwise) of the (R)-enantiomers and (S)-enantiomers of a compound of formula I.

In one embodiment the present invention is directed to the compounds of formula I or pharmaceutically acceptable salts or esters thereof wherein A, B, Q, and W are carbon.

In another embodiment the present invention is directed to the compounds of formula I or pharmaceutically acceptable salts or esters thereof wherein A is nitrogen and B, Q, and W are carbon.

In another embodiment the present invention is directed to the compounds of formula I or pharmaceutically acceptable salts or esters thereof wherein W is nitrogen and A, B, and Q are carbon.

In another embodiment the present invention is directed to the compounds of formula I or pharmaceutically acceptable salts or esters thereof wherein B is nitrogen and A, Q, and W are carbon.

In another embodiment the present invention is directed to the compounds of formula I or pharmaceutically acceptable salts or esters thereof wherein Q is nitrogen and A, B, and W are carbon.

In another embodiment the present invention is directed to the compounds of formula I or pharmaceutically acceptable salts or esters thereof wherein A and B are nitrogen and Q and W are carbon.

In another embodiment the present invention is directed to the compounds of formula I or pharmaceutically acceptable salts or esters thereof wherein A and Q are nitrogen and B and W are carbon.

In another embodiment the present invention is directed to the compounds of formula I or pharmaceutically acceptable salts or esters thereof wherein W and B are nitrogen and A and Q are carbon.

In another embodiment the present invention is directed to the compounds of formula I or pharmaceutically acceptable salts or esters thereof wherein W and Q are nitrogen and A and B are carbon.

In one embodiment the present invention is directed to the compounds of formula I or pharmaceutically acceptable salts or esters thereof wherein X is a direct bond.

In one embodiment the present invention is directed to the compounds of formula I or pharmaceutically acceptable salts or esters thereof wherein X is oxygen.

In one embodiment the present invention is directed to the compounds of formula I or pharmaceutically acceptable salts or esters thereof wherein X is —S(O)$_2$—.

In one embodiment the present invention is directed to the compounds of formula I or pharmaceutically acceptable salts or esters thereof wherein R$^1$ is hydrogen.

In another embodiment the present invention is directed to the compounds of formula I or pharmaceutically acceptable salts or esters thereof wherein R$^1$ is methyl.

In another embodiment the present invention is directed to the compounds of formula I or pharmaceutically acceptable salts or esters thereof wherein R$^2$ is selected from the group consisting of:
(1) hydrogen;
(2) bromo;
(3) chloro;
(4) methyl;
(5) isopropyl;
(6) trifluoromethyl; and
(7) 1-methylcyclopropyl.

In another embodiment the present invention is directed to the compounds of formula I or pharmaceutically acceptable salts or esters thereof wherein R$^2$ is selected from the group consisting of:
(1) hydrogen;
(2) bromo;
(3) chloro;
(4) methyl; and
(5) trifluoromethyl.

In another embodiment the present invention is directed to the compounds of formula I or pharmaceutically acceptable salts or esters thereof wherein R$^3$, R$^4$ and R$^5$, independently of each other, are selected from the group consisting of:
(1) hydrogen;
(2) halogen;
(3) nitro;
(4) lower alkyl optionally substituted by halogen or hydroxyl;
(5) lower alkoxy optionally substituted by halogen;
(6) lower alkanoyl; and
(7) carbamoyl, lower alkylaminocarbonyl, or lower dialkylaminocarbonyl; and
(8) lower alkylsulfonyl or lower cycloalkylsulfonyl.

In another embodiment the present invention is directed to the compounds of formula I or pharmaceutically acceptable salts or esters thereof wherein R$^3$, R$^4$ and R$^5$, independently of each other, are selected from the group consisting of:
(1) hydrogen;
(2) fluoro or chloro;
(3) nitro;
(4) isopropyl or tert-butyl;
(5) methoxy;
(6) acetyl;
(7) carbamoyl; and
(8) methylsulfonyl or ethylsulfonyl.

In another embodiment the present invention is directed to the compounds of formula I or pharmaceutically acceptable salts or esters thereof wherein R$^3$, R$^4$ and R$^5$, independently of each other, are selected from the group consisting of:
(1) hydrogen;
(2) hydroxyl;
(3) fluoro, chloro, or bromo;
(4) nitro;
(5) cyano;
(6) methyl, ethyl, isopropyl, or tert-butyl;
(7) difluoromethyl or trifluoromethyl;
(8) hydroxylethyl;
(9) methoxy, ethoxy or isopropoxy;
(10) trifluoromethoxy;
(11) acetyl;
(12) carbamoyl;
(13) methylcarbonylamino;
(14) methylsulfinyl or ethylsulfinyl; and
(15) methylsulfonyl or ethylsulfonyl.

In particular embodiments, preferred positions of R$^2$, R$^3$, R$^4$, R$^5$ and X are hereafter indicated by the following numbered positions (2, 3, 4, 5, 9, 10, and 11) of formula I as shown below:

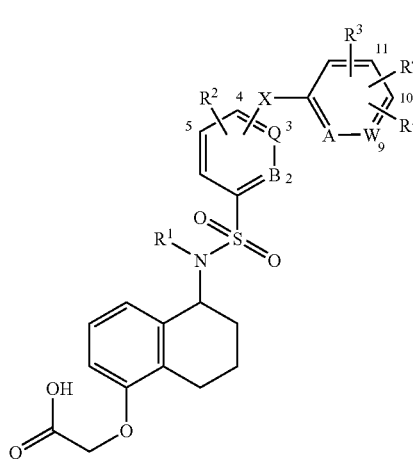

In a particular embodiment, X is attached to the 3 or 4 position and R$^2$ is attached to the 5 position on the ring containing B and Q.

In a more particular embodiment, X is a direct bond attached to the 4 position and R$^2$ is attached to the 5 position on the ring containing B and Q.

In a further particular embodiment, X is a direct bond attached to the 4 position and R$^2$ is chloro or trifluoromethyl attached to the 5 position on the ring containing B and Q.

In another particular embodiment, X is oxygen attached to the 4 position and R$^2$ is attached to the 5 position on the ring containing B and Q.

In a further particular embodiment, X is oxygen attached to the 4 position and R$^2$ is chloro or trifluoromethyl attached to the 5 position on the ring containing B and Q.

In another particular embodiment, when Q is nitrogen, X is a direct bond or oxygen attached to the 4 position and R$^2$ is attached to the 5 position on the ring containing B and Q.

In another particular embodiment, when Q is nitrogen, X is a direct bond or oxygen attached to the 4 position and R$^2$ is bromo attached to the 5 position on the ring containing B and Q.

In another embodiment, when B and Q are carbon, X is a direct bond or oxygen attached to the 4 position and R$^2$ is attached to the 5 position on the ring containing B and Q.

In a more particular embodiment, when B and Q are carbon, X is a direct bond or oxygen attached to the 4 position and R$^2$ is chloro attached to the 5 position on the ring containing B and Q.

In another more particular embodiment, when B and Q are carbon, X is a direct bond or oxygen attached to the 4 position and R$^2$ is trifluoromethyl attached to the 5 position on the ring containing B and Q.

In one embodiment at least one of R$^3$, R$^4$, and R$^5$ is hydrogen attached to position 10 and the two remaining R groups are attached to positions 9 and 11 on the ring containing A and W.

In another particular embodiment at least two of $R^3$, $R^4$, and $R^5$ are hydrogen and the remaining R group is attached to position 9 or 11 on the ring containing A and W.

In a more specific embodiment, the present invention is directed to a compound of formula I selected from the group consisting of:

[(R)-5-(4'-Methyl-biphenyl-4-sulfonylamino)-5,6,7,8-tetrahydro-naphthalen-1-yloxy]-acetic acid;
[5-(3-Phenoxy-benzenesulfonylamino)-5,6,7,8-tetrahydro-naphthalen-1-yloxy]-acetic acid;
[5-(Biphenyl-3-sulfonylamino)-5,6,7,8-tetrahydro-naphthalen-1-yloxy]-acetic acid;
[5-(4-Phenoxy-benzenesulfonylamino)-5,6,7,8-tetrahydro-naphthalen-1-yloxy]-acetic acid;
[5-(6-Phenoxy-pyridine-3-sulfonylamino)-5,6,7,8-tetrahydro-naphthalen-1-yloxy]-acetic acid;
[(R)-5-(4'-Fluoro-biphenyl-4-sulfonylamino)-5,6,7,8-tetrahydro-naphthalen-1-yloxy]-acetic acid;
[(R)-5-(4'-Methoxy-biphenyl-4-sulfonylamino)-5,6,7,8-tetrahydro-naphthalen-1-yloxy]-acetic acid;
[(R)-5-(4'-Chloro-biphenyl-4-sulfonylamino)-5,6,7,8-tetrahydro-naphthalen-1-yloxy]-acetic acid;
[(R)-5-(4'-Acetyl-biphenyl-4-sulfonylamino)-5,6,7,8-tetrahydro-naphthalen-1-yloxy]-acetic acid;
[(R)-5-(4'-Methyl-biphenyl-3-sulfonylamino)-5,6,7,8-tetrahydro-naphthalen-1-yloxy]-acetic acid;
[(R)-5-(4-Phenoxy-benzenesulfonylamino)-5,6,7,8-tetrahydro-naphthalen-1-yloxy]-acetic acid;
{(R)-5-[4-(2-Chloro-phenoxy)-benzenesulfonylamino]-5,6,7,8-tetrahydro-naphthalen-1-yloxy}-acetic acid;
{5-[5-Bromo-6-(2-chloro-4-fluoro-phenoxy)-pyridine-3-sulfonylamino]-5,6,7,8-tetrahydro-naphthalen-1-yloxy}-acetic acid;
{(R)-5-[3-Chloro-4-(4-chloro-phenoxy)-benzenesulfonylamino]-5,6,7,8-tetrahydro-naphthalen-1-yloxy}-acetic acid;
{5-[5-Bromo-6-(2-fluoro-phenoxy)-pyridine-3-sulfonylamino]-5,6,7,8-tetrahydro-naphthalen-1-yloxy}-acetic acid;
{5-[5-Bromo-6-(2-chloro-phenoxy)-pyridine-3-sulfonylamino]-5,6,7,8-tetrahydro-naphthalen-1-yloxy}-acetic acid;
{5-[5-Bromo-6-(3-chloro-phenoxy)-pyridine-3-sulfonylamino]-5,6,7,8-tetrahydro-naphthalen-1-yloxy}-acetic acid;
{5-[5-Bromo-6-(3-cyano-phenoxy)-pyridine-3-sulfonylamino]-5,6,7,8-tetrahydro-naphthalen-1-yloxy}-acetic acid;
{5-[5-Bromo-6-(4-cyano-phenoxy)-pyridine-3-sulfonylamino]-5,6,7,8-tetrahydro-naphthalen-1-yloxy}-acetic acid;
{5-[5-Bromo-6-(4-fluoro-phenoxy)-pyridine-3-sulfonylamino]-5,6,7,8-tetrahydro-naphthalen-1-yloxy}-acetic acid;
{5-[5-Bromo-6-(3-isopropyl-phenoxy)-pyridine-3-sulfonylamino]-5,6,7,8-tetrahydro-naphthalen-1-yloxy}-acetic acid;
{5-[5-Bromo-6-(4-isopropyl-phenoxy)-pyridine-3-sulfonylamino]-5,6,7,8-tetrahydro-naphthalen-1-yloxy}-acetic acid;
{5-[5-Bromo-6-(4-methoxy-phenoxy)-pyridine-3-sulfonylamino]-5,6,7,8-tetrahydro-naphthalen-1-yloxy}-acetic acid;
{5-[5-Bromo-6-(3,4-dimethyl-phenoxy)-pyridine-3-sulfonylamino]-5,6,7,8-tetrahydro-naphthalen-1-yloxy}-acetic acid;
{5-[5-Bromo-6-(4-chloro-2-methyl-phenoxy)-pyridine-3-sulfonylamino]-5,6,7,8-tetrahydro-naphthalen-1-yloxy}-acetic acid;
{5-[5-Bromo-6-(4-ethyl-phenoxy)-pyridine-3-sulfonylamino]-5,6,7,8-tetrahydro-naphthalen-1-yloxy}-acetic acid;
{5-[5-Bromo-6-(3,5-dimethyl-phenoxy)-pyridine-3-sulfonylamino]-5,6,7,8-tetrahydro-naphthalen-1-yloxy}-acetic acid;
[5-(5-Bromo-6-phenoxy-pyridine-3-sulfonylamino)-5,6,7,8-tetrahydro-naphthalen-1-yloxy]-acetic acid;
{5-[5-Bromo-6-(indan-5-yloxy)-pyridine-3-sulfonylamino]-5,6,7,8-tetrahydro-naphthalen-1-yloxy}-acetic acid;
[5-(5-Bromo-6-m-tolyloxy-pyridine-3-sulfonylamino)-5,6,7,8-tetrahydro-naphthalen-1-yloxy]-acetic acid;
[5-(5-Bromo-6-o-tolyloxy-pyridine-3-sulfonylamino)-5,6,7,8-tetrahydro-naphthalen-1-yloxy]-acetic acid;
[5-(5-Bromo-6-p-tolyloxy-pyridine-3-sulfonylamino)-5,6,7,8-tetrahydro-naphthalen-1-yloxy]-acetic acid;
{5-[5-Bromo-6-(4-chloro-phenoxy)-pyridine-3-sulfonylamino]-5,6,7,8-tetrahydro-naphthalen-1-yloxy}-acetic acid;
(5-{5-Bromo-6-[4-(2-hydroxy-ethyl)-phenoxy]-pyridine-3-sulfonylamino}-5,6,7,8-tetrahydro-naphthalen-1-yloxy)-acetic acid;
{(R)-5-[5-Chloro-6-(4-chloro-phenoxy)-pyridine-3-sulfonylamino]-5,6,7,8-tetrahydro-naphthalen-1-yloxy}-acetic acid;
{(R)-5-[5-Bromo-6-(4-fluoro-phenoxy)-pyridine-3-sulfonylamino]-5,6,7,8-tetrahydro-naphthalen-1-yloxy}-acetic acid;
{(R)-5-[5-Bromo-6-(4-chloro-phenoxy)-pyridine-3-sulfonylamino]-5,6,7,8-tetrahydro-naphthalen-1-yloxy}-acetic acid;
{(R)-5-[5-Bromo-6-(2-chloro-phenoxy)-pyridine-3-sulfonylamino]-5,6,7,8-tetrahydro-naphthalen-1-yloxy}-acetic acid;
{(R)-5-[5-Bromo-6-(3-chloro-phenoxy)-pyridine-3-sulfonylamino]-5,6,7,8-tetrahydro-naphthalen-1-yloxy}-acetic acid;
{(R)-5-[5-Bromo-6-(2-chloro-4-fluoro-phenoxy)-pyridine-3-sulfonylamino]-5,6,7,8-tetrahydro-naphthalen-1-yloxy}-acetic acid;
[(R)-5-(5-Bromo-6-phenoxy-pyridine-3-sulfonylamino)-5,6,7,8-tetrahydro-naphthalen-yloxy]-acetic acid;
{(R)-5-[3-Chloro-4-(3-chloro-phenoxy)-benzenesulfonylamino]-5,6,7,8-tetrahydro-naphthalen-1-yloxy}-acetic acid;
{(R)-5-[3-Chloro-4-(4-fluoro-phenoxy)-benzenesulfonylamino]-5,6,7,8-tetrahydro-naphthalen-1-yloxy}-acetic acid;
{(R)-5-[3-Chloro-4-(2-chloro-phenoxy)-benzenesulfonylamino]-5,6,7,8-tetrahydro-naphthalen-1-yloxy}-acetic acid;
{(R)-5-[3-Chloro-4-(4-chloro-2-fluoro-phenoxy)-benzenesulfonylamino]-5,6,7,8-tetrahydro-naphthalen-1-yloxy}-acetic acid;
{(R)-5-[3-Chloro-4-(2-chloro-4-fluoro-phenoxy)-benzenesulfonylamino]-5,6,7,8-tetrahydro-naphthalen-1-yloxy}-acetic acid;
[(R)-5-(3-Chloro-4-phenoxy-benzenesulfonylamino)-5,6,7,8-tetrahydro-naphthalen-1-yloxy]-acetic acid;
{(R)-5-[2-Chloro-4-(4-fluoro-phenoxy)-benzenesulfonylamino]-5,6,7,8-tetrahydro-naphthalen-1-yloxy}-acetic acid;
{(R)-5-[2-Chloro-4-(2-chloro-phenoxy)-benzenesulfonylamino]-5,6,7,8-tetrahydro-naphthalen-1-yloxy}-acetic acid;
{(R)-5-[2-Chloro-4-(2-chloro-4-fluoro-phenoxy)-benzenesulfonylamino]-5,6,7,8-tetrahydro-naphthalen-1-yloxy}-acetic acid;

[(R)-5-(2-Chloro-4-phenoxy-benzenesulfonylamino)-5,6,7,8-tetrahydro-naphthalen-1-yloxy]-acetic acid;
{(R)-5-[2-Chloro-4-(4-chloro-phenoxy)-benzenesulfonylamino]-5,6,7,8-tetrahydro-naphthalen-1-yloxy}-acetic acid;
{(R)-5-[2-Chloro-4-(3-chloro-phenoxy)-benzenesulfonylamino]-5,6,7,8-tetrahydro-naphthalen-1-yloxy}-acetic acid;
{(R)-5-[4-(4-Fluoro-phenoxy)-3-trifluoromethyl-benzenesulfonylamino]-5,6,7,8-tetrahydro-naphthalen-1-yloxy}-acetic acid;
{(R)-5-[4-(2-Chloro-phenoxy)-3-trifluoromethyl-benzenesulfonylamino]-5,6,7,8-tetrahydro-naphthalen-1-yloxy}-acetic acid;
{(R)-5-[4-(4-Chloro-2-fluoro-phenoxy)-3-trifluoromethyl-benzenesulfonylamino]-5,6,7,8-tetrahydro-naphthalen-1-yloxy}-acetic acid;
{(R)-5-[4-(2-Chloro-4-fluoro-phenoxy)-3-trifluoromethyl-benzenesulfonylamino]-5,6,7,8-tetrahydro-naphthalen-1-yloxy}-acetic acid;
[(R)-5-(4-Phenoxy-3-trifluoromethyl-benzenesulfonylamino)-5,6,7,8-tetrahydro-naphthalen-1-yloxy]-acetic acid;
{(R)-5-[4-(4-Chloro-phenoxy)-3-trifluoromethyl-benzenesulfonylamino]-5,6,7,8-tetrahydro-naphthalen-1-yloxy}-acetic acid;
{(R)-5-[4-(3-Chloro-phenoxy)-3-trifluoromethyl-benzenesulfonylamino]-5,6,7,8-tetrahydro-naphthalen-1-yloxy}-acetic acid;
{5-[4-(4-Fluoro-pyridin-2-yl)-benzenesulfonylamino]-5,6,7,8-tetrahydro-naphthalen-1-yloxy}-acetic acid;
[(R)-5-(2'-Chloro-biphenyl-4-sulfonylamino)-5,6,7,8-tetrahydro-naphthalen-1-yloxy]-acetic acid;
{5-[4-(2-Fluoro-pyridin-3-yl)-benzenesulfonylamino]-5,6,7,8-tetrahydro-naphthalen-1-yloxy}-acetic acid;
{5-[4-(6-Fluoro-pyridin-3-yl)-benzenesulfonylamino]-5,6,7,8-tetrahydro-naphthalen-1-yloxy}-acetic acid;
{5-[4-(5-Fluoro-pyridin-3-yl)-benzenesulfonylamino]-5,6,7,8-tetrahydro-naphthalen-1-yloxy}-acetic acid;
{5-[4-(6-Methyl-pyridin-3-yl)-benzenesulfonylamino]-5,6,7,8-tetrahydro-naphthalen-1-yloxy}-acetic acid;
{5-[4-(6-Methyl-pyridin-2-yl)-benzenesulfonylamino]-5,6,7,8-tetrahydro-naphthalen-1-yloxy}-acetic acid;
{5-[4-(3-Methyl-pyridin-2-yl)-benzenesulfonylamino]-5,6,7,8-tetrahydro-naphthalen-1-yloxy}-acetic acid;
{5-[4-(6-Methoxy-pyridin-2-yl)-benzenesulfonylamino]-5,6,7,8-tetrahydro-naphthalen-1-yloxy}-acetic acid;
{5-[4-(5-Methyl-pyridin-3-yl)-benzenesulfonylamino]-5,6,7,8-tetrahydro-naphthalen-1-yloxy}-acetic acid;
{5-[4-(6-Trifluoromethyl-pyridin-3-yl)-benzenesulfonylamino]-5,6,7,8-tetrahydro-naphthalen-1-yloxy}-acetic acid;
{5-[4-(2-Chloro-5-methyl-pyridin-3-yl)-benzenesulfonylamino]-5,6,7,8-tetrahydro-naphthalen-1-yloxy}-acetic acid;
{5-[4-(5-Methanesulfonyl-pyridin-3-yl)-benzenesulfonylamino]-5,6,7,8-tetrahydro-naphthalen-1-yloxy}-acetic acid;
{5-[4-(6-Fluoro-5-methyl-pyridin-3-yl)-benzenesulfonylamino]-5,6,7,8-tetrahydro-naphthalen-1-yloxy}-acetic acid;
{5-[4-(2-Methyl-pyridin-3-yl)-benzenesulfonylamino]-5,6,7,8-tetrahydro-naphthalen-1-yloxy}-acetic acid;
[5-(2'-Chloro-biphenyl-4-sulfonylamino)-5,6,7,8-tetrahydro-naphthalen-1-yloxy]-acetic acid;
[5-(3'-Chloro-biphenyl-4-sulfonylamino)-5,6,7,8-tetrahydro-naphthalen-1-yloxy]-acetic acid;
[5-(4'-Chloro-biphenyl-4-sulfonylamino)-5,6,7,8-tetrahydro-naphthalen-1-yloxy]-acetic acid;
[(R)-5-(4'-Hydroxy-biphenyl-4-sulfonylamino)-5,6,7,8-tetrahydro-naphthalen-1-yloxy]-acetic acid;
[(R)-5-(3'-Acetyl-biphenyl-4-sulfonylamino)-5,6,7,8-tetrahydro-naphthalen-1-yloxy]-acetic acid;
[(R)-5-(2',3'-Dichloro-biphenyl-4-sulfonylamino)-5,6,7,8-tetrahydro-naphthalen-1-yloxy]-acetic acid;
[(R)-5-(2',5'-Dimethoxy-biphenyl-4-sulfonylamino)-5,6,7,8-tetrahydro-naphthalen-1-yloxy]-acetic acid;
[(R)-5-(2',6'-Dimethoxy-biphenyl-4-sulfonylamino)-5,6,7,8-tetrahydro-naphthalen-1-yloxy]-acetic acid;
[(R)-5-(2',5'-Dichloro-biphenyl-4-sulfonylamino)-5,6,7,8-tetrahydro-naphthalen-1-yloxy]-acetic acid;
[(R)-5-(2',5'-Dimethyl-biphenyl-4-sulfonylamino)-5,6,7,8-tetrahydro-naphthalen-1-yloxy]-acetic acid;
[(R)-5-(4'-Dimethylcarbamoyl-biphenyl-4-sulfonylamino)-5,6,7,8-tetrahydro-naphthalen-1-yloxy]-acetic acid;
[(R)-5-(2',3'-Dimethoxy-biphenyl-4-sulfonylamino)-5,6,7,8-tetrahydro-naphthalen-1-yloxy]-acetic acid;
[(R)-5-(5'-Chloro-2'-methyl-biphenyl-4-sulfonylamino)-5,6,7,8-tetrahydro-naphthalen-1-yloxy]-acetic acid;
[(R)-5-(3'-Dimethylcarbamoyl-biphenyl-4-sulfonylamino)-5,6,7,8-tetrahydro-naphthalen-1-yloxy]-acetic acid;
[(R)-5-(2,4'-Dimethyl-biphenyl-4-sulfonylamino)-5,6,7,8-tetrahydro-naphthalen-1-yloxy]-acetic acid;
[(R)-5-(2,3'-Dimethyl-biphenyl-4-sulfonylamino)-5,6,7,8-tetrahydro-naphthalen-1-yloxy]-acetic acid;
[(R)-5-(2,2'-Dimethyl-biphenyl-4-sulfonylamino)-5,6,7,8-tetrahydro-naphthalen-1-yloxy]-acetic acid;
[(R)-5-(4'-Chloro-2-methyl-biphenyl-4-sulfonylamino)-5,6,7,8-tetrahydro-naphthalen-1-yloxy]-acetic acid;
[(R)-5-(4'-Ethoxy-2-methyl-biphenyl-4-sulfonylamino)-5,6,7,8-tetrahydro-naphthalen-1-yloxy]-acetic acid;
[(R)-5-(4'-Methoxy-2,3',5'-trimethyl-biphenyl-4-sulfonylamino)-5,6,7,8-tetrahydro-naphthalen-1-yloxy]-acetic acid;
[(R)-5-(3',4'-Dichloro-2-methyl-biphenyl-4-sulfonylamino)-5,6,7,8-tetrahydro-naphthalen-1-yloxy]-acetic acid;
[(R)-5-(3'-Nitro-biphenyl-4-sulfonylamino)-5,6,7,8-tetrahydro-naphthalen-1-yloxy]-acetic acid;
[(R)-5-(2',4'-Dichloro-biphenyl-4-sulfonylamino)-5,6,7,8-tetrahydro-naphthalen-1-yloxy]-acetic acid;
[(R)-5-(4'-Methyl-3'-nitro-biphenyl-4-sulfonylamino)-5,6,7,8-tetrahydro-naphthalen-1-yloxy]-acetic acid;
[(R)-5-(3'-Methylsulfanyl-biphenyl-4-sulfonylamino)-5,6,7,8-tetrahydro-napthalen-1-yloxy]-acetic acid;
[(R)-5-(3'-tert-Butyl-5'-methyl-biphenyl-4-sulfonylamino)-5,6,7,8-tetrahydro-naphthalen-1-yloxy]-acetic acid;
[(R)-5-(3'-Trifluoromethyl-biphenyl-4-sulfonylamino)-5,6,7,8-tetrahydro-naphthalen-1-yloxy]-acetic acid;
[(R)-5-(3'-Isopropyl-biphenyl-4-sulfonylamino)-5,6,7,8-tetrahydro-naphthalen-1-yloxy]-acetic acid;
{(R)-5-[5-(3-tert-Butyl-5-methyl-phenyl)-pyridine-2-sulfonylamino]-5,6,7,8-tetrahydro-naphthalen-1-yloxy}-acetic acid;
[(R)-5-(5'-Fluoro-3'-methoxy-biphenyl-4-sulfonylamino)-5,6,7,8-tetrahydro-naphthalen-1-yloxy]-acetic acid;
{(R)-5-[5-(3-Isopropyl-phenyl)-pyridine-2-sulfonylamino]-5,6,7,8-tetrahydro-naphthalen-1-yloxy}-acetic acid;
[(R)-5-(3'-Isopropoxy-biphenyl-4-sulfonylamino)-5,6,7,8-tetrahydro-naphthalen-1-yloxy]-acetic acid;
{(R)-5-[4-(5-Methyl-pyridin-3-yl)-benzenesulfonylamino]-5,6,7,8-tetrahydro-naphthalen-1-yloxy}-acetic acid;
[(R)-5-(3'-Methyl-biphenyl-4-sulfonylamino)-5,6,7,8-tetrahydro-naphthalen-1-yloxy]-acetic acid;

[(R)-5-(3'-Chloro-biphenyl-4-sulfonylamino)-5,6,7,8-tetrahydro-naphthalen-1-yloxy]-acetic acid;
[(R)-5-(3'-Methyl-biphenyl-3-sulfonylamino)-5,6,7,8-tetrahydro-naphthalen-1-yloxy]-acetic acid;
[(R)-5-(3'-Isopropyl-biphenyl-3-sulfonylamino)-5,6,7,8-tetrahydro-naphthalen-1-yloxy]-acetic acid;
[(R)-5-(2',3'-Dimethyl-biphenyl-3-sulfonylamino)-5,6,7,8-tetrahydro-naphthalen-1-yloxy]-acetic acid;
[(R)-5-(4'-Methoxy-3',5'-dimethyl-biphenyl-3-sulfonylamino)-5,6,7,8-tetrahydro-naphthalen-1-yloxy]-acetic acid;
{5-[5-(3-Trifluoromethyl-phenyl)-pyridine-2-sulfonylamino]-5,6,7,8-tetrahydro-naphthalen-1-yloxy}-acetic acid;
(5-{5-[3-(2-Hydroxy-ethyl)-phenyl]-pyridine-2-sulfonylamino}-5,6,7,8-tetrahydro-naphthalen-1-yloxy)-acetic acid;
{5-[5-(3-Ethoxy-phenyl)-pyridine-2-sulfonylamino]-5,6,7,8-tetrahydro-naphthalen-1-yloxy}-acetic acid;
{5-[5-(4-Trifluoromethoxy-phenyl)-pyridine-2-sulfonylamino]-5,6,7,8-tetrahydro-naphthalen-1-yloxy}-acetic acid;
{5-[6-(2-Trifluoromethyl-phenyl)-pyridine-3-sulfonylamino]-5,6,7,8-tetrahydro-naphthalen-1-yloxy}-acetic acid;
{5-[6-(4-Trifluoromethoxy-phenyl)-pyridine-3-sulfonylamino]-5,6,7,8-tetrahydro-naphthalen-1-yloxy}-acetic acid;
{5-[4-(5-Methyl-pyridin-2-yl)-benzenesulfonylamino]-5,6,7,8-tetrahydro-naphthalen-1-yloxy}-acetic acid;
{5-[4-(5-Fluoro-6-methyl-pyridin-2-yl)-benzenesulfonylamino]-5,6,7,8-tetrahydro-naphthalen-1-yloxy}-acetic acid;
[5-([2,3']Bipyridinyl-5-sulfonylamino)-5,6,7,8-tetrahydro-naphthalen-1-yloxy]-acetic acid;
{5-[6-(3-Cyano-phenyl)-pyridine-3-sulfonylamino]-5,6,7,8-tetrahydro-naphthalen-1-yloxy}-acetic acid;
{5-[4-(4-Methyl-pyridin-2-yl)-benzenesulfonylamino]-5,6,7,8-tetrahydro-naphthalen-1-yloxy}-acetic acid;
{5-[5-(2-Chloro-phenyl)-pyridine-2-sulfonylamino]-5,6,7,8-tetrahydro-naphthalen-1-yloxy}-acetic acid;
{5-[5-(3-Methoxy-phenyl)-pyridine-2-sulfonylamino]-5,6,7,8-tetrahydro-naphthalen-1-yloxy}-acetic acid;
{5-[5-(4-Methoxy-phenyl)-pyridine-2-sulfonylamino]-5,6,7,8-tetrahydro-naphthalen-1-yloxy}-acetic acid;
{5-[5-(4-Chloro-phenyl)-pyridine-2-sulfonylamino]-5,6,7,8-tetrahydro-naphthalen-1-yloxy}-acetic acid;
{5-[6-(3-Ethoxy-phenyl)-pyridine-3-sulfonylamino]-5,6,7,8-tetrahydro-naphthalen-1-yloxy}-acetic acid;
{5-[6-(5-Fluoro-2-methoxy-phenyl)-pyridine-3-sulfonylamino]-5,6,7,8-tetrahydro-naphthalen-1-yloxy}-acetic acid;
{5-[6-(3-Methoxy-phenyl)-pyridine-3-sulfonylamino]-5,6,7,8-tetrahydro-naphthalen-1-yloxy}-acetic acid;
{5-[6-(2-Chloro-phenyl)-pyridine-3-sulfonylamino]-5,6,7,8-tetrahydro-naphthalen-1-yloxy}-acetic acid;
{5-[6-(3-Chloro-4-fluoro-phenyl)-pyridine-3-sulfonylamino]-5,6,7,8-tetrahydro-naphthalen-1-yloxy}-acetic acid;
{5-[6-(3-Fluoro-phenyl)-pyridine-3-sulfonylamino]-5,6,7,8-tetrahydro-naphthalen-1-yloxy}-acetic acid;
{5-[6-(4-Chloro-phenyl)-pyridine-3-sulfonylamino]-5,6,7,8-tetrahydro-naphthalen-1-yloxy}-acetic acid;
{5-[6-(4-Fluoro-phenyl)-pyridine-3-sulfonylamino]-5,6,7,8-tetrahydro-naphthalen-1-yloxy}-acetic acid;
{5-[6-(2-Fluoro-phenyl)-pyridine-3-sulfonylamino]-5,6,7,8-tetrahydro-naphthalen-1-yloxy}-acetic acid;
{5-[6-(4-Fluoro-3-methyl-phenyl)-pyridine-3-sulfonylamino]-5,6,7,8-tetrahydro-naphthalen-1-yloxy}-acetic acid;
{5-[6-(3-Trifluoromethyl-phenyl)-pyridine-3-sulfonylamino]-5,6,7,8-tetrahydro-naphthalen-1-yloxy}-acetic acid;
{5-[6-(4-Methoxy-phenyl)-pyridine-3-sulfonylamino]-5,6,7,8-tetrahydro-naphthalen-1-yloxy}-acetic acid;
(5-{6-[3-(2-Hydroxy-ethyl)-phenyl]-pyridine-3-sulfonylamino}-5,6,7,8-tetrahydro-naphthalen-1-yloxy)-acetic acid;
[5-(6-m-Tolyl-pyridine-3-sulfonylamino)-5,6,7,8-tetrahydro-naphthalen-1-yloxy]-acetic acid;
[(R)-5-(3'-Methanesulfinyl-biphenyl-4-sulfonylamino)-5,6,7,8-tetrahydro-naphthalen-1-yloxy]-acetic acid;
[(R)-5-(3'-Methanesulfonyl-biphenyl-4-sulfonylamino)-5,6,7,8-tetrahydro-naphthalen-1-yloxy]-acetic acid;
((R)-5-{[3-Chloro-4-(4-chloro-phenoxy)-benzenesulfonyl]-methyl-amino}-5,6,7,8-tetrahydro-naphthalen-1-yloxy)-acetic acid;
((R)-5-{[3-Chloro-4-(2-chloro-phenoxy)-benzenesulfonyl]-methyl-amino}-5,6,7,8-tetrahydro-naphthalen-1-yloxy)-acetic acid;
((R)-5-{[3-Chloro-4-(4-fluoro-phenoxy)-benzenesulfonyl]-methyl-amino}-5,6,7,8-tetrahydro-naphthalen-1-yloxy)-acetic acid;
((R)-5-{[5-(3-isopropyl-phenyl)-pyridine-2-sulfonyl]-methyl-amino}-5,6,7,8-tetrahydro-naphthalen-1-yloxy)-acetic acid;
{(R)-5-[Methyl-(5-m-tolyl-pyridine-2-sulfonyl)-amino]-5,6,7,8-tetrahydro-naphthalen-1-yloxy}-acetic acid;
((R)-5-{[5-(2,3-Dimethyl-phenyl)-pyridine-2-sulfonyl]-methyl-amino}-5,6,7,8-tetrahydro-naphthalen-1-yloxy)-acetic acid;
((R)-5-{[5-(3-tert-Butyl-5-methyl-phenyl)-pyridine-2-sulfonyl]-methyl-amino}-5,6,7,8-tetrahydro-naphthalen-1-yloxy)-acetic acid;
((R)-5-{[3-(4-Chloro-benzenesulfonyl)-5-trifluoromethyl-benzenesulfonyl]-methyl-amino}-5,6,7,8-tetrahydro-naphthalen-1-yloxy)-acetic acid;
((R)-5-{[3-(4-Fluoro-benzenesulfonyl)-5-trifluoromethyl-benzenesulfonyl]-methyl-amino}-5,6,7,8-tetrahydro-naphthalen-1-yloxy)-acetic acid; and
and any pharmaceutically acceptable salt or ester thereof.

Another embodiment of the present invention is a compound selected from the group consisting of:
[5-(4-Pyridin-4-yl-benzenesulfonylamino)-5,6,7,8-tetrahydro-naphthalen-1-yloxy]-acetic acid;
{5-[4-(2-Methoxy-pyridin-4-yl)-benzenesulfonylamino]-5,6,7,8-tetrahydro-naphthalen-1-yloxy}-acetic acid;
{5-[4-(2-Fluoro-pyridin-4-yl)-benzenesulfonylamino]-5,6,7,8-tetrahydro-naphthalen-1-yloxy}-acetic acid;
{5-[4-(2-Methyl-pyridin-4-yl)-benzenesulfonylamino]-5,6,7,8-tetrahydro-naphthalen-1-yloxy}-acetic acid;
{5-[4-(2,6-Difluoro-pyridin-4-yl)-benzenesulfonylamino]-5,6,7,8-tetrahydro-naphthalen-1-yloxy}-acetic acid;
[5-(6-Thiophen-3-yl-pyridine-3-sulfonylamino)-5,6,7,8-tetrahydro-naphthalen-1-yloxy]-acetic acid; and
and any pharmaceutically acceptable salt or ester thereof.

General Synthesis of Compounds According to the Invention

The compounds of the present invention can be prepared by any conventional means. Suitable processes for synthesizing these compounds are described in the examples. Generally, compounds of formula I can be prepared according to the schemes illustrated below.
Compounds of interest Ia can be prepared according to Scheme 1. Starting with naphthalene-1,5-diol (II), palladium catalyzed hydrogenation gives 5-hydroxy-3,4-dihydro-2H-
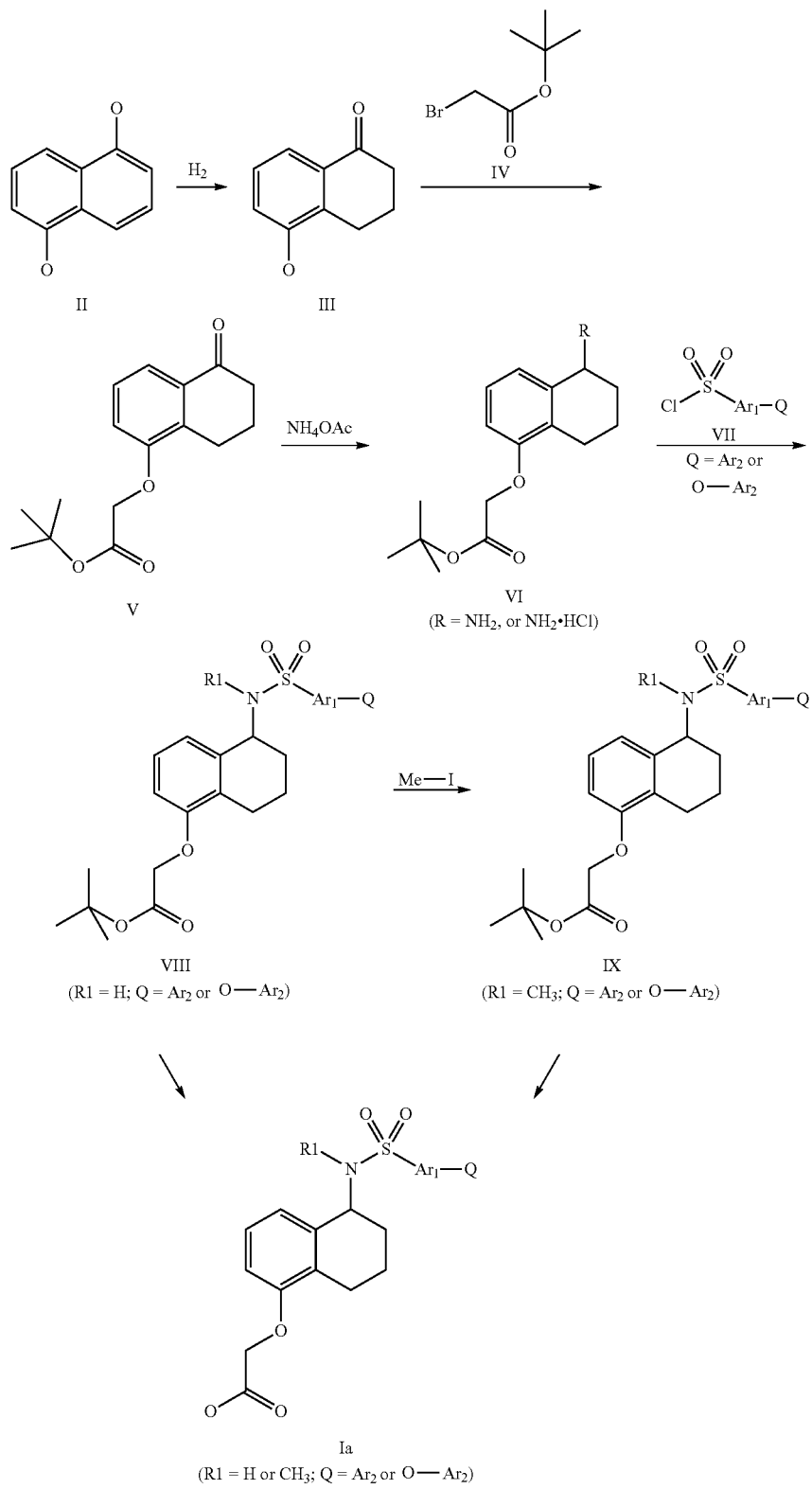
Scheme 1 naphthalen-1-one (III), which undergoes nucleophilic substitution with tert-butyl bromoacetate (IV) under basic conditions to generate the ether compound V. Reductive amination of intermediate V with ammonium acetate yields the corresponding amino derivative VI. Sulfonylation of VI (or its hydrochloride salt) with a variety of biaryl sulfonyl chlorides VII affords sulfonamides of structures VIII. N-Methylation of the sulfonamides VII gives compounds IX. Ester hydrolysis of either VIII or IX produces compounds of interest Ia. Racemic compounds Ia can be resolved using chiral chromatography to give the enantiomerically pure R and S forms of compounds of interest. Alternatively, the chiral separation can be performed with intermediates VI, VIII, or IX to generate either of the pure enantiomers of VI, VIII or IX, which can be carried through the same synthetic route described above to produce optically pure compounds of interest Ia.

Hydrogenation of naphthalene-1,5-diol (II) to give 5-hydroxy-3,4-dihydro-2H-naphthalen-1-one (III) can be carried out in the presence of 10% palladium on carbon under 100 psi pressure of hydrogen under basic conditions in a solvent such as isopropanol, ethanol, ethyl acetate, or methanol, at 80° C. for several hours.

Nucleophilic substitution reaction of 5-hydroxy-3,4-dihydro-2H-naphthalen-1-one (III) with tert-butyl bromoacetate (IV) to give the ether compound V can be accomplished using the methods that are well known to someone skilled in the art. The reaction is typically carried out in the presence of a carbonate base (e.g. cesium carbonate, potassium carbonate, or the like) or an organic base (e.g. diisopropylethylamine, triethylamine, or the like) in an aprotic solvent such as acetone, acetonitrile, N,N-dimethylformamide, or dimethyl sulfoxide, at a temperature between room temperature and 150° C. for several hours.

Transformation of the ketone V to its amine derivative VI can be achieved via reductive amination. The process can be carried out in stepwise fashion by treating the ketone V with an amine such as ammonium acetate or ammonia to generate the corresponding imine, which can then be isolated and reduced with a suitable reducing agent (e.g. sodium borohydride). It is also possible to carry out the same sequence all in one pot, with the imine formation and reduction occurring concurrently with reducing agents such as sodium cyanoborohydride ($NaBH_3CN$) or sodium triacetoxyborohydride ($NaBH(OCOCH_3)_3$). The reaction is typically carried out in a solvent such as methanol or tetrahydrofuran, at a temperature between room temperature and reflux temperature for several hours.

Sulfonylation of the amine VI (or its hydrochloride salt) with the biaryl sulfonyl chlorides of structures VII to give sulfonamides VIII can be easily accomplished using methods well known to someone skilled in the art. The reaction is typically carried out in the presence of a base such as triethylamine, pyridine, or dimethyl-pyridin-4-yl-amine in a suitable inert solvent such as dichloromethane, acetonitrile, 1,4-dioxane, tetrahydrofuran or mixtures thereof, at room temperature for 16 hours.

N-Methylation of compounds VIII to produce the derivatives IX can be achieved by treating compounds IX with methyl iodide in the presence of a weak base such as potassium carbonate or sodium carbonate, in an inert solvent such as N,N-dimethylformamide, acetonitrile, or tetrahydrofuran, at 65° C. for 5 hours.

Hydrolysis of compounds VIII or IX gives the compounds of interest of formula Ia. The reaction can be carried out in the presence of an aqueous inorganic base such as sodium hydroxide or potassium hydroxide, in an inert solvent such as dichloromethane or tetrahydrofuran, at room temperature for several hours. Alternatively, ester hydrolysis can also be accomplished under acidic conditions in the presence of an acid such as trifluoroacetic acid, dilute hydrochloric acid, or sulfonic acid, in a solvent such as dichloromethane, water, or mixtures thereof, at room temperature for several hours.

Racemic compounds Ia can be resolved using chiral chromatography to give the enantiomerically pure R and S forms of compounds of interest. Alternatively, the chiral separation can be performed with intermediates VI, VII, or IX to generate either of the pure enantiomers of VI, VIII or IX, which can be carried through the same synthetic route described above to produce optically pure compounds of interest Ia.

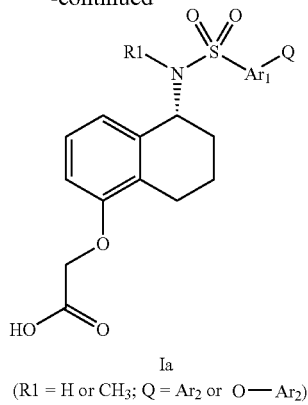

Ia
(R1 = H or CH₃; Q = Ar₂ or O—Ar₂)

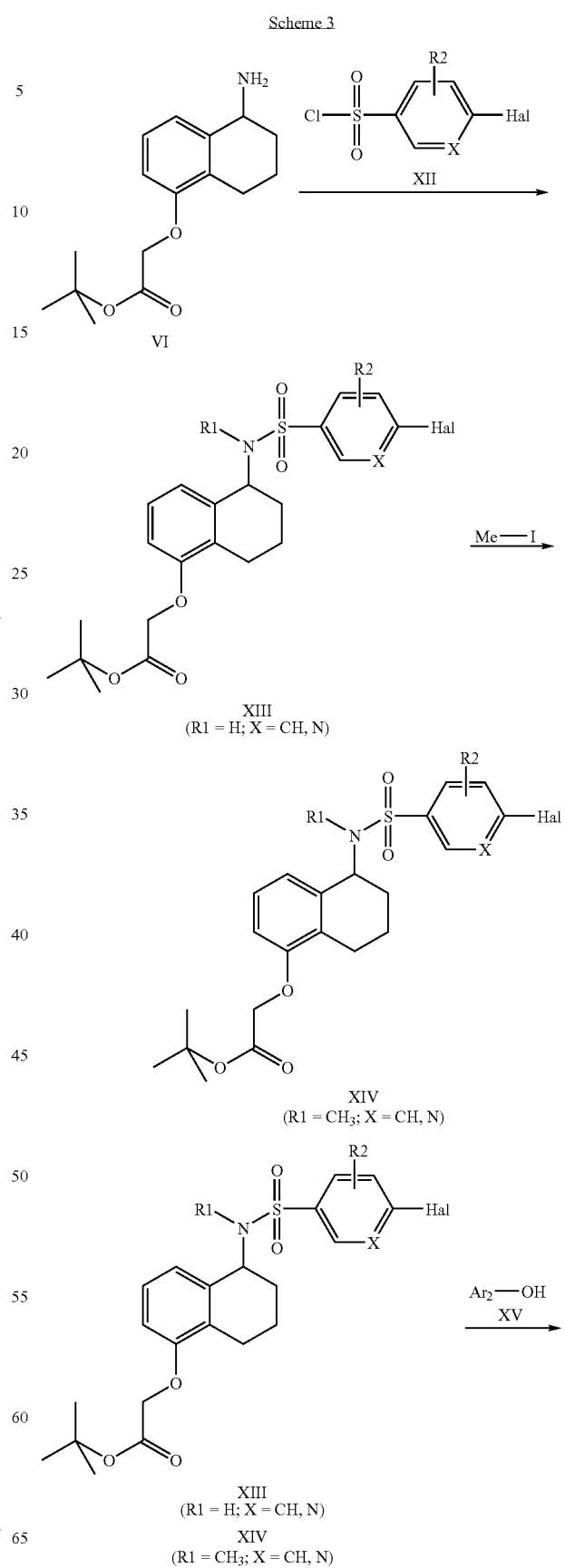

Alternatively, the key chiral intermediate VI can be prepared via an asymmetric synthesis approach shown in Scheme 2. Reduction of the ketone V to the corresponding hydroxyl compound XI can be done enantioselectively by using the chiral catalyst of formula X (or a similar catalyst containing cymene in place of mesitylene) in the presence of formic acid-triethylamine azeotropes. The hydroxyl compound XI is then converted to the amine hydrochloride salt VI via a two step process: First, the alcohol XI is converted to the corresponding azido analogue (with high preference for inversion of stereochemistry) using diphenylphosphoryl azide (DPPA) and 1,8-diazabicyclo[5.4.0]undec-7-ene (DBU). Hydrogenation of the azido derivative, followed by treatment with chlorotrimethylsilane and methanol, gives the amine hydrochloride VI bearing the desired stereochemistry. The key intermediate VI can then be converted to compounds of interest Ia, as previously described in Scheme 1.

Reduction of the ketone V to the hydroxyl compound XI can be done enantioselectively by using a catalyst such as chloro-[(1S,2S)—N-(p-toluenesulfonyl)-1,2-diphenylethane-diamine](cymene)ruthenium(II) (X) (or a similar catalyst containing cymene in place of mesitylene) in formic acid-triethylamine azeotropes (5:2 molar ratio) at room temperature for several hours, and then at 45° C. for another few hours (references: Fujii, A. et al., *J. Am. Chem. Soc.* 118 (1996) 2521; Wagner, K. *Angew. Chem., Int. Ed. Engl.* 9 (1970), 50).

Displacement of the hydroxyl group of structure XI to give the corresponding azido analogue (with a high selectivity for inversion of stereochemistry) can be achieved by treating a mixture of compound XI and diphenylphosphoryl azide (DPPA) with 1,8-diazabicyclo[5.4.0]undec-7-ene (DBU) under anhydrous conditions at a temperature between 0° C. and 10° C. for 18 hours in an inert solvent such as toluene or N,N-dimethylformamide.

Hydrogenation the above azido derivative to give the corresponding amine VI with retained chirality can be carried out in the presence of 5% palladium on carbon under 350 psi pressure of hydrogen, at room temperature for 1.5 hour, in an organic solvent such as ethyl acetate, methanol, or ethanol.

The conversion of key intermediate VI to the compounds of interest Ia is then carried as previously described in Scheme 1 above.

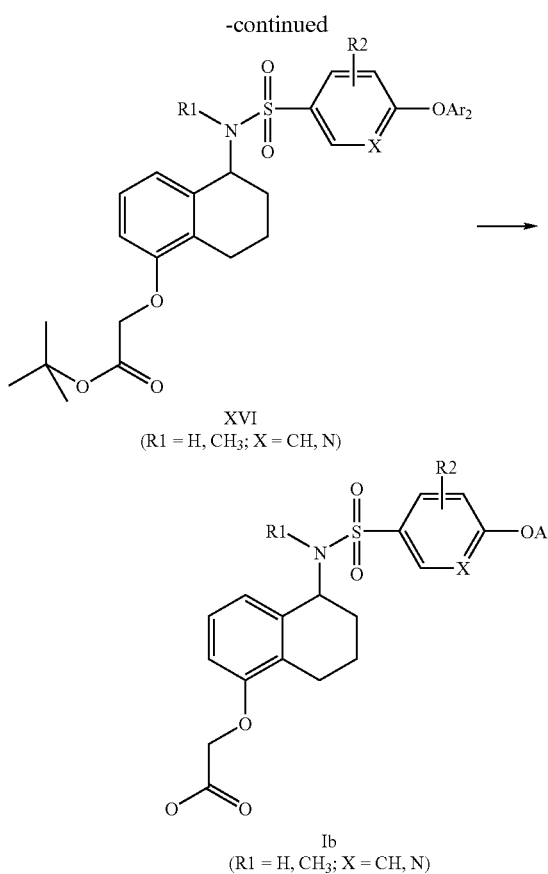

XVI
(R1 = H, CH₃; X = CH, N)

Ib
(R1 = H, CH₃; X = CH, N)

Compounds of interest Ib, bearing an ether linkage, can be prepared according to Scheme 3. In this sequence, the first step involves a sulfonylation reaction (similar to Scheme 1), where the aryl sulfonyl chlorides XII (X=N or CH) bear a halogen group (Hal=Cl if X=N, or Hal=F if X=CH) on the aromatic ring. Methylation of compounds XIII generates the corresponding N-methyl derivatives XIV. Nucleophilic substitution of the halogen group of compounds XIII or XIV with phenols XV, followed by ester hydrolysis, produces compounds Ib. Racemic compounds Ib can be resolved using chiral chromatography to give the enantiomerically pure R and S forms of compounds of interest. Alternatively, the optically pure compounds of interest Ib can be obtained by starting with the corresponding optically pure form of the amine VI following the exact synthetic route described above.

Sulfonylation of the amine compound VI (or its hydrochloride salt) with aryl sulfonyl chlorides of structures XII to give sulfonamides XIII can be easily accomplished using methods well known to someone skilled in the art. The reaction is typically carried out in the presence of a base such as triethylamine, diisopropylethylamine, pyridine, or dimethyl-pyridin-4-yl-amine in a suitable inert solvent such as dichloromethane, acetonitrile, 1,4-dioxane, tetrahydrofuran or mixtures thereof, at room temperature for 16 hours.

The corresponding N-methyl compounds XIV can be readily formed by methylation of compounds XIII with methyl iodide. The reaction can be carried out in the presence of a weak base such as potassium carbonate or sodium carbonate, in an inert solvent such as N,N-dimethylformamide, acetonitrile or tetrahydrofuran, at 65° C. for 5 hours.

Conversion of halides XIII or XIV (wherein R₁ could be H, or CH₃; halogen=Cl if X=N, or halogen=F if X=CH) to ethers XVI can be achieved by nucleophilic substitution reactions with phenols XV, which is well known to those skilled in the art, in the presence of a base such as sodium hydride or potassium carbonate, in an inert solvent such as N,N-dimethylformamide at a temperature between 100 and 150° C. for several hours. Alternatively, the reaction can be carried out at a temperature between 100° C. and 180° C. for a period of 15 to 60 minutes under microwave irradiation.

Hydrolysis of compounds XVI (wherein R₁ could be H, or CH₃) gives the compounds of interest of formula Ib. The reaction can be carried out in the presence of an aqueous inorganic base such as sodium hydroxide or potassium hydroxide, in an inert solvent such as 1,4-dioxane or tetrahydrofuran, at room temperature for several hours.

Racemic compounds Ib can be resolved using chiral chromatography to give the enantiomerically pure R and S forms of compounds of interest. Alternatively, the optically pure compounds of interest Ib can be obtained by starting with the corresponding optically pure form of the amine VI (or its hydrochloride salt) following the exact synthetic route described above.

Scheme 4

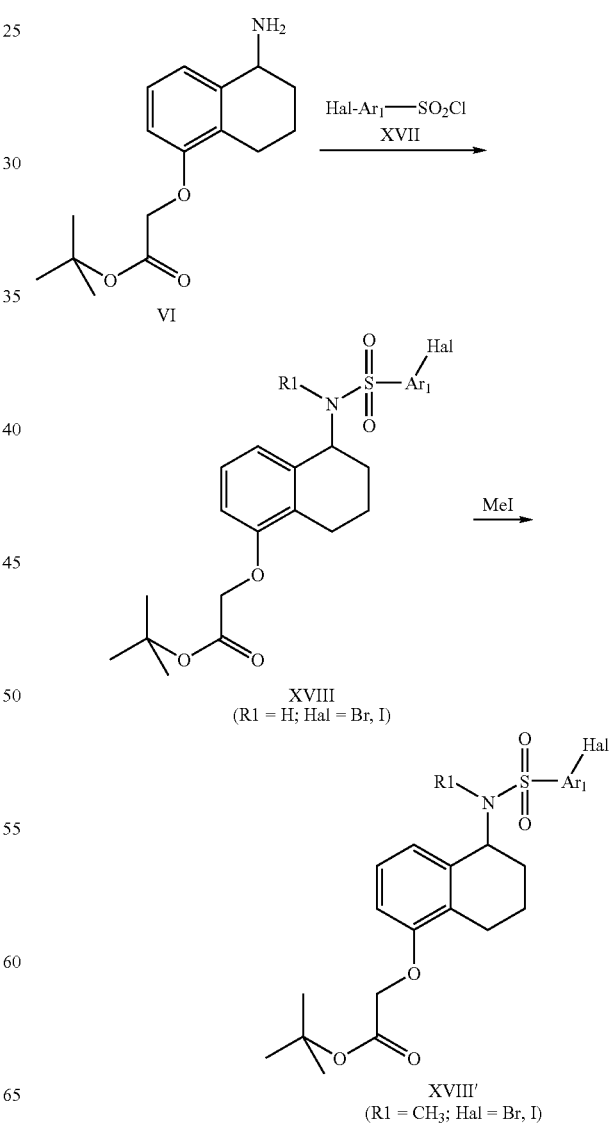

VI

XVIII
(R1 = H; Hal = Br, I)

XVIII'
(R1 = CH₃; Hal = Br, I)

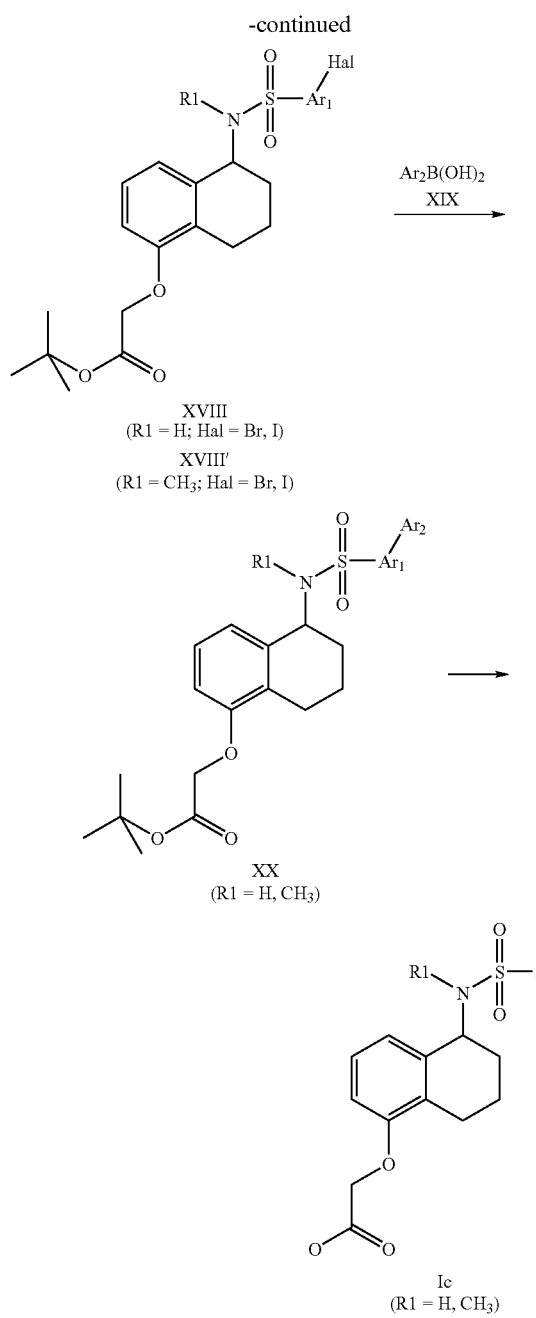

Synthesis of the compounds of interest Ic containing bi-aryl sulfonamides is illustrated in Scheme 4. In this process, the first step involves a sulfonylation reaction, similar to that described in Scheme 1, utilizing sulfonyl chlorides XVII bearing an aryl halide (Hal=Br, I) to produce intermediates XVIII. N-Methylation of XVIII gives the corresponding derivative XVIII'. Suzuki coupling reactions of compounds XVIII or XVIII' with aryl boronic acids XIX, followed by hydrolysis produce compounds of interest Ic. Racemic compounds Ic can be resolved using chiral chromatography to give the enantiomerically pure R and S forms of compounds of interest. Alternatively, the optically pure compounds of interest Ic can be obtained by starting with the corresponding optically pure form of the amine VI (or its hydrochloride salt) following the exact synthetic route described above.

Sulfonylation of the amine compound VI (or its hydrochloride salt) with the aryl sulfonyl chlorides of structures XVII to give sulfonamides XVIII can be easily accomplished using methods well known to someone skilled in the art. For example, the reaction can be carried out in the presence of a base such as triethylamine, diisopropylethylamine, pyridine, or dimethyl-pyridin-4-yl-amine in a suitable inert solvent such as dichloromethane, acetonitrile, 1,4-dioxane, tetrahydrofuran or mixtures thereof, at room temperature for 16 hours.

The corresponding N-methyl compounds XVIII' can be readily formed by methylation of compound XVIII with methyl iodide. The reaction can be carried out in the presence of a weak base such as potassium carbonate or sodium carbonate, in an inert solvent such as N,N-dimethylformamide, acetonitrile or tetrahydrofuran, at 65° C. for 5 hours.

Suzuki coupling reactions between aryl boronic acids XIX and aryl halides XVIII or XVIII' (wherein R1=H, CH$_3$; Hal=Br, I) to give compounds XX can be achieved in the presence of a palladium catalyst such as tetrakis(triphenylphosphine)palladium(0), [1,1'-bis(diphenylphosphino)ferrocene]dichloropalladium(II) (PdCl$_2$(dppf)), palladium (II) acetate, or a polymer bound form of the above palladium catalysts, and a base such as potassium tert-butoxide, sodium carbonate, or sodium hydroxide, in an inert solvent such as ethanol, tetrahydrofuran, toluene, N,N-dimethylformamide, 1,2-dimethoxyethane, dimethyl sulfoxide, PEG-400 [poly(ethylene glycol-400)], water or mixtures thereof, at a heated temperature between room temperature and reflux for several hours. Alternatively, the reactions can be carried out at a temperature between 110 and 180° C. for a period of 15 to 30 minutes under microwave irradiation (Lee S. et al., *Bioorg. Med. Chem. Lett.* 15 (2005) 2998).

Hydrolysis of compounds XX gives the compounds of interest of formula Ic. The reaction can be carried out in the presence of an aqueous inorganic base such as sodium hydroxide or potassium hydroxide, in an inert solvent such as 1,4-dioxane or tetrahydrofuran, at room temperature for several hours.

Racemic compounds Ic can be resolved using chiral chromatography to give the enantiomerically pure R and S forms of compounds of interest. Alternatively, the optically pure compounds of interest Ic can be obtained by starting with the corresponding optically pure form of the amine VI (or its hydrochloride salt) following the exact synthetic route described above.

Scheme 5

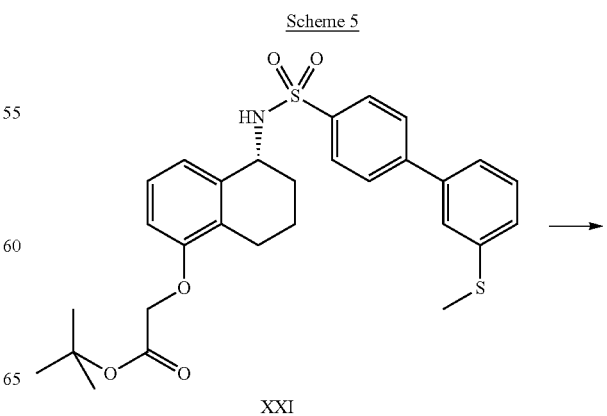

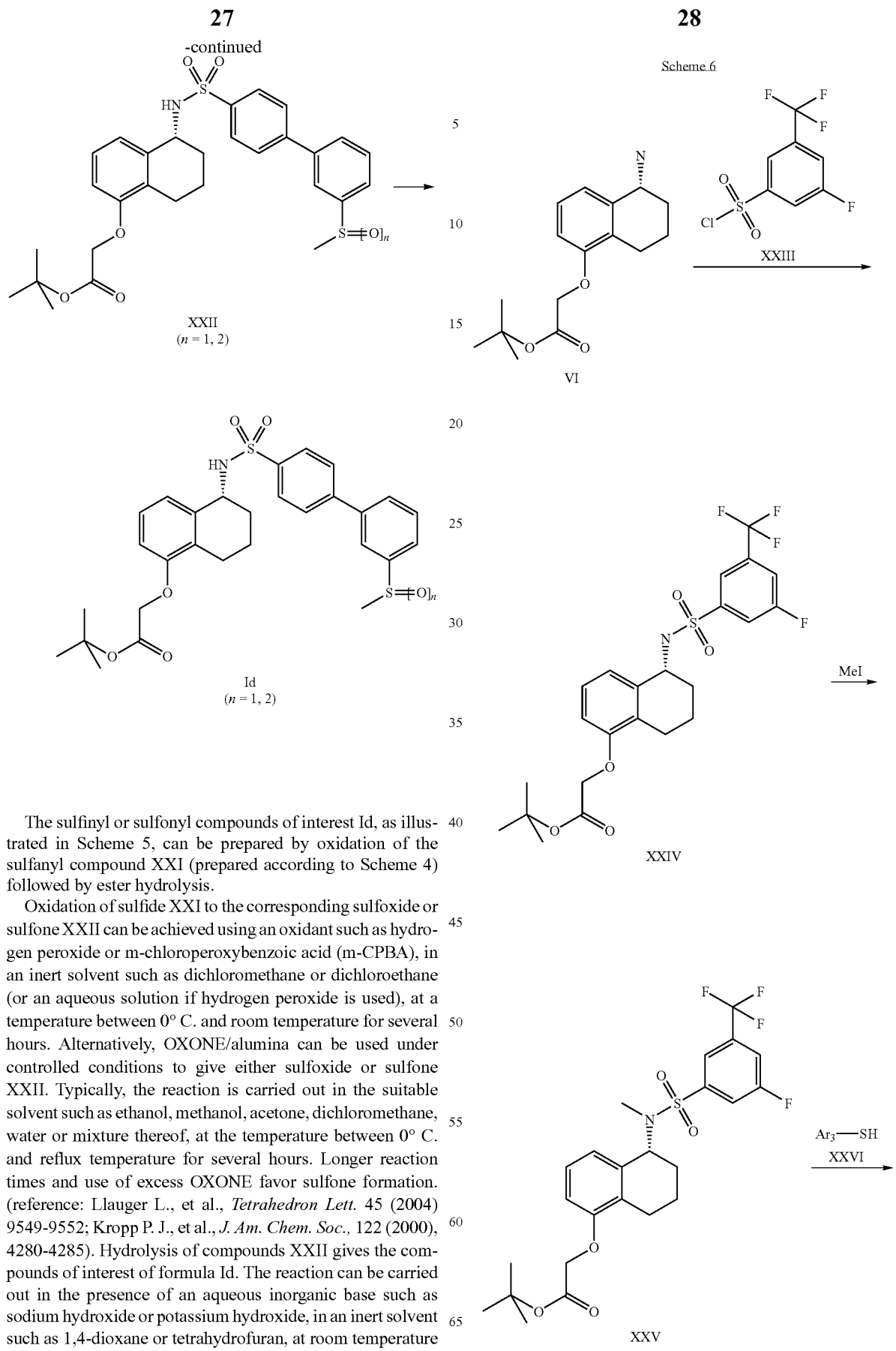

Scheme 6

The sulfinyl or sulfonyl compounds of interest Id, as illustrated in Scheme 5, can be prepared by oxidation of the sulfanyl compound XXI (prepared according to Scheme 4) followed by ester hydrolysis.

Oxidation of sulfide XXI to the corresponding sulfoxide or sulfone XXII can be achieved using an oxidant such as hydrogen peroxide or m-chloroperoxybenzoic acid (m-CPBA), in an inert solvent such as dichloromethane or dichloroethane (or an aqueous solution if hydrogen peroxide is used), at a temperature between 0° C. and room temperature for several hours. Alternatively, OXONE/alumina can be used under controlled conditions to give either sulfoxide or sulfone XXII. Typically, the reaction is carried out in the suitable solvent such as ethanol, methanol, acetone, dichloromethane, water or mixture thereof, at the temperature between 0° C. and reflux temperature for several hours. Longer reaction times and use of excess OXONE favor sulfone formation. (reference: Llauger L., et al., *Tetrahedron Lett.* 45 (2004) 9549-9552; Kropp P. J., et al., *J. Am. Chem. Soc.*, 122 (2000), 4280-4285). Hydrolysis of compounds XXII gives the compounds of interest of formula Id. The reaction can be carried out in the presence of an aqueous inorganic base such as sodium hydroxide or potassium hydroxide, in an inert solvent such as 1,4-dioxane or tetrahydrofuran, at room temperature for several hours.

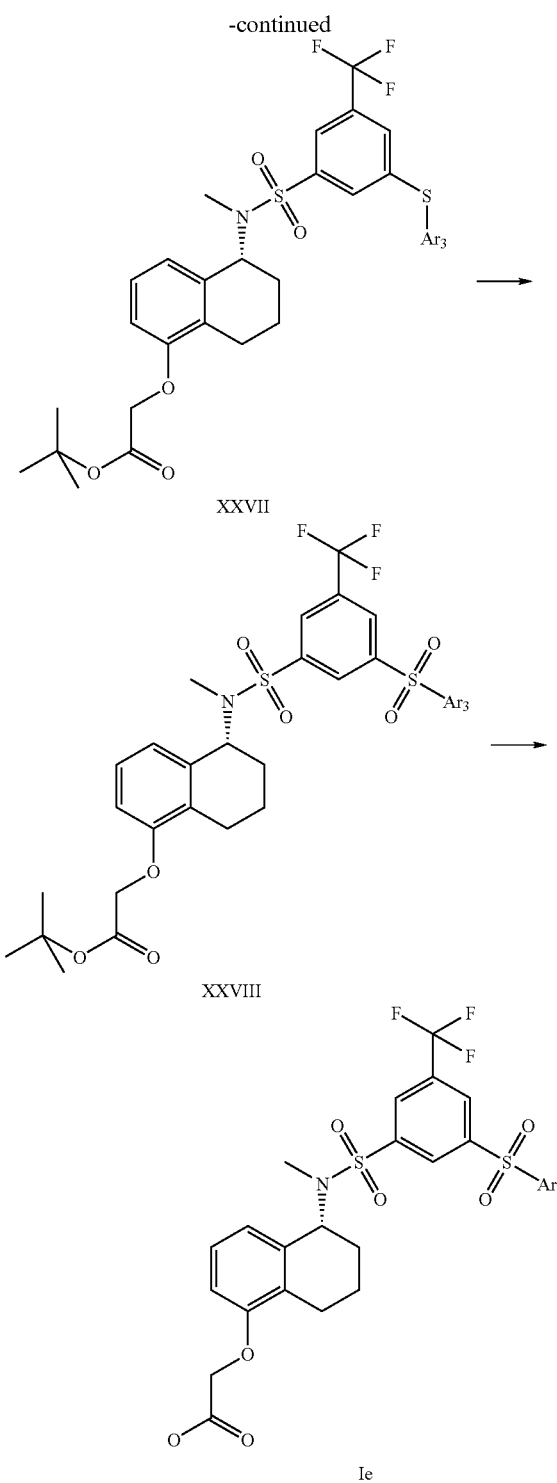

The compounds of interest of structure Ie can be prepared as designated in Scheme 6. Sulfonylation of the amine VI (or its hydrochloride salt) with 3-fluoro-5-trifluoromethyl-benzenesulfonyl chloride (XXIII) gives the sulfonamide XXIV, which can be further methylated to give the N-methylated intermediate XXV. Nucleophilic substitution of the fluoro-substituted compound XXV with the aryl thiols XXVI generates the sulfides XXVII. Further oxidation of the sulfide intermediates to sulfones XXVIII, followed by ester hydrolysis produce the compounds of interest Ie.

Sulfonylation of the amine VI (or its hydrochloride salt) with 3-fluoro-5-trifluoromethyl-benzenesulfonyl chloride (XXIII) to give sulfonamide XXIV can be easily accomplished using methods well known to someone skilled in the art. The reaction is typically carried out in the presence of a base such as triethylamine, diisopropylethylamine, pyridine, or dimethyl-pyridin-4-yl-amine in a suitable inert solvent such as dichloromethane, acetonitrile, 1,4-dioxane, tetrahydrofuran or mixtures thereof, at room temperature for 16 hours.

The corresponding N-methyl compound XXV can be readily formed by methylation of compound XXIV with methyl iodide. The reaction can be carried out in the presence of a weak base such as potassium carbonate or sodium carbonate, in an inert solvent such as N,N-dimethylformamide, acetonitrile or tetrahydrofuran, at 65° C. for 5 hours.

Nucleophilic substitution of the fluoro-substituted compound XXV with the aryl thiols XXVI to give the 3-arylsulfanyl analogues XXVII can be done in the presence of a base, such as potassium carbonate, cesium carbonate, sodium acetate, or triethylamine, in a solvent such as N,N-dimethylformamide, dimethyl sulfoxide, ethanol, water or mixtures thereof, at a temperature between 100 and 150° C. for about 30 to 60 minutes under microwave irradiation. Alternatively, the reaction can be also carried out without the use of a microwave at a moderately elevated temperature over a longer reaction time.

Oxidation of the sulfanyl compounds XXVII to the sulfonyl analogues XXVIII can be achieved using an oxidant such as hydrogen peroxide or m-chloroperoxybenzoic acid (m-CPBA), in an inert solvent such as dichloromethane or dichloroethane (or an aqueous solution if hydrogen peroxide is used), at a temperature between 0° C. and room temperature for several hours. Alternatively, OXONE/alumina can be used under controlled conditions to give sulfone XXVIII. Typically, the reaction is carried out in a suitable solvent such as ethanol, methanol, acetone, dichloromethane, water or a mixture thereof, at the temperature between 0° C. and the reflux temperature for several hours. (reference: Llauger L., et al., *Tetrahedron Lett.* 45 (2004) 9549-9552; Kropp P. J., et al., *J. Am. Chem. Soc.*, 122 (2000), 4280-4285).

Hydrolysis of compounds XXVIII gives the compounds of interest of formula Ie. The reaction can be carried out in the presence of an aqueous inorganic base such as sodium hydroxide or potassium hydroxide, in an inert solvent such as 1,4-dioxane or tetrahydrofuran, at room temperature for several hours.

EXAMPLES

Although certain exemplary embodiments are depicted and described herein, the compounds of the present invention can be prepared using appropriate starting materials according to the methods described generally herein and/or by methods available to one of ordinary skill in the art.

Materials and Instrumentation in General

Intermediates and final compounds were purified by either flash chromatography and/or preparative HPLC (high performance liquid chromatography). Flash chromatography was performed using (1) the Biotage SP1™ system and the Quad 12/25 Cartridge module from Biotage AB) or (2) the ISCO CombiFlash® chromatography instrument (from Teledyne Isco, Inc.); unless otherwise noted. The silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Preparative HPLC was performed on a reversed phase column using an Xbridge™ Prep $C_{18}$ (5 µm, OBD™ 30×100 mm) column (from Waters Corporation), a SunFire™ Prep $C_{18}$ (5 µm, OBD™ 30×100 mm) column (from Waters Corporation), or a Varian Pursuit® C-18 column 20×150 mm (from Varian, Inc.).

Mass spectrometry (MS) or high resolution mass spectrometry (HRMS) was performed using a Waters® ZQ™ 4000 (from Waters Corporation), a Waters® Alliance® 2795-ZQ™2000 (from Waters Corporation), a Waters® Quattro Micro™ API (from Waters Corporation), or an MDS ScieX™ API-2000™n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the HNMR spectrum acquired at 300 MHz) and a Varian® Inova400 NMR spectrometer (for the HNMR spectrum acquired at 400 MHz) both from Varian Inc. NMR data is provided for a particular intermediate or compound where indicated.

The microwave assisted reactions were carried out in a Biotage Initiator™ Sixty (or its early models) (from Biotage AB) or by a CEM Discover® model (with gas addition accessory) (from CEM Corporation).

Chiral separation was performed by supercritical fluid chromatography (SFC) using a Multigram® III instrument (from Thar Technologies, Inc.).

All reactions involving air-sensitive reagents were performed under an inert atmosphere. Reagents were used as received from commercial suppliers unless otherwise noted.

Part I

Preparation of Preferred Intermediates

Preparation of 2-Methyl-5-pyridinylboronic acid

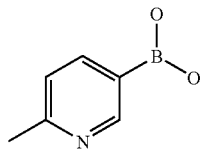

To a stirred solution of 5-bromo-2-methyl-pyridine (992 mg, 5.8 mmol) in diethyl ether (5 mL) was slowly added n-butyl lithium in hexane (1.4 M, 5 mL, 7 mmol) at −78° C. over a span of 10 minutes under nitrogen atmosphere. The reaction mixture was stirred at −78° C. for 90 minutes. At this time, tri-isopropyl borate (1.30 g, 6.9 mmol) was slowly added, and the resulting mixture was allowed to warm to room temperature and stirred for an additional 90 minutes. The reaction was quenched with 5% aqueous sodium hydroxide solution (6 mL) at 0° C. and was extracted with diethyl ether (25 mL×4). The pH of the aqueous solution was adjusted to about 7 by the slow addition of 2N hydrochloric acid. The aqueous layer was extracted with ethyl acetate (50 mL×3). The combined organic layers were dried over anhydrous sodium sulfate, filtered and concentrated under reduced pressure to give 2-methyl-5-pyridinylbronic acid, which was used without further purification.

The following boronic acids were prepared in an analogous manner as described for 2-methyl-5-pyridinylbronic acid starting from the corresponding commercially available aryl bromides.

| Aryl bromide | Aryl boronic acid |
| --- | --- |
| 5-Bromo-2-trifluoromethyl-pyridine | 2-Trifluoromethyl-5-pyridinylboronic acid |
| 2-Bromo-3-methyl-pyridine | 3-Methylpyridine-2-boronic acid |
| 2-Bromo-5-methyl-pyridine | 5-Methylpyridine-2-boronic acid |
| 2-Bromo-6-methyl-pyridine | 6-Methylpyridine-2-boronic acid |
| 2-Bromo-6-methoxyl-pyridine | 6-Methoxylpyridine-2-boronic acid |
| 6-Bromo-3-fluoro-2-methyl-pyridine | 5-Fluoro-6-methylpyridine-2-yl-2-boronic acid |

Preparation of 4-Methylpyridine-2-boronic acid

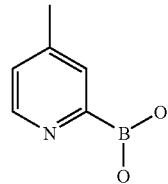

To a stirred solution of 2-bromo-4-methylpyridine (0.5 g, 2.9 mmol) in diethyl ether (5 mL) was added a 1M solution of ethylmagnesium bromide in tetrahydrofuran (3.48 mL, 3.48 mmol) slowly at 0° C. over 10 minutes under a nitrogen atmosphere. The reaction mixture was slowly warmed to room temperature and stirred for 3 hours. To the above mixture was added tri-isopropyl borate (0.65 g, ~0.8 mL, 3.48 mmol) dropwise at 0° C. The reaction mixture was slowly warmed to room temperature and stirred for another 1 hour. The reaction was quenched with saturated aqueous ammonium chloride solution (6 mL) at 0° C. and then extracted with diethyl ether (50 mL×4). The combined organic layers were dried over anhydrous sodium sulfate, filtered and concentrated under reduced pressure to give 4-methylpyridine-2-boronic acid, which was used without further purification.

Preparation of 6-Bromo-pyridine-3-sulfonyl chloride

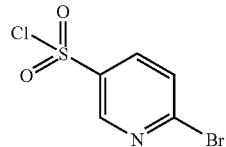

To a cooled (0° C.-5° C.) stirred solution of 5-amino-2-bromopyridine (1.5 g, 8.6 mmol) in 12 N hydrochloric acid (26.5 mL), was slowly added a solution of sodium nitrite (0.66 g, 7.76 mmol) in water (7 mL). In a separate flask, sulfur dioxide was bubbled through a stirred solution of copper(II) chloride dihydrate (0.63 g, 3.50 mmol) in glacial acetic acid at 0° C. for 30 minutes, and then the diazotized reaction mixture prepared above was added. The resulting mixture was slowly warmed to room temperature and stirred for 30 minutes, then was poured into ice water (100 mL), and extracted with ethyl acetate (50 mL×3). The combined organic layers were dried over anhydrous sodium sulfate, filtered, and concentrated under reduced pressure to afford the crude 6-bromo-pyridine-3-sulfonyl chloride, which was immediately used in the next step.

Part II

Preparation of Compounds of Interest

Example 1-1

Method A

[5-(Biphenyl-4-sulfonylamino)-5,6,7,8-tetrahydro-naphthalen-1-yloxy]-acetic acid

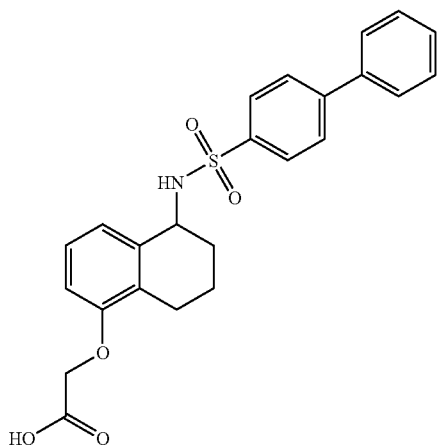

5-Hydroxy-3,4-dihydro-2H-naphthalen-1-one

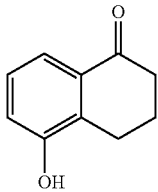

To a mixture of 1,5-dihydroxynaphthalene (25.0 g, 156 mmol) in isopropanol (150 mL) and an aqueous (40 mL) solution of sodium hydroxide (6.3 g, 157 mmol) was added 10% palladium on carbon (3.9 g) at room temperature. The reaction mixture was put under 100 psi hydrogen in a Parr autoclave (from Parr Instrument Company) at 80° C. for 20 hours. After being cooled to room temperature, the reaction mixture was filtered through a pad of Celite® (a diatomite filter from World Minerals Inc.), and then washed with isopropanol (200 mL). The combined filtrates were treated with charcoal at 50° C. for 1 hour, and then were filtered through a pad of Celite® (diatomite filter). Isopropanol was removed, and the resulting solution was adjusted to a pH of about 2 by the slow addition of concentrated hydrochloric acid, during which a solid precipitate appeared. The solid was collected, and washed with water (100 mL×2), and then dried under high vacuum at 50° C. to give 5-hydroxy-3,4-dihydro-2H-naphthalen-1-one (15.0 g, 60%) as a dark brown solid, which was used in the next step without further purification. MS cald. (calculated) for $C_{10}H_{10}O_2$ 162, obsd. (observed) 163 [(M+H)$^+$].

(5-Oxo-5,6,7,8-tetrahydro-naphthalen-1-yloxy)-acetic acid tert-butyl ester

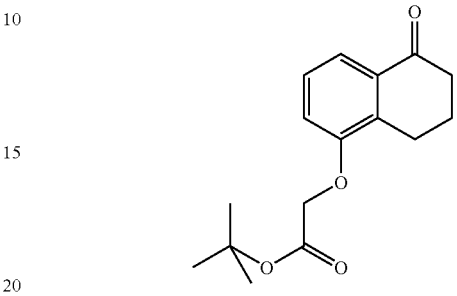

To a stirred mixture of 5-hydroxy-3,4-dihydro-2H-naphthalen-1-one (10.0 g, 61.7 mmol) and cesium carbonate (58.5 g, 180 mmol) in acetonitrile (300 mL) was added tert-butyl bromoacetate (29.0 g, 148 mmol) at room temperature under nitrogen. After being stirred at room temperature overnight, the reaction mixture was filtered through a pad of Celite® (a diatomite filter), and washed with ethyl acetate (100 mL). The combined filtrates were concentrated under reduced pressure. The residue was partitioned between ethyl acetate (500 mL) and water (200 mL×3). The organic layer was concentrated under reduced pressure. Column chromatography (silica gel, 100-200 mesh, 5-10% ethyl acetate in hexane) gave (5-oxo-5,6,7,8-tetrahydro-naphthalen-1-yloxy)-acetic acid tert-butyl ester (12.1 g, 71%). MS cald. for $C_{16}H_{20}O_4$ 276, obsd. 277 [(M+H)$^+$].

(5-Amino-5,6,7,8-tetrahydro-naphthalen-1-yloxy)-acetic acid tert-butyl ester

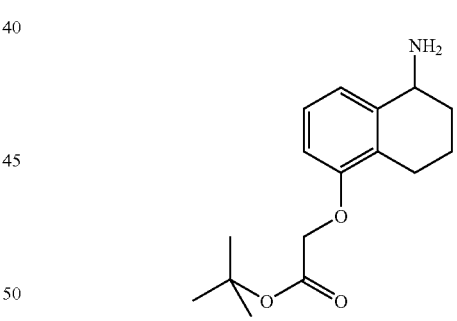

To a stirred solution of (5-oxo-5,6,7,8-tetrahydro-naphthalen-1-yloxy)-acetic acid tert-butyl ester (10.0 g, 36.2 mmol) in methanol (300 mL) was added ammonium acetate (55.0 g, 714 mmol) at room temperature under nitrogen. After being stirred for 4 hours at room temperature, the reaction mixture was cooled to 0° C. and sodium cyanoborohydride (5.7 g, 90 mmol) was added. The resulting mixture was allowed to warm to room temperature and stirred for an additional 48 hours. The reaction mixture was then concentrated under reduced pressure. To the residue was added saturated sodium carbonate solution to adjust the pH to about 7, and the resulting solution was extracted with ethyl acetate (500 mL×3). The combined organic layers were dried over anhydrous sodium sulfate, filtered, and concentrated in vacuo. Column chromatography (silica gel, 100-200 mesh, 2% to 5% methanol in dichloromethane) gave (5-amino-5,6,7,8-tetrahydro-naphthalen-1-yloxy)-acetic acid tert-butyl ester (4.6 g, 46%) as a solid. MS cald. for $C_{16}H_{23}NO_3$ 277. obsd. 278 $[(M+H)^+]$.

[5-(Biphenyl-4-sulfonylamino)-5,6,7,8-tetrahydro-naphthalen-1-yloxy]-acetic acid tert-butyl ester

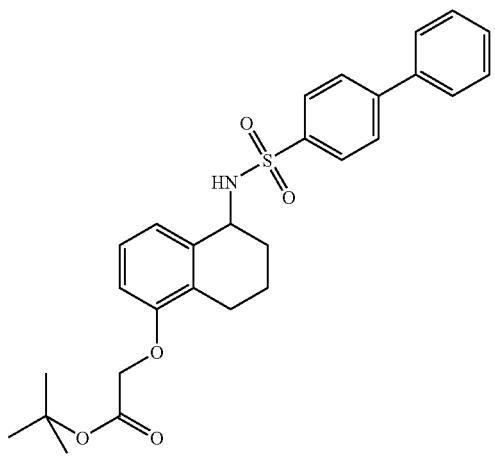

To a solution of (5-amino-5,6,7,8-tetrahydro-naphthalen-1-yloxy)-acetic acid tert-butyl ester (199 mg, 0.72 mmol) and biphenyl-4-sulfonyl chloride (217 mg, 0.86 mmol) in dry tetrahydrofuran (10 mL) was added diisopropylethylamine (186 mg, 1.44 mmol) at 0° C. The reaction mixture was stirred at room temperature for 12 hours, and then concentrated under reduced pressure. The residue was partitioned between water and ethyl acetate. The combined organic layers were washed with water, dried over sodium sulfate, and evaporated in vacuo. Column chromatography (silica gel, 100-200 mesh, 10-15% ethyl acetate in hexane) gave [5-(biphenyl-4-sulfonylamino)-5,6,7,8-tetrahydro-naphthalen-1-yloxy]-acetic acid tert-butyl ester. MS cald. for $C_{28}H_{31}NO_5S$ 493, obsd. 494 $[(M+H)^+]$.

[5-(Biphenyl-4-sulfonylamino)-5,6,7,8-tetrahydro-naphthalen-1-yloxy]-acetic acid

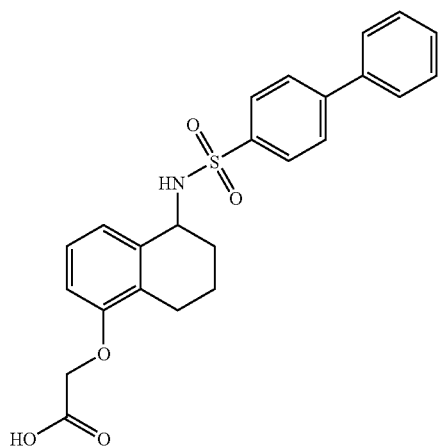

To a solution of 5-(biphenyl-4-sulfonylamino)-5,6,7,8-tetrahydro-naphthalen-1-yloxy]-acetic acid tert-butyl ester (100 mg, 0.202 mmol) in tetrahydrofuran (8 mL) was added a solution of lithium hydroxide monohydrate (26 mg, 0.608 mmol) in water (2 mL). The reaction mixture was stirred at room temperature for 48 hours. The solvent was removed under reduced pressure, and the residue was partitioned between water and ethyl acetate. The aqueous layer was acidified with aqueous hydrochloric acid and extracted with ethyl acetate (25 mL×3). The combined organic layers were dried over sodium sulfate, filtered, and evaporated under reduced pressure to give pure [5-(biphenyl-4-sulfonylamino)-5,6,7,8-tetrahydro-naphthalen-1-yloxy]-acetic acid (31 mg, 78%). MS cald. for $C_{24}H_{23}NO_5S$ 437, obsd. 436 $[(M-H)^-]$.

Example 1-2

Method B

[(R)-5-(4'-Methyl-biphenyl-4-sulfonylamino)-5,6,7,8-tetrahydro-naphthalen-1-yloxy]-acetic acid

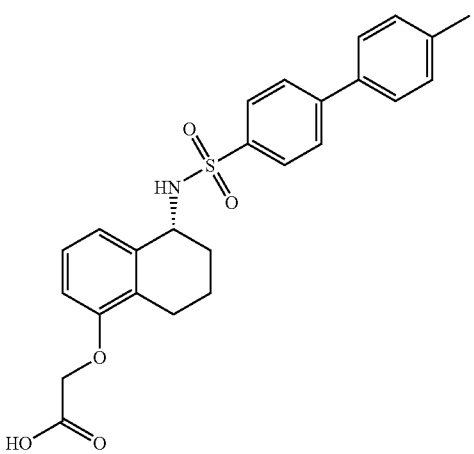

(R)-(5-Amino-5,6,7,8-tetrahydro-naphthalen-1-yloxy)-acetic acid tert-butyl ester

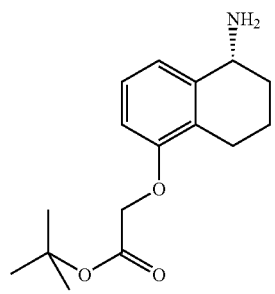

From (5-amino-5,6,7,8-tetrahydro-naphthalen-1-yloxy)-acetic acid tert-butyl ester (example 1-1, $3^{rd}$ step), chiral separation by supercritical fluid chromatography (SFC) (using Thar Technologies, Inc.'s Multigram® III instrument, Daicel® OD column 3×25 cm, 25% methanol containing 0.2% triethylamine, 70 mL/min) afforded (R)-(5-amino-5,6,7,8-tetrahydro-naphthalen-1-yloxy)-acetic acid tert-butyl ester.

The absolute stereochemistry assignment was established by X-ray structure determination of the 4-iodophenylsulfonamide derivative.

[(R)-5-(4'-Methyl-biphenyl-4-sulfonylamino)-5,6,7,8-tetrahydro-naphthalen-1-yloxy]-acetic acid tert-butyl ester

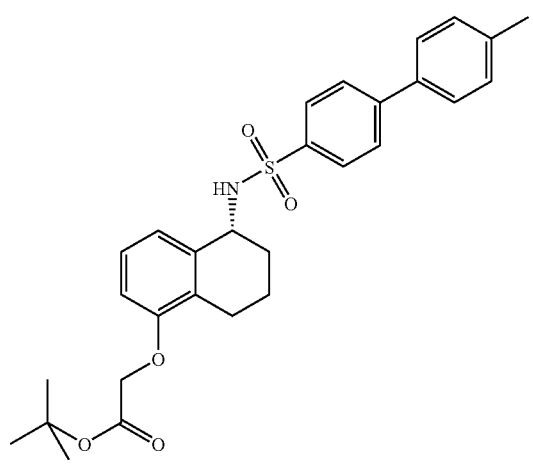

Starting from (R)-(5-amino-5,6,7,8-tetrahydro-naphthalen-1-yloxy)-acetic acid tert-butyl ester (28 mg, 0.1 mmol), triethylamine (0.02 mL, 0.11 mmol) and 4'-methyl-biphenyl-4-sulfonyl chloride (29 mg, 0.11 mmol), using the method analogous to the one for example 1-1, method A, 4$^{th}$ step, crude [(R)-5-(4'-methyl-biphenyl-4-sulfonylamino)-5,6,7,8-tetrahydro-naphthalen-1-yloxy]-acetic acid tert-butyl ester was obtained, which was used in the next step without further purification. MS cald. for $C_{29}H_{33}NO_5S$ 507, obsd. 508 [(M+H)$^+$].

[(R)-5-(4'-Methyl-biphenyl-4-sulfonylamino)-5,6,7,8-tetrahydro-naphthalen-1-yloxy]-acetic acid

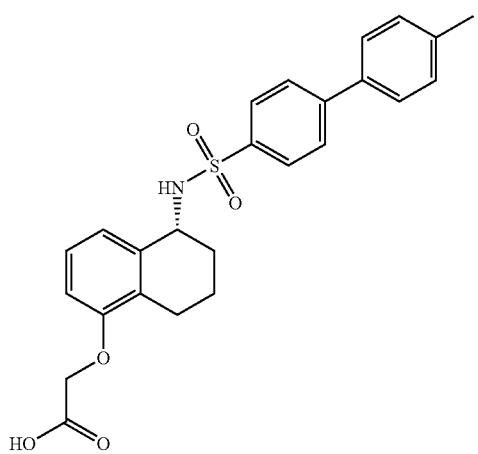

The crude [(R)-5-(4'-methyl-biphenyl-4-sulfonylamino)-5,6,7,8-tetrahydro-naphthalen-1-yloxy]-acetic acid tert-butyl ester was treated with 10% trifluoroacetic acid (0.02 mL) in dichloromethane (1 mL) at room temperature for 2 hours. The mixture was concentrated in vacuo. The residue was purified by reverse phase HPLC (Pursuit C-18, 20×150 mm, water/acetonitrile/0.05% trifluoroacetic acid) to give [(R)-5-(4'-methyl-biphenyl-4-sulfonylamino)-5,6,7,8-tetrahydro-naphthalen-1-yloxy]-acetic acid (4.3 mg, 9.5% over two steps). $^1$H NMR (400 MHz, DMSO-d$_6$) δ ppm 13.02 (br. s, 1H), 8.13 (d, J=8.5 Hz, 1H), 7.78-8.00 (m, 4H), 7.68 (d, J=8.0 Hz, 2H), 7.33 (d, J=8.0 Hz, 2H), 7.03 (t, J=7.9 Hz, 1H), 6.73 (d, J=7.9 Hz, 1H), 6.66 (d, J=7.9 Hz, 1H), 4.62 (s, 2H), 4.29-4.44 (m, 1H), 2.42-2.62 (m, 2H), 2.37 (s, 3H), 1.79 (br. s, 1H), 1.56 (d, 3H); MS cald. for $C_{25}H_{25}NO_5S$ 451, obsd. 452 [(M+H)$^+$].

Alternative preparation of ((R)-5-amino-5,6,7,8-tetrahydro-naphthalen-1-yloxy)-acetic acid tert-butyl ester hydrochloride salt (VI) according to Scheme 2

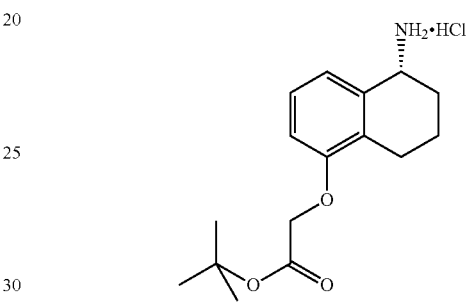

((S)-5-Hydroxy-5,6,7,8-tetrahydro-naphthalen-1-yloxy)-acetic acid tert-butyl ester (XI)

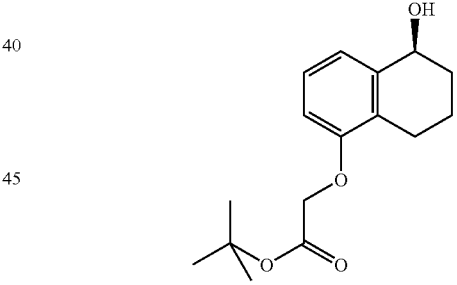

To a flask containing 124 mg (0.203 mmol) of di-mu-chlorobis[(p-cymene)chlororuthenium(II) ([RuCl$_2$(C$_{10}$H$_{14}$)]$_2$, Strem Chemicals, Inc., CAS No. 52462-29-0) and 153 mg (0.416 mmol) of (1S,2S)-(+)-N-p-tosyl-1,2-diphenylethylenediamine (Aldrich, CAS No. 167316-27-0) was added 50 mL of a pre-formed mixture of formic acid and triethylamine (in 5:2 molar ratio), and the resulting mixture was stirred at room temperature for 45 minutes (gas evolution was observed). Then 10 g (36.19 mmol) of (5-oxo-5,6,7,8-tetrahydro-naphthalen-1-yloxy)-acetic acid tert-butyl ester (V, prepared as described above) was added, and the reaction mixture was stirred at 42° C. internal temperature. Upon gas evolution and foaming, the reaction mixture was cooled to 33° C. internal temperature over 1 hour, and then stirred for an additional 24 hours at 33° C. The reaction mixture was then cooled in an ice-water bath, diluted with 50 mL of de-ionized water, and extracted with 100 mL of toluene. The organic layer was separated and washed with 1 M aqueous citric acid (50 mL), saturated aqueous sodium bicarbonate (50 mL), and water (50 mL). The organic phase was then dried over MgSO$_4$, and concentrated azeotropically at 35° C./20 mmHg to a total volume of 30 mL. The resulting solution was co-evaporated with 2×100 mL of toluene to a total volume of 20 mL (product and toluene), which was used in the next step without further purification.

((R)-5-Azido-5,6,7,8-tetrahydro-naphthalen-1-yloxy)-acetic acid tert-butyl ester

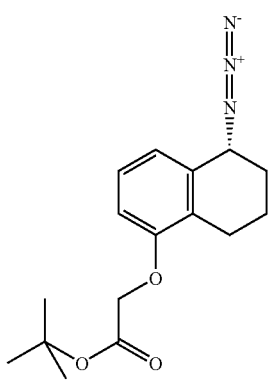

The toluene solution of chiral alcohol XI prepared above (36.19 mmol, assumed 100% conversion) was diluted with an additional 100 mL of toluene, and cooled in an ice-water bath, then treated with diphenylphosphoryl azide (13.64 g, 49.57 mmol). To this solution was added 1,8-diazabicyclo[5.4.0]undec-7-ene (DBU, 8.0 g, 52.46 mmol), dropwise over 20 minutes at such a rate so as to maintain the internal temperature between 1-4° C. The reaction mixture was then stirred at an internal temperature of 1-2° C. for an additional 45 minutes, then warmed to room temperature (with a water bath), and stirred at room temperature overnight. After 20 hours, the reaction mixture was treated with ice-cold water (50 mL), while maintaining the internal temperature below 24° C. The organic layer was separated and washed with 1 M aqueous citric acid solution (50 mL), saturated aqueous sodium bicarbonate (50 mL), and water (50 mL). The resulting organic phase was then concentrated under vacuum at 20 mmHg/26° C., to provide 15 g of an oil, which was used in the next step without further purification.

((R)-5-Amino-5,6,7,8-tetrahydro-naphthalen-1-yloxy)-acetic acid tert-butyl ester hydrochloride salt (VI)

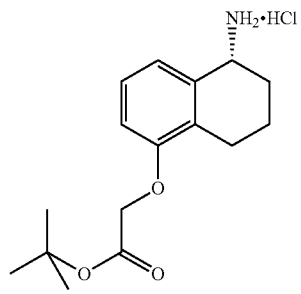

To a solution of ((R)-5-azido-5,6,7,8-tetrahydro-naphthalen-1-yloxy)-acetic acid tert-butyl ester prepared above (36.19 mmol, assumed 100% conversion) in 100 mL of methanol in a 300 mL Parr-reactor was added water (1.6 mL) and 5% Pd/C (1.4 g). The reaction mixture was stirred under a 350 psi pressure of hydrogen. After 90 minutes, the reaction was filtered through a pad of Celite, washed with methanol, and concentrated in vacuo to provide 16.0 g of an oil. The crude oil was dissolved in 10 mL of methanol and 50 mL of methyl tert-butyl ether. Water was removed azeotropically, to provide 14.0 g of an oil, which was dissolved in 10 mL of methanol, and 50 mL of methyl tert-butyl ether. To this solution was added a solution of chlorotrimethylsilane (5.722 mL, 43.42 mmol) in 50 mL of methyl tert-butyl ether at room temperature, dropwise over 40 minutes. The resulting mixture was stirred for 2 hours. The resulting precipitate was filtered, to provide 8.8 g (78% yield over 3 steps) of ((R)-5-amino-5,6,7,8-tetrahydro-naphthalen-1-yloxy)-acetic acid tert-butyl ester hydrochloride salt (VI).

Examples 1-3 to 1-12

The following examples 1-3 to 1-13 were prepared in an analogous manner to examples 1-1 or 1-2 starting with naphthalene-1,5-diol and the appropriate biaryl sulfonyl chlorides.

| Example No.* | Systematic Name | $^1$H NMR (400 MHz, DMSO-d$_6$) δ ppm | MS [(M − H)] | Structure |
| --- | --- | --- | --- | --- |
| 1-3(A) | [5-(3-Phenoxy-benzene-sulfonylamino)-5,6,7,8-tetrahydro-naphthalen-1-yloxy]-acetic acid | 12.98 (br. s, 1 H), 8.17 (d, J = 8.6 Hz, 1 H), 7.58-7.69 (m, 2 H), 7.40-7.49 (m, 2 H), 7.36-7.40 (m, 1 H), 7.29-7.36 (m, 1 H), 7.17-7.26 (m, 1 H), 7.06-7.12 (m, 2 H), 7.04 (t, J = 8.0 Hz, 1 H), 6.67 (d, J = 8.0 Hz, 1 H), 6.64 (d, J = 8.0 Hz, 1 H), 4.65 (s, 2 H), 4.21-4.37 (m, 1 H), 2.51-2.62 (m, 2 H), 1.68-1.86 (m, 1 H), 1.54 (br. s, 3 H) | 452 | 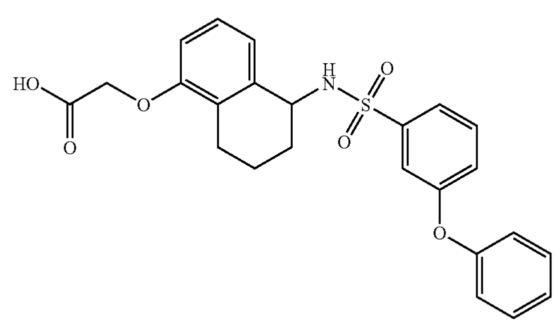 |

| Example No.* | Systematic Name | ¹H NMR (400 MHz, DMSO-$d_6$) δ ppm | MS [(M − H)] | Structure |
| --- | --- | --- | --- | --- |
| 1-4(A) | [5-(Biphenyl-3-sulfonylamino)-5,6,7,8-tetrahydro-naphthalen-1-yloxy]-acetic acid | 12.94 (br. s, 1 H), 8.08-8.16 (m, 2 H), 7.94 (m, 1 H), 7.84 (m, 1 H), 7.62-7.76 (m, 3 H), 7.50 (t, J = 7.5 Hz, 2 H), 7.38-7.45 (m, 1 H), 6.98 (t, J = 8.3 Hz, 1 H), 6.64 (d, J = 8.3 Hz, 1 H), 6.64 (d, J = 8.3 Hz, 1 H), 4.62 (s, 2 H), 4.31-4.43 (m, 1 H), 2.51-2.62 (m, 2 H), 1.65-1.83 (m, 1 H), 1.53 (br. s, 3 H) | 436 | 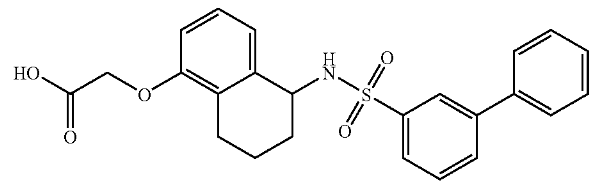 |
| 1-5(A) | [5-(4-Phenoxy-benzene-sulfonylamino)-5,6,7,8-tetrahydro-naphthalen-1-yloxy]-acetic acid | 12.97 (br. s, 1 H), 8.05 (d, J = 8.6 Hz, 1 H), 7.87 (d, J = 8.8 Hz, 2 H), 7.48 (t, J = 8.0 Hz, 2 H), 7.26 (t, J = 7.5 Hz, 1 H), 7.12-7.20 (m, 4 H), 7.04 (t, J = 8.0 Hz, 1 H), 6.67 (d, J = 8.0 Hz, 2 H), 4.66 (s, 2 H), 4.32 (br. s, 1 H), 2.53-2.61 (m, 2 H), 1.79 (br. s, 1 H), 1.56 (br. s, 3 H) | 452 | 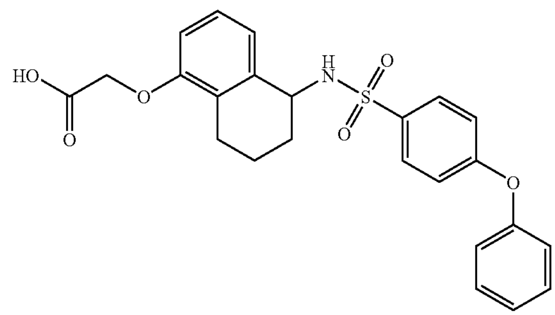 |
| 1-6(A) | [5-(6-Phenoxy-pyridine-3-sulfonylamino)-5,6,7,8-tetrahydro-naphthalen-1-yloxy]-acetic acid | 12.97 (br. s, 1 H), 8.58 (d, J = 2.3 Hz, 1 H), 8.25 (d, J = 8.3 Hz, 2 H), 7.41-7.54 (m, 2 H), 7.16-7.34 (m, 4 H), 7.07 (t, J = 8.0 Hz, 1 H), 6.73 (d, J = 8.0 Hz, 1 H), 6.69 (d, J = 8.0 Hz, 1 H), 4.66 (s, 2 H), 4.37-4.45 (m, 1 H), 2.51-2.63 (m, 2 H), 1.70-1.89 (m, 1 H), 1.51-1.70 (m, 3 H) | 453 | 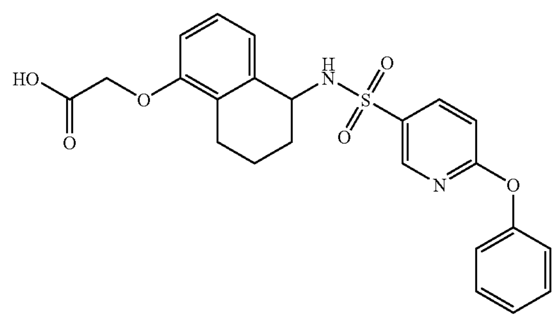 |
| 1-7(B) | [(R)-5-(4'-Fluoro-biphenyl-4-sulfonylamino)-5,6,7,8-tetrahydro-naphthalen-1-yloxy]-acetic acid | (300 MHz) 13.00 (br. s, 1 H), 8.15 (d, J = 8.6 Hz, 1 H), 7.96 (d, J = 8.9 Hz, 2 H), 7.91 (d, J = 8.9 Hz, 2 H), 7.84 (dd, J = 8.8, 5.5 Hz, 2 H) 7.35 (app t, J = 8.8, 8.8 Hz, 2 H) 7.03 (t, J = 8.0 Hz, 1 H) 6.73 (d, J = 7.8 Hz, 1 H), 6.66 (d, J = 8.2 Hz, 1 H) 4.62 (s, 2 H), 4.38 (br m, 1 H), 2.53 (br m, 2 H), 1.78 (br m, 1 H), 1.56 (br m, 3 H) | 454 | 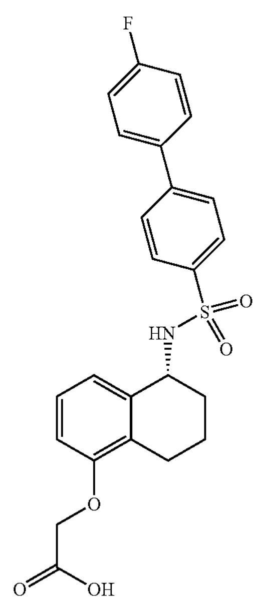 |

-continued

| Example No.* | Systematic Name | 1H NMR (400 MHz, DMSO-d6) δ ppm | MS [(M − H)] | Structure |
|---|---|---|---|---|
| 1-8(B) | [(R)-5-(4'-Methoxy-biphenyl-4-sulfonylamino)-5,6,7,8-tetrahydro-naphthalen-1-yloxy]-acetic acid | 13.00 (br. s, 1 H), 8.11 (d, J = 8.5 Hz, 1 H), 7.80-7.97 (m, 4 H), 7.74 (d, J = 8.9 Hz, 2 H), 7.08 (d, J = 8.9 Hz, 2 H), 7.04 (t, J = 8.1 Hz, 1 H), 6.75 (d, J = 8.1 Hz, 1 H), 6.67 (d, J = 8.1 Hz, 1 H), 4.64 (s, 2 H), 4.30-4.42 (m, 1 H), 3.83 (s, 3 H), 2.42-2.63 (m, 2 H), 1.68-1.92 (m, 1 H), 1.46-1.66 (m, 3 H) | 466 | 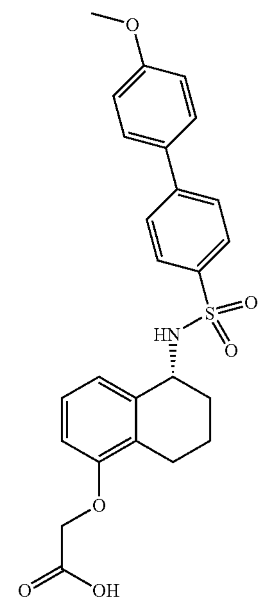 |
| 1-9(B) | [(R)-5-(4'-Chloro-biphenyl-4-sulfonylamino)-5,6,7,8-tetrahydro-naphthalen-1-yloxy]-acetic acid | N/A | 470 | 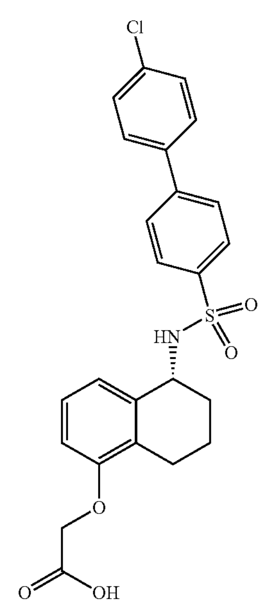 |

| Example No.* | Systematic Name | $^1$H NMR (400 MHz, DMSO-$d_6$) δ ppm | MS [(M − H)] | Structure |
|---|---|---|---|---|
| 1-10(B) | [(R)-5-(4'-Acetyl-biphenyl-4-sulfonylamino)-5,6,7,8-tetrahydro-naphthalen-1-yloxy]-acetic acid | (300 MHz) 13.00 (br. s, 1 H), 8.20 (d, J = 8.3 Hz, 1 H), 8.09 (d, J = 8.5 Hz, 2 H), 8.01 (d, J = 8.9 Hz, 2 H), 7.98 (d, J = 8.9 Hz, 2 H), 7.94 (d, J = 8.5 Hz, 2 H) 7.03 (t, J = 8.0 Hz, 1 H), 6.73 (d, J = 7.8 Hz, 1 H), 6.65 (d, J = 8.2 Hz, 1 H) 4.60 (s, 2 H), 4.39 (br m, 1 H), 2.64 (s, 3 H), 2.50 (br m, 2 H), 1.78 (br m, 1 H), 1.57 (br m, 3 H) | 478 | 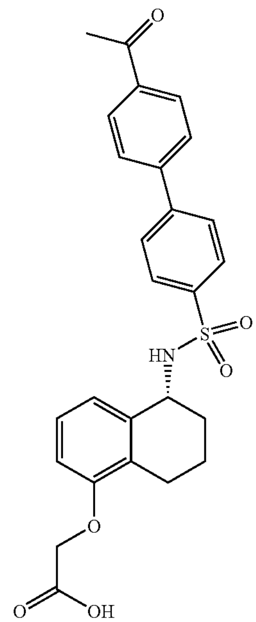 |
| 1-11(B) | [(R)-5-(4'-Methyl-biphenyl-3-sulfonylamino)-5,6,7,8-tetrahydro-naphthalen-1-yloxy]-acetic acid | 12.98 (br. s, 1 H), 8.13 (d, J = 8.3 Hz, 1 H), 8.11 (t, J = 1.8 Hz, 1 H), 7.94 (ddd, J = 7.8, 1.8, 0.9 Hz, 1 H), 7.81-7.86 (m, 1 H), 7.69 (t, J = 7.8 Hz, 1 H), 7.63 (d, J = 7.9 Hz, 2 H), 7.33 (d, J = 7.9 Hz, 2 H), 7.00 (t, J = 8.0 Hz, 1 H), 6.67 (d, J = 8.0 Hz, 1 H), 6.66 (d, J = 8.0 Hz, 1 H), 4.64 (s, 2 H), 4.34-4.43 (m, 1 H), 2.42-2.64 (m, 2 H), 2.37 (s, 3 H), 1.67-1.87 (m, 1 H), 1.50-1.64 (m, 3 H) | 450 | 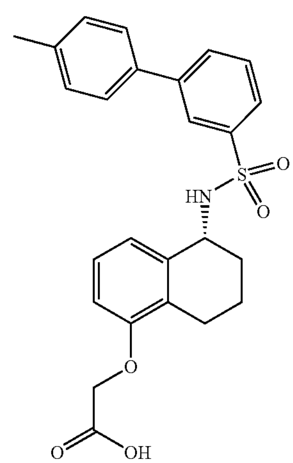 |

| Example No.* | Systematic Name | ¹H NMR (400 MHz, DMSO-$d_6$) δ ppm | MS [(M − H)] | Structure |
| --- | --- | --- | --- | --- |
| 1-12(B) | [(R)-5-(4-Phenoxy-benzene-sulfonylamino)-5,6,7,8-tetrahydro-naphthalen-1-yloxy]-acetic acid | 13.01 (br. s, 1 H), 8.04 (d, J = 8.5 Hz, 1 H), 7.87 (d, J = 9.0 Hz, 2 H), 7.42-7.55 (m, 2 H), 7.22-7.32 (m, 1 H), 7.12-7.20 (m, 4 H), 7.04 (t, J = 8.0 Hz, 1 H), 6.67 (d, J = 8.0 Hz, 2 H), 4.63 (s, 2 H), 4.25-4.38 (m, 1 H), 2.53-2.58 (m, 2 H), 1.71-1.86 (m, 1 H), 1.57 (br. s, 3 H) | 452 | 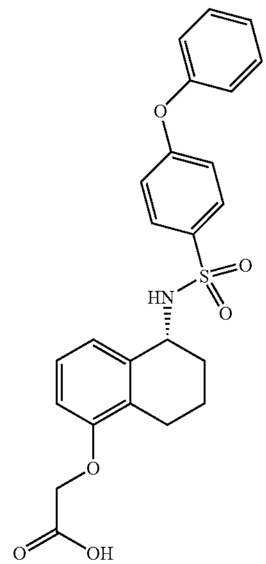 |
| 1-13(B) | {(R)-5-[4-(2-Chloro-phenoxy)-benzene-sulfonylamino]-5,6,7,8-tetrahydro-naphthalen-1-yloxy}-acetic acid | 13.00 (br. s, 1 H), 8.04 (d, J = 8.5 Hz, 1 H), 7.87 (d, J = 9.0 Hz, 2 H), 7.62-7.71 (m, 1 H), 7.43-7.53 (m, 1 H), 7.29-7.39 (m, 2 H), 7.09 (d, J = 9.0 Hz, 2 H), 7.02 (t, J = 7.9 Hz, 1 H), 6.67 (d, J = 7.9 Hz, 1 H), 6.63 (d, J = 7.9 Hz, 1 H), 4.64 (s, 2 H), 4.26-4.36 (m, 1 H), 2.41-2.63 (m, 2 H), 1.69-1.85 (m, 1 H), 1.56 (br. s, 3 H) | 486 | 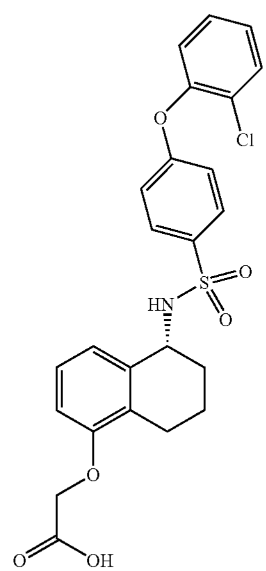 |

*Method of preparation A or B indicated in parentheses.

Example 2-1

Method C

{5-[5-Bromo-6-(2-chloro-4-fluoro-phenoxy)-pyridine-3-sulfonylamino]-5,6,7,8-tetrahydro-naphthalen-1-yloxy}-acetic acid

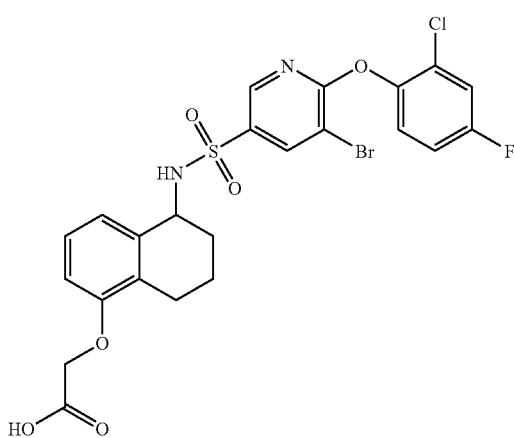

[5-(5-Bromo-6-chloro-pyridine-3-sulfonylamino)-5,6,7,8-tetrahydro-naphthalen-1-yloxy]-acetic acid tert-butyl ester

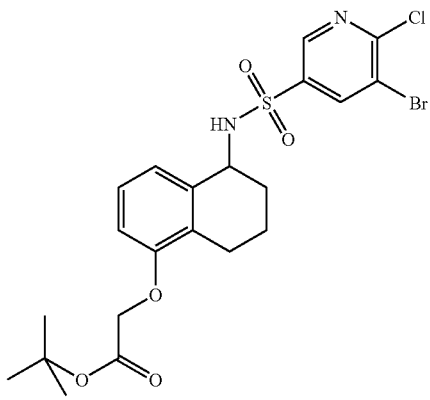

Starting with (5-amino-5,6,7,8-tetrahydro-naphthalen-1-yloxy)-acetic acid tert-butyl ester (example 1-1, method A, 3$^{rd}$ step) (2.0 g, 7.2 mmol), diisopropylethylamine (2.0 g, 15.5 mmol) and 5-bromo-6-chloro-pyridine-3-sulfonyl chloride (2.1 g, 7.3 mmol), using the method analogous to the one for example 1-1, method A, 4$^{th}$ step, [5-(5-bromo-6-chloro-pyridine-3-sulfonylamino)-5,6,7,8-tetrahydro-naphthalen-1-yloxy]-acetic acid tert-butyl ester (2.1 g, 55%) was obtained. MS cald. for $C_{21}H_{24}BrClN_2O_5S$ 530, obsd. 531 [(M+H)$^+$].

{5-[5-Bromo-6-(2-chloro-4-fluoro-phenoxy)-pyridine-3-sulfonylamino]-5,6,7,8-tetrahydro-naphthalen-1-yloxy}-acetic acid tert-butyl ester

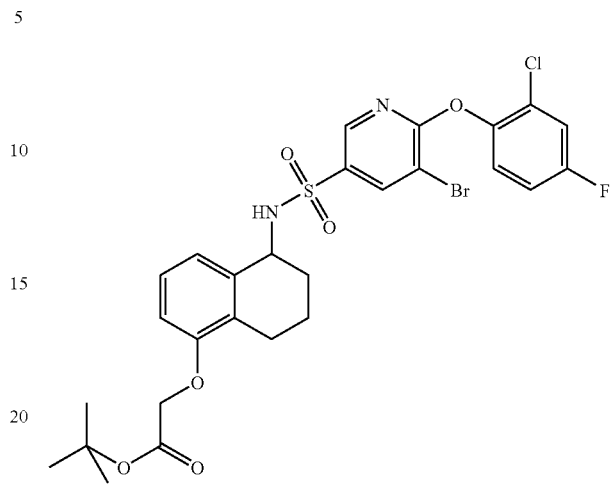

To a stirred solution of 2-chloro-4-fluoro-phenol (292 mg, 2.0 mmol) in N,N-dimethylformamide (5 mL) was added sodium hydride (28.8 mg, 1.2 mmol) portionwise at 0° C. under nitrogen and stirred at the same temperature for 15 minutes. To the above mixture was added [5-(5-bromo-6-chloro-pyridine-3-sulfonylamino)-5,6,7,8-tetrahydro-naphthalen-1-yloxy]-acetic acid tert-butyl ester (212 mg, 0.4 mmol) portionwise at 0° C. Then the reaction mixture was heated at 100° C. overnight. After being cooled to room temperature, the reaction was quenched with water (2 mL), and diluted with ethyl acetate (50 mL). The resulting solution was washed subsequently with water (10 mL), 1N sodium hydroxide solution (10 mL), and brine (10 mL). The organic layer was dried over anhydrous sodium sulfate, filtered, and concentrated in vacuo to give {5-[5-bromo-6-(2-chloro-4-fluoro-phenoxy)-pyridine-3-sulfonylamino]-5,6,7,8-tetrahydro-naphthalen-1-yloxy}-acetic acid tert-butyl ester, which was used in the next step without further purification. MS cald. for $C_{27}H_{27}BrClFN_2O_6S$ 640, obsd. 641 [(M+H)$^+$].

{5-[5-Bromo-6-(2-chloro-4-fluoro-phenoxy)-pyridine-3-sulfonylamino]-5,6,7,8-tetrahydro-naphthalen-1-yloxy}-acetic acid

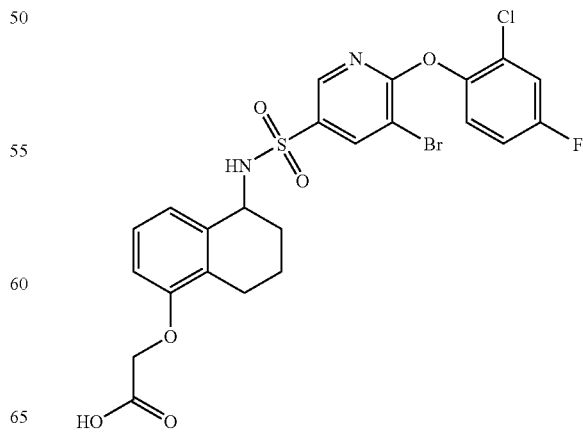

To a stirred solution of {5-[5-bromo-6-(2-chloro-4-fluoro-phenoxy)-pyridine-3-sulfonylamino]-5,6,7,8-tetrahydro-naphthalen-1-yloxy}-acetic acid tert-butyl ester (192 mg, 0.3 mmol) in tetrahydrofuran-water (5:1, 6 mL) was added lithium hydroxide (30 mg, 0.91 mmol). The reaction mixture was stirred at room temperature overnight. Tetrahydrofuran was removed under reduced pressure. The residue was diluted with ethyl acetate (20 mL), and then extracted with 10% aqueous sodium hydroxide (10 mL×3). The combined aqueous layers were neutralized to a pH of about 7 by the addition of 2N acetic acid at 0-5° C. The resulting solution was extracted with ethyl acetate (15 mL×3). The combined organic layers were dried over anhydrous sodium sulfate, filtered, and concentrated in vacuo. The crude product was recrystallized from hot ethyl acetate to afford {5-[5-bromo-6-(2-chloro-4-fluoro-phenoxy)-pyridine-3-sulfonylamino]-5,6,7,8-tetrahydro-naphthalen-1-yloxy}-acetic acid tert-butyl ester yield (149.6 mg, 64% over two steps) MS cald. for $C_{23}H_{20}BrClFN_2O_6S$ 584, obsd. 583 [(M−H)$^-$]; $^1$H NMR (400 MHz, DMSO-d$_6$) δ ppm 8.52 (s, 1H), 8.50 (br. s, 1H), 8.27 (br. s, 1H), 7.67 (dd, J=8.3, 2.9 Hz, 1H), 7.57 (dd, J=8.9, 5.4 Hz, 1H), 7.37 (td, J=8.9, 2.9 Hz, 1H), 6.92 (t, J=8.1 Hz, 1H), 6.54 (d, J=7.8 Hz, 1H), 6.47 (d, J=7.8 Hz, 1H), 4.38 (br. s, 1H), 4.08 (s, 2H), 2.37-2.63 (m, 2H), 1.69-1.85 (m, 1H), 1.61 (br. s, 3H).

Example 2-2

Method D

{(R)-5-[3-Chloro-4-(4-chloro-phenoxy)-benzene-sulfonylamino]-5,6,7,8-tetrahydro-naphthalen-1-yloxy}-acetic acid

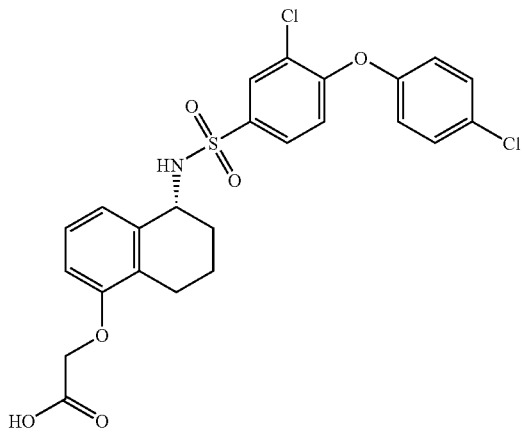

((R)-5-Amino-5,6,7,8-tetrahydro-naphthalen-1-yloxy)-acetic acid tert-butyl ester hydrochloride salt

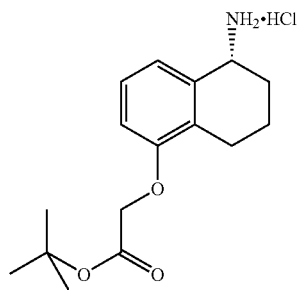

To a stirred solution of (5-oxo-5,6,7,8-tetrahydro-naphthalen-1-yloxy)-acetic acid tert-butyl ester (example 1-1, method A, 3$^{rd}$ step) (76.6 g, 0.028 mol) in methanol (1100 mL) was added ammonium acetate (299.0 g, 3.88 mol), followed by a dropwise addition of a solution of sodium cyanoborohydride (17.4 g, 0.28 mol) in methanol (100 mL) at room temperature under nitrogen. The reaction mixture was stirred at room temperature for 4 days until no starting material remained (monitored by TLC, ethyl acetate:methanol=10:1). The reaction mixture was then concentrated under reduced pressure. To the residue was added saturated sodium carbonate solution (700 mL), and the resulting solution was extracted with dichloromethane (1000 mL×3). The combined organic layers were dried over anhydrous sodium sulfate, filtered, and concentrated in vacuo to afford a crude product as a brownish semi-solid. The crude product was triturated with diethyl ether (150 mL), and then treated with 8M hydrochloric acid in ethyl acetate (70 mL). The resulting white precipitate was filtered, and washed with anhydrous diethyl ether. The collected solid was dried at 55° C. in an oven to afford (5-amino-5,6,7,8-tetrahydro-naphthalen-1-yloxy)-acetic acid tert-butyl ester hydrochloride salt (54 g, 62%) as a white solid. Chiral separation by supercritical fluid chromatography (SFC) (using Thar Technologies, Inc.'s Multigram® III instrument, Daicel® OD column 5×25 cm, 30% methanol, 200 ml/min) afforded the R-(5-amino-5,6,7,8-tetrahydro-naphthalen-1-yloxy)-acetic acid tert-butyl ester hydrochloride salt. MS cald. for C16H23NO3 277. obsd. 278 (ESI$^+$) [(M+H)$^+$].

The absolute stereochemistry assignment was established by x-ray structure determination of the 4-iodophenylsulfonamide derivative.

(R)-[5-(3-Chloro-4-fluoro-benzenesulfonylamino)-5,6,7,8-tetrahydro-naphthalen-1-yloxy]-acetic acid tert-butyl ester

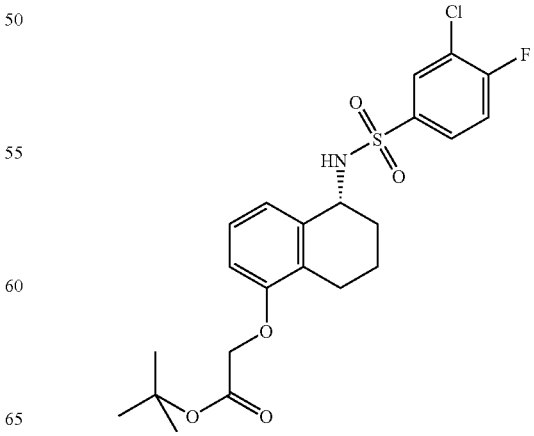

A solution of dimethyl-pyridin-4-yl-amine (1.17 g, 9.60 mmol) in tetrahydrofuran (10 mL) was added dropwise to a solution of (R)-(5-amino-5,6,7,8-tetrahydro-naphthalen-1-yloxy)-acetic acid tert-butyl ester hydrochloride salt (1 g, 3.18 mmol) and 3-chloro-4-fluoro-benzenesulfonyl chloride (0.68 mL, 4.77 mmol) in tetrahydrofuran (10 mL). The reaction mixture was stirred at room temperature overnight, and then concentrated. The residue was purified by column chromatography (gradient elution, 0-5% methanol in dichloromethane) to afford (R)-[5-(3-chloro-4-fluoro-benzenesulfonylamino)-5,6,7,8-tetrahydro-naphthalen-1-yloxy]-acetic acid tert-butyl ester (1.4 g, 93.8%) as a white solid. MS calcd. for $C_{22}H_{25}ClFNO_5S$ 469, obsd 470 ($ESI^+$) [$(M+H)^+$].

(R)-{5-[3-Chloro-4-(4-chloro-phenoxy)-benzenesulfonylamino]-5,6,7,8-tetrahydro-naphthalen-1-yloxy}-acetic acid tert-butyl ester A mixture of (R)-[5-(3-chloro-4-fluoro-benzenesulfonylamino)-5,6,7,8-tetrahydro-naphthalen-1-yloxy]-acetic acid tert-butyl ester (100 mg, 0.21 mmol), sodium hydride (60% dispersed in mineral oil, 50 mg, 1.25 mmol) and 4-chlorophenol (315 mg, 2.45 mmol) in N,N-dimethylformamide (2 mL) was heated in a microwave oven at 130° C. for 15 minutes. The resulting mixture was then acidified with 0.1N hydrochloric acid to pH 5. The precipitate was collected by filtration and purified by preparative HPLC to afford (R)-{5-[3-chloro-4-(4-chloro-phenoxy)-benzenesulfonylamino]-5,6,7,8-tetrahydro-naphthalen-1-yloxy}-acetic acid tert-butyl ester (87.2 mg, 72%) as a white powder. MS cald. for $C_{28}H_{29}Cl_2NO_6S$ 577, obsd. 578 ($ESI^+$) [$(M+H)^+$].

(R)-{5-[3-Chloro-4-(4-chloro-phenoxy)-benzenesulfonylamino]-5,6,7,8-tetrahydro-naphthalen-1-yloxy}-acetic acid

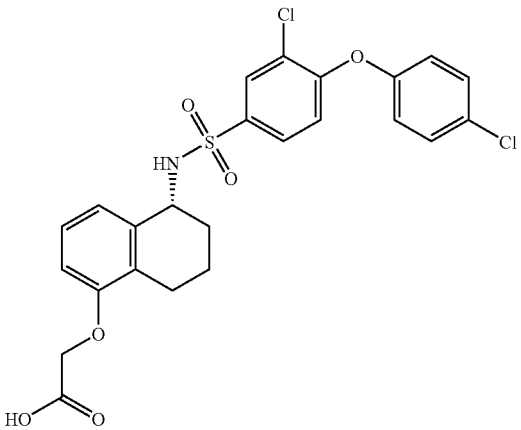

To a solution of (R)-{5-[3-chloro-4-(4-chloro-phenoxy)benzenesulfonylamino]-5,6,7,8-tetrahydro-naphthalen-1-yloxy}-acetic acid tert-butyl ester (160 mg, 0.277 mmol) in tetrahydrofuran (3 mL) was added 1N sodium hydroxide (3 mL). The reaction mixture was stirred at room temperature for 2 hours, and then extracted with diethyl ether (10 mL). The organic layer was discarded. The aqueous layer was acidified with concentrated hydrochloric acid to pH 4 and stirred with diethyl ether (3 mL) and petroleum ether (9 mL) at room temperature for 2 hours. The precipitate was collected by filtering through a glass funnel to afford (R)-{5-[3-chloro-4-(4-chloro-phenoxy)-benzenesulfonylamino]-5,6,7,8-tetrahydro-naphthalen-1-yloxy}-acetic acid (114 mg, 79%) as a white powder. $^1$H NMR (400 MHz, DMSO-$d_6$) δ ppm 8.21 (d, J=8.59 Hz, 1H), 8.02 (d, J=2.27 Hz, 1H), 7.82 (dd, J=8.59, 2.27 Hz, 1H), 7.53 (d, J=8.84 Hz, 2H), 7.13-7.23 (m, 2H), 7.05 (t, J=8.08 Hz, 1H), 6.67 (dd, J=11.75, 7.96 Hz, 2H), 4.65 (s, 2H), 4.39 (d, J=8.08 Hz, 1H), 1.78 (m, 2H), 1.59 (m, 4H); MS cald. For $C_{24}H_{21}Cl_2NO_6S$ 521, obsd. 522 ($ESI^+$) [$(M+H)^+$].

Examples 2-3 to 2-48

The following examples 2-3 to 2-48 were prepared in the analogous manner to examples 2-1 or 2-2 using either method C or D, starting with naphthalene-1,5-diol, aryl sulfonyl chlorides (5-bromo-6-chloro-pyridine-3-sulfonyl chloride, 5-chloro-6-chloro-pyridine-3-sulfonyl chloride, 3-chloro-4-fluoro-benzenesulfonyl chloride, 2-chloro-4-fluoro-benzenesulfonyl chloride, or 4-fluoro-3-trifluoromethyl-benzenesulfonyl chloride) and the appropriate commercially available phenols.

| Example No* | Systematic Name | 1H NMR (400 MHz, DMSO-d$_6$) δ ppm | MS [(M − H)] | Structure |
|---|---|---|---|---|
| 2-3(C) | {5-[5-Bromo-6-(2-fluoro-phenoxy)-pyridine-3-sulfonylamino]-5,6,7,8-tetrahydro-naphthalen-1-yloxy}-acetic acid | 13.01 (br. s, 1 H), 8.55 (m, 1 H), 8.32 (d, J = 8.3 Hz, 2 H), 7.25-7.55 (m, 4 H), 7.04 (t, J = 8.0 Hz, 1 H), 6.68 (d, J = 8.0 Hz, 1 H), 6.63 (d, J = 8.0 Hz, 1 H), 4.62 (s, 2 H), 4.41-4.55 (m, 1 H), 2.51-2.63 (m, 2 H), 1.73-1.86 (m, 1 H), 1.61 (br. s, 3 H) | 551$^a$ | 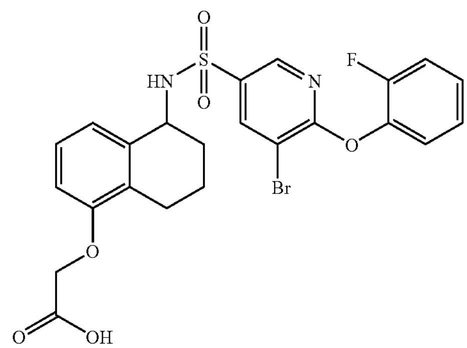 |
| 2-4(C) | {5-[5-Bromo-6-(2-chloro-phenoxy)-pyridine-3-sulfonylamino]-5,6,7,8-tetrahydro-naphthalen-1-yloxy}-acetic acid | 8.55 (d, J = 2.2 Hz, 1 H), 8.53 (d, J = 2.2 Hz, 1 H), 8.31 (d, J = 8.3 Hz, 1 H), 7.64 (d, J = 8.8 Hz, 1 H), 7.43-7.55 (m, 2 H), 7.32-7.42 (m, 1 H), 7.01 (t, J = 8.2 Hz, 1 H), 6.67 (d, J = 8.2 Hz, 2 H), 6.58 (d, J = 7.3 Hz, 1 H), 4.55 (br. s, 2 H), 4.40-4.50 (m, 1 H), 2.40-2.63 (m, 2 H), 1.72-1.84 (m, 1 H), 1.51-1.71 (m, 3 H) | 565 | 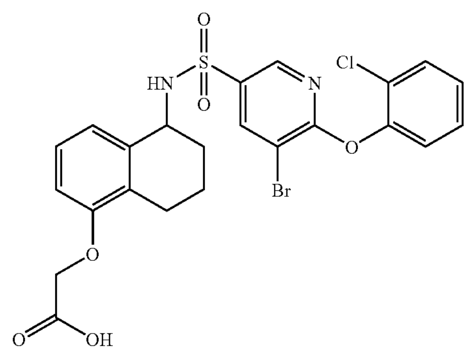 |
| 2-5(C) | {5-[5-Bromo-6-(3-chloro-phenoxy)-pyridine-3-sulfonylamino]-5,6,7,8-tetrahydro-naphthalen-1-yloxy}-acetic acid | 13.02 (br. s, 1 H), 8.55 (d, J = 2.2 Hz, 1 H), 8.52 (d, J = 2.2 Hz, 1 H), 8.31 (d, J = 8.3 Hz, 1 H), 7.51 (t, J = 7.8 Hz, 1 H), 7.47 (t, J = 2.0 Hz, 1 H), 7.39 (d, J = 7.8 Hz, 1 H), 7.27 (d, 1 H), 7.08 (t, J = 8.0 Hz, 1 H), 6.72 (d, J = 8.0 Hz, 1 H), 6.70 (d, J = 8.0 Hz, 1 H), 4.65 (s, 2 H), 4.41-4.53 (m, 1 H), 2.40-2.63 (m, 2 H), 1.75-1.87 (m, 1 H), 1.55-1.71 (m, 3 H) | 565 | 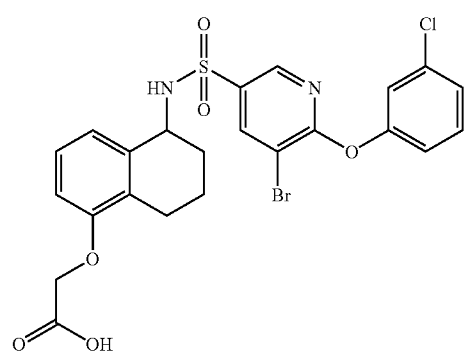 |
| 2-6(C) | {5-[5-Bromo-6-(3-cyano-phenoxy)-pyridine-3-sulfonylamino]-5,6,7,8-tetrahydro-naphthalen-1-yloxy}-acetic acid | d: 8.55 (d, J = 2.1 Hz, 1 H), 8.54 (d, J = 2.1 Hz, 1 H), 8.28-8.37 (m, 1 H), 7.88-7.94 (m, 1 H), 7.79 (ddd, J = 6.0, 2.8, 1.5 Hz, 1 H), 7.67-7.70 (m, 2 H), 6.99 (t, J = 7.9 Hz, 1 H), 6.54-6.61 (m, 2 H), 4.45 (br. s, 1 H), 4.14 (s, 2 H), 2.54-2.63 (m, 2 H), 1.77 (br. s, 1 H), 1.61 (br. s, 3 H) | 556 | 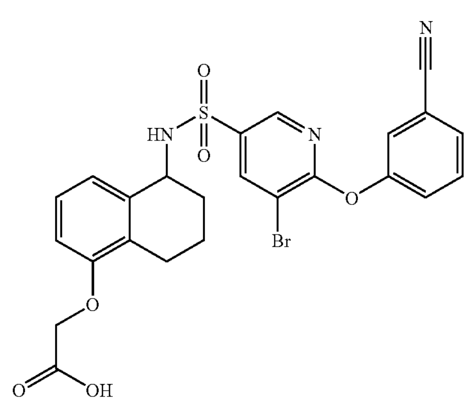 |

-continued

| Example No* | Systematic Name | 1H NMR (400 MHz, DMSO-d₆) δ ppm | MS [(M − H)] | Structure |
|---|---|---|---|---|
| 2-7(C) | {5-[5-Bromo-6-(4-cyano-phenoxy)-pyridine-3-sulfonylamino]-5,6,7,8-tetrahydro-naphthalen-1-yloxy}-acetic acid | 8.56 (d, J = 2.0 Hz, 1 H), 8.54 (d, J = 2.0 Hz, 1 H), 8.33 (br. s, 1 H), 7.98 (d, J = 8.7 Hz, 2 H), 7.52 (d, J = 8.7 Hz, 2 H), 6.97 (t, J = 7.8 Hz, 1 H), 6.56 (d, J = 7.8 Hz, 1 H), 6.55 (d, J = 7.8 Hz, 1 H), 4.44 (br. s, 1 H), 4.07 (s, 2 H), 2.44-2.63 (m, 2 H), 1.71-1.85 (m, 1 H), 1.60 (br. s, 3 H) | 556 | 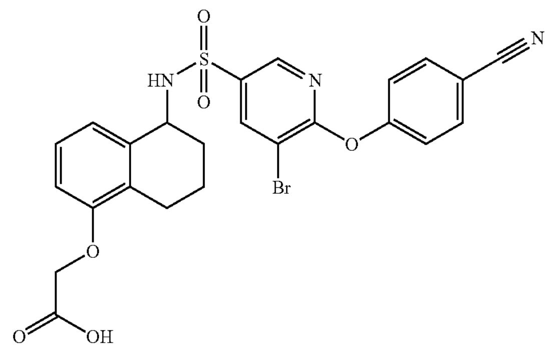 |
| 2-8(C) | {5-[5-Bromo-6-(4-fluoro-phenoxy)-pyridine-3-sulfonylamino]-5,6,7,8-tetrahydro-naphthalen-1-yloxy}-acetic acid | 8.51 (s, 2 H), 8.30 (d, J = 8.07 Hz, 1 H), 7.28-7.34 (m, 4 H), 6.95-7.02 (m, 2 H), 6.71-6.78 (m, 1 H), 6.57-6.64 (m, 2 H), 4.44 (br. s, 1 H) 4.23 (br. s, 2 H) 1.72-1.77 (m, 1 H), 1.62-1.70 (m, 3 H), 1.22-1.26 (m, 2 H), 0.80-0.86 (m, 2 H) | 549 | 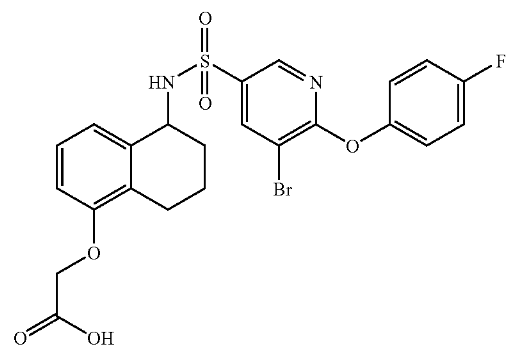 |
| 2-9(C) | {5-[5-Bromo-6-(3-isopropyl-phenoxy)-pyridine-3-sulfonylamino]-5,6,7,8-tetrahydro-naphthalen-1-yloxy}-acetic acid | 8.52 (d, J = 2.2 Hz, 1 H), 8.51 (d, J = 2.2 Hz, 1 H), 8.29 (d, J = 7.8 Hz, 1 H), 7.38 (t, J = 8.1 Hz, 1 H), 7.18 (d, J = 8.1 Hz, 1 H), 7.12 (t, J = 2.0 Hz, 1 H), 7.05 (dd, J = 8.1, 2.0 Hz, 1 H), 6.97 (t, J = 7.9 Hz, 1 H), 6.55 (d, J = 7.9 Hz, 2 H), 4.38-4.49 (m, 1 H), 4.09 (s, 2 H), 2.85-3.00 (m, 1 H), 2.44-2.61 (m, 2 H), 1.70-1.87 (m, 1 H), 1.61 (br. s, 3 H), 1.21 (d, 6 H) | 573 | 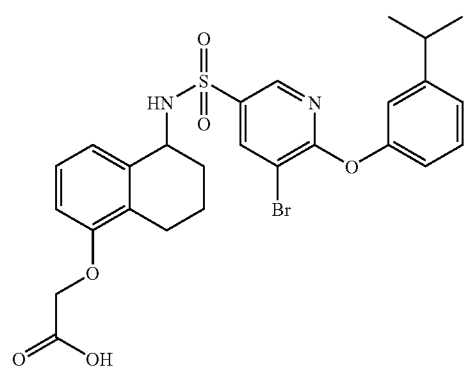 |
| 2-10(C) | {5-[5-Bromo-6-(4-isopropyl-phenoxy)-pyridine-3-sulfonylamino]-5,6,7,8-tetrahydro-naphthalen-1-yloxy}-acetic acid | 8.52 (d, J = 2.2 Hz, 1 H), 8.50 (d, J = 2.2 Hz, 1 H), 8.28 (br. s, 1 H), 7.33 (d, J = 8.6 Hz, 2 H), 7.16 (d, J = 8.6 Hz, 2 H), 6.97 (t, J = 8.0 Hz, 1 H), 6.54 (d, J = 8.0 Hz, 2 H), 4.42 (br. s, 1 H), 4.06 (s, 2 H), 2.84-2.99 (m, 1 H), 2.51-2.62 (m, 2 H), 1.72-1.84 (m, 1 H), 1.48-1.69 (m, 3 H), 1.23 (d, 6 H) | 573 | 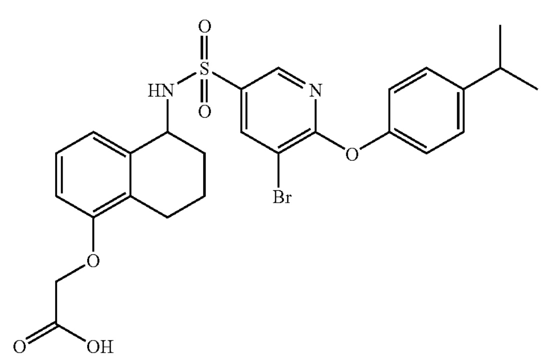 |

-continued

| Example No* | Systematic Name | 1H NMR (400 MHz, DMSO-d$_6$) δ ppm | MS [(M − H)] | Structure |
|---|---|---|---|---|
| 2-11(C) | {5-[5-Bromo-6-(4-methoxy-phenoxy)-pyridine-3-sulfonylamino]-5,6,7,8-tetrahydro-naphthalen-1-yloxy}-acetic acid | 8.47 (d, J = 2.0 Hz, 1 H), 8.44 (d, J = 2.0 Hz, 1 H), 7.05-7.13 (m, 2 H), 6.93-7.02 (m, 3 H), 6.64 (d, J = 8.3 Hz, 1 H), 6.52 (d, J = 7.8 Hz, 1 H), 4.41-4.47 (m, 1 H), 4.37 (s, 2 H), 3.82 (s, 3 H), 2.74-2.90 (m, 1 H), 2.52-2.71 (m, 1 H), 1.64-1.96 (m, 4 H) | 563$^a$ | 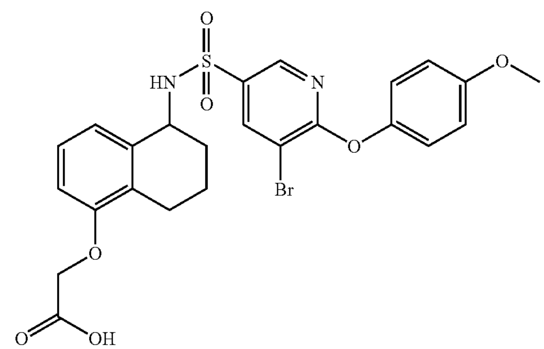 |
| 2-12(C) | {5-[5-Bromo-6-(3,4-dimethyl-phenoxy)-pyridine-3-sulfonylamino]-5,6,7,8-tetrahydro-naphthalen-1-yloxy}-acetic acid | 8.50 (br. s, 2 H), 8.22-8.33 (m, 1 H), 7.21 (d, J = 7.3 Hz, 1 H), 7.00-7.06 (m, 1 H), 6.87-7.00 (m, 2 H), 6.50-6.59 (m, 2 H), 4.42 (br. s, 1 H), 4.05 (s, 2 H), 2.51-2.62 (m, 2 H), 2.23 (s, 6 H), 1.78 (br. s, 1 H), 1.60 (br. s, 3 H) | 559 | 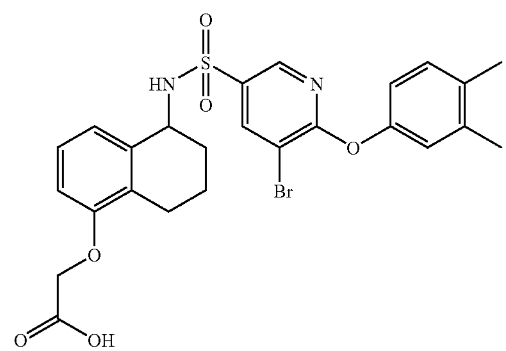 |
| 2-13(C) | {5-[5-Bromo-6-(4-chloro-2-methyl-phenoxy)-pyridine-3-sulfonylamino]-5,6,7,8-tetrahydro-naphthalen-1-yloxy}-acetic acid | 8.53 (d, J = 2.2 Hz, 1 H), 8.51 (d, J = 2.2 Hz, 1 H), 8.31 (d, J = 8.1 Hz, 1 H), 7.47 (d, J = 2.6 Hz, 1 H), 7.36 (dd, J = 8.9, 2.6 Hz, 1 H), 7.27 (d, J = 8.9 Hz, 1 H), 7.02 (t, J = 8.0 Hz, 1 H), 6.67 (d, J = 8.0 Hz, 1 H), 6.61 (d, J = 8.0 Hz, 1 H), 4.61 (s, 2 H), 4.42-4.49 (m, 1 H), 2.51-2.64 (m, 2 H), 2.06 (s, 3 H), 1.71-1.88 (m, 1 H), 1.61 (br. s, 3 H) | 581$^a$ | 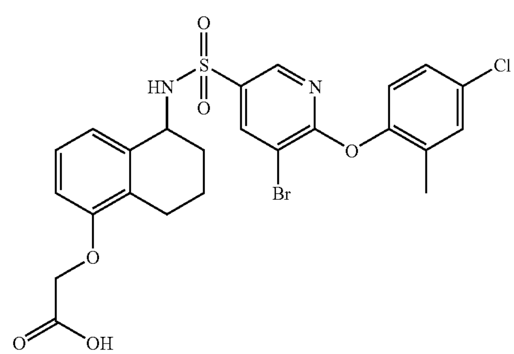 |
| 2-14(C) | {5-[5-Bromo-6-(4-ethyl-phenoxy)-pyridine-3-sulfonylamino]-5,6,7,8-tetrahydro-naphthalen-1-yloxy}-acetic acid | 8.51 (d, J = 2.2 Hz, 1 H), 8.49 (d, J = 2.2 Hz, 1 H), 8.27 (br. s, 1 H), 7.30 (d, J = 8.8 Hz, 2 H), 7.15 (d, J = 8.8 Hz, 2 H), 6.97 (t, J = 7.8 Hz, 1 H), 6.51-6.58 (m, 2 H), 4.38-4.46 (m, 1 H), 4.07 (s, 2 H), 2.64 (q, J = 7.3 Hz, 2 H), 2.51-2.64 (m, 2 H), 1.72-1.85 (m, 1 H), 1.60 (br. s, 3 H), 1.21 (t, J = 7.3 Hz, 3 H) | 559 | 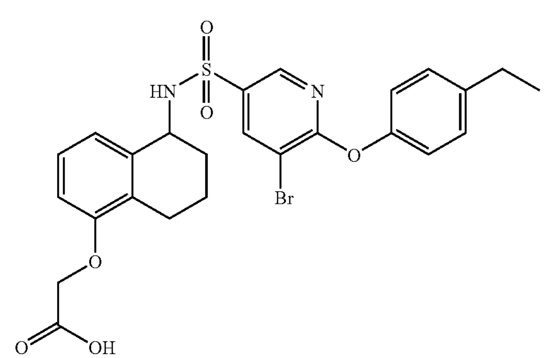 |

| Example No* | Systematic Name | 1H NMR (400 MHz, DMSO-d$_6$) δ ppm | MS [(M − H)] | Structure |
|---|---|---|---|---|
| 2-15(C) | {5-[5-Bromo-6-(3,5-dimethyl-phenoxy)-pyridine-3-sulfonylamino]-5,6,7,8-tetrahydro-naphthalen-1-yloxy}-acetic acid | 8.52 (d, J = 2.2 Hz, 1 H), 8.50 (d, J = 2.2 Hz, 1 H), 8.26 (br. s, 1 H), 6.97 (t, J = 7.8 Hz, 1 H), 6.93 (s, 1 H), 6.85 (s, 2 H), 6.50-6.58 (m, 2 H), 4.43 (br. s, 1 H), 4.06 (s, 2 H), 2.39-2.65 (m, 2 H), 2.29 (s, 6 H), 1.71-1.84 (m, 1 H), 1.53-1.67 (m, 3 H) | 559 | 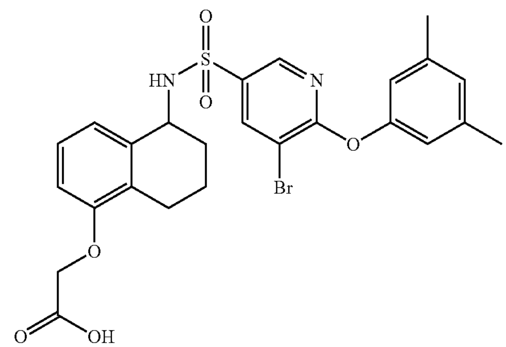 |
| 2-16(C) | [5-(5-Bromo-6-phenoxy-pyridine-3-sulfonylamino)-5,6,7,8-tetrahydro-naphthalen-1-yloxy]-acetic acid | 12.99 (br. s, 1 H), 8.52 (d, J = 2.2 Hz, 1 H), 8.52 (d, J = 2.2 Hz, 1 H), 8.31 (d, J = 8.3 Hz, 1 H), 7.43-7.51 (m, 2 H), 7.28-7.34 (m, 1 H), 7.23-7.28 (m, 2 H), 7.08 (t, J = 8.1 Hz, 1 H), 6.66-6.75 (m, 2 H), 4.67 (s, 2 H), 4.41-4.51 (m, 1 H), 2.51-2.59 (m, 2 H), 1.73-1.87 (m, 1 H), 1.61 (br. s, 3 H) | 533$^a$ | 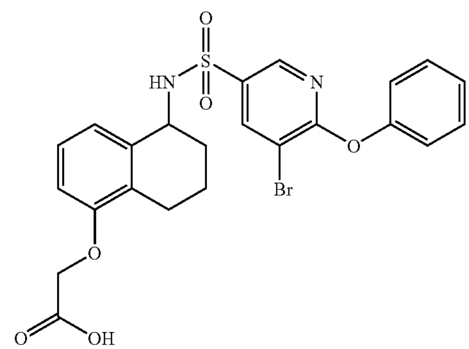 |
| 2-17(C) | {5-[5-Bromo-6-(indan-5-yloxy)-pyridine-3-sulfonylamino]-5,6,7,8-tetrahydro-naphthalen-1-yloxy}-acetic acid | 8.50 (d, J = 2.2 Hz, 1 H), 8.49 (d, J = 2.2 Hz, 1 H), 8.25 (br. s, 1 H), 7.28 (d, J = 8.1 Hz, 1 H), 7.08 (d, J = 2.2 Hz, 1 H), 6.91-7.01 (m, 1 H), 6.51-6.56 (m, 2 H), 4.42 (br. s, 1 H), 4.05 (s, 2 H), 2.84-2.92 (m, 4 H), 2.51-2.59 (m, 2 H), 1.96-2.15 (m, 2 H), 1.78 (br. s, 1 H), 1.60 (br. s, 3 H) | 571 | 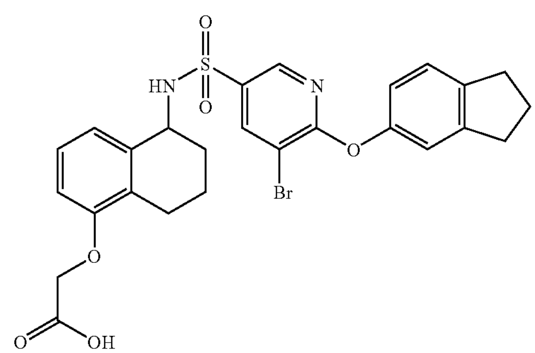 |
| 2-18(C) | [5-(5-Bromo-6-m-tolyloxy-pyridine-3-sulfonylamino)-5,6,7,8-tetrahydro-naphthalen-1-yloxy]-acetic acid | 8.48 (d, J = 2.2 Hz, 1 H), 8.46 (d, J = 2.2 Hz, 1 H), 7.32 (t, J = 7.7 Hz, 1 H), 7.11 (d, J = 7.7 Hz, 1 H), 6.93-7.03 (m, 3 H), 6.65 (d, J = 8.1 Hz, 1 H), 6.60 (d, J = 7.8 Hz, 1 H), 4.50 (s, 2 H), 4.40-4.49 (m, 1 H), 2.71-2.87 (m, 1 H), 2.52-2.69 (m, 1 H), 2.38 (s, 3 H), 1.64-1.93 (m, 4 H) | 547$^a$ | 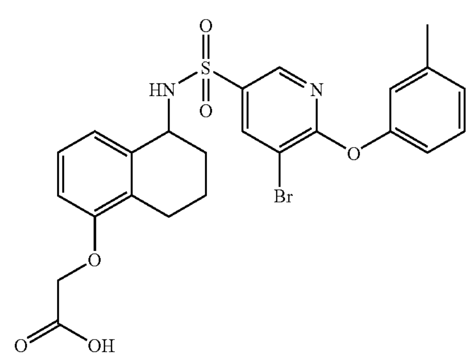 |

| Example No* | Systematic Name | 1H NMR (400 MHz, DMSO-d$_6$) δ ppm | MS [(M − H)] | Structure |
|---|---|---|---|---|
| 2-19(C) | [5-(5-Bromo-6-o-tolyloxy-pyridine-3-sulfonylamino)-5,6,7,8-tetrahydro-naphthalen-1-yloxy]-acetic acid | 12.98 (br. s, 1 H), 8.51 (d, J = 2.0 Hz, 1 H), 8.28 (d, J = 8.3 Hz, 1 H), 7.36 (d, J = 7.3 Hz, 1 H), 7.30 (t, J = 6.8 Hz, 1 H), 7.16-7.26 (m, 2 H), 7.03 (t, J = 7.8 Hz, 1 H), 6.69 (d, J = 7.8 Hz, 1 H), 6.62 (d, J = 7.8 Hz, 1 H), 4.64 (s, 2 H), 4.37-4.55 (m, 1 H), 2.53-2.60 (m, 2 H), 2.06 (s, 3 H), 1.70-1.88 (m, 1 H), 1.45-1.70 (m, 3 H) | 545 | 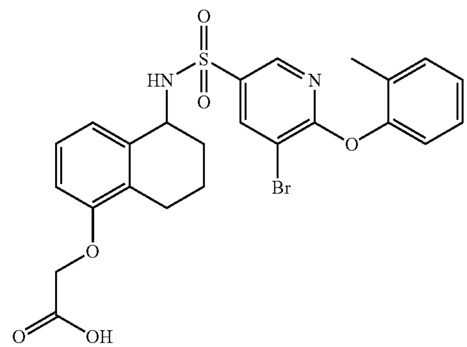 |
| 2-20(C) | [5-(5-Bromo-6-p-tolyloxy-pyridine-3-sulfonylamino)-5,6,7,8-tetrahydro-naphthalen-1-yloxy]-acetic acid | (CD$_3$OD-d$_4$) 8.48 (d, J = 2.2 Hz, 1 H), 8.46 (d, J = 2.2 Hz, 1 H), 7.26 (d, J = 8.3 Hz, 2 H), 7.05 (d, J = 8.3 Hz, 2 H), 6.99-7.06 (m, 1 H), 6.67 (d, J = 8.1 Hz, 1 H), 6.64 (d, J = 8.1 Hz, 1 H), 4.63 (br. s, 2 H), 4.46 (br. s, 1 H), 2.68-2.88 (m, 1 H), 2.51-2.70 (m, 1 H), 2.38 (s, 3 H), 1.82-1.95 (m, 1 H), 1.68-1.82 (m, 3 H) | 545 | 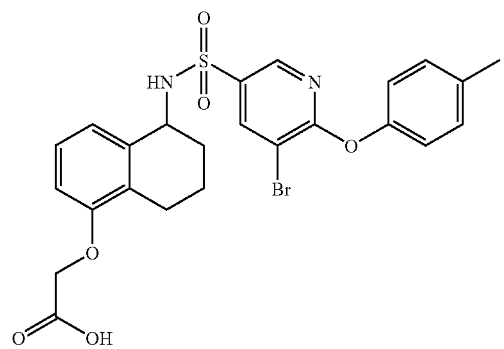 |
| 2-21(C) | {5-[5-Bromo-6-(4-chloro-phenoxy)-pyridine-3-sulfonylamino]-5,6,7,8-tetrahydro-naphthalen-1-yloxy}-acetic acid | (CD$_3$OD-d$_4$) 8.51 (d, J = 2.2 Hz, 1 H), 8.49 (d, J = 2.2 Hz, 1 H), 7.46 (d, J = 9.0 Hz, 2 H), 7.21 (d, J = 9.0 Hz, 2 H), 7.02 (t, J = 7.8 Hz, 1 H), 6.66 (d, J = 7.8 Hz, 1 H), 6.61 (d, J = 7.8 Hz, 1 H), 4.55 (s, 2 H), 4.41-4.49 (m, 1 H), 2.72-2.86 (m, 1 H), 2.56-2.68 (m, 1 H), 1.67-1.96 (m, 4 H) | 565 | 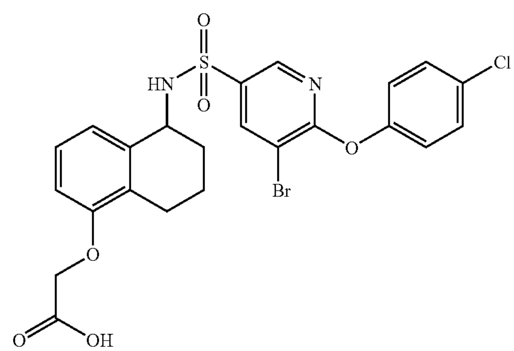 |
| 2-22(C) | (5-{5-Bromo-6-[4-(2-hydroxy-ethyl)-phenoxy]-pyridine-3-sulfonylamino}-5,6,7,8-tetrahydro-naphthalen-1-yloxy)-acetic acid | (CD$_3$OD-d$_4$) 8.46 (s, 2 H), 7.32 (d, J = 8.5 Hz, 2 H), 7.10 (d, J = 8.5 Hz, 2 H), 7.00 (t, J = 7.8 Hz, 1 H), 6.65 (d, J = 7.8 Hz, 1 H), 6.60 (d, J = 7.8 Hz, 1 H), 4.49 (s, 2 H), 4.42-4.47 (m, 1 H), 3.78 (t, J = 7.0 Hz, 2 H), 2.86 (t, J = 7.0 Hz, 2 H), 2.78 (m, 1 H), 2.51-2.68 (m, 1 H), 1.68-1.96 (m, 4 H) | 577[a] | 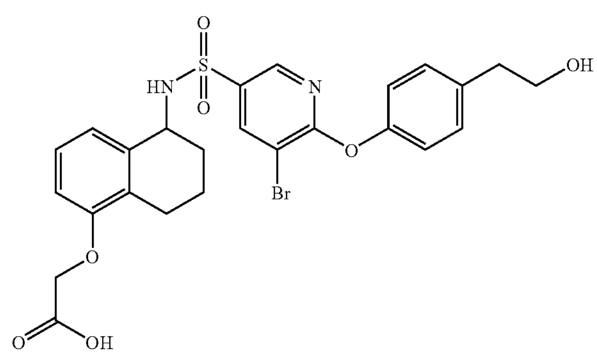 |

-continued

| Example No* | Systematic Name | 1H NMR (400 MHz, DMSO-d$_6$) δ ppm | MS [(M − H)] | Structure |
|---|---|---|---|---|
| 2-23(D) | {(R)-5-[5-Chloro-6-(4-chloro-phenoxy)-pyridine-3-sulfonylamino]-5,6,7,8-tetrahydro-naphthalen-1-yloxy}-acetic acid | (300 MHz, DMSO-d$_6$) d: 12.97 (s, 1 H), 8.47 (d, J = 2.2 Hz, 1 H), 8.40 (d, J = 2.2 Hz, 1 H), 8.31 (d, J = 8.2 Hz, 1 H), 7.52 (d, J = 8.8 Hz, 2 H), 7.32 (d, J = 8.8 Hz, 2 H), 7.06 (t, J = 7.8 Hz, 1 H), 6.71 (d, J = 7.8 Hz, 1 H), 6.68 (d, J = 7.8 Hz, 1 H), 4.65 (s, 2 H), 4.37-4.53 (m, 1 H), 2.51-2.58 (m, 2 H), 1.69-1.88 (m, 1 H), 1.48-1.68 (m, 3 H) | 523.049[b] | 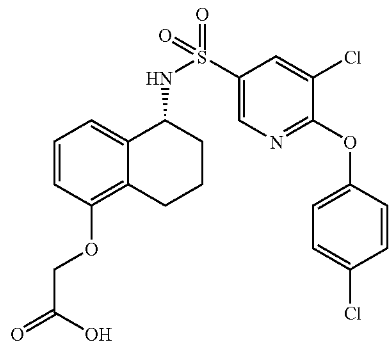 |
| 2-24(D) | {(R)-5-[5-Bromo-6-(4-fluoro-phenoxy)-pyridine-3-sulfonylamino]-5,6,7,8-tetrahydro-naphthalen-1-yloxy}-acetic acid | 8.48-8.53 (m, 2 H), 7.27-7.34 (m, 4 H), 7.01-7.10 (m, 1 H), 6.69 (d, J = 7.83 Hz, 2 H), 4.51-4.62 (m, 2 H), 4.41-4.49 (m, 1 H), 2.54-2.69 (m, 2 H), 1.73-1.85 (m, 1 H), 1.51-1.68 (m, 3 H) | 551[a] | 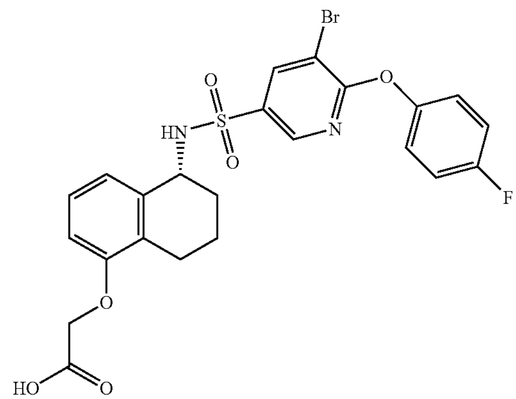 |
| 2-25(D) | {(R)-5-[5-Bromo-6-(4-chloro-phenoxy)-pyridine-3-sulfonylamino]-5,6,7,8-tetrahydro-naphthalen-1-yloxy}-acetic acid | (CD3OD-d$_4$) 7.94 (d, 2 H), 7.60 (q, 1 H), 7.43 (m, 1 H), 7.26 (m, 2 H), 7.07 (d, 2 H), 6.70 (s, 1 H), 4.80 (s, 2 H), 4.37 (t, 1 H), 2.60-2.48 (m, 2 H), 1.94-1.75 (m, 4 H) | 567[a] | 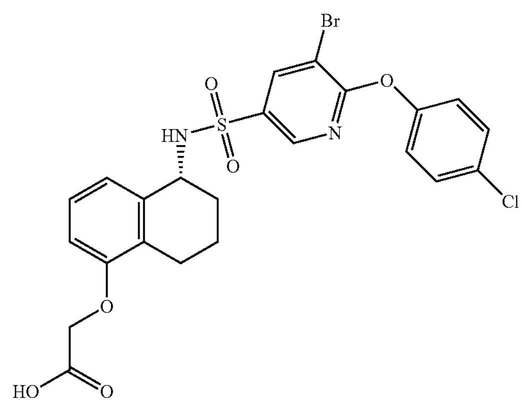 |
| 2-26(D) | {(R)-5-[5-Bromo-6-(2-chloro-phenoxy)-pyridine-3-sulfonylamino]-5,6,7,8-tetrahydro-naphthalen-1-yloxy}-acetic acid | 8.50-8.53 (m, 2 H), 8.28 (d, J = 8.34 Hz, 1 H), 7.60 (d, J = 1.26 Hz, 1 H), 7.43-7.49 (m, 2 H), 7.32-7.38 (m, 1 H), 6.97-7.04 (m, 1 H), 6.67 (d, J = 7.58 Hz, 1 H), 6.57-6.61 (m, 1 H), 4.63 (s, 2 H), 4.40-4.47 (m, 1 H), 2.53-2.65 (m, 2 H), 1.70-1.82 (m, 1 H), 1.53-1.65 (m, 3 H) | 567[a] | 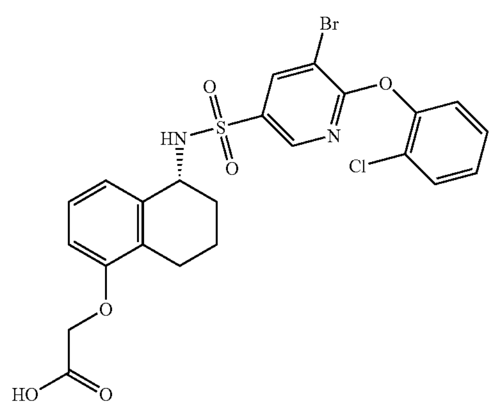 |

| Example No* | Systematic Name | 1H NMR (400 MHz, DMSO-d$_6$) δ ppm | MS [(M − H)] | Structure |
|---|---|---|---|---|
| 2-27(D) | {(R)-5-[5-Bromo-6-(3-chloro-phenoxy)-pyridine-3-sulfonylamino]-5,6,7,8-tetrahydro-naphthalen-1-yloxy}-acetic acid | 8.51-8.56 (m, 2 H), 8.31 (d, J = 8.59 Hz, 1 H), 7.46-7.51 (m, 2 H), 7.38 (dd, J = 7.20, 1.89 Hz, 1 H), 7.27 (dd, J = 7.71, 1.89 Hz, 1 H), 7.08 (t, J = 7.83 Hz, 1 H), 6.72 (dd, J = 10.99, 7.96 Hz, 2 H), 4.66 (s, 2 H), 4.44-4.51 (m, 1 H), 2.53-2.65 (m, 2 H), 1.74-1.85 (m, 1 H), 1.53-1.69 (m, 3 H) | 567[a] | 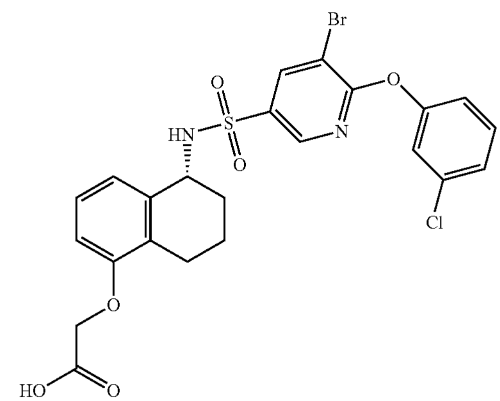 |
| 2-28(D) | {(R)-5-[5-Bromo-6-(2-chloro-4-fluoro-phenoxy)-pyridine-3-sulfonylamino]-5,6,7,8-tetrahydro-naphthalen-1-yloxy}-acetic acid | 8.53 (s, 2 H), 7.67 (dd, J = 8.46, 2.91 Hz, 1 H), 7.58 (dd, J = 9.22, 5.18 Hz, 1 H), 7.33-7.42 (m, 1 H), 7.02 (t, J = 7.96 Hz, 1 H), 6.69 (s, 1 H), 6.61 (s, 1 H), 4.59 (s, 2 H), 4.43-4.50 (m, 1 H), 2.51-2.70 (m, 2 H), 1.72-1.84 (m, 1 H), 1.50-1.69 (m, 3 H) | 585[a] | 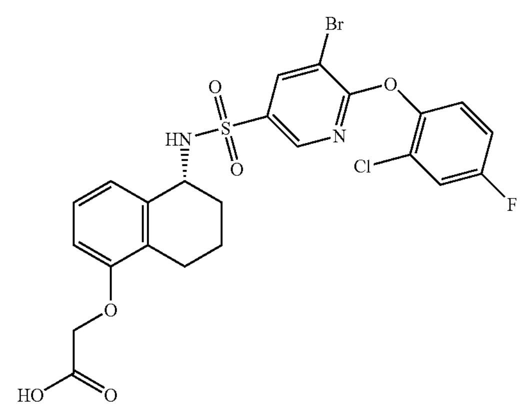 |
| 2-29(D) | [(R)-5-(5-Bromo-6-phenoxy-pyridine-3-sulfonylamino)-5,6,7,8-tetrahydro-naphthalen-1-yloxy]-acetic acid | 8.51 (q, J = 2.19 Hz, 2 H) 8.29 (d, J = 8.34 Hz, 1 H) 7.45-7.50 (m, 1 H) 7.48 (t, J = 7.96 Hz, 2 H) 7.30 (t, J = 7.45 Hz, 1 H) 7.25 (d, J = 7.58 Hz, 2 H) 7.07 (t, J = 7.96 Hz, 1 H) 6.71 (t, J = 7.83 Hz, 2 H) 4.66 (s, 2 H) 4.47 (br. s, 1 H) 2.57 (d, J = 7.33 Hz, 2 H) 1.79 (d, J = 7.58 Hz, 1 H) 1.61 (t, J = 6.82 Hz, 3 H) | 533[a] | 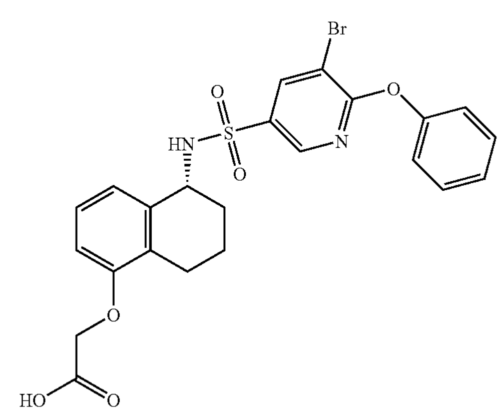 |

| Example No* | Systematic Name | 1H NMR (400 MHz, DMSO-d$_6$) δ ppm | MS [(M − H)] | Structure |
|---|---|---|---|---|
| 2-30(D) | {(R)-5-[3-Chloro-4-(3-chloro-phenoxy)-benzenesulfonyl-amino]-5,6,7,8-tetrahydro-naphthalen-1-yloxy}-acetic acid | (CD3OD) 8.06 (d, J = 2.02 Hz, 1 H), 7.85 (dd, J = 8.72, 2.15 Hz, 1 H), 7.41 (t, J = 8.21 Hz, 1 H), 7.23 (dd, J = 7.71, 1.39 Hz, 1 H), 7.19 (d, J = 8.59 Hz, 1 H), 7.07 (t, J = 2.15 Hz, 1 H), 6.99 (d, J = 2.53 Hz, 1 H), 6.64-6.70 (m, 1 H), 6.57 (d, J = 7.83 Hz, 1 H), 4.57-4.77 (m, 1 H), 4.41-4.46 (m, 5 H), 2.72-2.84 (m, 1 H), 2.54-2.66 (m, 1 H), 1.82-1.94 (m, 1 H), 1.64-1.81 (m, 3 H) | 522$^a$ | 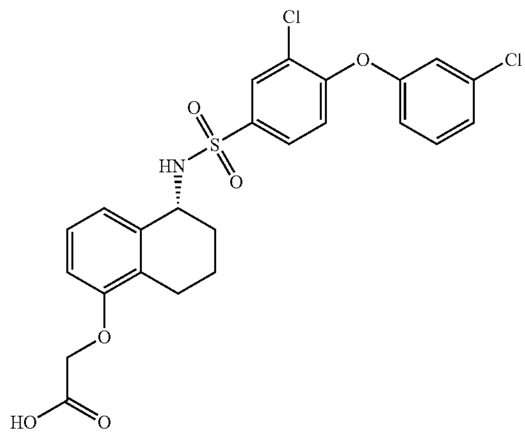 |
| 2-31(D) | {(R)-5-[3-Chloro-4-(4-fluoro-phenoxy)-benzenesulfonyl-amino]-5,6,7,8-tetrahydro-naphthalen-1-yloxy}-acetic acid | 8.19 (d, J = 8.34 Hz, 1 H), 8.01 (d, J = 2.27 Hz, 1 H), 7.79 (dd, J = 8.59, 2.27 Hz, 1 H), 7.31 (d, J = 8.59 Hz, 1 H), 7.20-7.25 (m, 2 H), 7.10 (d, J = 8.59 Hz, 1 H), 7.05 (t, J = 7.83 Hz, 1 H), 6.68 (t, J = 7.71 Hz, 2 H) 4.65 (s, 2 H), 4.39 (m, 1 H) 2.66 (s, 2 H), 1.78 (m, 1 H), 1.58 (m, 3 H) | 506$^a$ | 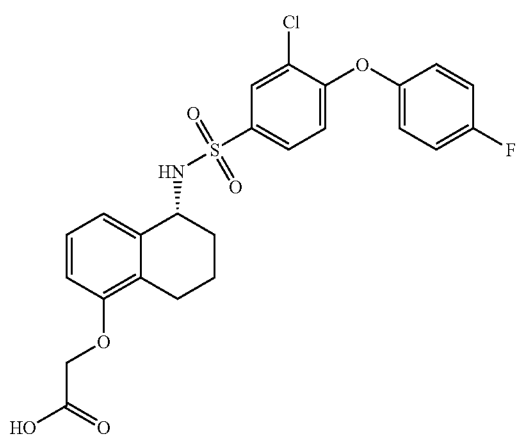 |
| 2-32(D) | {(R)-5-[3-Chloro-4-(2-chloro-phenoxy)-benzenesulfonyl-amino]-5,6,7,8-tetrahydro-naphthalen-1-yloxy}-acetic acid | 8.18-8.21 (m, 1 H), 8.01-8.04 (m, 1 H), 7.77-7.82 (m, 1 H), 7.67-7.71 (m, 1 H), 7.45-7.49 (m, 1 H), 7.35-7.39 (m, 1 H), 7.32 (d, 1 H), 7.00-7.04 (m, 1 H), 6.97 (d, 1 H), 6.64-6.68 (m, 1 H), 6.55-6.61 (m, 1 H), 4.54-4.62 (m, 2 H), 2.54-2.61 (m, 1 H), 2.30-2.38 (m, 1 H), 1.75-1.81 (m, 1 H), 1.54-1.63 (m, 3 H) | 522$^a$ | 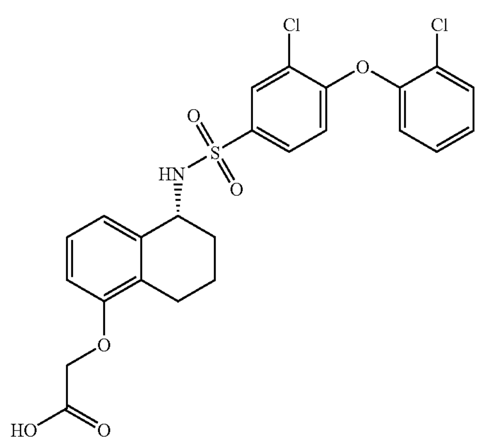 |

| Example No* | Systematic Name | 1H NMR (400 MHz, DMSO-d$_6$) δ ppm | MS [(M − H)] | Structure |
|---|---|---|---|---|
| 2-33(D) | {(R)-5-[3-Chloro-4-(4-chloro-2-fluoro-phenoxy)-benzenesulfonyl-amino]-5,6,7,8-tetrahydro-naphthalen-1-yloxy}-acetic acid | 8.21 (d, J = 8.59 Hz, 1 H) 8.03 (d, J = 2.02 Hz, 1 H), 7.74-7.82 (m, 2 H), 7.73-7.76 (m, 1 H), 7.39-7.43 (m, 1 H), 7.16 (d, J = 8.84 Hz, 1 H), 7.03 (t, J = 7.83 Hz, 1 H), 6.66-6.71 (m, 1 H), 6.62 (d, J = 7.58 Hz, 1 H), 4.62-4.67 (s, 2 H), 4.35-4.42 (m, 1 H), 2.54-2.68 (m, 1 H), 1.73-1.85 (m, 1 H), 1.52-1.66 (m, 3 H) | 540[a] | 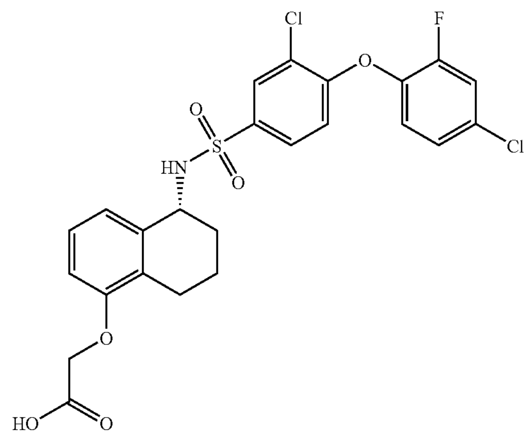 |
| 2-34(D) | {(R)-5-[3-Chloro-4-(2-chloro-4-fluoro-phenoxy)-benzenesulfonyl-amino]-5,6,7,8-tetrahydro-naphthalen-1-yloxy}-acetic acid | 8.19 (d, J = 8.59 Hz, 1 H), 8.02 (d, J = 2.27 Hz, 1 H), 7.72-7.79 (m, 2 H), 7.45 (d, J = 5.31 Hz, 1 H), 7.39 (dd, J = 8.08, 3.03 Hz, 1 H), 7.02 (t, J = 7.96 Hz, 1 H) 6.96 (d, J = 8.59 Hz, 1 H), 6.68 (d, J = 8.08 Hz, 1 H), 6.60 (d, J = 7.33 Hz, 1 H), 4.65 (s, 2 H), 4.32-4.40 (m, 1 H), 2.54-2.68 (m, 1 H), 2.31-2.44 (m, 1 H), 1.72-1.84 (m, 1 H), 1.52-1.65 (m, 3 H) | 540[a] | 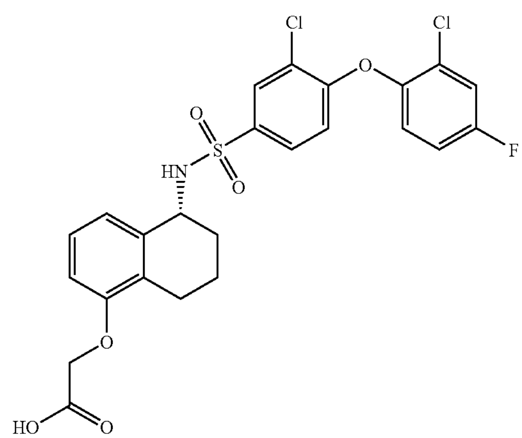 |
| 2-35(D) | [(R)-5-(3-Chloro-4-phenoxy-benzenesulfonyl-amino)-5,6,7,8-tetrahydro-naphthalen-1-yloxy]-acetic acid | 8.20 (d, J = 8.34 Hz, 1 H), 8.02 (d, J = 2.27 Hz, 1 H), 7.79-7.84 (m, 1 H), 7.48 (dd, 2 H) 7.27 (t, J = 7.45 Hz, 1 H), 7.13 (dd, J = 8.21, 2.65 Hz, 2 H), 7.05 (t, J = 7.83 Hz, 1 H) 6.67 (dd, J = 13.26, 7.71 Hz, 2 H), 4.61-4.67 (m, 2 H), 4.35-4.42 (m, 1 H), 2.55-2.64 (m, 1 H), 2.29-2.41 (m, 1 H), 1.72-1.86 (m, 1 H), 1.53-1.66 (m, 3 H) | 488[a] | 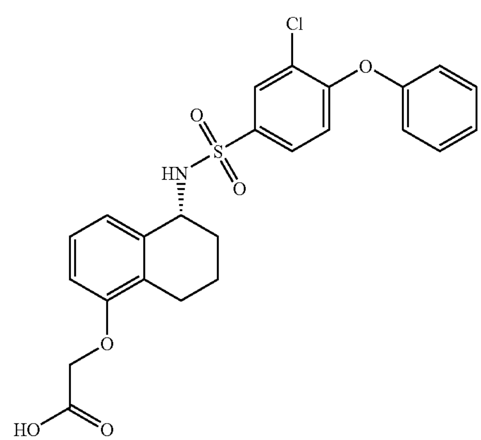 |

| Example No* | Systematic Name | 1H NMR (400 MHz, DMSO-d$_6$) δ ppm | MS [(M − H)] | Structure |
|---|---|---|---|---|
| 2-36(D) | {(R)-5-[2-Chloro-4-(4-fluoro-phenoxy)-benzenesulfonyl-amino]-5,6,7,8-tetrahydro-naphthalen-1-yloxy}-acetic acid | 8.32 (d, J = 9.09 Hz, 1 H), 8.03 (d, J = 8.84 Hz, 1 H), 7.33 (t, J = 8.84 Hz, 2 H), 7.27 (dd, J = 11.62, 3.54 Hz, 2 H), 7.05-7.12 (m, 1 H), 7.02 (dd, J = 8.84, 2.53 Hz, 1 H), 6.81 (s, 1 H), 6.68 (d, J = 8.34 Hz, 1 H), 4.65 (s, 2 H), 4.27-4.33 (m, 1 H), 2.53-2.68 (m, 1 H), 2.31-2.36 (m, 1 H), 1.84-1.90 (m, 1 H), 1.52-1.68 (m, 3 H) | 506[a] | 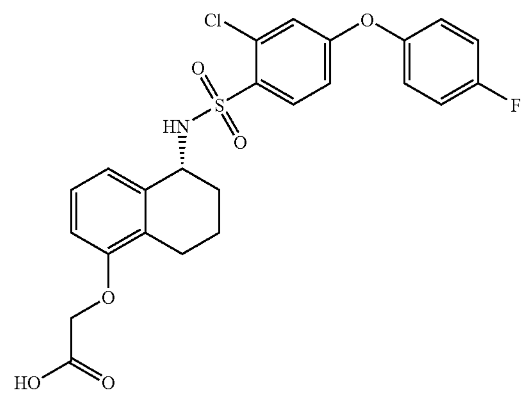 |
| 2-37(D) | {(R)-5-[2-Chloro-4-(2-chloro-phenoxy)-benzenesulfonyl-amino]-5,6,7,8-tetrahydro-naphthalen-1-yloxy}-acetic acid | 8.34 (d, J = 9.09 Hz, 1 H), 8.05 (d, J = 8.84 Hz, 1 H), 7.68 (dd, J = 7.83, 1.52 Hz, 1 H), 7.47-7.52 (m, 2 H), 7.35-7.43 (m, 1 H), 7.25 (d, J = 2.53 Hz, 1 H), 7.06 (t, J = 7.96 Hz, 1 H), 6.97 (dd, J = 8.84, 2.53 Hz, 1 H), 6.75 (d, J = 7.83 Hz, 1 H), 6.68 (d, J = 8.08 Hz, 1 H), 4.66 (s, 2 H), 4.27-4.34 (m, 1 H), 2.51-2.62 (m, 2 H), 1.80-1.92 (m, 1 H), 1.53-1.65 (m, 3 H) | 522[a] | 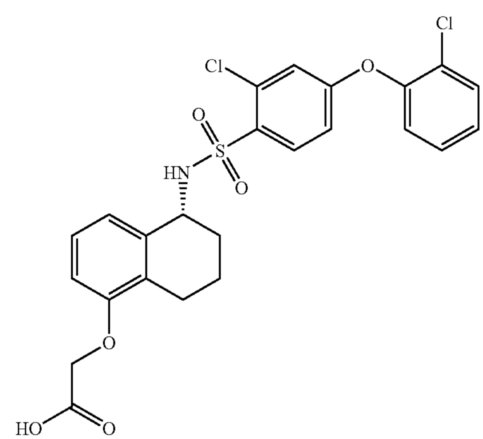 |
| 2-38(D) | {(R)-5-[2-Chloro-4-(2-chloro-4-fluoro-phenoxy)-benzenesulfonyl-amino]-5,6,7,8-tetrahydro-naphthalen-1-yloxy}-acetic acid | 8.34 (d, J = 9.09 Hz, 1 H), 8.04 (d, J = 8.84 Hz, 1 H), 7.72 (dd, J = 8.34, 3.03 Hz, 1 H), 7.51 (dd, J = 8.97, 5.18 Hz, 1 H), 7.35-7.41 (m, 1 H), 7.27 (d, J = 2.53 Hz, 1 H), 7.06 (t, J = 7.96 Hz, 1 H), 6.98 (dd, J = 8.84, 2.53 Hz, 1 H), 6.75 (d, J = 7.58 Hz, 1 H), 6.68 (d, J = 8.08 Hz, 1H, 4.65 (s, 2 H), 4.27-4.34 (m, 1 H), 2.55 (d, J = 11.62 Hz, 2 H), 1.81-1.93 (m, 1 H), 1.54-1.65 (m, 3 H) | 540[a] | 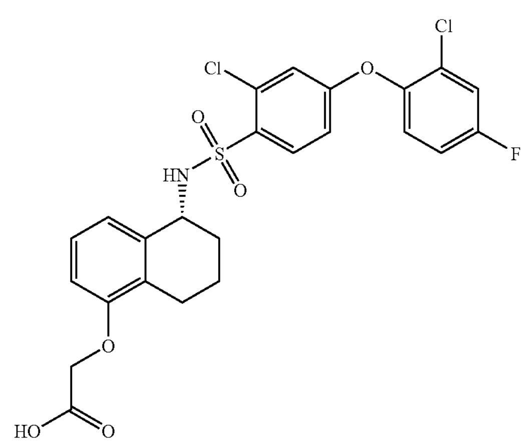 |

| Example No* | Systematic Name | 1H NMR (400 MHz, DMSO-d$_6$) δ ppm | MS [(M − H)] | Structure |
|---|---|---|---|---|
| 2-39(D) | [(R)-5-(2-Chloro-4-phenoxy-benzenesulfonyl-amino)-5,6,7,8-tetrahydro-naphthalen-1-yloxy]-acetic acid | 8.32 (d, J = 9.09 Hz, 1 H), 8.04 (d, J = 8.84 Hz, 1 H), 7.47-7.53 (m, 2 H), 7.30 (t, J = 7.45 Hz, 1 H) 7.26 (d, J = 2.53 Hz, 1 H), 7.18-7.22 (m, 2 H), 7.08 (t, J = 7.96 Hz, 1 H), 7.04 (dd, J = 8.84, 2.53 Hz, 1 H), 6.80 (d, J = 7.58 Hz, 1 H), 6.68 (d, J = 8.08 Hz, 2 H), 4.66 (s, 2 H), 4.27-4.34 (m, 1 H), 2.52-2.60 (m, 2 H), 1.83-1.91 (m, 1 H), 1.55-1.65 (m, 3 H) | 488$^a$ | 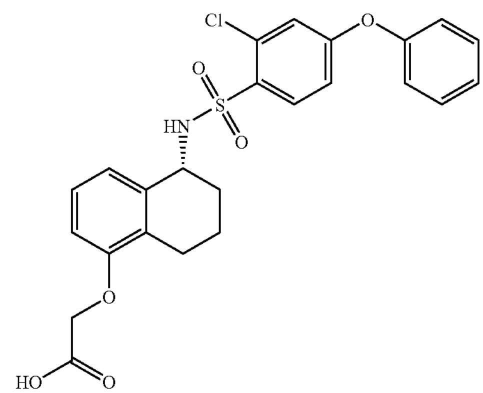 |
| 2-40(D) | {(R)-5-[2-Chloro-4-(4-chloro-phenoxy)-benzenesulfonyl-amino]-5,6,7,8-tetrahydro-naphthalen-1-yloxy}-acetic acid | 8.34 (d, J = 9.09 Hz, 1 H), 8.05 (d, J = 8.84 Hz, 1 H), 7.54 (d, J = 8.84 Hz, 2 H), 7.32 (d, J = 2.53 Hz, 1 H), 7.22-7.26 (m, 2 H), 7.07 (d, J = 8.84 Hz, 2 H), 6.80 (d, J = 7.83 Hz, 1 H), 6.68 (d, J = 8.34 Hz, 1 H), 4.65 (s, 2 H), 4.25-4.34 (m, 1 H), 2.51-2.68 (m, 2 H), 1.84-1.92 (m, 1 H), 1.54-1.65 (m, 3 H) | 522$^a$ | 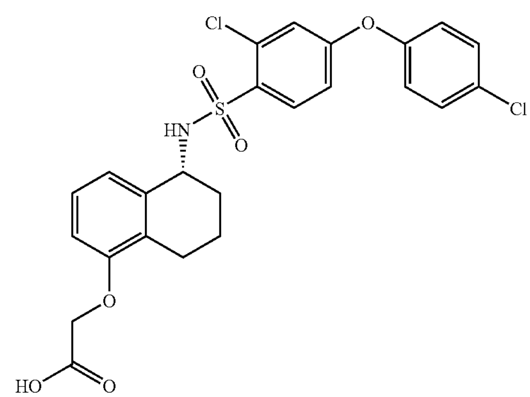 |
| 2-41(D) | {(R)-5-[2-Chloro-4-(3-chloro-phenoxy)-benzenesulfonyl-amino]-5,6,7,8-tetrahydro-naphthalen-1-yloxy}-acetic acid | 8.35 (d, J = 9.09 Hz, 1 H), 8.06 (d, J = 8.84 Hz, 1 H), 7.50 (d, J = 7.83 Hz, 1 H), 7.32-7.37 (m, 3 H), 7.15-7.20 (m, 1 H), 7.05-7.12 (m, 2 H), 6.79 (d, J = 8.08 Hz, 1 H), 6.68 (d, J = 8.59 Hz, 1 H), 4.66 (s, 2 H), 4.27-4.35 (m, 1 H), 2.53-2.63 (m, 2 H), 1.82-1.92 (m, 1 H), 1.54-1.67 (m, 3 H) | 522$^a$ | 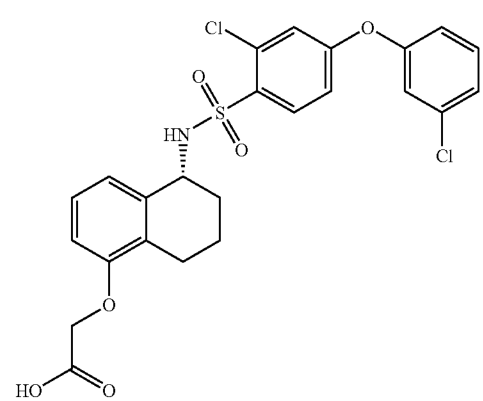 |

| Example No* | Systematic Name | 1H NMR (400 MHz, DMSO-d$_6$) δ ppm | MS [(M − H)] | Structure |
|---|---|---|---|---|
| 2-42(D) | {(R)-5-[4-(4-Fluoro-phenoxy)-3-trifluoromethyl-benzenesulfonyl-amino]-5,6,7,8-tetrahydro-naphthalen-1-yloxy}-acetic acid | 8.26 (d, J = 8.34 Hz, 1 H), 8.17 (d, J = 2.27 Hz, 1 H), 8.09 (dd, J = 8.84, 2.27 Hz, 1 H), 7.32-7.38 (m, 2 H), 7.26-7.30 (m, 2 H), 7.13 (d, J = 8.59 Hz, 1 H), 7.04 (t, J = 7.83 Hz, 1 H), 6.68 (d, J = 8.08 Hz, 1 H), 6.63 (d, J = 7.58 Hz, 1 H), 4.64 (s, 2 H), 4.34-4.41 (m, 1 H), 2.52-2.70 (m, 2 H), 1.71-1.84 (m, 1 H), 1.52-1.64 (m, 3 H) | 540$^a$ | 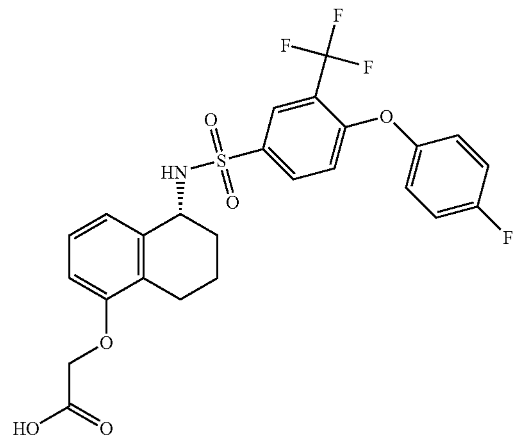 |
| 2-43(D) | {(R)-5-[4-(2-Chloro-phenoxy)-3-trifluoromethyl-benzenesulfonyl-amino]-5,6,7,8-tetrahydro-naphthalen-1-yloxy}-acetic acid | 8.26 (d, J = 8.34 Hz, 1 H), 8.19 (d, J = 2.02 Hz, 1 H), 8.09 (dd, J = 8.84, 2.27 Hz, 1 H), 7.71 (dd, J = 7.96, 1.39 Hz, 1 H), 7.49-7.54 (m, 1 H), 7.39-7.45 (m, 2 H), 6.97 (d, J = 8.84 Hz, 2 H), 6.68 (d, J = 8.08 Hz, 1 H), 6.55 (d, J = 7.83 Hz, 1 H), 4.64 (s, 2 H), 4.36 (d, J = 7.83 Hz, 1 H), 2.52-2.68 (m, 2 H), 1.71-1.82 (m, 1 H), 1.52-1.65 (m, 3 H) | 556$^a$ | 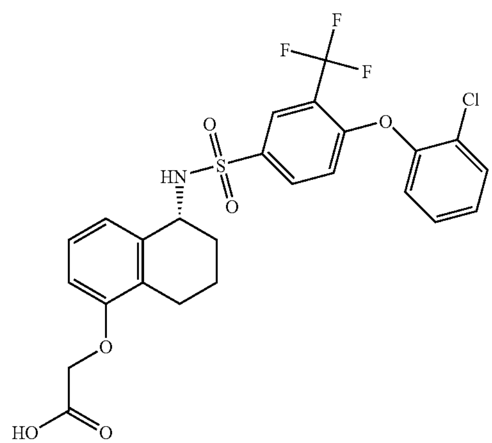 |
| 2-44(D) | {(R)-5-[4-(4-Chloro-2-fluoro-phenoxy)-3-trifluoromethyl-benzenesulfonyl-amino]-5,6,7,8-tetrahydro-naphthalen-1-yloxy}-acetic acid | 8.29 (d, J = 8.34 Hz, 1 H), 8.19 (d, J = 1.77 Hz, 1 H), 8.09 (dd, J = 8.97, 1.89 Hz, 1 H), 7.77 (dd, J = 10.61, 2.27 Hz, 1 H), 7.50 (t, J = 8.59 Hz, 1 H), 7.41-7.46 (m, 1 H), 7.21 (d, J = 8.59 Hz, 1 H), 7.01 (t, J = 7.96 Hz, 1 H), 6.68 (d, J = 8.08 Hz, 1 H), 6.57 (d, J = 7.83 Hz, 1 H), 4.65 (s, 2 H), 4.33-4.41 (m, 1 H), 2.52-2.68 (m, 2 H), 1.74 (m, 1 H) 1.51-1.65 (m, 3 H) | 574$^a$ | 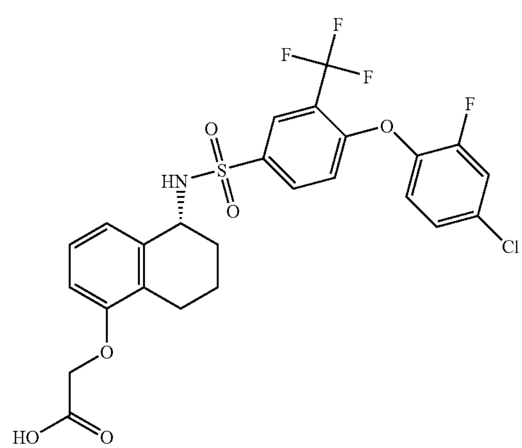 |

| Example No* | Systematic Name | 1H NMR (400 MHz, DMSO-d$_6$) δ ppm | MS [(M − H)] | Structure |
| --- | --- | --- | --- | --- |
| 2-45(D) | {(R)-5-[4-(2-Chloro-4-fluoro-phenoxy)-3-trifluoromethyl-benzenesulfonyl-amino]-5,6,7,8-tetrahydro-naphthalen-1-yloxy}-acetic acid | 8.30 (d, J = 8.34 Hz, 1 H), 8.22 (d, J = 2.02 Hz, 1 H), 8.11 (dd, J = 8.72, 2.15 Hz, 1 H), 7.79 (dd, J = 8.34, 3.03 Hz, 1 H), 7.57 (dd, J = 9.09, 5.05 Hz, 1 H), 7.44 (td, J = 8.59, 3.03 Hz, 5 H), 7.01-7.07 (m, 2 H), 6.71 (d, J = 8.08 Hz, 1 H), 6.59 (d, J = 7.83 Hz, 1 H), 4.67 (s, 2 H), 4.36-4.44 (m, 1 H), 2.55-2.71 (m, 2 H), 1.73-1.87 (m, 1 H), 1.54-1.68 (m, 3 H) | 574$^a$ | 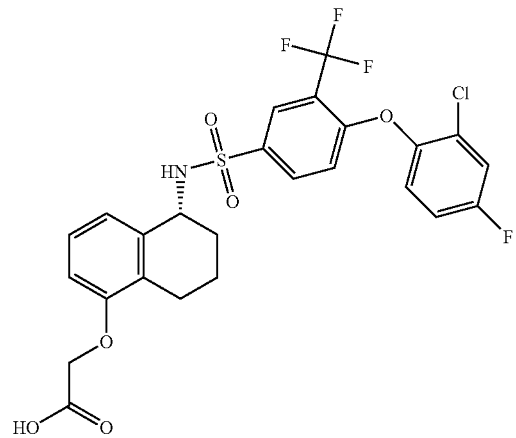 |
| 2-46(D) | [(R)-5-(4-Phenoxy-3-trifluoromethyl- | 8.27 (d, J = 8.34 Hz, 1 H), 8.18 (d, J = 2.27 Hz, 1 H), 8.10 (dd, J = 8.84, 2.27 Hz, 5 H), 7.52 (t, J = 7.96 Hz, 2 H), 7.32 (t, J = 7.45 Hz, 1 H), 7.20 (d, J = 7.58 Hz, 2 H), 7.14 (d, J = 8.84 Hz, 1 H), 7.04 (t, J = 8.08 Hz, 1 H), 6.69 (d, J = 8.08 Hz, 1 H) 6.63 (d, J = 7.83 Hz, 1 H), 4.65 (s, 2 H), 4.34-4.41 (m, 1 H), 2.51-2.67 (m, 2 H), 1.73-1.84 (m, 1 H), 1.53-1.65 (m, 3 H) | 522$^a$ | 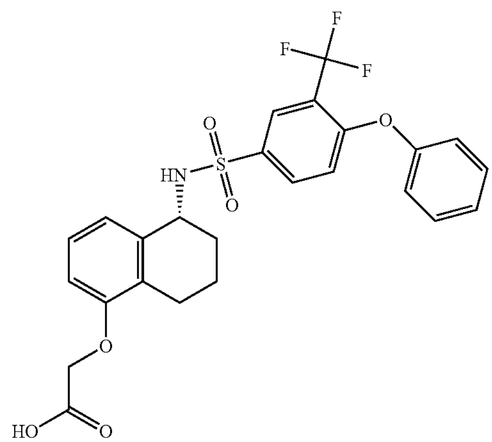 |
| 2-47(D) | {(R)-5-[4-(4-Chloro-phenoxy)-3-trifluoromethyl-benzenesulfonyl-amino]-5,6,7,8-tetrahydro-naphthalen-1-yloxy}-acetic acid | 8.28 (d, J = 8.34 Hz, 1 H), 8.18 (d, J = 1.77 Hz, 1 H) 8.10 (dd, J = 8.72, 2.15 Hz, 1 H), 7.56 (d, J = 9.09 Hz, 2 H), 7.24 (d, J = 9.09 Hz, 2 H), 7.21 (d, J = 8.84 Hz, 1 H), 7.04 (t, J = 7.96 Hz, 2 H), 6.69 (d, J = 8.08 Hz, 1 H), 6.63 (d, J = 7.83 Hz, 1 H), 4.65 (s, 2 H), 4.35-4.42 (m, 1 H), 2.52-2.64 (m, 2 H), 1.72-1.84 (m, 1 H), 1.52-1.65 (m, 3 H) | 556$^a$ | 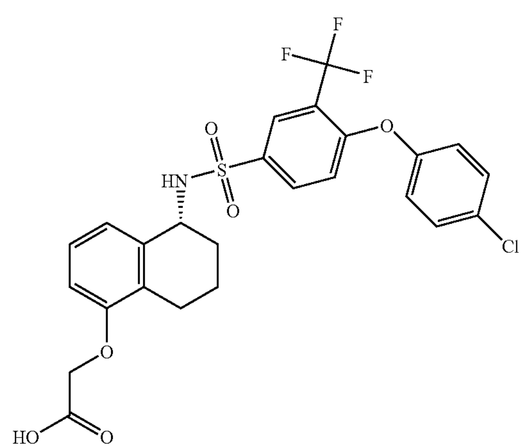 |

| Example No* | Systematic Name | 1H NMR (400 MHz, DMSO-d$_6$) δ ppm | MS [(M − H)] | Structure |
|---|---|---|---|---|
| 2-48(D) | {(R)-5-[4-(3-Chloro-phenoxy)-3-trifluoromethyl-benzenesulfonyl-amino]-5,6,7,8-tetrahydro-naphthalen-1-yloxy}-acetic acid | 8.29 (d, J = 8.34 Hz, 1 H), 8.19 (d, J = 2.02 Hz, 1 H), 8.13 (dd, J = 8.72, 2.15 Hz, 1 H), 7.53 (t, J = 8.08 Hz, 1 H), 7.39 (d, J = 1.01 Hz, 1 H), 7.34 (t, J = 2.15 Hz, 1 H), 7.27 (d, J = 8.84 Hz, 1 H), 7.17 (dd, J = 8.34, 1.77 Hz, 1 H), 7.03 (t, J = 7.96 Hz, 1 H), 6.68 (d, J = 8.34 Hz, 1 H), 6.61 (d, J = 8.08 Hz, 1 H), 4.64 (s, 2 H), 4.34-4.43 (m, 1 H), 2.52-2.69 (m, 2 H), 1.72-1.84 (m, 1 H), 1.52-1.66 (m, 3 H) | 556$^a$ | 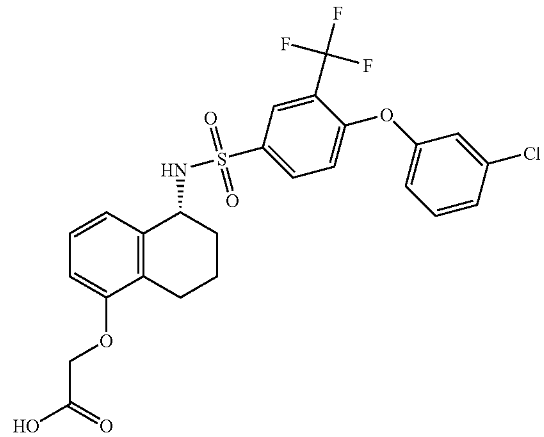 |

*Method of preparation C or D indicated in parentheses;
$^a$MS [M + H]$^+$,
$^b$HRMS: [M + H]$^+$

Example 3-1

Method E

{5-[4-(4-Fluoro-pyridin-2-yl)-benzenesulfonylamino]-5,6,7,8-tetrahydro-naphthalen-1-yloxy}-acetic acid

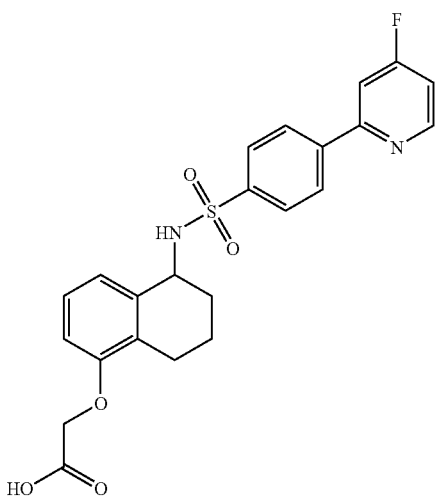

[5-(4-Bromo-benzenesulfonylamino)-5,6,7,8-tetrahydro-naphthalen-1-yloxy]-acetic acid tert-butyl ester

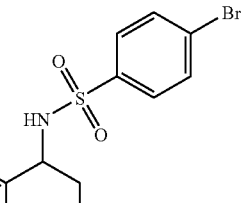

Starting with (5-amino-5,6,7,8-tetrahydro-naphthalen-1-yloxy)-acetic acid tert-butyl ester (example 1-1, method A, 3$^{rd}$ step) (0.500 g, 1.8 mmol), diisopropylamine (0.553 g, 2.1 mmol) and 4-bromobenzenesulfonyl chloride (0.465 g, 1.8 mmol), using the method analogous to the one described for example 1-1, method A, 4$^{th}$ step, [5-(4-bromo-benzenesulfonylamino)-5,6,7,8-tetrahydro-naphthalen-1-yloxy]-acetic acid tert-butyl ester (0.53 g, 61%) was obtained. MS cald. for C$_{22}$H$_{26}$BrNO$_5$S 495, obsd. 496 [(M+H)$^+$].

{5-[4-(4-Fluoro-pyridin-2-yl)-benzenesulfonylamino]-5,6,7,8-tetrahydro-naphthalen-1-yloxy}-acetic acid tert-butyl ester

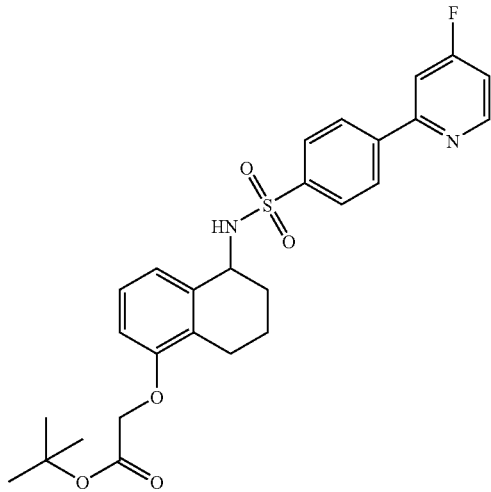

To a degassed, stirred mixture of [5-(4-bromo-benzenesulfonylamino)-5,6,7,8-tetrahydro-naphthalen-1-yloxy]-acetic acid tert-butyl ester (150 mg, 0.30 mmol) in 1,4-dioxane (10 mL) and a 1 M aqueous solution of potassium carbonate (0.89 mL, 0.89 mmol) was added 4-fluoro-pyridine-2-boronic acid (51 mg, 0.36 mmol) and tetrakis(triphenylphosphine)palladium(0) (16 mg, 0.014 mmol) under argon at room temperature. The mixture was heated at reflux for 4 hours. After being cooled to room temperature, the solvents were removed under reduced pressure. The crude residue was diluted with ethyl acetate (50 mL), washed with water (10 mL×2), dried over anhydrous sodium sulfate, and concentrated in vacuo to give crude {5-[4-(4-fluoro-pyridin-2-yl)-benzenesulfonylamino]-5,6,7,8-tetrahydro-naphthalen-1-yloxy}-acetic acid tert-butyl ester, which was used without further purification. MS cald. for $C_{27}H_{29}FN_2O_5S$ 512, obsd. 513 [(M+H)$^+$].

{5-[4-(4-Fluoro-pyridin-2-yl)-benzenesulfonylamino]-5,6,7,8-tetrahydro-naphthalen-1-yloxy}-acetic acid

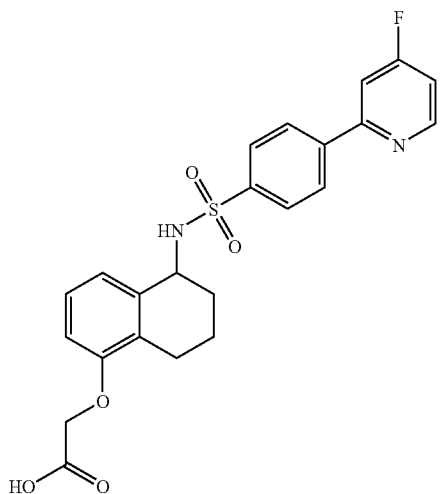

Starting with {5-[4-(4-fluoro-pyridin-2-yl)-benzenesulfonylamino]-5,6,7,8-tetrahydro-naphthalen-1-yloxy}-acetic acid tert-butyl ester, and using the method analogous to the one described for example 2-1, 3$^{rd}$ step, {5-[4-(4-fluoro-pyridin-2-yl)-benzenesulfonylamino]-5,6,7,8-tetrahydro-naphthalen-1-yloxy}-acetic acid (9.3 mg, 7.2% over two steps) was obtained. MS cald. for $C_{23}H_{21}FN_2O_5S$ 456, obsd. 457 [(M+H)$^+$].

Example 3-2

Method F

[(R)-5-(2'-Chloro-biphenyl-4-sulfonylamino)-5,6,7,8-tetrahydro-naphthalen-1-yloxy]-acetic acid

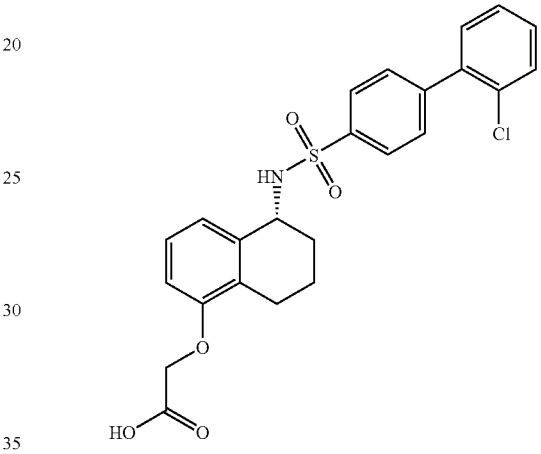

[(R)-5-(4-Iodo-benzenesulfonylamino)-5,6,7,8-tetrahydro-naphthalen-1-yloxy]-acetic acid tert-butyl ester

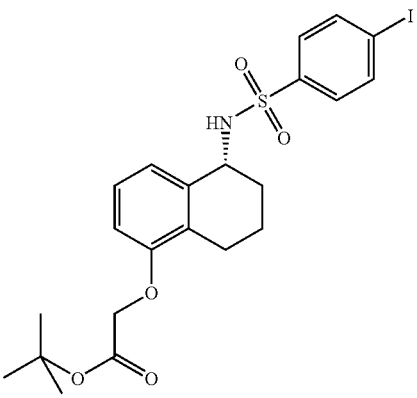

Starting with (R)-(5-amino-5,6,7,8-tetrahydro-naphthalen-1-yloxy)-acetic acid tert-butyl ester (example 1-2, method B, 1$^{st}$ step) and 4-iodobenzenesulfonyl chloride, using the method analogous to the one used for example 1-1, method A, 4$^{th}$ step, (R)-[5-(4-iodo-benzenesulfonylamino)-5,6,7,8-tetrahydro-naphthalen-1-yloxy]-acetic acid tert-butyl ester was obtained. MS cald. for $C_{22}H_{26}INO_5S$ 543, obsd. 544 [(M+H)$^+$].

85

[(R)-5-(2'-Chloro-biphenyl-4-sulfonylamino)-5,6,7,
8-tetrahydro-naphthalen-1-yloxy]-acetic acid tert-
butyl ester

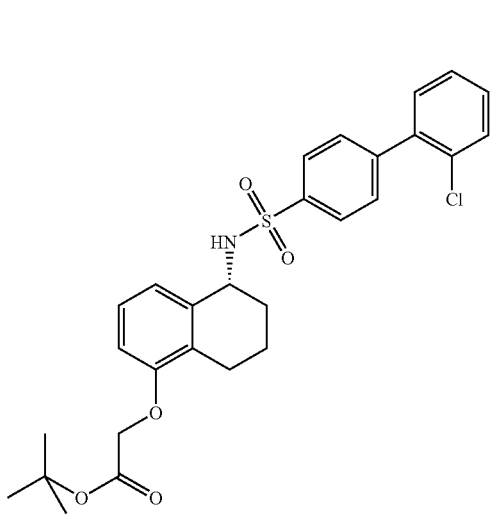

To a mixture of 2-chlorophenylboronic acid (7 mg, 0.044 mmol) and polymer bound tetrakis(triphenylphosphine) palladium (0.5 mmol/g, 11 mg, 0.0036 mmol) in a microwave vial was added (R)-5-(4-iodo-benzenesulfonylamino)-5,6,7,8-tetrahydro-naphthalen-1-yloxy]-acetic acid tert-butyl ester (20 mg, 0.036 mmol) in 1:1 tetrahydrofuran:ethanol solution (1 mL), followed by 1 M potassium carbonate (0.05 mL, 0.048 mmol). The resulting mixture was heated in a Biotage microwave at 110° C. for 15 minutes. The reaction mixture was filtered, and washed with dichloromethane. The combined filtrate was concentrated to dryness in vacuo to give crude (R)-[5-(2'-chloro-biphenyl-4-sulfonylamino)-5,6,7,8-tetrahydro-naphthalen-1-yloxy]-acetic acid tert-butyl ester, which was used in the next step without further purification. MS cald. for $C_{28}H_{30}ClNO_5S$ 527, obsd. 528 [(M+H)$^+$].

86

[(R)-5-(2'-Chloro-biphenyl-4-sulfonylamino)-5,6,7,
8-tetrahydro-naphthalen-1-yloxy]-acetic acid

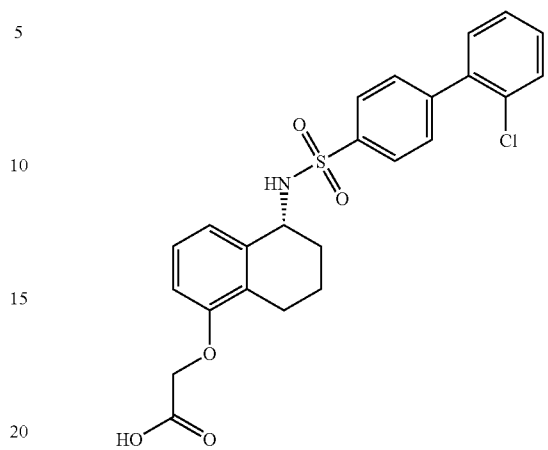

(R)-[5-(2'-Chloro-biphenyl-4-sulfonylamino)-5,6,7,8-tetrahydro-naphthalen-1-yloxy]-acetic acid tert-butyl ester was treated with aqueous lithium hydroxide (0.2 M, 1 mL) in tetrahydrofuran (1 mL) overnight, at room temperature. The reaction mixture was concentrated in vacuo. Reverse phase HPLC (Pursuit C-18, 20×150 mm, water/acetonitrile/0.05% trifluoroacetic acid) gave (R)-[5-(2'-chloro-biphenyl-4-sulfonylamino)-5,6,7,8-tetrahydro-naphthalen-1-yloxy]-acetic acid (8.5 mg, 43% over two steps). MS cald. for $C_{24}H_{22}ClNO_5S$ 471, obsd. 472 [(M+H)$^+$].

Examples 3-3 to 3-89

The following examples 3-3 to 3-89 were prepared in the analogous manner to examples 3-1 or 3-2, using method E or method F, starting with naphthalene-1,5-diol, commercially available or prepared bromo or iodo aryl sulfonyl chlorides (4-bromobenzenesulfonyl chloride, 4-iodobenzenesulfonyl chloride, 4-bromo-3-methylbenzenesulfonyl chloride, 5-bromo-pyridine-2-sulfonyl chloride, 6-bromo-pyridine-3-sulfonyl chloride) and the appropriate commercially available or prepared aryl boronic acids.

| Example No.* | Systematic Name | $^1$H NMR (400 MHz, DMSO-d$_6$) δ ppm | MS [(M + H)$^+$] | Structure |
| --- | --- | --- | --- | --- |
| 3-3(E) | {5-[4-(2-Fluoro-pyridin-3-yl)-benzenesulfonyl-amino]-5,6,7,8-tetrahydro-naphthalen-1-yloxy}-acetic acid | 13.09 (s, 1 H), 8.32 (d, J = 4.9 Hz, 1 H), 8.18-8.28 (m, 2 H), 8.00 (d, J = 8.3 Hz, 2 H), 7.87 (d, J = 8.3 Hz, 2 H), 7.53 (ddd, J = 6.8, 4.9, 1.5 Hz, 1 H), 7.03 (t, J = 7.8 Hz, 1 H), 6.71 (d, J = 7.8 Hz, 1 H), 6.67 (d, J = 7.8 Hz, 1 H), 4.64 (s, 2 H), 4.33-4.46 (m, 1 H), 2.50-2.64 (m, 2 H), 1.73-1.85 (m, 1 H), 1.59 (d, 3 H) | 455$^c$ | 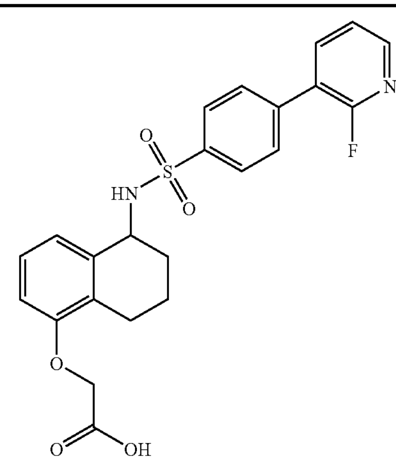 |

| Example No.* | Systematic Name | ¹H NMR (400 MHz, DMSO-d₆) δ ppm | MS [(M + H)⁺] | Structure |
|---|---|---|---|---|
| 3-4(E) | {5-[4-(6-Fluoro-pyridin-3-yl)-benzenesulfonyl-amino]-5,6,7,8-tetrahydro-naphthalen-1-yloxy}-acetic acid | 12.95 (br. s, 1 H), 8.68 (d, J = 2.6 Hz, 1 H), 8.41 (td, J = 8.2, 2.7 Hz, 1 H), 8.19 (d, J = 8.8 Hz, 1 H), 7.89-8.06 (m, 4 H), 7.35 (dd, J = 8.2, 2.6 Hz, 1 H), 7.04 (t, J = 7.8 Hz, 1 H), 6.75 (d, J = 7.8 Hz, 1 H), 6.67 (d, J = 7.8 Hz, 1 H), 4.64 (s, 2 H), 4.27-4.46 (m, 1 H), 2.36-2.61 (m, 2 H), 1.72-1.87 (m, 1 H), 1.48-1.64 (m, 3 H) | 457 | 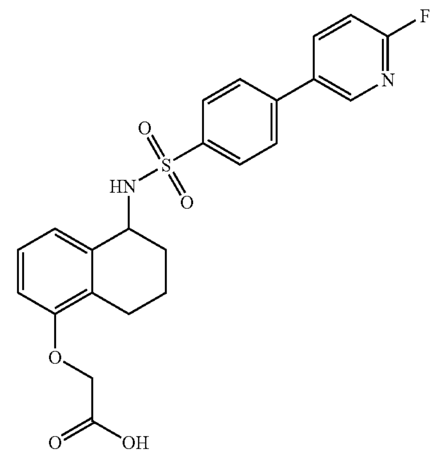 |
| 3-5(E) | [5-(4-Pyridin-4-yl-benzenesulfonyl-amino)-5,6,7,8-tetrahydro-naphthalen-1-yloxy]-acetic acid | 8.71 (d, J = 4.7 Hz, 2 H), 8.16-8.29 (m, 1 H), 8.06 (d, J = 8.3 Hz, 2 H), 8.00 (d, J = 8.3 Hz, 2 H), 7.82 (d, J = 4.7 Hz, 2 H), 7.00 (t, J = 8.0 Hz, 1 H), 6.68 (d, J = 8.0 Hz, 1 H), 6.62 (d, J = 8.0 Hz, 1 H), 4.28-4.51 (m, 3 H), 2.51-2.64 (m, 2 H), 1.78 (br. s, 1 H), 1.57 (br. s, 3 H) | 439 | 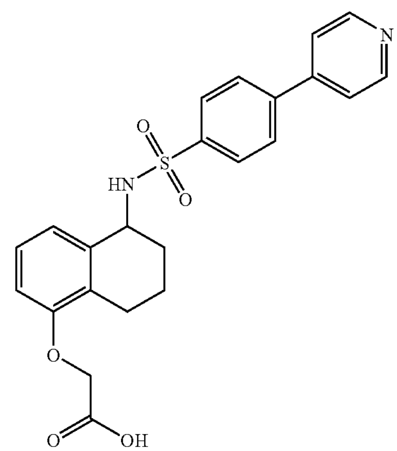 |
| 3-6(E) | {5-[4-(5-Fluoro-pyridin-3-yl)-benzenesulfonyl-amino]-5,6,7,8-tetrahydro-naphthalen-1-yloxy}-acetic acid | 13.13 (s, 1 H), 8.88 (s, 1 H), 8.63 (d, J = 2.4 Hz, 1 H), 8.19 (d, J = 8.8 Hz, 2 H), 8.03 (d, J = 8.3 Hz, 2 H), 7.96 (d, J = 8.3 Hz, 2 H), 7.02 (t, J = 8.0 Hz, 1 H), 6.72 (d, J = 8.0 Hz, 1 H), 6.64 (d, J = 8.0 Hz, 1 H), 4.62 (s, 2 H), 4.28-4.43 (m, 1 H), 2.51-2.64 (m, 2 H), 1.67-1.81 (m, 1 H), 1.54 (br. 2, 3 H) | 457 | 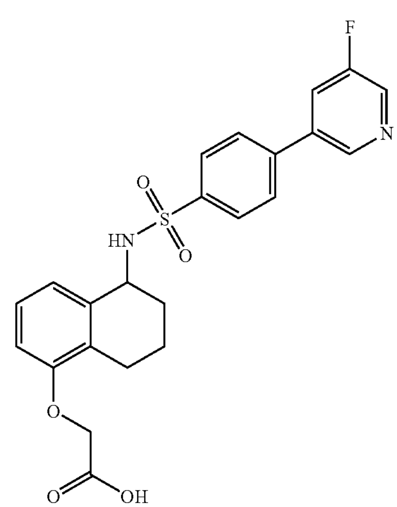 |

| Example No.* | Systematic Name | $^1$H NMR (400 MHz, DMSO-$d_6$) δ ppm | MS [(M + H)$^+$] | Structure |
|---|---|---|---|---|
| 3-7(E) | {5-[4-(6-Methyl-pyridin-3-yl)-benzenesulfonyl-amino]-5,6,7,8-tetrahydro-naphthalen-1-yloxy}-acetic acid | 8.86 (d, J = 2.2 Hz, 1 H), 8.17 (d, J = 8.3 Hz, 1 H), 8.09 (dd, J = 8.1, 2.2 Hz, 1 H), 7.96 (s, 4 H), 7.40 (d, J = 8.1 Hz, 1 H), 6.98 (t, J = 8.0 Hz, 1 H), 6.66 (d, J = 8.0 Hz, 1 H), 6.58 (d, J = 8.0 Hz, 1 H), 4.28-4.42 (m, 3 H), 2.54 (br. s, 3 H), 2.51-2.64 (m, 2 H), 1.78 (br. s, 1 H), 1.56 (br. s, 3 H) | 453 | 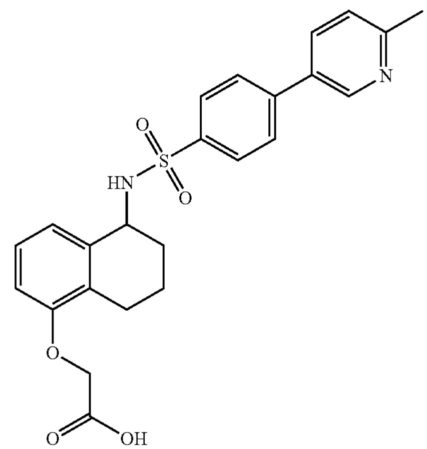 |
| 3-8(E) | {5-[4-(2-Methoxy-pyridin-4-yl)-benzenesulfonyl-amino]-5,6,7,8-tetrahydro-naphthalen-1-yloxy}-acetic acid | 12.93 (br. s, 1 H), 8.29 (d, J = 5.4 Hz, 1 H), 8.23 (d, J = 8.3 Hz, 1 H), 8.04 (d, J = 8.3 Hz, 2 H), 7.97 (d, J = 8.3 Hz, 2 H), 7.41 (dd, J = 5.4, 1.3 Hz, 1 H), 7.23 (s, 1 H), 7.04 (t, J = 8.1 Hz, 1 H), 6.73 (d, J = 8.1 Hz, 1 H), 6.67 (d, J = 8.1 Hz, 1 H), 4.66 (s, 2 H), 4.34-4.45 (m, 1 H), 3.92 (s, 3 H), 2.45-2.62 (m, 2 H), 1.72-1.84 (m, 1 H), 1.56 (br. s, 3 H) | 469 | 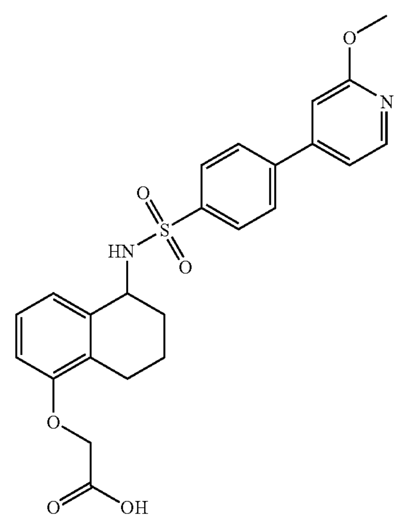 |
| 3-9(E) | {5-[4-(6-Methyl-pyridin-2-yl)-benzenesulfonyl-amino]-5,6,7,8-tetrahydro-naphthalen-1-yloxy}-acetic acid | 13.20 (br. s, 1 H), 8.31 (d, J = 8.6 Hz, 2 H), 8.17 (d, J = 8.6 Hz, 1 H), 7.97 (d, J = 8.6 Hz, 2 H), 7.89 (d, J = 7.6 Hz, 1 H), 7.84 (t, J = 7.6 Hz, 1 H), 7.31 (d, J = 7.6 Hz, 1 H), 7.02 (t, J = 7.9 Hz, 1 H), 6.73 (d, J = 7.9 Hz, 1 H), 6.65 (d, J = 7.9 Hz, 1 H), 4.61 (br. s, 2 H), 4.30-4.44 (m, 1 H), 2.57 (s, 3 H), 2.45-2.62 (m, 2 H), 1.78 (br. s, 1 H), 1.55 (br. s, 3 H) | 459 | 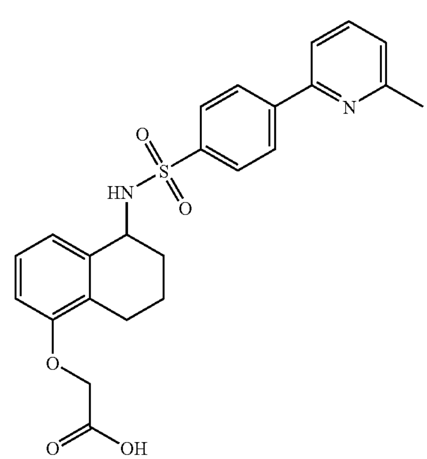 |

-continued

| Example No.* | Systematic Name | ¹H NMR (400 MHz, DMSO-d₆) δ ppm | MS [(M + H)⁺] | Structure |
|---|---|---|---|---|
| 3-10(E) | {5-[4-(3-Methyl-pyridin-2-yl)-benzenesulfonyl-amino]-5,6,7,8-tetrahydro-naphthalen-1-yloxy}-acetic acid | 8.53 (d, J = 4.4 Hz, 1 H), 8.19 (d, J = 7.6 Hz, 1 H), 7.96 (d, J = 8.2 Hz, 2 H), 7.78 (d, J = 8.2 Hz, 3 H), 7.37 (dd, J = 7.9, 4.4 Hz, 1 H), 7.00 (t, J = 7.9 Hz, 1 H), 6.59-6.68 (m, 2 H), 4.56 (br. s, 2 H), 4.38 (br. s, 1 H), 2.45-2.62 (m, 2 H), 2.35 (s, 3 H), 1.79 (br. s, 1 H), 1.58 (br. s, 3 H) | 453 | 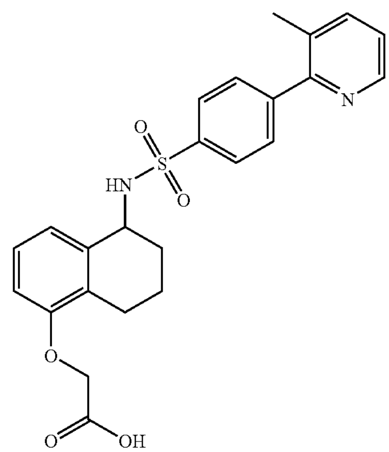 |
| 3-11(E) | {5-[4-(6-Methoxy-pyridin-2-yl)-benzenesulfonyl-amino]-5,6,7,8-tetrahydro-naphthalen-1-yloxy}-acetic acid | 12.98 (br. s, 1 H), 8.34 (d, J = 8.8 Hz, 2 H), 8.17 (d, J = 8.8 Hz, 1 H), 7.97 (d, J = 8.8 Hz, 2 H), 7.85 (dd, J = 8.3, 7.3 Hz, 1 H), 7.71 (d, J = 7.3 Hz, 1 H), 7.04 (t, J = 8.0 Hz, 1 H), 6.88 (d, J = 8.3 Hz, 1 H), 6.76 (d, J = 8.0 Hz, 1 H), 6.67 (d, J = 8.0 Hz, 1 H), 4.65 (s, 2 H), 4.34-4.43 (m, 1 H), 3.99 (s, 3 H), 2.43-2.48 (m, 2 H), 1.71-1.83 (m, 1 H), 1.56 (br. s, 3 H) | 469 | 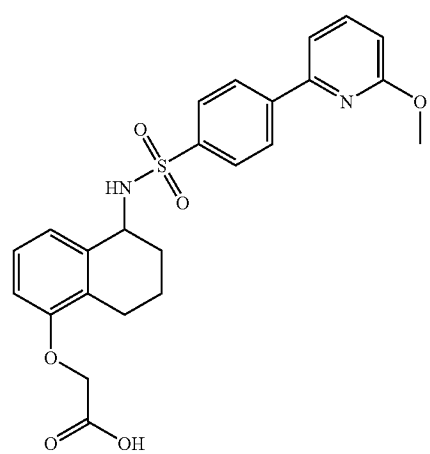 |
| 3-12(E) | {5-[4-(5-Methyl-pyridin-3-yl)-benzenesulfonyl-amino]-5,6,7,8-tetrahydro-naphthalen-1-yloxy}-acetic acid | 12.70 (br. s, 1 H), 8.79 (d, J = 2.0 Hz, 1 H), 8.49 (s, 1 H), 8.17 (d, J = 8.8 Hz, 1 H), 8.03 (s, 1 H), 7.98 (s, 4 H), 7.04 (t, J = 7.8 Hz, 1 H), 6.74 (d, J = 7.8 Hz, 1 H), 6.67 (d, J = 7.8 Hz, 1 H), 4.64 (s, 2 H), 4.30-4.47 (m, 1 H), 2.40 (s, 3 H), 2.33-2.45 (m, 2 H), 1.79 (br. s, 1 H), 1.47-1.69 (m, 3 H) | 453 | 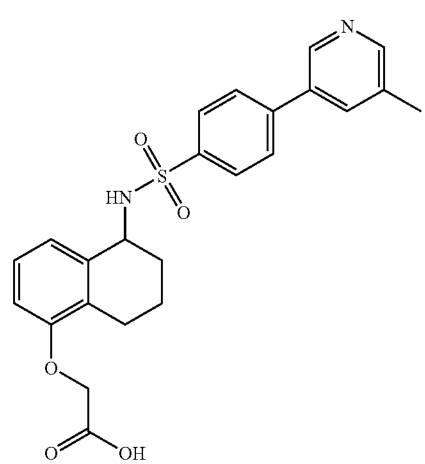 |

| Example No.* | Systematic Name | ¹H NMR (400 MHz, DMSO-d₆) δ ppm | MS [(M + H)⁺] | Structure |
|---|---|---|---|---|
| 3-13(E) | {5-[4-(2-Fluoro-pyridin-4-yl)-benzenesulfonyl-amino]-5,6,7,8-tetrahydro-naphthalen-1-yloxy}-acetic acid | 13.06 (br. s, 1 H), 8.38 (d, J = 5.4 Hz, 1 H), 8.24 (d, J = 8.3 Hz, 1 H), 8.11 (d, J = 8.5 Hz, 2 H), 8.01 (d, J = 8.5 Hz, 2 H), 7.81 (dt, J = 5.4, 1.7 Hz, 1 H), 7.67 (s, 1 H), 7.04 (t, J = 8.1 Hz, 1 H), 6.74 (d, J = 8.1 Hz, 1 H), 6.68 (d, J = 8.1 Hz, 1 H), 4.65 (s, 2 H), 4.29-4.48 (m, 1 H), 2.44 (br. s, 2 H), 1.71-1.85 (m, 1 H), 1.47-1.64 (m, 3 H) | 455ᶜ | 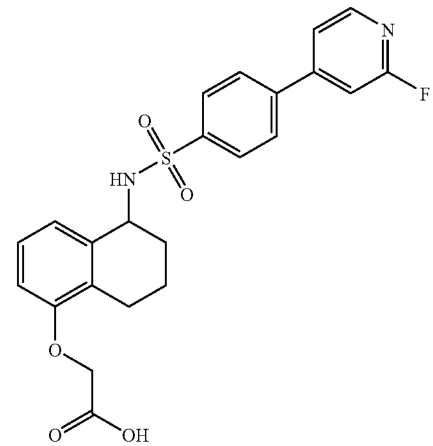 |
| 3-14(E) | {5-[4-(6-Trifluoromethyl-pyridin-3-yl)-benzenesulfonyl-amino]-5,6,7,8-tetrahydro-naphthalen-1-yloxy}-acetic acid | 9.20 (d, J = 2.2 Hz, 1 H), 8.49 (dd, J = 8.4, 2.2 Hz, 1 H), 8.25 (d, J = 8.3 Hz, 1 H), 8.09 (d, J = 8.6 Hz, 2 H), 8.06 (d, J = 8.4 Hz, 1 H), 8.02 (d, J = 8.6 Hz, 1 H), 7.02 (t, J = 7.8 Hz, 1 H), 6.70 (d, J = 7.8 Hz, 1 H), 6.63 (d, J = 7.8 Hz, 1 H), 4.50 (br. s, 2 H), 4.36-4.45 (m, 1 H), 2.54-2.60 (m, 2 H), 1.78 (br. s, 1 H), 1.57 (br. s, 3 H) | 507 | 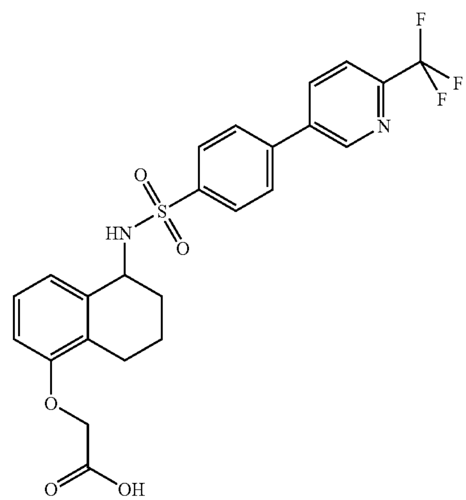 |
| 3-15(E) | {5-[4-(2-Chloro-5-methyl-pyridin-3-yl)-benzenesulfonyl-amino]-5,6,7,8-tetrahydro-naphthalen-1-yloxy}-acetic acid | 12.98 (br. s, 1 H), 8.33 (br. s, 1 H), 8.21 (dd, J = 8.56, 3.18 Hz, 1 H), 7.97 (d, J = 7.83 Hz, 1 H), 7.78-7.88 (m, 2 H), 7.72 (d, J = 8.31 Hz, 1 H), 6.95-7.14 (m, 1 H), 6.55-6.78 (m, 2 H), 4.65 (s, 2 H), 4.25-4.48 (m, 1 H), 2.36 (s, 2 H), 1.70-1.88 (m, 1 H), 1.43-1.67 (m, 3 H) + small amount of impurities | 487 | 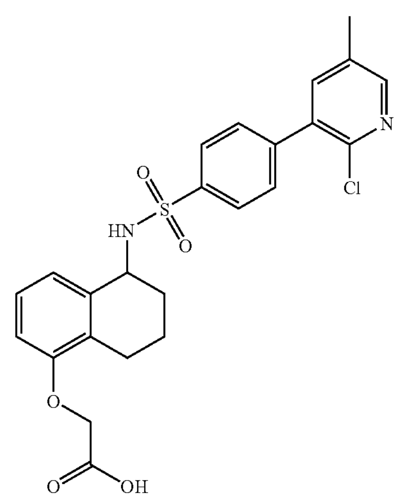 |

| Example No.* | Systematic Name | $^1$H NMR (400 MHz, DMSO-d$_6$) δ ppm | MS [(M + H)$^+$] | Structure |
| --- | --- | --- | --- | --- |
| 3-16(E) | {5-[4-(5-Methanesulfonyl-pyridin-3-yl)-benzenesulfonyl-amino]-5,6,7,8-tetrahydro-naphthalen-1-yloxy}-acetic acid | 9.34 (d, J = 1.8 Hz, 1 H), 9.11 (d, J = 1.8 Hz, 1 H), 8.67 (br. s, 1 H), 8.24 (d, J = 8.6 Hz, 1 H), 8.08-8.18 (m, J = 8.4 Hz, 2 H), 8.03 (d, J = 8.4 Hz, 2 H), 7.02 (t, J = 7.8 Hz, 1 H), 6.72 (d, J = 7.8 Hz, 1 H), 6.63 (d, J = 7.8 Hz, 1 H), 4.34-4.45 (m, 1 H), 4.05 (br. s, 2 H), 3.43 (s, 3 H), 2.54-2.60 (m, 2 H), 1.77 (br. s, 1 H), 1.57 (br. s, 3 H) | 517 | 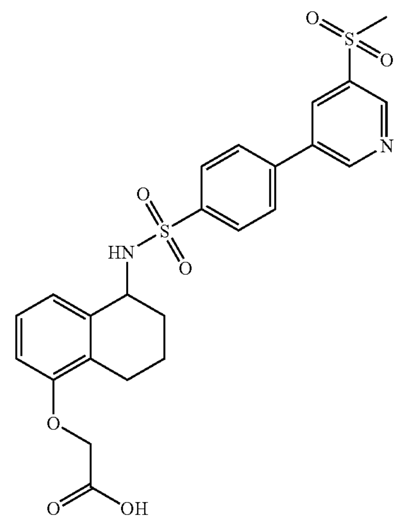 |
| 3-17(E) | {5-[4-(6-Fluoro-5-methyl-pyridin-3-yl)-benzenesulfonyl-amino]-5,6,7,8-tetrahydro-naphthalen-1-yloxy}-acetic acid | 8.47 (br. s, 1 H), 8.30 (d, J = 9.5 Hz, 1 H), 8.20 (d, J = 8.6 Hz, 1 H), 7.90-8.10 (m, 4 H), 7.04 (t, J = 8.0 Hz, 1 H), 6.74 (d, J = 8.0 Hz, 1 H), 6.67 (d, J = 8.0 Hz, 1 H), 4.65 (s, 2 H), 4.33-4.44 (m, 1 H), 2.54-2.61 (m, 2 H), 2.34 (s, 3 H), 1.72-1.85 (m, 1 H), 1.56 (br. s, 3 H) | 469$^c$ | 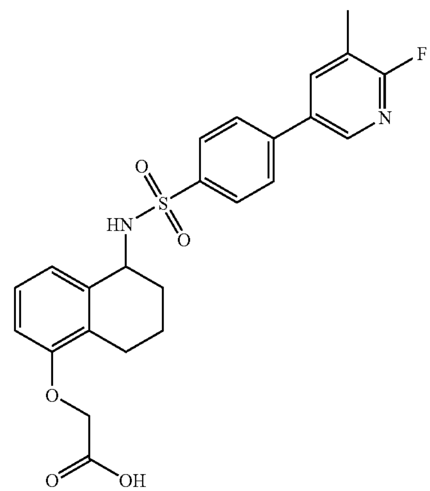 |
| 3-18(E) | {5-[4-(2-Methyl-pyridin-4-yl)-benzenesulfonyl-amino]-5,6,7,8-tetrahydro-naphthalen-1-yloxy}-acetic acid | 12.97 (br. s, 1 H), 8.74 (d, J = 5.9 Hz, 1 H), 8.27 (d, J = 8.3 Hz, 1 H), 8.10-8.18 (d, J = 8.3 Hz, 2 H), 8.00-8.08 (m, 3 H), 7.87-8.00 (m, 1 H), 7.04 (t, J = 7.8 Hz, 1 H), 6.74 (d, J = 7.8 Hz, 1 H), 6.68 (d, J = 7.8 Hz, 1 H), 4.66 (s, 2 H), 4.34-4.51 (m, 1 H), 2.67 (s, 3 H), 2.41-2.47 (m, 2 H), 1.79 (br. s, 1 H), 1.56 (br. s, 3 H) | 453 | 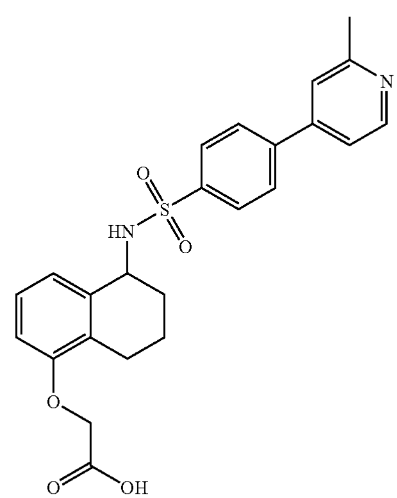 |

-continued

| Example No.* | Systematic Name | ¹H NMR (400 MHz, DMSO-d$_6$) δ ppm | MS [(M + H)$^+$] | Structure |
| --- | --- | --- | --- | --- |
| 3-19(E) | {5-[4-(2-Methyl-pyridin-3-yl)-benzenesulfonyl-amino]-5,6,7,8-tetrahydro-naphthalen-1-yloxy}-acetic acid | 13.08 (br. s, 1 H), 8.52 (dd, J = 4.9, 1.7 Hz, 1 H), 8.18 (d, J = 8.8 Hz, 1 H), 7.96 (d, J = 8.3 Hz, 2 H), 7.69 (dd, J = 7.6, 1.7 Hz, 1 H), 7.65 (d, J = 8.3 Hz, 2 H), 7.35 (dd, J = 7.6, 4.9 Hz, 1 H), 7.00 (t, J = 7.8 Hz, 1 H), 6.66 (d, J = 7.8 Hz, 1 H), 6.60 (d, J = 7.8 Hz, 1 H), 4.61 (s, 2 H), 4.34-4.45 (m, 1 H), 2.52-2.61 (m, 2 H), 2.45 (s, 3 H), 1.81 (br. s, 1 H), 1.60 (br. 2, 3 H) | 453 | 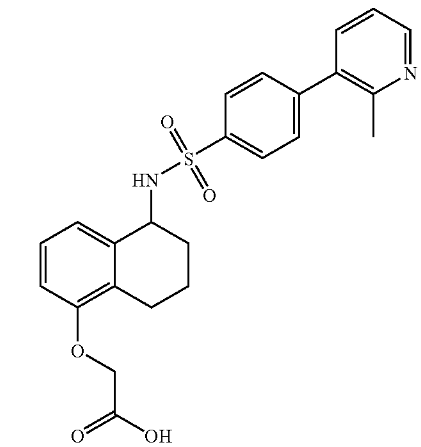 |
| 3-20(E) | [5-(2'-Chloro-biphenyl-4-sulfonylamino)-5,6,7,8-tetrahydro-naphthalen-1-yloxy]-acetic acid | 12.96 (br. s, 1 H), 8.19 (d, J = 8.5 Hz, 1 H), 7.96 (d, J = 8.5 Hz, 2 H), 7.68 (d, J = 8.5 Hz, 2 H), 7.61-7.65 (m, 1 H), 7.42-7.53 (m, 3 H), 7.00 (t, J = 8.1 Hz, 1 H), 6.67 (d, J = 8.1 Hz, 1 H), 6.62 (d, J = 8.1 Hz, 1 H), 4.65 (s, 2 H), 4.34-4.47 (m, 1 H), 2.42-2.64 (m, 2 H), 1.70-1.93 (m, 1 H), 1.49-1.69 (m, 3 H) | 472 | 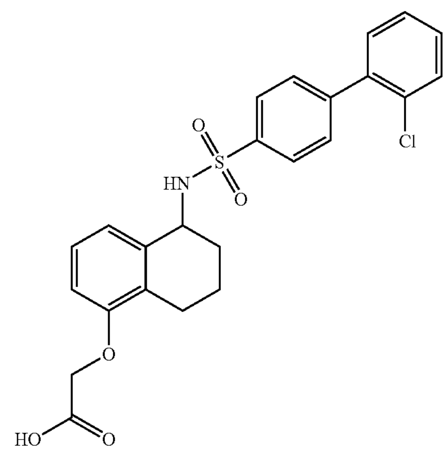 |
| 3-21(F) | [5-(3'-Chloro-biphenyl-4-sulfonylamino)-5,6,7,8-tetrahydro-naphthalen-1-yloxy]-acetic acid | N/A | 472 | 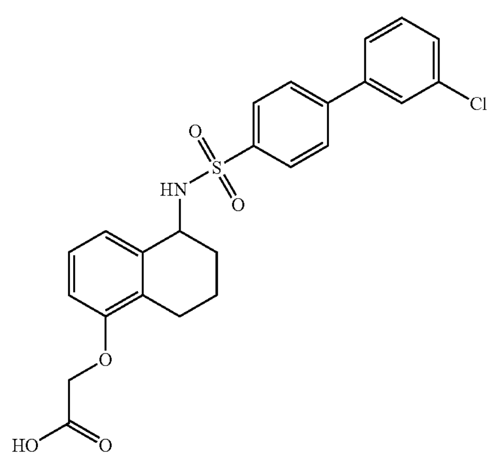 |

-continued

| Example No.* | Systematic Name | ¹H NMR (400 MHz, DMSO-d$_6$) δ ppm | MS [(M + H)$^+$] | Structure |
|---|---|---|---|---|
| 3-22(F) | [5-(4'-Chloro-biphenyl-4-sulfonylamino)-5,6,7,8-tetrahydro-naphthalen-1-yloxy]-acetic acid | N/A | 472 | 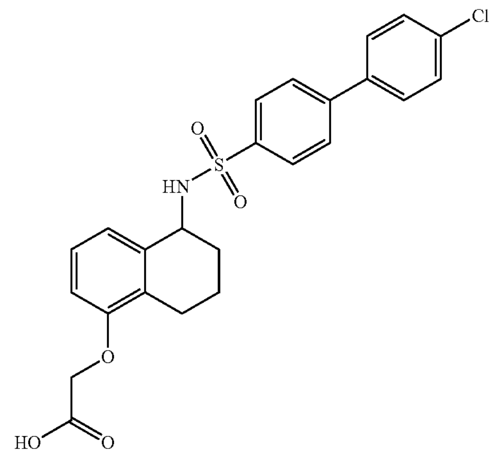 |
| 3-23(F) | [(R)-5-(4'-Hydroxy-biphenyl-4-sulfonylamino)-5,6,7,8-tetrahydro-naphthalen-1-yloxy]-acetic acid | N/A | 454 | 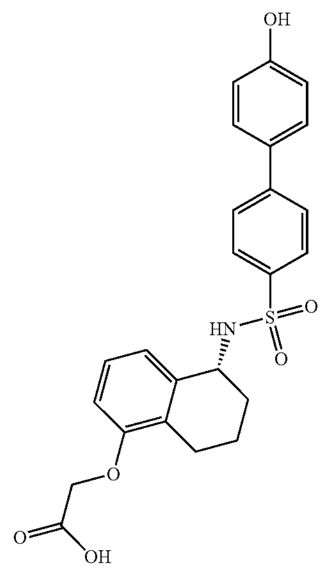 |
| 3-24(F) | [(R)-5-(3'-Acetyl-biphenyl-4-sulfonylamino)-5,6,7,8-tetrahydro-naphthalen-1-yloxy]-acetic acid | 8.30 (t, J = 1.7 Hz, 1 H), 8.18 (d, J = 8.7 Hz, 1 H), 7.95-8.09 (m, 6 H), 7.69 (t, J = 7.8 Hz, 1 H), 6.99-7.07 (m, 1 H), 6.73 (d, J = 7.9 Hz, 1 H), 6.65 (d, J = 8.1 Hz, 1 H), 4.56 (s, 2 H), 4.34-4.44 (m, 1 H), 2.54 (s, 3 H), 2.50-2.63 (m, 2 H), 1.78 (m, 1 H), 1.58 (m, 3 H) | 480 | 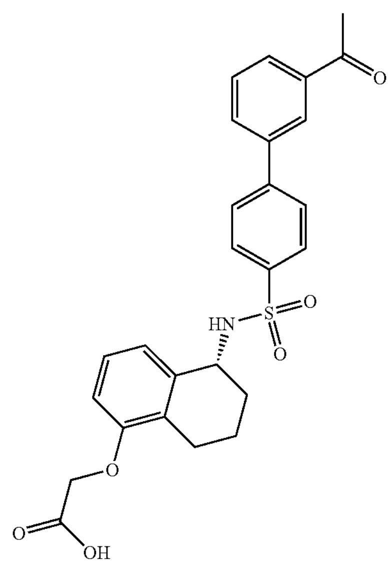 |

| Example No.* | Systematic Name | $^1$H NMR (400 MHz, DMSO-d$_6$) δ ppm | MS [(M + H)$^+$] | Structure |
|---|---|---|---|---|
| 3-25(F) | [(R)-5-(2',3'-Dichloro-biphenyl-4-sulfonylamino)-5,6,7,8-tetrahydro-naphthalen-1-yloxy]-acetic acid | 12.97 (br. s, 1 H), 8.21 (d, J = 8.3 Hz, 1 H), 7.97 (d, J = 8.6 Hz, 2 H), 7.74 (dd, J = 7.7, 1.9 Hz, 1 H), 7.68 (d, J = 8.6 Hz, 2 H), 7.50 (t, J = 7.7 Hz, 1 H), 7.46 (dd, J = 7.7, 1.9 Hz, 1 H), 7.00 (t, J = 7.8 Hz, 1 H), 6.66 (d, J = 7.8 Hz, 1 H), 6.59 (d, J = 7.8 Hz, 1 H), 4.60 (s, 2 H), 4.35-4.45 (m, 1 H), 2.45-2.64 (m, 2 H), 1.74-1.86 (m, 1 H), 1.61 (br. s, 3 H) | 507 | 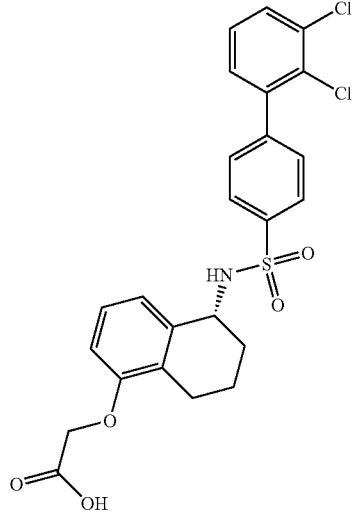 |
| 3-26(F) | [(R)-5-(2',5'-Dimethoxy-biphenyl-4-sulfonylamino)-5,6,7,8-tetrahydro-naphthalen-1-yloxy]-acetic acid | 8.12 (d, J = 8.5 Hz, 1 H), 7.89 (d, J = 8.3 Hz, 2 H), 7.72 (d, J = 8.3 Hz, 2 H), 7.10 (d, J = 8.7 Hz, 1 H), 7.02 (t, J = 8.1 Hz, 1 H), 6.92-6.99 (m, 2 H), 6.69 (d, J = 8.1 Hz, 1 H), 6.66 (d, J = 8.1 Hz, 1 H), 4.60 (s, 2 H), 4.33-4.43 (m, 1 H), 3.77 (s, 3 H), 3.73 (s, 3 H), 2.52-2.59 (m, 2 H), 1.80 (br. s, 1 H), 1.60 (br. s, 3 H) | 498 | 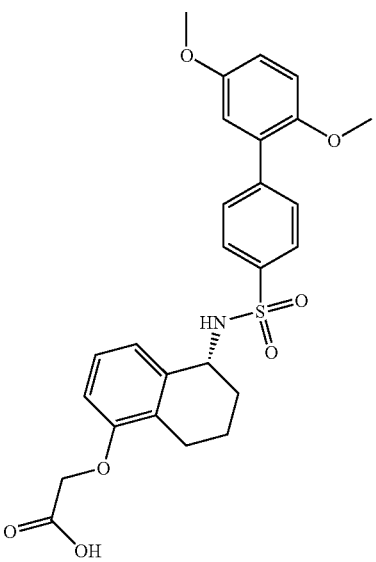 |

-continued

| Example No.* | Systematic Name | $^1$H NMR (400 MHz, DMSO-d$_6$) δ ppm | MS [(M + H)$^+$] | Structure |
|---|---|---|---|---|
| 3-27(F) | [(R)-5-(2',6'-Dimethoxy-biphenyl-4-sulfonylamino)-5,6,7,8-tetrahydro-naphthalen-1-yloxy]-acetic acid | N/A | 498 | 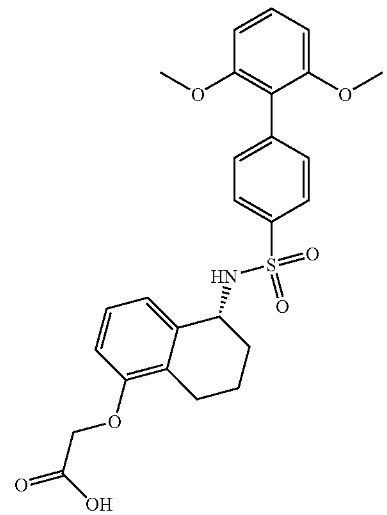 |
| 3-28(F) | [(R)-5-(2',5'-Dichloro-biphenyl-4-sulfonylamino)-5,6,7,8-tetrahydro-naphthalen-1-yloxy]-acetic acid | 12.97 (br. s, 1 H), 8.21 (d, J = 8.7 Hz, 1 H), 7.97 (d, J = 8.7 Hz, 2 H), 7.70 (d, J = 8.7 Hz, 2 H), 7.67 (d, J = 8.6 Hz, 1 H), 7.61 (d, J = 2.7 Hz, 1 H), 7.56 (dd, J = 8.6, 2.7 Hz, 1 H), 7.01 (t, J = 8.1 Hz, 1 H), 6.67 (d, J = 8.1 Hz, 1 H), 6.63 (d, J = 8.1 Hz, 1 H), 4.64 (s, 2 H), 4.32-4.45 (m, 1 H), 2.43-2.64 (m, 2 H), 1.73-1.87 (m, 1 H), 1.60 (br. s, 3 H) | 507 | 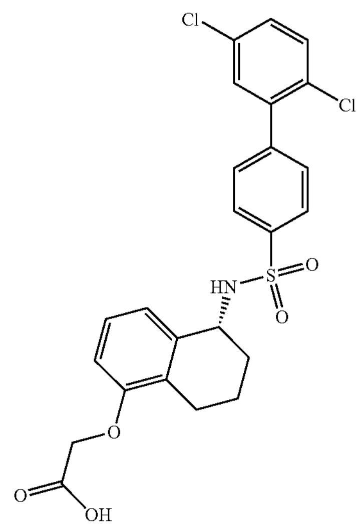 |
| 3-29(F) | [(R)-5-(2',5'-Dimethyl-biphenyl-4-sulfonylamino)-5,6,7,8-tetrahydro-naphthalen-1-yloxy]-acetic acid | 12.97 (br. s, 1 H), 8.14 (d, J = 8.3 Hz, 1 H), 7.92 (d, J = 8.5 Hz, 2 H), 7.57 (d, J = 8.5 Hz, 2 H), 7.23 (d, J = 7.8 Hz, 1 H), 7.14 (dd, J = 7.8, 1.6 Hz, 1 H), 7.09 (d, J = 1.6 Hz, 1 H), 7.00 (t, J = 8.0 Hz, 1 H), 6.67 (d, J = 8.0 Hz, 1 H), 6.61 (d, J = 8.0 Hz, 1 H), 4.61-4.67 (m, 2 H), 4.32-4.43 (m, 1 H), 2.53-2.70 (m, 2 H), 2.32 (s, 3 H), 2.20 (s, 3 H), 1.72-1.89 (m, 1 H), 1.53-1.66 (m, 3 H) | 466 | 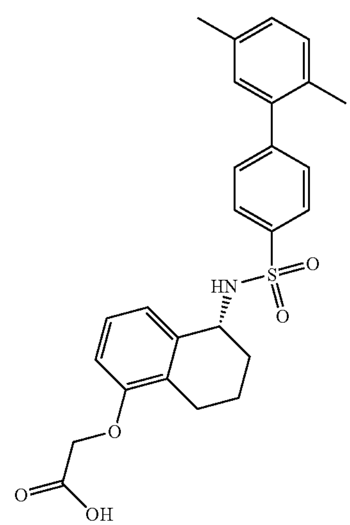 |

-continued

| Example No.* | Systematic Name | $^1$H NMR (400 MHz, DMSO-d$_6$) δ ppm | MS [(M + H)$^+$] | Structure |
|---|---|---|---|---|
| 3-30(F) | [(R)-5-(4'-Dimethylcarbamoyl-biphenyl-4-sulfonylamino)-5,6,7,8-tetrahydro-naphthalen-1-yloxy]-acetic acid | 12.95 (br. s, 1 H), 8.17 (d, J = 8.5 Hz, 1 H), 7.97 (s, 4 H), 7.85 (d, J = 8.3 Hz, 2 H), 7.55 (d, J = 8.3 Hz, 2 H), 7.03 (t, J = 8.1 Hz, 1 H), 6.73 (d, J = 8.1 Hz, 1 H), 6.67 (d, J = 8.1 Hz, 1 H), 4.64 (s, 2 H), 4.32-4.45 (m, 1 H), 3.01 (br. s, 3 H), 2.96 (br. s, 3 H), 2.42-2.62 (m, 2 H), 1.71-1.86 (m, 1 H), 1.46-1.66 (m, 3 H) | 509 | 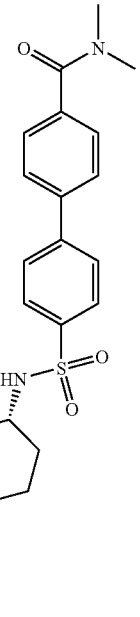 |
| 3-31(F) | [(R)-5-(2',3'-Dimethoxy-biphenyl-4-sulfonylamino)-5,6,7,8-tetrahydro-naphthalen-1-yloxy]-acetic acid | 8.13 (d, J = 8.3 Hz, 1 H), 7.92 (d, J = 8.6 Hz, 2 H), 7.71 (d, J = 8.6 Hz, 2 H), 7.16-7.23 (m, 1 H), 7.14 (dd, J = 8.5, 1.9 Hz, 1 H), 6.96-7.03 (m, 2 H), 6.61-6.69 (m, 2 H), 4.62 (s, 2 H), 4.33-4.44 (m, 1 H), 3.87 (s, 3 H), 3.55 (s, 3 H), 2.50-2.63 (m, 2 H), 1.71-1.89 (m, 1 H), 1.50-1.69 (m, 3 H) | 498 | 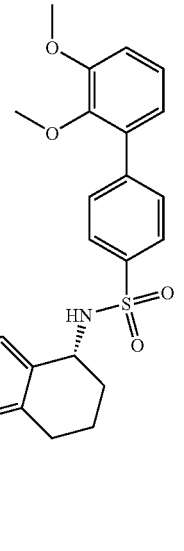 |

| Example No.* | Systematic Name | ¹H NMR (400 MHz, DMSO-d₆) δ ppm | MS [(M + H)⁺] | Structure |
|---|---|---|---|---|
| 3-32(F) | [(R)-5-(5'-Chloro-2'-methyl-biphenyl-4-sulfonylamino)-5,6,7,8-tetrahydro-naphthalen-1-yloxy]-acetic acid | 8.18 (d, J = 8.5 Hz, 1 H), 7.94 (d, J = 8.5 Hz, 2 H), 7.61 (d, J = 8.5 Hz, 2 H), 7.40 (d, J = 1.9 Hz, 1 H), 7.39 (s, 1 H), 7.34 (d, J = 1.9 Hz, 1 H), 7.00 (t, J = 8.0 Hz, 1 H), 6.66 (d, J = 8.0 Hz, 1 H), 6.60 (d, J = 8.0 Hz, 1 H), 4.60 (br. s, 2 H), 4.39 (br. s, 1 H), 2.37-2.59 (m, 2 H), 2.22 (s, 3 H), 1.73-1.87 (m, 1 H), 1.59 (br. s, 3 H) | 486 | 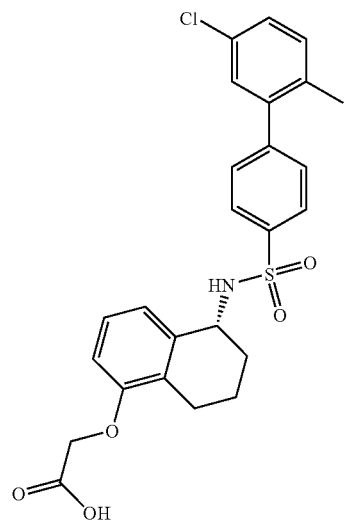 |
| 3-33(F) | [(R)-5-(3'-Dimethylcarbamoyl-biphenyl-4-sulfonylamino)-5,6,7,8-tetrahydro-naphthalen-1-yloxy]-acetic acid | 13.01 (br. s, 1 H), 8.17 (d, J = 8.5 Hz, 1 H), 7.96 (s, 4 H), 7.86 (dt, J = 7.6, 1.6 Hz, 1 H), 7.78 (t, J = 1.6 Hz, 1 H), 7.59 (t, J = 7.6 Hz, 1 H), 7.46 (dt, J = 7.6, 1.6 Hz, 1 H), 7.03 (t, J = 8.1 Hz, 1 H), 6.73 (d, J = 8.1 Hz, 1 H), 6.66 (d, J = 8.1 Hz, 1 H), 4.61 (s, 2 H), 4.29-4.51 (m, 1 H), 3.02 (br. s, 3 H), 2.96 (br. s, 3 H), 2.42-2.62 (m, 2 H), 1.71-1.87 (m, 1 H), 1.57 (br. s, 3 H) | 509 | 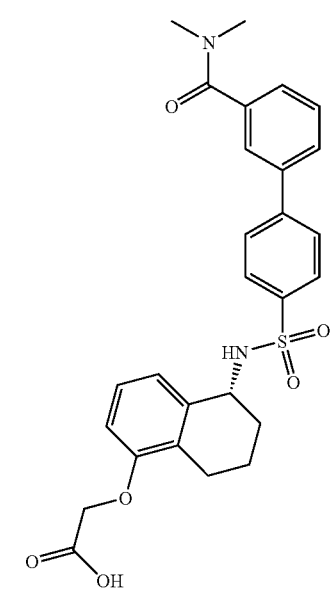 |

| Example No.* | Systematic Name | $^1$H NMR (400 MHz, DMSO-d$_6$) δ ppm | MS [(M + H)$^+$] | Structure |
|---|---|---|---|---|
| 3-34(F) | [(R)-5-(2,4'-Dimethyl-biphenyl-4-sulfonylamino)-5,6,7,8-tetrahydro-naphthalen-1-yloxy]-acetic acid | N/A | 466 | 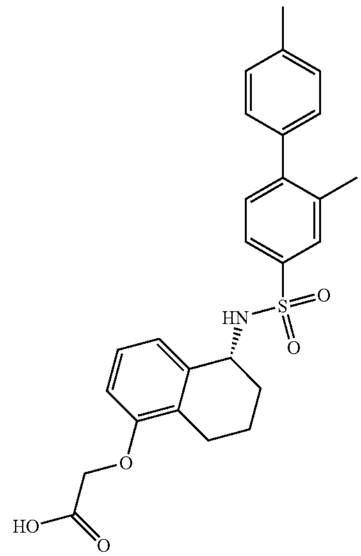 |
| 3-35(F) | [(R)-5-(2,3'-Dimethyl-biphenyl-4-sulfonylamino)-5,6,7,8-tetrahydro-naphthalen-1-yloxy]-acetic acid | 8.09 (d, J = 8.7 Hz, 1 H), 7.78-7.82 (m, 1 H), 7.71-7.78 (m, 1 H), 7.42 (d, J = 7.9 Hz, 1 H), 7.38 (t, J = 7.5 Hz, 1 H), 7.16-7.27 (m, 3 H), 7.05 (t, J = 7.9 Hz, 1 H), 6.72 (d, J = 7.9 Hz, 1 H), 6.67 (d, J = 7.9 Hz, 1 H), 4.63 (s, 2 H), 4.32-4.42 (m, 1 H), 2.41-2.61 (m, 2 H), 2.38 (s, 3 H), 2.32 (s, 3 H), 1.70-1.95 (m, 1 H), 1.49-1.70 (m, 3 H) | 466 | 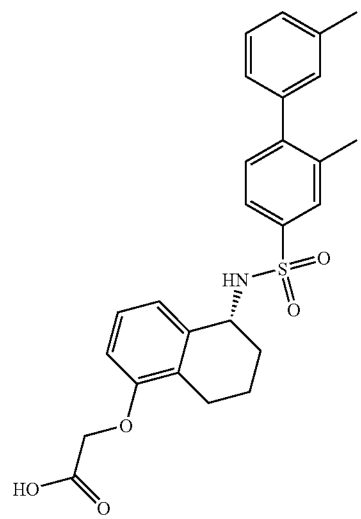 |
| 3-36(F) | [(R)-5-(2,2'-Dimethyl-biphenyl-4-sulfonylamino)-5,6,7,8-tetrahydro-naphthalen-1-yloxy]-acetic acid | N/A | 466 | 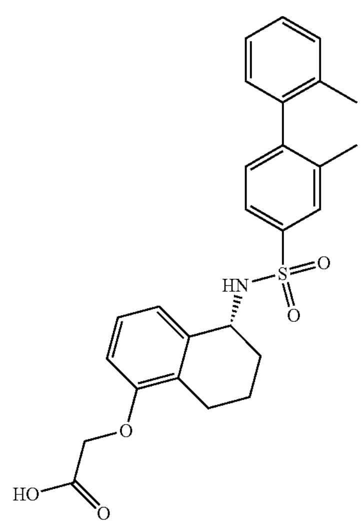 |

| Example No.* | Systematic Name | ¹H NMR (400 MHz, DMSO-d$_6$) δ ppm | MS [(M + H)$^+$] | Structure |
|---|---|---|---|---|
| 3-37(F) | [(R)-5-(4'-Chloro-2-methyl-biphenyl-4-sulfonylamino)-5,6,7,8-tetrahydro-naphthalen-1-yloxy]-acetic acid | 8.12 (d, J = 8.5 Hz, 1 H), 7.81 (d, J = 1.3 Hz, 1 H), 7.73-7.78 (m, 1 H), 7.55 (d, J = 8.3 Hz, 2 H), 7.43-7.47 (d, J = 8.3 Hz, 2 H), 7.02 (t, J = 8.4 Hz, 1 H), 6.67 (d, J = 8.4 Hz, 1 H), 6.63 (d, J = 8.4 Hz, 1 H), 4.47 (br. s, 2 H), 4.33-4.43 (m, 1 H), 2.51-2.62 (m, 2 H), 2.32 (s, 3 H), 1.67-1.88 (m, 1 H), 1.47-1.65 (m, 3 H) | 486 | 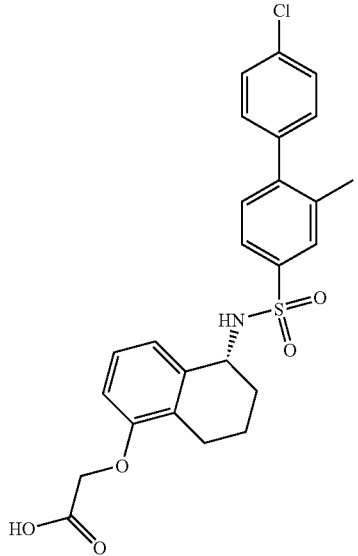 |
| 3-38(F) | [(R)-5-(4'-Ethoxy-2-methyl-biphenyl-4-sulfonylamino)-5,6,7,8-tetrahydro-naphthalen-1-yloxy]-acetic acid | 13.02 (br. s, 1 H), 8.07 (d, J = 8.7 Hz, 1 H), 7.78 (d, J = 1.3 Hz, 1 H), 7.70-7.74 (m, 1 H), 7.41 (d, J = 8.1 Hz, 1 H), 7.34 (d, J = 8.9 Hz, 2 H), 7.02 (d, J = 8.9 Hz, 2 H), 6.98-7.07 (m, 1 H), 6.67-6.73 (m, 1 H), 6.62-6.67 (m, 1 H), 4.54 (s, 2 H), 4.26-4.45 (m, 1 H), 4.09 (q, J = 6.9 Hz, 2 H), 2.42-2.62 (m, 2 H), 2.33 (s, 3 H), 1.74-1.88 (m, 1 H), 1.51-1.67 (m, 3 H), 1.36 (t, J = 6.9 Hz, 3 H) | 496 | 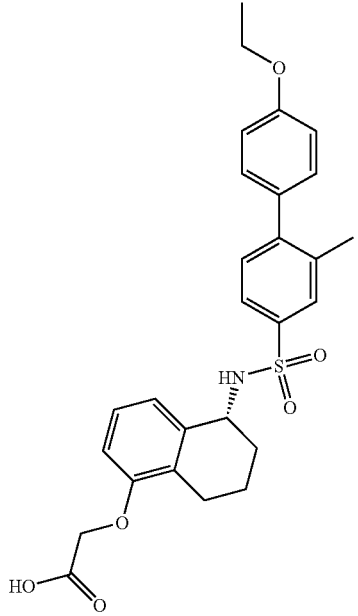 |

| Example No.* | Systematic Name | ¹H NMR (400 MHz, DMSO-d$_6$) δ ppm | MS [(M + H)⁺] | Structure |
|---|---|---|---|---|
| 3-39(F) | [(R)-5-(4'-Methoxy-2,3',5'-trimethyl-biphenyl-4-sulfonylamino)-5,6,7,8-tetrahydro-naphthalen-1-yloxy]-acetic acid | N/A | 510 | 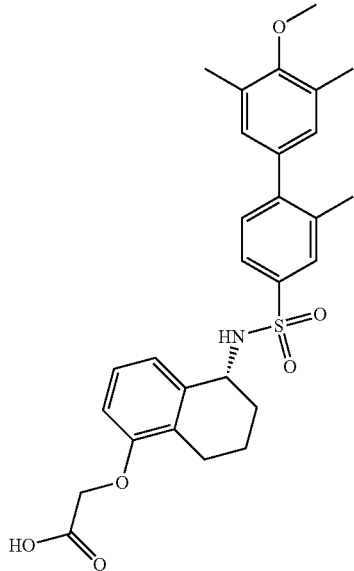 |
| 3-40(F) | [(R)-5-(3',4'-Dichloro-2-methyl-biphenyl-4-sulfonylamino)-5,6,7,8-tetrahydro-naphthalen-1-yloxy]-acetic acid | N/A | 521 | 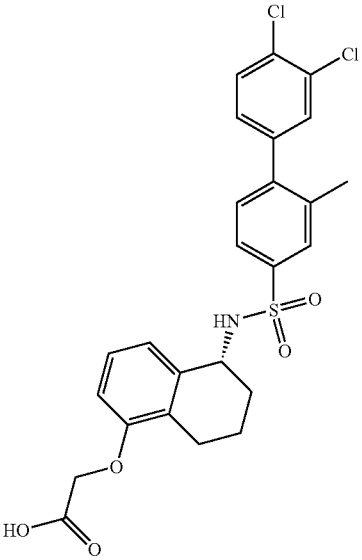 |
| 3-41(F) | [(R)-5-(3'-Nitro-biphenyl-4-sulfonylamino)-5,6,7,8-tetrahydro-naphthalen-1-yloxy]-acetic acid | 13.09 (br. s, 1 H), 8.56 (t, J = 1.9 Hz, 1 H), 8.30 (ddd, J = 8.0, 2.3, 1.0 Hz, 1 H), 8.27 (ddd, J = 8.0, 1.6, 1.0 Hz, 1 H), 8.22 (d, J = 8.5 Hz, 1 H), 8.07 (d, J = 8.6 Hz, 2 H), 8.00 (d, J = 8.6 Hz, 2 H), 7.83 (t, J = 8.0 Hz, 1 H), 7.04 (t, J = 7.9 Hz, 1 H), 6.75 (d, J = 7.9 Hz, 1 H), 6.67 (d, J = 7.9 Hz, 1 H), 4.63 (s, 2 H), 4.30-4.44 (m, 1 H), 2.42-2.62 (m, 2 H), 1.73-1.87 (m, 1 H), 1.58 (br. s, 3 H) | 483 | 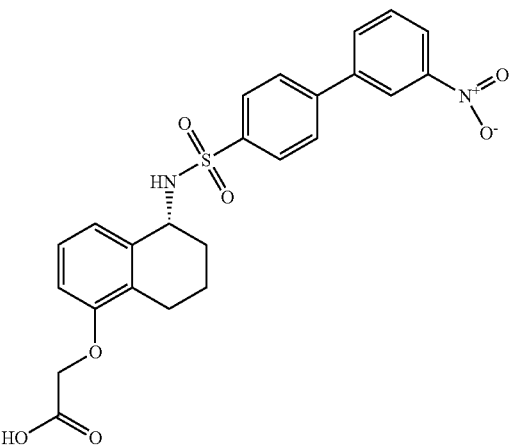 |

-continued

| Example No.* | Systematic Name | $^1$H NMR (400 MHz, DMSO-$d_6$) δ ppm | MS [(M + H)$^+$] | Structure |
|---|---|---|---|---|
| 3-42(F) | [(R)-5-(2',4'-Dichloro-biphenyl-4-sulfonylamino)-5,6,7,8-tetrahydro-naphthalen-1-yloxy]-acetic acid | N/A | 507 | 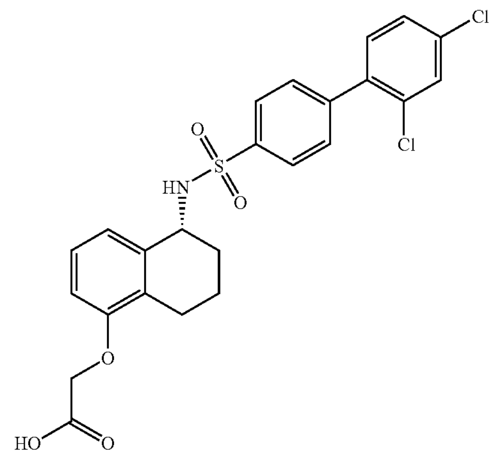 |
| 3-43(F) | [(R)-5-(4'-Methyl-3'-nitro-biphenyl-4-sulfonylamino)-5,6,7,8-tetrahydro-naphthalen-1-yloxy]-acetic acid | 13.00 (br. s, 1 H), 8.36 (d, J = 1.9 Hz, 2 H), 8.20 (d, J = 8.5 Hz, 2 H), 8.07 (dd, J = 8.0, 1.8 Hz, 2 H), 8.00-8.05 (m, J = 8.7 Hz, 2 H), 7.98 (d, J = 8.5 Hz, 2 H), 7.66 (d, J = 8.1 Hz, 1 H), 7.04 (t, J = 8.1 Hz, 1 H), 6.74 (d, J = 7.7 Hz, 1 H), 6.67 (d, J = 7.9 Hz, 1 H), 4.63 (s, 2 H), 4.29-4.47 (m, 1 H), 2.57 (s, 3 H), 2.48-2.59 (m, 2 H), 1.70-1.91 (m, 1 H), 1.45-1.67 (m, 3 H) | 497 | 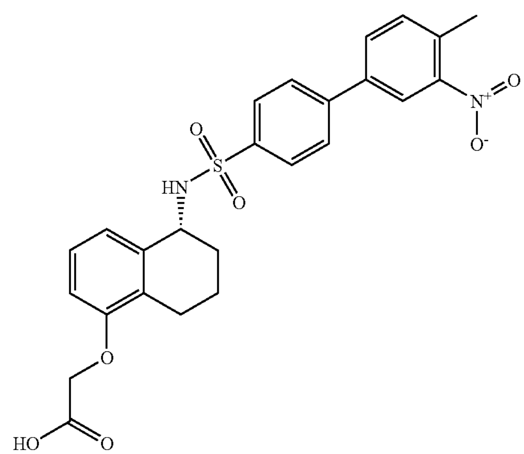 |
| 3-44(F) | [(R)-5-(3'-Methylsulfanyl-biphenyl-4-sulfonylamino)-5,6,7,8-tetrahydro-naphthalen-1-yloxy]-acetic acid | 13.00 (br. s, 1 H), 8.16 (d, J = 8.5 Hz, 1 H), 7.95 (s, 4 H), 7.61 (t, J = 1.7 Hz, 1 H), 7.50-7.56 (m, 1 H), 7.46 (t, J = 7.7 Hz, 1 H), 7.31-7.37 (m, 1 H), 7.03 (t, J = 8.1 Hz, 1 H), 6.73 (d, J = 8.1 Hz, 1 H), 6.66 (d, J = 8.1 Hz, 1 H), 4.59 (br. s, 2 H), 4.31-4.44 (m, 1 H), 2.57 (s, 3 H), 2.53-2.58 (m, 2 H), 1.68-1.87 (m, 1 H), 1.57 (br. s, 3 H) | 484 | 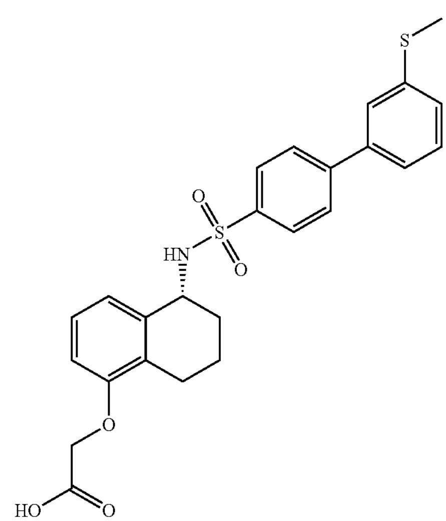 |

| Example No.* | Systematic Name | ¹H NMR (400 MHz, DMSO-d₆) δ ppm | MS [(M + H)⁺] | Structure |
|---|---|---|---|---|
| 3-45(F) | [(R)-5-(3'-tert-Butyl-5'-methyl-biphenyl-4-sulfonylamino)-5,6,7,8-tetrahydro-naphthalen-1-yloxy]-acetic acid | 13.12 (br. s, 1 H), 8.14 (d, J = 8.7 Hz, 1 H), 7.92-7.96 (d, J = 8.7 Hz, 2 H), 7.90 (d, J = 8.7 Hz, 2 H), 7.52 (s, 1 H), 7.39 (s, 1 H), 7.29 (s, 1 H), 7.03 (t, J = 8.0 Hz, 1 H), 6.74 (d, J = 8.0 Hz, 1 H), 6.66 (d, J = 8.0 Hz, 1 H), 4.61 (s, 2 H), 4.31-4.48 (m, 1 H), 2.45-2.64 (m, 2 H), 2.40 (s, 3 H), 1.67-1.88 (m, 1 H), 1.47-1.65 (m, 3 H), 1.34 (s, 9 H) | 508 | 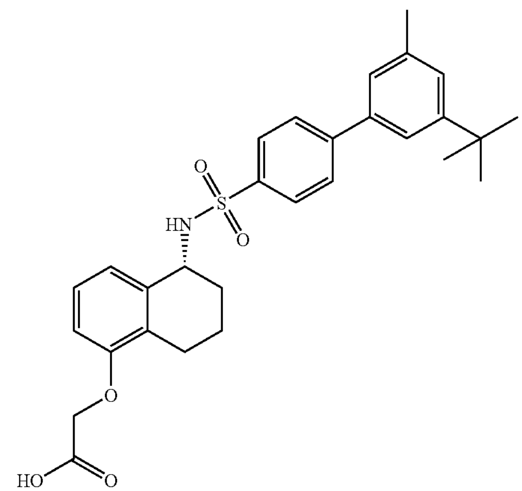 |
| 3-46(F) | [(R)-5-(3'-Trifluoromethyl-biphenyl-4-sulfonylamino)-5,6,7,8-tetrahydro-naphthalen-1-yloxy]-acetic acid | 12.93 (br. s, 1 H), 8.20 (d, J = 8.5 Hz, 1 H), 8.07-8.16 (m, 2 H), 8.03 (d, J = 8.7 Hz, 2 H), 7.98 (d, J = 8.7 Hz, 2 H), 7.82 (d, J = 8.0 Hz, 1 H), 7.77 (t, J = 8.0 Hz, 1 H), 7.04 (t, J = 8.0 Hz, 1 H), 6.75 (d, J = 8.0 Hz, 1 H), 6.67 (d, J = 8.0 Hz, 1 H), 4.62 (s, 2 H), 4.34-4.45 (m, 1 H), 2.51-2.58 (m, 2 H), 1.72-1.83 (m, 1 H), 1.49-1.66 (m, 3 H) | 506 | 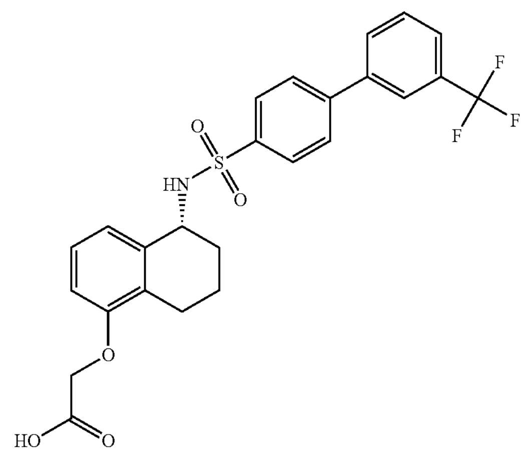 |
| 3-47(F) | [(R)-5-(3'-Isopropyl-biphenyl-4-sulfonylamino)-5,6,7,8-tetrahydro-naphthalen-1-yloxy]-acetic acid | 13.05 (br. s, 1 H), 8.14 (d, J = 8.5 Hz, 1 H), 7.85-7.99 (m, 4 H), 7.63 (t, J = 1.5 Hz, 1 H), 7.58 (dt, J = 7.7, 1.5 Hz, 1 H), 7.44 (t, J = 7.7 Hz, 1 H), 7.33 (d, J = 7.7 Hz, 1 H), 7.03 (t, J = 8.0 Hz, 1 H), 6.74 (d, J = 8.0 Hz, 1 H), 6.66 (d, J = 8.0 Hz, 1 H), 4.61 (s, 2 H), 4.33-4.43 (m, J = 7.5 Hz, 1 H), 3.00 (quin, J = 6.8 Hz, 1 H), 2.42-2.62 (m, 2 H), 1.70-1.88 (m, 1 H), 1.47-1.67 (m, 3 H), 1.28 (d, J = 6.8 Hz, 6 H) | 480 | 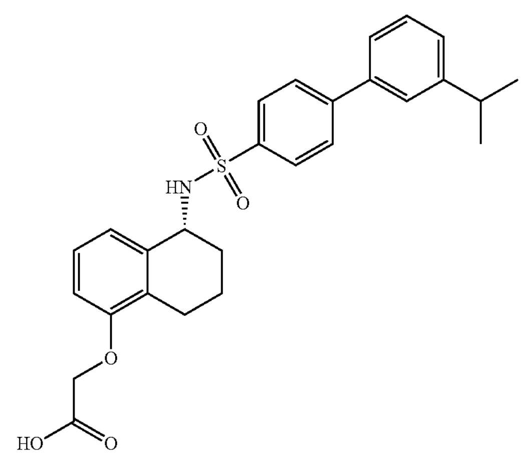 |

| Example No.* | Systematic Name | $^1$H NMR (400 MHz, DMSO-$d_6$) δ ppm | MS [(M + H)$^+$] | Structure |
|---|---|---|---|---|
| 3-48(F) | {(R)-5-[5-(3-tert-Butyl-5-methyl-phenyl)-pyridine-2-sulfonylamino]-5,6,7,8-tetrahydro-naphthalen-1-yloxy}-acetic acid | N/A | 509 | 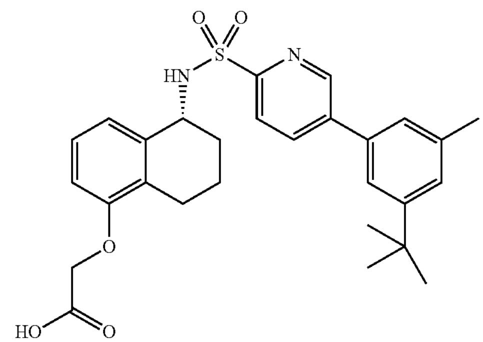 |
| 3-49(F) | [(R)-5-(5'-Fluoro-3'-methoxy-biphenyl-4-sulfonylamino)-5,6,7,8-tetrahydro-naphthalen-1-yloxy]-acetic acid | 12.97 (br. s, 1 H), 8.18 (d, J = 8.5 Hz, 1 H), 7.85-8.02 (m, 4 H), 7.23 (dt, J = 10.0, 1.9 Hz, 1 H), 7.19 (t, J = 1.9 Hz, 1 H), 7.04 (t, J = 8.1 Hz, 1 H), 6.92 (dt, J = 10.9, 1.9 Hz, 1 H), 6.75 (d, J = 8.1 Hz, 1 H), 6.67 (d, J = 8.1 Hz, 1 H), 4.65 (s, 2 H), 4.33-4.44 (m, 1 H), 3.87 (s, 3 H), 2.37-2.71 (m, 2 H), 1.66-1.90 (m, 1 H), 1.56 (d, J = 5.5 Hz, 3 H) | 486 | 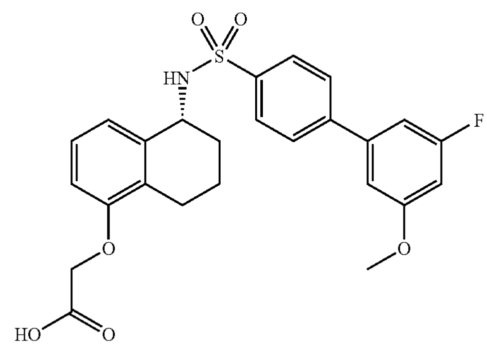 |
| 3-50(F) | {(R)-5-[5-(3-Isopropyl-phenyl)-pyridine-2-sulfonylamino]-5,6,7,8-tetrahydro-naphthalen-1-yloxy}-acetic acid | 13.02 (br. s, 1 H), 9.10 (d, J = 2.0 Hz, 1 H), 8.38 (dd, J = 8.2, 2.0 Hz, 1 H), 8.33 (d, J = 8.5 Hz, 1 H), 8.05 (d, J = 8.2 Hz, 1 H), 7.71 (s, 1 H), 7.66 (d, J = 7.7 Hz, 1 H), 7.48 (t, J = 7.7 Hz, 1 H), 7.39 (d, J = 7.7 Hz, 1 H), 7.06 (t, J = 7.9 Hz, 1 H), 6.89 (d, J = 7.9 Hz, 1 H), 6.67 (d, J = 7.9 Hz, 1 H), 4.64 (s, 2 H), 4.51-4.60 (m, 1 H), 2.95-3.07 (m, 1 H), 2.53-2.60 (m, 2 H), 1.50-1.94 (m, 4 H), 1.28 (d, J = 6.8 Hz, 6 H) | 481 | 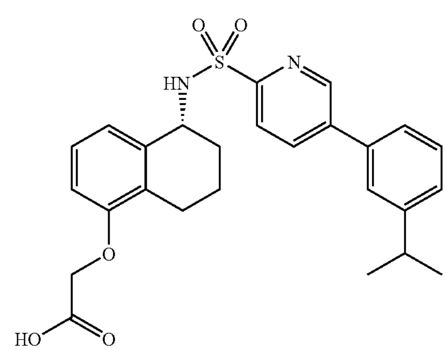 |
| 3-51(F) | [(R)-5-(3'-Isopropoxy-biphenyl-4-sulfonylamino)-5,6,7,8-tetrahydro-naphthalen-1-yloxy]-acetic acid | 12.98 (s, 1 H), 8.15 (d, J = 8.7 Hz, 1 H), 7.92 (s, 4 H), 7.41 (t, J = 8.0 Hz, 1 H), 7.28-7.33 (m, 1 H), 7.27 (t, J = 2.0 Hz, 1 H), 7.03 (dd, J = 8.1, 7.6 Hz, 1 H), 7.00 (dd, J = 8.0, 2.0 Hz, 1 H), 6.74 (d, J = 8.1 Hz, 1 H), 6.67 (d, J = 7.6 Hz, 1 H), 4.76 (quin, J = 6.1 Hz, 1 H), 4.64 (s, 2 H), 4.30-4.44 (m, 1 H), 2.39-2.64 (m, 2 H), 1.70-1.87 (m, 1 H), 1.50-1.65 (m, 3 H), 1.31 (d, J = 6.1 Hz, 6 H) | 496 | 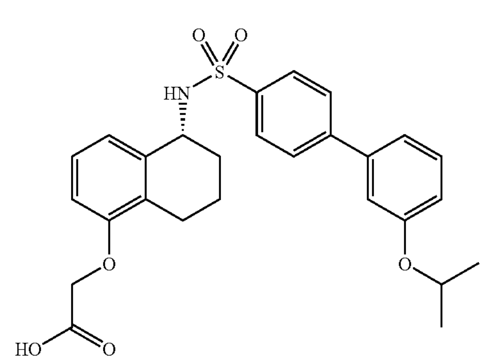 |

| Example No.* | Systematic Name | $^1$H NMR (400 MHz, DMSO-$d_6$) δ ppm | MS [(M + H)$^+$] | Structure |
|---|---|---|---|---|
| 3-52(F) | {(R)-5-[4-(5-Methyl-pyridin-3-yl)-benzenesulfonyl-amino]-5,6,7,8-tetrahydro-naphthalen-1-yloxy}-acetic acid | 12.98 (br. s, 1 H), 8.80 (d, J = 2.1 Hz, 1 H), 8.49 (d, J = 1.5 Hz, 1 H), 8.19 (d, J = 8.5 Hz, 1 H), 8.03 (br. s, 1 H), 7.98 (s, 4 H), 7.04 (t, J = 7.9 Hz, 1 H), 6.75 (d, J = 7.7 Hz, 1 H), 6.68 (d, J = 8.1 Hz, 1 H), 4.65 (s, 2 H), 4.35-4.44 (m, 1 H), 2.39-2.49 (m, 2 H), 2.40 (s, 3 H), 1.69-1.86 (m, 1 H), 1.44-1.68 (m, 3 H) | 453 | 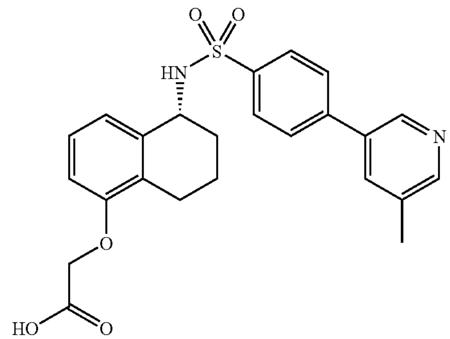 |
| 3-53(F) | [(R)-5-(3'-Methyl-biphenyl-4-sulfonylamino)-5,6,7,8-tetrahydro-naphthalen-1-yloxy]-acetic acid | 12.98 (br. s, 1 H), 8.14 (d, J = 8.5 Hz, 1 H), 7.82-7.99 (m, 4 H), 7.60 (s, 1 H), 7.56 (d, J = 7.7 Hz, 1 H), 7.41 (t, J = 7.7 Hz, 1 H), 7.26 (d, J = 7.7 Hz, 1 H), 7.04 (t, J = 7.9 Hz, 1 H), 6.74 (d, J = 7.9 Hz, 1 H), 6.67 (d, J = 7.9 Hz, 1 H), 4.65 (s, 2 H), 4.32-4.43 (m, 1 H), 2.46-2.60 (m, 2 H), 2.41 (s, 3 H), 1.70-1.88 (m, 1 H), 1.49-1.65 (m, 3 H) | 452 | 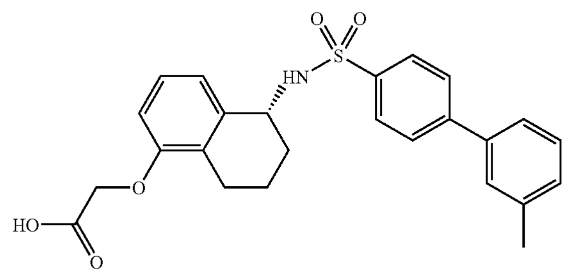 |
| 3-54(F) | [(R)-5-(3'-Chloro-biphenyl-4-sulfonylamino)-5,6,7,8-tetrahydro-naphthalen-1-yloxy]-acetic acid | 12.99 (br. s, 1 H), 8.18 (d, J = 8.5 Hz, 1 H), 7.90-8.02 (m, 4 H), 7.86 (t, J = 1.7 Hz, 1 H), 7.76 (dt, J = 7.9, 1.7 Hz, 1 H), 7.56 (t, J = 7.9 Hz, 1 H), 7.52 (dt, J = 7.9, 1.7 1 H), 7.04 (t, J = 7.9 Hz, 1 H), 6.74 (d, J = 7.9 Hz, 1 H), 6.67 (d, J = 7.9 Hz, 1 H), 4.65 (s, 2 H), 4.30-4.45 (m, 1 H), 2.38-2.62 (m, 2 H), 1.69-1.88 (m, 1 H), 1.45-1.66 (m, 3 H) | 472 | 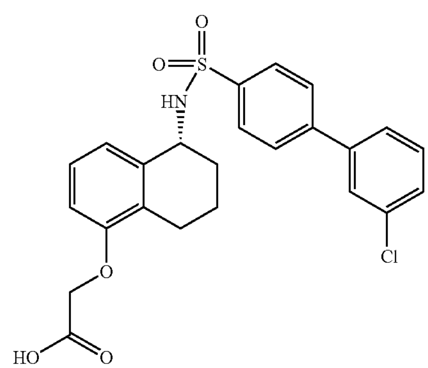 |
| 3-55(F) | [(R)-5-(3'-Methyl-biphenyl-3-sulfonylamino)-5,6,7,8-tetrahydro-naphthalen-1-yloxy]-acetic acid | 12.98 (br. s, 1 H), 8.10-8.17 (m, 2 H), 7.95 (dd, J = 6.3, 1.4 Hz, 1 H), 7.86 (dd, J = 6.6, 1.7 Hz, 1 H), 7.70 (t, J = 7.9 Hz, 1 H), 7.55 (s, 1 H), 7.51 (d, J = 7.7 Hz, 1 H), 7.41 (t, J = 7.7 Hz, 1 H), 7.26 (d, J = 7.7 Hz, 1 H), 7.01 (t, J = 8.0 Hz, 1 H), 6.68 (d, J = 7.7 Hz, 1 H), 6.67 (d, J = 8.3 Hz, 1 H), 4.65 (s, 2 H), 4.34-4.45 (m, 1 H), 2.41-2.72 (m, 2 H), 2.40 (s, 3 H), 1.66-1.88 (m, 1 H), 1.40-1.66 (m, 3 H) | 452 | 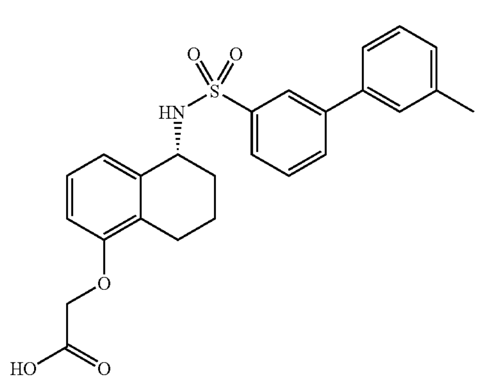 |

| Example No.* | Systematic Name | $^1$H NMR (400 MHz, DMSO-d$_6$) δ ppm | MS [(M + H)$^+$] | Structure |
|---|---|---|---|---|
| 3-56(F) | [(R)-5-(3'-Isopropyl-biphenyl-3-sulfonylamino)-5,6,7,8-tetrahydro-naphthalen-1-yloxy]-acetic acid | 12.99 (br. s, 1 H), 8.15 (d, J = 8.3 Hz, 1 H), 8.12 (t, J = 1.6 Hz, 1 H), 7.96 (dt, J = 7.9, 1.6 Hz, 1 H), 7.87 (dt, J = 7.9, 1.6 Hz, 1 H), 7.71 (t, J = 7.9 Hz, 1 H), 7.55-7.58 (m, 1 H), 7.50-7.55 (m, 1 H), 7.44 (t, J = 7.6 Hz, 1 H), 7.33 (d, J = 7.6 Hz, 1 H), 7.01 (t, J = 7.9 Hz, 1 H), 6.69 (d, J = 7.9 Hz, 1 H), 6.67 (d, J = 7.9 Hz, 1 H), 4.64 (s, 2 H), 4.31-4.47 (m, 1 H), 2.99 (quin, J = 6.9 Hz, 1 H), 2.42-2.64 (m, 2 H), 1.68-1.86 (m, 1 H), 1.46-1.65 (m, 3 H), 1.27 (d, J = 6.9 Hz, 6 H) | 480 | 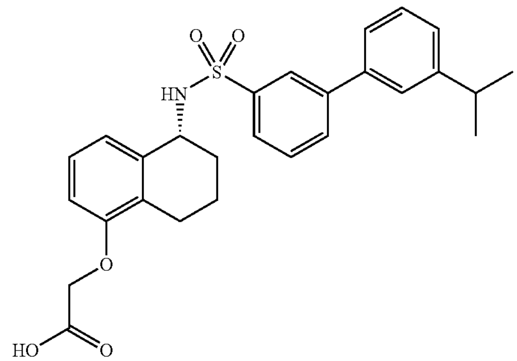 |
| 3-57(F) | [(R)-5-(2',3'-Dimethyl-biphenyl-3-sulfonylamino)-5,6,7,8-tetrahydro-naphthalen-1-yloxy]-acetic acid | 12.99 (br. s, 1 H), 8.15 (d, J = 8.3 Hz, 1 H), 8.12 (t, J = 1.6 Hz, 1 H), 7.96 (dt, J = 7.9, 1.6 Hz, 1 H), 7.87 (dt, J = 7.9, 1.6 Hz, 1 H), 7.71 (t, J = 7.9 Hz, 1 H), 7.55-7.58 (m, 1 H), 7.50-7.55 (m, 1 H), 7.44 (t, J = 7.6 Hz, 1 H), 7.33 (d, J = 7.6 Hz, 1 H), 7.01 (t, J = 7.9 Hz, 1 H), 6.69 (d, J = 7.9 Hz, 1 H), 6.67 (d, J = 7.9 Hz, 1 H), 4.64 (s, 2 H), 4.31-4.47 (m, 1 H), 2.99 (quin, J = 6.9 Hz, 1 H), 2.42-2.64 (m, 2 H), 1.68-1.86 (m, 1 H), 1.46-1.65 (m, 3 H), 1.27 (d, J = 6.9 Hz, 6 H) | 466 | 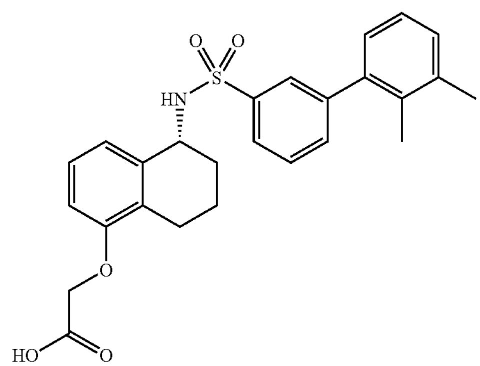 |
| 3-58(F) | [(R)-5-(4'-Methoxy-3',5'-dimethyl-biphenyl-3-sulfonylamino)-5,6,7,8-tetrahydro-naphthalen-1-yloxy]-acetic acid | 13.03 (br. s, 1 H), 8.11 (d, J = 8.3 Hz, 1 H), 8.08 (t, J = 1.6 Hz, 1 H), 7.91 (dt, J = 7.7, 1.6 Hz, 1 H), 7.79-7.87 (m, 1 H), 7.67 (t, J = 7.7 Hz, 1 H), 7.40 (s, 2 H), 7.01 (t, J = 8.0 Hz, 1 H), 6.68 (d, J = 7.7 Hz, 1 H), 6.67 (d, J = 8.3 Hz, 1 H), 4.65 (s, 2 H), 4.28-4.48 (m, 1 H), 3.70 (s, 3 H), 2.41-2.63 (m, 2 H), 2.31 (s, 6 H), 1.65-1.89 (m, 1 H), 1.40-1.69 (m, 3 H) | 496 | 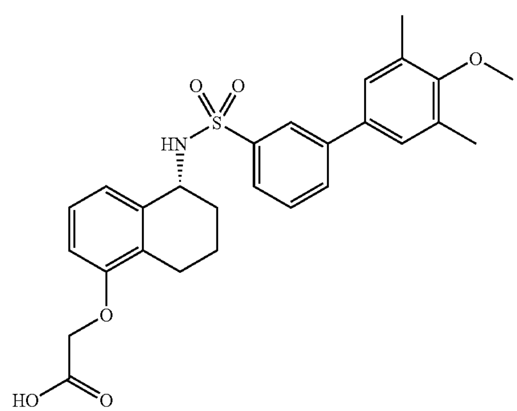 |

| Example No.* | Systematic Name | $^1$H NMR (400 MHz, DMSO-$d_6$) δ ppm | MS [(M + H)$^+$] | Structure |
|---|---|---|---|---|
| 3-59(F) | {5-[5-(3-Trifluoromethyl-phenyl)-pyridine-2-sulfonylamino]-5,6,7,8-tetrahydro-naphthalen-1-yloxy}-acetic acid | 12.97 (br. s, 1 H), 9.19 (dd, J = 2.4, 1.0 Hz, 1 H), 8.49 (dd, J = 8.3, 2.4 Hz, 1 H), 8.37 (d, J = 8.3 Hz, 1 H), 8.22 (s, 1 H), 8.18 (d, J = 7.8 Hz, 1 H), 8.08 (dd, J = 8.3, 1.0 Hz, 1 H), 7.87 (d, J = 7.8 Hz, 1 H), 7.80 (t, J = 7.8 Hz, 1 H), 7.07 (t, J = 7.8 Hz, 1 H), 6.91 (d, J = 7.8 Hz, 1 H), 6.68 (d, J = 7.8 Hz, 1 H), 4.65 (s, 2 H), 4.50-4.62 (m, 1 H), 2.52-2.60 (m, 2 H), 1.79-1.97 (m, 1 H), 1.44-1.79 (m, 3 H) | 507 | 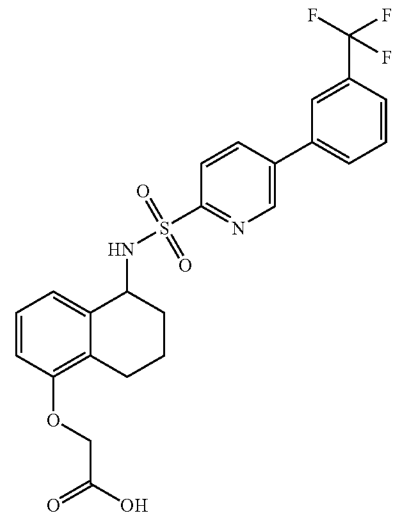 |
| 3-60(E) | (5-{5-[3-(2-Hydroxy-ethyl)-phenyl]-pyridine-2-sulfonylamino}-5,6,7,8-tetrahydro-naphthalen-1-yloxy)-acetic acid | 12.98 (br. s, 1 H), 9.09 (d, J = 2.4 Hz, 1 H), 8.36 (dd, J = 8.2, 2.4 Hz, 1 H), 8.33 (d, J = 8.6 Hz, 1 H), 8.05 (d, J = 8.2 Hz, 1 H), 7.70 (s, 1 H), 7.67 (d, J = 7.7 Hz, 1 H), 7.46 (t, J = 7.7 Hz, 1 H), 7.35 (d, J = 7.7 Hz, 1 H), 7.06 (t, J = 8.1 Hz, 1 H), 6.88 (d, J = 8.1 Hz, 1 H), 6.67 (d, J = 8.1 Hz, 1 H), 4.67-4.74 (m, 1 H), 4.66 (s, 2 H), 4.48-4.59 (m, 1 H), 3.60-3.75 (m, 2 H), 2.83 (t, J = 7.0 Hz, 2 H), 2.53-2.56 (m, 2 H), 1.84 (br. s, 1 H), 1.61 (br. s, 3 H) | 483 | 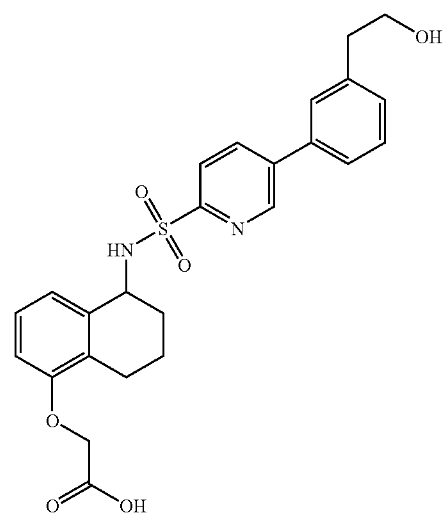 |
| 3-61(E) | {5-[5-(3-Ethoxy-phenyl)-pyridine-2-sulfonylamino]-5,6,7,8-tetrahydro-naphthalen-1-yloxy}-acetic acid | 12.95 (br. s, 1 H), 9.10 (d, J = 2.4 Hz, 1 H), 8.38 (dd, J = 8.3, 2.4 Hz, 1 H), 8.32 (d, J = 8.8 Hz, 1 H), 8.04 (d, J = 8.3 Hz, 1 H), 7.42-7.50 (m, 1 H), 7.34-7.43 (m, 2 H), 7.01-7.11 (m, 2 H), 6.89 (d, J = 7.8 Hz, 1 H), 6.67 (d, J = 7.8 Hz, 1 H), 4.66 (s, 2 H), 4.49-4.59 (m, 1 H), 4.14 (q, J = 6.8 Hz, 2 H), 2.52-2.59 (m, 2 H), 1.80-1.96 (m, 1 H), 1.55-1.78 (m, 3 H), 1.37 (t, J = 6.8 Hz, 3 H) | 483 | 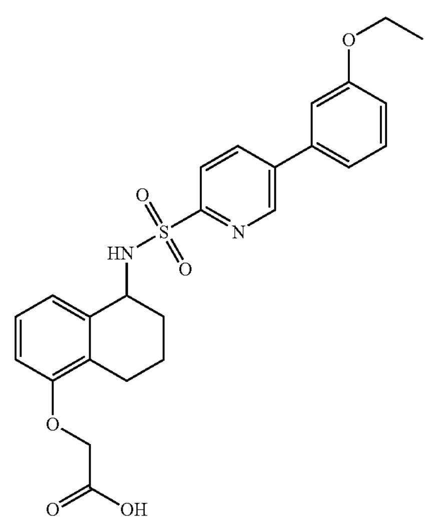 |

| Example No.* | Systematic Name | $^1$H NMR (400 MHz, DMSO-$d_6$) δ ppm | MS [(M + H)$^+$] | Structure |
|---|---|---|---|---|
| 3-62(E) | {5-[5-(4-Trifluoromethoxy-phenyl)-pyridine-2-sulfonylamino]-5,6,7,8-tetrahydro-naphthalen-1-yloxy}-acetic acid | 12.96 (br. s, 1 H), 9.12 (d, J = 2.3 Hz, 1 H), 8.41 (dd, J = 8.3, 2.3 Hz, 1 H), 8.36 (d, J = 8.6 Hz, 1 H), 8.07 (d, J = 8.3 Hz, 1 H), 8.00 (d, J = 8.4 Hz, 2 H), 7.56 (d, J = 8.4 Hz, 2 H), 7.05 (t, J = 8.1 Hz, 1 H), 6.88 (d, J = 8.1 Hz, 1 H), 6.67 (d, J = 8.1 Hz, 1 H), 4.66 (s, 2 H), 4.49-4.60 (m, 1 H), 2.55 (br. s, 2 H), 1.84 (br. s, 1 H), 1.54-1.77 (m, 3 H) | 523 | 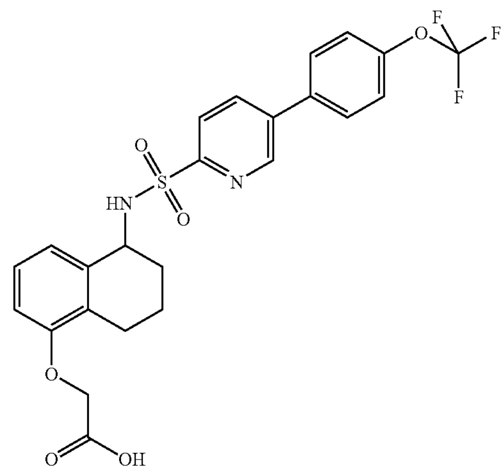 |
| 3-63(E) | {5-[6-(2-Trifluoromethyl-phenyl)-pyridine-3-sulfonylamino]-5,6,7,8-tetrahydro-naphthalen-1-yloxy}-acetic acid | 12.98 (br. s, 1 H), 9.08 (d, J = 2.3 Hz, 1 H), 8.44 (d, J = 8.8 Hz, 1 H), 8.35 (dd, J = 8.0, 2.3 Hz, 1 H), 7.92 (d, J = 8.0 Hz, 1 H), 7.80-7.86 (m, 1 H), 7.78 (d, J = 8.3 Hz, 1 H), 7.71-7.76 (m, 1 H), 7.63 (d, J = 7.3 Hz, 1 H), 7.00 (t, J = 7.8 Hz, 1 H), 6.68 (d, J = 7.8 Hz, 1 H), 6.58 (d, J = 7.8 Hz, 1 H), 4.62 (s, 2 H), 4.44-4.53 (m, 1 H), 2.42-2.48 (m, 2 H), 1.69-1.89 (m, 1 H), 1.64 (br. s, 3 H) | 507 | 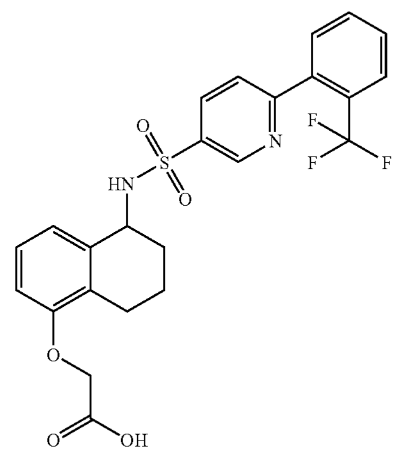 |
| 3-64(E) | {5-[6-(4-Trifluoromethoxy-phenyl)-pyridine-3-sulfonylamino]-5,6,7,8-tetrahydro-naphthalen-1-yloxy}-acetic acid | 13.00 (br. s, 1 H), 9.10 (d, J = 2.4 Hz, 1 H), 8.41 (d, J = 8.3 Hz, 1 H), 8.30-8.36 (m, 3 H), 8.25-8.30 (m, 1 H), 7.55 (d, J = 8.1 Hz, 2 H), 7.05 (t, J = 7.8 Hz, 1 H), 6.74 (d, J = 7.8 Hz, 1 H), 6.68 (d, J = 7.8 Hz, 1 H), 4.65 (s, 2 H), 4.41-4.57 (m, 1 H), 2.55-2.62 (m, 2 H), 2.49-2.53 (m, 2 H), 1.70-1.87 (m, 1 H), 1.59 (br. s, 3 H) | 523 | 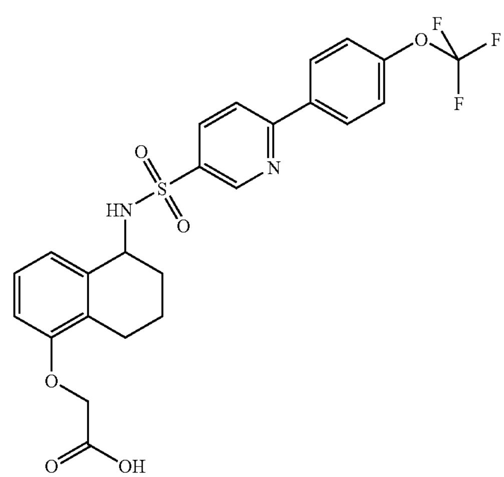 |

| Example No.* | Systematic Name | $^1$H NMR (400 MHz, DMSO-d$_6$) δ ppm | MS [(M + H)$^+$] | Structure |
|---|---|---|---|---|
| 3-65(E) | {5-[4-(2,6-Difluoro-pyridin-4-yl)-benzenesulfonyl-amino]-5,6,7,8-tetrahydro-naphthalen-1-yloxy}-acetic acid | 12.96 (br. s, 1 H), 8.27 (d, J = 8.8 Hz, 1 H), 8.16 (d, J = 8.5 Hz, 2 H), 8.01 (d, J = 8.5 Hz, 2 H), 7.70 (s, 2 H), 7.04 (t, J = 7.8 Hz, 1 H), 6.74 (d, J = 7.8 Hz, 1 H), 6.68 (d, J = 7.8 Hz, 1 H), 4.65 (s, 2 H), 4.32-4.50 (m, 1 H), 2.39-2.46 (m, 2 H), 1.72-1.87 (m, 1 H), 1.56 (br. s, 3 H) | 475 | 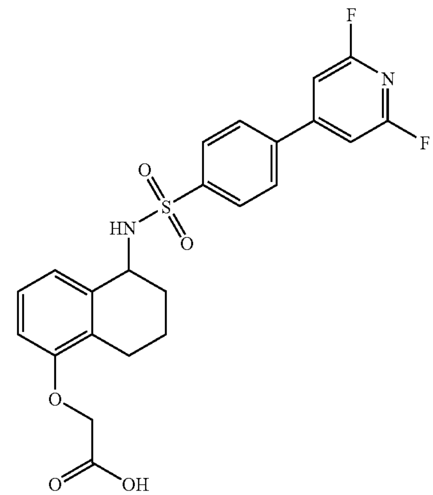 |
| 3-66(E) | {5-[4-(5-Methyl-pyridin-2-yl)-benzenesulfonyl-amino]-5,6,7,8-tetrahydro-naphthalen-1-yloxy}-acetic acid | 8.86 (br. s, 1 H), 8.17 (d, J = 8.3 Hz, 1 H), 8.09 (d, J = 6.8 Hz, 1 H), 7.96 (s, 4 H), 7.40 (d, J = 7.8 Hz, 1 H), 7.01 (t, J = 7.8 Hz, 1 H), 6.71 (d, J = 7.8 Hz, 1 H), 6.63 (d, J = 7.8 Hz, 1 H), 4.52 (br. s, 2 H), 4.33-4.43 (m, 1 H), 2.54 (br. s, 3 H), 2.50 (m, 2 H), 1.78 (br. s, 1 H), 1.57 (br. s, 3 H) | 453 | 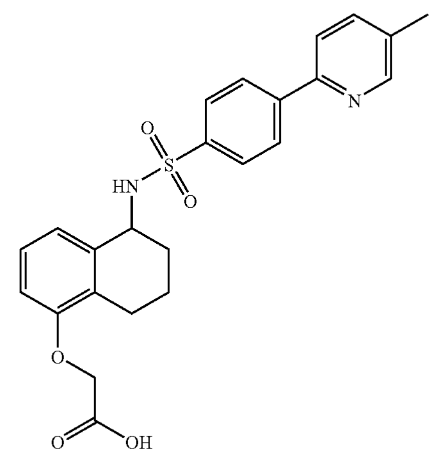 |
| 3-67(E) | {5-[4-(5-Fluoro-6-methyl-pyridin-2-yl)-benzenesulfonyl-amino]-5,6,7,8-tetrahydro-naphthalen-1-yloxy}-acetic acid | 8.27 (d, J = 8.3 Hz, 2 H), 8.13 (d, J = 8.3 Hz, 1 H), 8.00 (dd, J = 8.6, 3.4 Hz, 1 H), 7.97 (d, J = 8.3 Hz, 2 H), 7.78 (t, J = 8.6 Hz, 1 H), 6.92 (t, J = 7.8 Hz, 1 H), 6.58 (d, J = 7.8 Hz, 1 H), 6.52 (d, J = 7.8 Hz, 1 H), 4.27-4.43 (m, 1 H), 4.04 (s, 2 H), 2.55 (d, J = 2.9 Hz, 3 H), 2.45-2.49 (m, 2 H), 1.67-1.84 (m, 1 H), 1.54 (br. s, 3 H) | 471 | 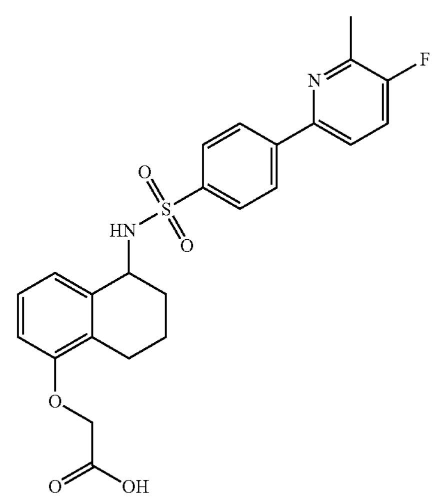 |

-continued

| Example No.* | Systematic Name | ¹H NMR (400 MHz, DMSO-d$_6$) δ ppm | MS [(M + H)$^+$] | Structure |
|---|---|---|---|---|
| 3-68(E) | [5-([2,3']Bipyridinyl-5-sulfonylamino)-5,6,7,8-tetrahydro-naphthalen-1-yloxy]-acetic acid | 9.36 (d, J = 2.2 Hz, 1 H), 9.12 (d, J = 2.0 Hz, 1 H), 8.71 (dd, J = 4.7, 2.0 Hz, 1 H), 8.52-8.58 (m, 1 H), 8.42 (br. s, 1 H), 8.30-8.37 (m, 2 H), 7.59 (dd, J = 7.5, 4.7 Hz, 1 H), 6.96 (t, J = 8.0 Hz, 1 H), 6.61 (d, J = 8.0 Hz, 1 H), 6.54 (d, J = 8.0 Hz, 1 H), 4.46 (br. s, 1 H), 4.10 (br. s, 2 H), 2.55 (br. s, 2 H), 1.71-1.82 (m, 1 H), 1.58 (br. s, 3 H) | 440 | 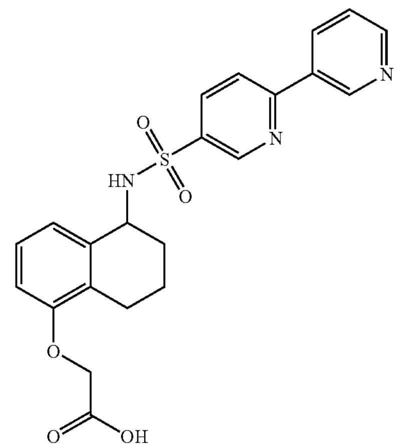 |
| 3-69(E) | {5-[6-(3-Cyano-phenyl)-pyridine-3-sulfonylamino]-5,6,7,8-tetrahydro-naphthalen-1-yloxy}-acetic acid | 12.96 (br. s, 1 H), 9.12 (s, 1 H), 8.63 (s, 1 H), 8.54 (d, J = 8.3 Hz, 1 H), 8.43 (d, J = 8.3 Hz, 1 H), 8.37 (s, 2 H), 8.00 (d, J = 7.3 Hz, 1 H), 7.78 (t, J = 7.8 Hz, 1 H), 7.05 (t, J = 7.8 Hz, 1 H), 6.75 (d, J = 7.8 Hz, 1 H), 6.68 (d, J = 7.8 Hz, 1 H), 4.66 (s, 2H), 4.42-4.56 (m, 1H), 2.49-2.53 (m, 2 H), 1.77 (br. s, 1 H), 1.48-1.68 (m, 3 H) | 464 | 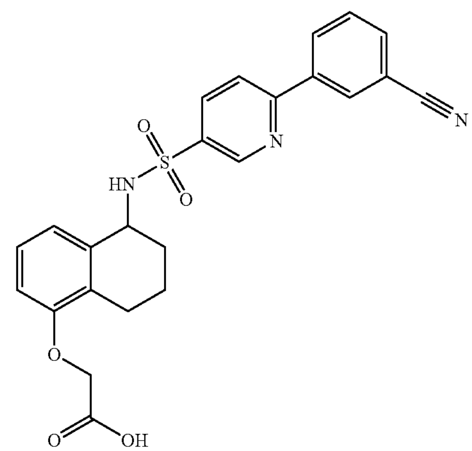 |
| 3-70(E) | {5-[4-(4-Methyl-pyridin-2-yl)-benzenesulfonyl-amino]-5,6,7,8-tetrahydro-naphthalen-1-yloxy}-acetic acid | 12.97 (br. s, 1 H), 8.58 (d, J = 4.9 Hz, 1 H), 8.32 (d, J = 8.3 Hz, 2 H), 8.17 (d, J = 8.6 Hz, 1 H), 7.94-8.06 (m, 3 H), 7.28 (d, J = 4.9 Hz, 1 H), 7.03 (t, J = 8.1 Hz, 1 H), 6.72 (d, J = 8.1 Hz, 1 H), 6.66 (d, J = 8.1 Hz, 1 H), 4.63 (s, 2 H), 4.33-4.43 (m, 1 H), 2.53-2.59 (m, 2 H), 2.42 (s, 3 H), 1.71-1.88 (m, 1 H), 1.56 (br. s, 3 H) | 453 | 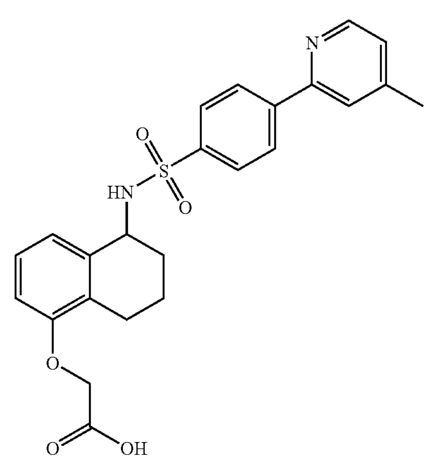 |

| Example No.* | Systematic Name | ¹H NMR (400 MHz, DMSO-d₆) δ ppm | MS [(M + H)⁺] | Structure |
|---|---|---|---|---|
| 3-71(E) | {5-[5-(2-Chloro-phenyl)-pyridine-2-sulfonylamino]-5,6,7,8-tetrahydro-naphthalen-1-yloxy}-acetic acid | 12.97 (br. s, 1 H), 8.85 (d, J = 2.0 Hz, 1 H), 8.39 (d, J = 8.6 Hz, 1 H), 8.19 (dd, J = 8.1, 2.0 Hz, 1 H), 8.09 (d, J = 8.1 Hz, 1 H), 7.49-7.71 (m, 4 H), 7.03 (t, J = 8.0 Hz, 1 H), 6.78 (d, J = 8.0 Hz, 1 H), 6.67 (d, J = 8.0 Hz, 1 H), 4.66 (s, 2 H), 4.51-4.61 (m, 1 H), 2.53-2.61 (m, 2 H), 1.78-1.96 (m, 1 H), 1.68 (br. s, 3 H) | 473 | 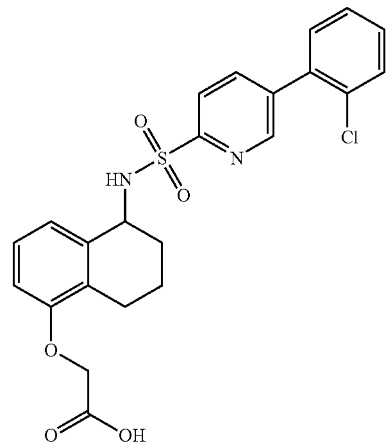 |
| 3-72(E) | {5-[5-(3-Methoxy-phenyl)-pyridine-2-sulfonylamino]-5,6,7,8-tetrahydro-naphthalen-1-yloxy}-acetic acid | 12.97 (br. s, 1 H), 9.11 (d, J = 2.0 Hz, 1 H), 8.39 (dd, J = 8.0, 2.0 Hz, 1 H), 8.34 (d, J = 8.6 Hz, 1 H), 8.05 (d, J = 8.1 Hz, 1 H), 7.45-7.52 (m, 1 H), 7.38-7.44 (m, 2 H), 7.02-7.10 (m, 2 H), 6.89 (d, J = 7.8 Hz, 1 H), 6.67 (d, J = 8.1 Hz, 1 H), 4.66 (s, 2 H), 4.51-4.58 (m, 1 H), 3.86 (s, 3 H), 2.52-2.60 (m, 2 H), 1.54-1.92 (m, 4 H) | 467ᶜ | 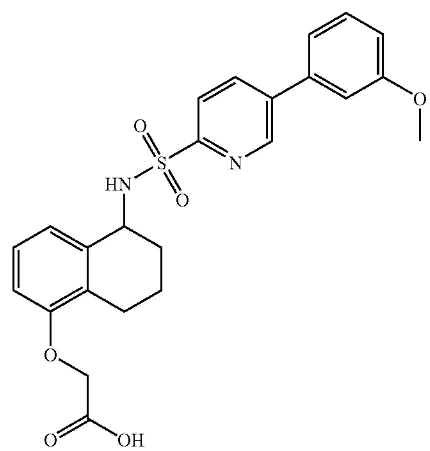 |
| 3-73(E) | {5-[5-(4-Methoxy-phenyl)-pyridine-2-sulfonylamino]-5,6,7,8-tetrahydro-naphthalen-1-yloxy}-acetic acid | 12.95 (br. s, 1 H), 9.07 (d, J = 2.4 Hz, 1 H), 8.32 (dd, J = 8.3, 2.4 Hz, 1 H), 8.28 (d, J = 8.8 Hz, 1 H), 8.01 (d, J = 8.3 Hz, 1 H), 7.82 (d, J = 8.6 Hz, 2 H), 7.11 (d, J = 8.6 Hz, 2 H), 7.05 (t, J = 8.0 Hz, 1 H), 6.88 (d, J = 8.0 Hz, 1 H), 6.67 (d, J = 8.0 Hz, 1 H), 4.64 (s, 2 H), 4.48-4.57 (m, 1 H), 3.84 (s, 3 H), 2.52-2.58 (m, 2 H), 1.53-1.89 (m, 4 H) | 469 | 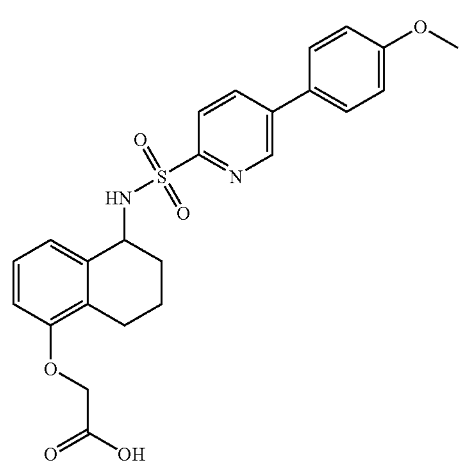 |

-continued

| Example No.* | Systematic Name | $^1$H NMR (400 MHz, DMSO-$d_6$) δ ppm | MS [(M + H)$^+$] | Structure |
|---|---|---|---|---|
| 3-74(E) | {5-[5-(4-Chloro-phenyl)-pyridine-2-sulfonylamino]-5,6,7,8-tetrahydro-naphthalen-1-yloxy}-acetic acid | 12.98 (br. s, 1 H), 9.11 (d, J = 2.2 Hz, 1 H), 8.39 (dd, J = 8.3, 2.2 Hz, 1 H), 8.34 (d, J = 8.3 Hz, 1 H), 8.06 (d, J = 8.3 Hz, 1 H), 7.90 (d, J = 8.3 Hz, 2 H), 7.63 (d, J = 8.3 Hz, 2 H), 7.05 (t, J = 7.8 Hz, 1 H), 6.88 (d, J = 7.8 Hz, 1 H), 6.67 (d, J = 7.8 Hz, 1 H), 4.65 (s, 2 H), 4.47-4.58 (m, 1 H), 2.52-2.59 (m, 2 H), 1.78-1.90 (m, 1 H), 1.52-1.78 (m, 3 H) | 473 | 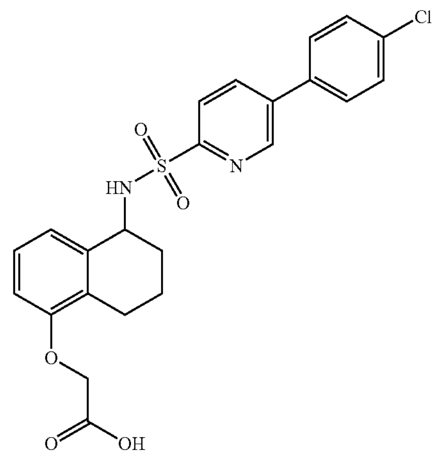 |
| 3-75(E) | {5-[6-(3-Ethoxy-phenyl)-pyridine-3-sulfonylamino]-5,6,7,8-tetrahydro-naphthalen-1-yloxy}-acetic acid | 13.09 (br. s, 1 H), 9.07 (d, J = 2.4 Hz, 1 H), 8.37 (d, J = 8.8 Hz, 1 H), 8.29 (dd, J = 8.4, 2.4 Hz, 1 H), 8.25 (d, J = 8.4 Hz, 1 H), 7.70-7.77 (m, 2 H), 7.45 (t, J = 7.9 Hz, 1 H), 7.08 (dd, J = 7.9, 2.0 Hz, 1 H), 7.04 (t, J = 8.1 Hz, 1 H), 6.73 (d, J = 8.1 Hz, 1 H), 6.66 (d, J = 8.1 Hz, 1 H), 4.58 (br. s, 2 H), 4.43-4.51 (m, 1 H), 4.14 (q, J = 7.2 Hz, 2 H), 2.43-2.47 (m, 2 H), 1.77 (br. s, 1 H), 1.59 (br. s, 3 H), 1.37 (t, J = 7.2 Hz, 3 H) | 483 | 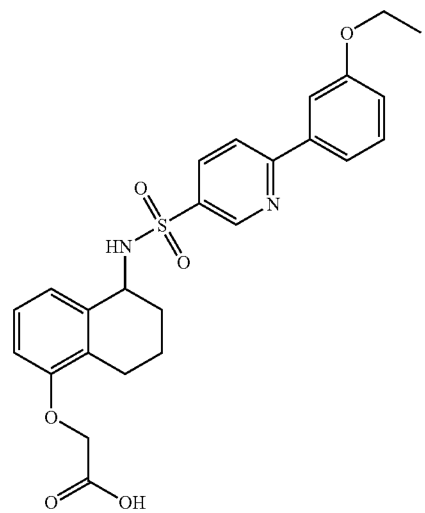 |
| 3-76(E) | {5-[6-(5-Fluoro-2-methoxy-phenyl)-pyridine-3-sulfonylamino]-5,6,7,8-tetrahydro-naphthalen-1-yloxy}-acetic acid | 12.98 (br. s, 1 H), 9.09 (dd, J = 2.4, 0.8 Hz, 1 H), 8.40 (d, J = 8.6 Hz, 1 H), 8.28 (dd, J = 8.4, 2.4 Hz, 1 H), 8.19 (dd, J = 8.4, 0.8 Hz, 1 H), 7.68 (dd, J = 9.7, 3.3 Hz, 1 H), 7.35 (ddd, J = 9.1, 8.1, 3.3 Hz, 1 H), 7.24 (dd, J = 9.1, 4.4 Hz, 1 H), 7.05 (t, J = 7.8 Hz, 1 H), 6.73 (d, J = 7.8 Hz, 1 H), 6.68 (d, J = 7.8 Hz, 1 H), 4.65 (s, 2 H), 4.42-4.52 (m, 1 H), 3.88 (s, 3 H), 2.53-2.62 (m, 2 H), 1.71-1.85 (m, 1 H), 1.51-1.70 (m, 3 H) | 487 | 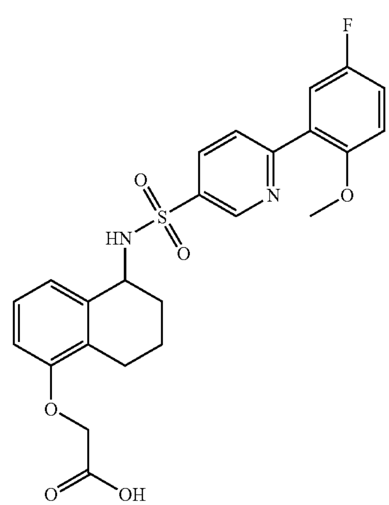 |

-continued

| Example No.* | Systematic Name | ¹H NMR (400 MHz, DMSO-$d_6$) δ ppm | MS [(M + H)$^+$] | Structure |
|---|---|---|---|---|
| 3-77(E) | {5-[6-(3-Methoxy-phenyl)-pyridine-3-sulfonylamino]-5,6,7,8-tetrahydro-naphthalen-1-yloxy}-acetic acid | 9.08 (d, J = 2.2 Hz, 1 H), 8.37 (d, J = 8.3 Hz, 1 H), 8.30 (dd, J = 8.4, 2.2 Hz, 1 H), 8.25 (d, J = 8.4 Hz, 1 H), 7.77 (d, J = 7.8 Hz, 1 H), 7.73-7.75 (m, 1 H), 7.47 (t, J = 8.1 Hz, 1 H), 7.10 (dd, J = 8.1, 2.2 Hz, 1 H), 6.99-7.07 (m, 1 H), 6.74 (d, J = 7.8 Hz, 1 H), 6.66 (d, J = 8.3 Hz, 1 H), 4.59 (s, 2 H), 4.41-4.54 (m, 1 H), 3.86 (s, 3 H), 2.35-2.48 (m, 2 H), 1.70-1.85 (m, 1 H), 1.49-1.69 (m, 3 H) | 469 | 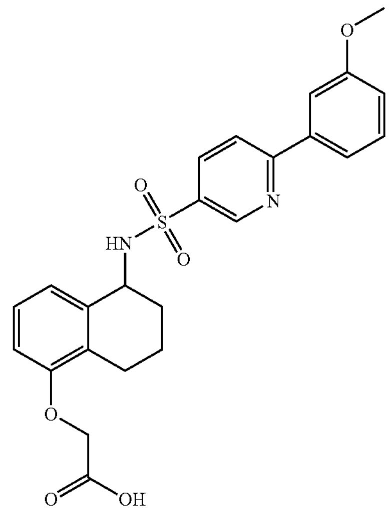 |
| 3-78(E) | {5-[6-(2-Chloro-phenyl)-pyridine-3-sulfonylamino]-5,6,7,8-tetrahydro-naphthalen-1-yloxy}-acetic acid | 13.05 (br. s, 1 H), 9.12 (dd, J = 2.3, 0.8 Hz, 1 H), 8.45 (d, J = 8.3 Hz, 1 H), 8.34 (dd, J = 8.4, 2.3 Hz, 1 H), 7.93 (dd, J = 8.4, 0.8 Hz, 1 H), 7.62-7.71 (m, 2 H), 7.48-7.58 (m, 2 H), 7.02 (t, J = 8.1 Hz, 1 H), 6.68 (d, J = 8.1 Hz, 1 H), 6.63 (d, J = 8.1 Hz, 1 H), 4.65 (s, 2 H), 4.43- 4.55 (m, 1 H), 2.52-2.63 (m, 2 H), 1.72-1.86 (m, 1 H), 1.63 (br. s, 3 H) | 473 | 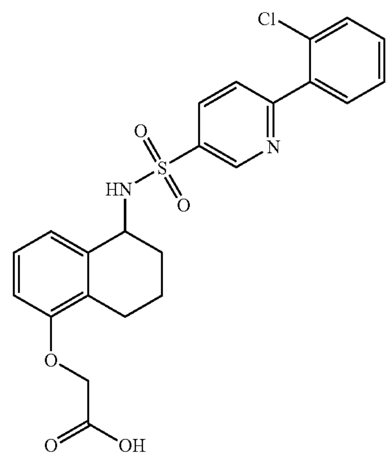 |
| 3-79(E) | {5-[6-(3-Chloro-4-fluoro-phenyl)-pyridine-3-sulfonylamino]-5,6,7,8-tetrahydro-naphthalen-1-yloxy}-acetic acid | 12.99 (br. s, 1 H), 9.05-9.13 (m, 1 H), 8.38-8.44 (m, 2 H), 8.31-8.34 (m, 2 H), 8.24 (ddd, J = 8.8, 4.7, 2.2 Hz, 1 H), 7.62 (t, J = 8.8 Hz, 1 H), 7.05 (t, J = 8.0 Hz, 1 H), 6.74 (d, J = 8.0 Hz, 1 H), 6.68 (d, J = 8.0 Hz, 1 H), 4.65 (s, 2 H), 4.45-4.53 (m, 1 H), 2.42-2.63 (m, 2 H), 1.78 (br. s, 1 H), 1.49-1.68 (m, 3 H) | 489$^c$ | 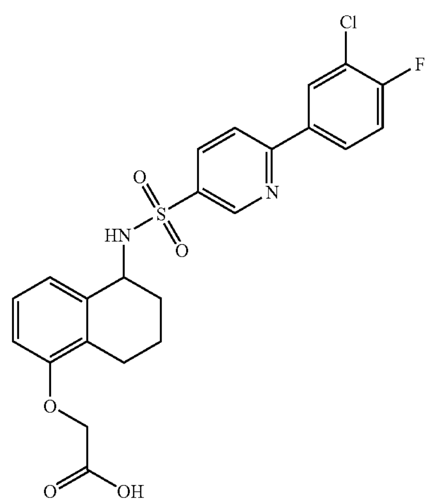 |

-continued

| Example No.* | Systematic Name | ¹H NMR (400 MHz, DMSO-d$_6$) δ ppm | MS [(M + H)$^+$] | Structure |
| --- | --- | --- | --- | --- |
| 3-80(E) | {5-[6-(3-Fluoro-phenyl)-pyridine-3-sulfonylamino]-5,6,7,8-tetrahydro-naphthalen-1-yloxy}-acetic acid | 13.20 (br. s, 1 H), 9.10 (d, J = 2.2 Hz, 1 H), 8.41 (d, J = 8.6 Hz, 1 H), 8.33 (dd, J = 8.6, 2.2 Hz, 1 H), 8.30 (d, J = 8.6 Hz, 1 H), 8.06 (d, J = 7.9 Hz, 1 H), 8.01 (ddd, J = 10.2, 2.4, 1.9 Hz, 1 H), 7.61 (td, J = 7.9, 6.0 Hz, 1 H), 7.38 (td, J = 7.9, 2.4 Hz, 1 H), 7.05 (t, J = 8.0 Hz, 1 H), 6.74 (d, J = 8.0 Hz, 1 H), 6.68 (d, J = 8.0 Hz, 1 H), 4.65 (s, 2 H), 4.39-4.53 (m, 1 H), 2.50-2.64 (m, 2 H), 1.69-1.87 (m, 2 H), 1.58 (br. s, 3 H) | 457 | 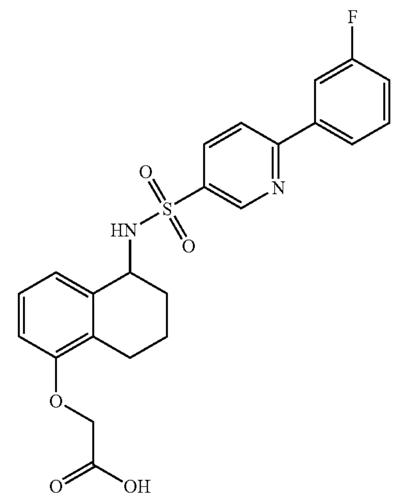 |
| 3-81(E) | {5-[6-(4-Chloro-phenyl)-pyridine-3-sulfonylamino]-5,6,7,8-tetrahydro-naphthalen-1-yloxy}-acetic acid | 9.08 (d, J = 2.4 Hz, 1 H), 8.39 (br. s, 1 H), 8.32 (dd, J = 8.5, 2.4 Hz, 1 H), 8.26 (d, J = 8.5 Hz, 1 H), 8.22 (d, J = 8.8 Hz, 2 H), 7.62 (d, J = 8.8 Hz, 2 H), 7.03 (t, J = 8.3 Hz, 1 H), 6.72 (d, J = 8.3 Hz, 1 H), 6.66 (d, J = 8.3 Hz, 1 H), 4.56 (br. s, 2 H), 4.43-4.53 (m, 1 H), 2.39-2.48 (m, 2 H), 1.78 (br. s, 1 H), 1.59 (br. s, 3 H) | 471$^c$ | 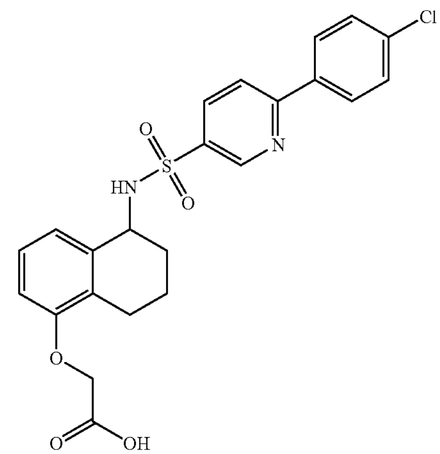 |
| 3-82(E) | {5-[6-(4-Fluoro-phenyl)-pyridine-3-sulfonylamino]-5,6,7,8-tetrahydro-naphthalen-1-yloxy}-acetic acid | 12.98 (br. s, 1 H), 9.07 (d, J = 2.0 Hz, 1 H), 8.38 (d, J = 8.6 Hz, 1 H), 8.30 (dd, J = 8.3, 2.0 Hz, 1 H), 8.21-8.28 (m, 3 H), 7.39 (t, J = 8.8 Hz, 2 H), 7.05 (t, J = 7.9 Hz, 1 H), 6.75 (d, J = 7.9 Hz, 1 H), 6.68 (d, J = 7.9 Hz, 1 H), 4.65 (s, 2 H), 4.44-4.56 (m, 1 H), 2.67 (br. 2, 2 H), 1.77 (br. s, 1 H), 1.58 (br. s, 3 H) | 457 | 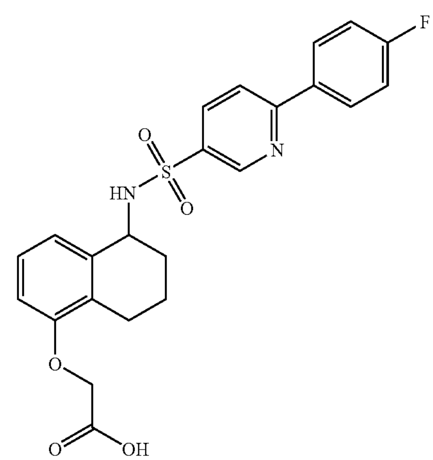 |

| Example No.* | Systematic Name | $^1$H NMR (400 MHz, DMSO-$d_6$) δ ppm | MS [(M + H)$^+$] | Structure |
|---|---|---|---|---|
| 3-83(E) | {5-[6-(2-Fluoro-phenyl)-pyridine-3-sulfonylamino]-5,6,7,8-tetrahydro-naphthalen-1-yloxy}-acetic acid | 12.98 (br. s, 1 H), 9.14 (d, J = 2.1 Hz, 1 H), 8.44 (d, J = 8.6 Hz, 1 H), 8.35 (dd, J = 8.3, 2.1 Hz, 1 H), 7.98-8.10 (m, 2 H), 7.53-7.64 (m, 1 H), 7.36-7.46 (m, 2 H), 7.00-7.09 (m, 1 H), 6.72 (d, J = 7.7 Hz, 1 H), 6.68 (d, J = 7.7 Hz, 1 H), 4.66 (br. s, 2 H), 4.43-4.55 (m, 1 H), 2.67 (br. s, 2 H), 1.79 (br. s, 1 H), 1.60 (br. s, 3 H) | 457 | 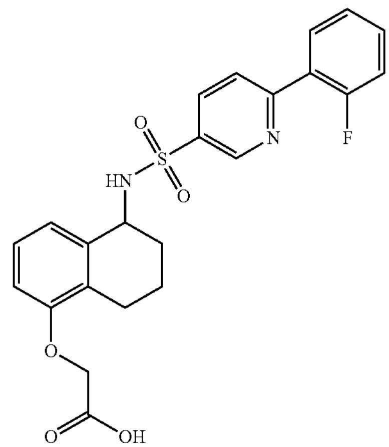 |
| 3-84(E) | {5-[6-(4-Fluoro-3-methyl-phenyl)-pyridine-3-sulfonylamino]-5,6,7,8-tetrahydro-naphthalen-1-yloxy}-acetic acid | 12.95 (br. s, 1 H), 9.06 (d, J = 2.0 Hz, 1 H), 8.36 (d, J = 8.8 Hz, 1 H), 8.29 (dd, J = 8.3, 2.0 Hz, 1 H), 8.21 (d, J = 8.3 Hz, 1 H), 8.16 (dd, J = 7.8, 2.1 Hz, 1 H), 8.06 (ddd, J = 8.8, 5.4, 2.1 Hz, 1 H), 7.31 (t, J = 8.8 Hz, 1 H), 7.05 (t, J = 7.8 Hz, 1 H), 6.75 (d, J = 7.8 Hz, 1 H), 6.68 (d, J = 7.8 Hz, 1 H), 4.66 (s, 2 H), 4.41-4.54 (m, 1 H), 2.42-2.47 (m, 2 H), 2.35 (s, 3 H), 1.69-1.88 (m, 1 H), 1.50-1.69 (m, 3 H) | 471 | 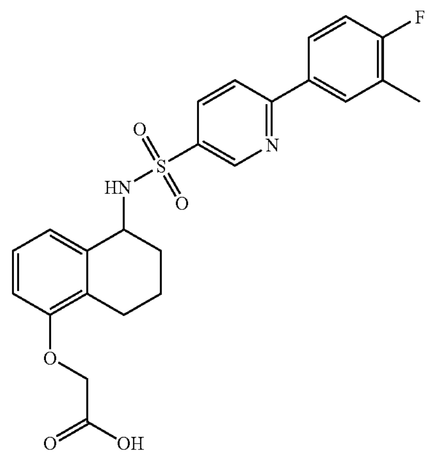 |
| 3-85(E) | {5-[6-(3-Trifluoromethyl-phenyl)-pyridine-3-sulfonylamino]-5,6,7,8-tetrahydro-naphthalen-1-yloxy}-acetic acid | 12.98 (br. s, 1 H), 9.14 (d, J = 2.4 Hz, 1 H), 8.53 (br. s, 1 H), 8.51 (d, J = 7.8 Hz, 1 H), 8.38-8.45 (m, 2 H), 8.36 (dd, J = 8.3, 2.4 Hz, 1 H), 7.91 (d, J = 7.8 Hz, 1 H), 7.81 (t, J = 7.8 Hz, 1 H), 7.00-7.13 (t, J = 7.8 Hz, 1 H), 6.76 (d, J = 7.8 Hz, 1 H), 6.68 (d, J = 7.8 Hz, 1 H), 4.65 (s, 2 H), 4.43-4.55 (m, 1 H), 2.53 (m, 2 H), 1.72-1.85 (m, 1 H), 1.59 (br. s, 3 H) | 507 | 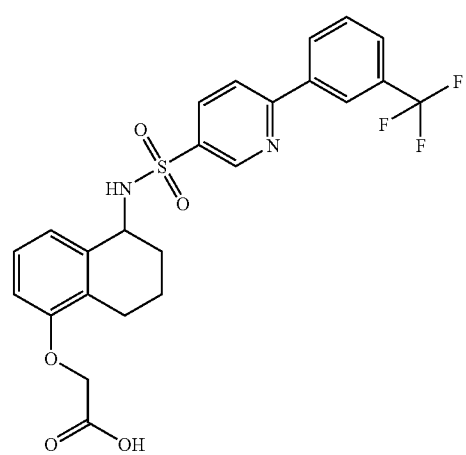 |

| Example No.* | Systematic Name | $^1$H NMR (400 MHz, DMSO-$d_6$) δ ppm | MS [(M + H)$^+$] | Structure |
|---|---|---|---|---|
| 3-86(E) | {5-[6-(4-Methoxy-phenyl)-pyridine-3-sulfonylamino]-5,6,7,8-tetrahydro-naphthalen-1-yloxy}-acetic acid | 12.94 (br. s, 1 H), 9.02 (d, J = 2.1 Hz, 1 H), 8.31 (d, J = 8.3 Hz, 1 H), 8.24 (dd, J = 8.6, 2.1 Hz, 1 H), 8.13-8.20 (m, 3 H), 7.10 (d, J = 8.8 Hz, 2 H), 7.05 (t, J = 7.8 Hz, 1 H), 6.76 (d, J = 7.8 Hz, 1 H), 6.68 (d, J = 7.8 Hz, 1 H), 4.66 (s, 2 H), 4.41-4.51 (m, 1 H), 3.85 (s, 3 H), 2.44-2.48 (m, 2 H), 1.77 (br. s, 1 H), 1.59 (br. s, 3 H) | 469 | 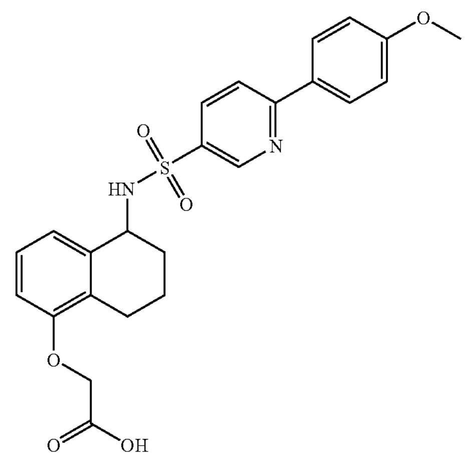 |
| 3-87(E) | (5-{6-[3-(2-Hydroxy-ethyl)-phenyl]-pyridine-3-sulfonylamino}-5,6,7,8-tetrahydro-naphthalen-1-yloxy)-acetic acid | 12.94 (br. s, 1 H), 9.08 (d, J = 2.4 Hz, 1 H), 8.36 (d, J = 8.8 Hz, 1 H), 8.30 (dd, J = 8.3, 2.4 Hz, 1 H), 8.22 (d, J = 8.3 Hz, 1 H), 8.05 (s, 1 H), 8.00 (d, J = 7.8 Hz, 1 H), 7.46 (t, J = 7.8 Hz, 1 H), 7.38 (d, J = 7.8 Hz, 1 H), 7.05 (t, J = 8.1 Hz, 1 H), 6.75 (d, J = 8.1 Hz, 1 H), 6.68 (d, J = 8.1 Hz, 1 H), 4.66 (s, 2 H), 4.42-4.53 (m, 1 H), 3.68 (t, J = 6.8 Hz, 2 H), 2.84 (t, J = 6.8 Hz, 2 H), 2.42-2.47 (m, 2 H), 1.67-1.85 (m, 1 H), 1.52-1.69 (m, 3 H) | 483$^c$ | 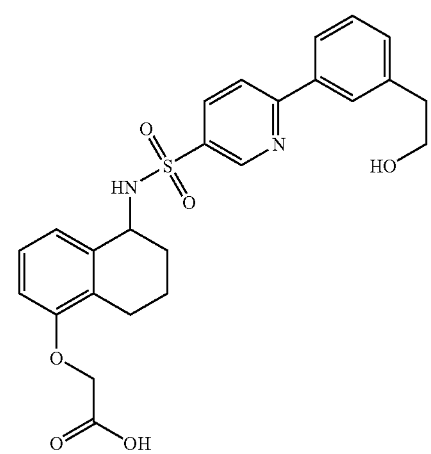 |
| 3-88(E) | [5-(6-Thiophen-3-yl-pyridine-3-sulfonylamino)-5,6,7,8-tetrahydro-naphthalen-1-yloxy]-acetic acid | 12.96 (br. s, 1 H), 9.00 (s, 1 H), 8.41 (br. s, 1 H), 8.32 (d, J = 7.8 Hz, 1 H), 8.22-8.28 (m, 1 H), 8.12 (d, J = 8.3 Hz, 1 H), 7.85 (d, J = 5.4 Hz, 1 H), 7.72 (dd, J = 4.6, 2.7 Hz, 1 H), 7.05 (t, J = 7.8 Hz, 1 H), 6.75 (d, J = 7.8 Hz, 1 H), 6.67 (d, J = 7.8 Hz, 1 H), 4.64 (br. s, 2 H), 4.39-4.53 (m, 1 H), 2.48-2.54 (m, 2 H), 1.76 (br. s, 1 H), 1.56 (br. s, 3 H) | 445 | 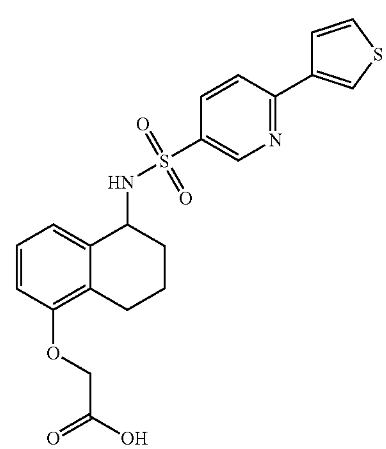 |

| Example No.* | Systematic Name | $^1$H NMR (400 MHz, DMSO-$d_6$) δ ppm | MS [(M + H)$^+$] | Structure |
|---|---|---|---|---|
| 3-89(E) | [5-(6-m-Tolyl-pyridine-3-sulfonylamino)-5,6,7,8-tetrahydro-naphthalen-1-yloxy]-acetic acid | 12.59 (br. s, 1 H), 9.07 (d, J = 2.4 Hz, 1 H), 8.36 (d, J = 8.8 Hz, 1 H), 8.29 (dd, J = 8.3, 2.4 Hz, 1 H), 8.21 (d, J = 8.3 Hz, 1 H), 8.03 (s, 1 H), 7.98 (d, J = 7.8 Hz, 1 H), 7.44 (t, J = 7.8 Hz, 1 H), 7.34 (d, J = 7.8 Hz, 1 H), 7.04 (t, J = 7.8 Hz, 1 H), 6.73 (d, J = 7.8 Hz, 1 H), 6.67 (d, J = 7.8 Hz, 1 H), 4.61 (s, 2 H), 4.41-4.54 (m, 1 H), 2.44-2.48 (m, 2 H), 2.42 (s, 3 H), 1.77 (br. s, 1 H), 1.46-1.70 (m, 3 H) | 453 | 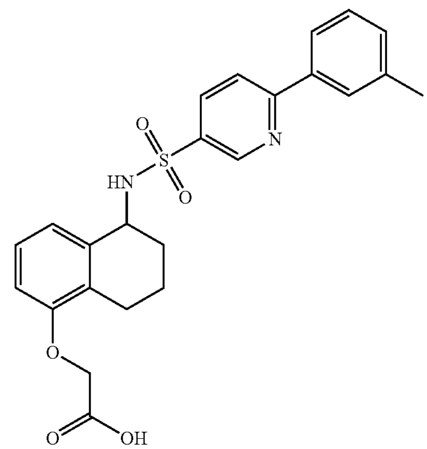 |

*Method of preparation E or F indicated in parentheses;
$^c$[M − H]$^−$

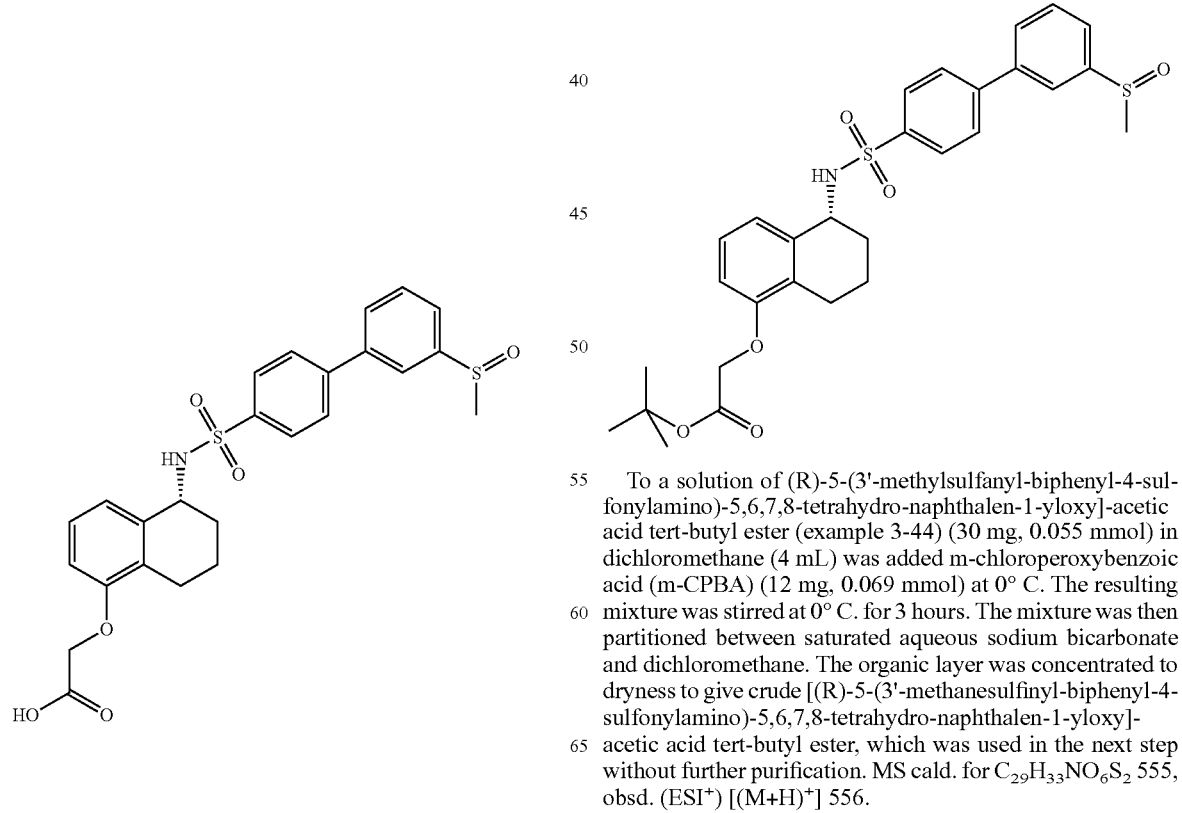

Example 4-1

[(R)-5-(3'-Methanesulfinyl-biphenyl-4-sulfonylamino)-5,6,7,8-tetrahydro-naphthalen-1-yloxy]-acetic acid

[(R)-5-(3'-Methanesulfinyl-biphenyl-4-sulfonylamino)-5,6,7,8-tetrahydro-naphthalen-1-yloxy]-acetic acid tert-butyl ester To a solution of (R)-5-(3'-methylsulfanyl-biphenyl-4-sulfonylamino)-5,6,7,8-tetrahydro-naphthalen-1-yloxy]-acetic acid tert-butyl ester (example 3-44) (30 mg, 0.055 mmol) in dichloromethane (4 mL) was added m-chloroperoxybenzoic acid (m-CPBA) (12 mg, 0.069 mmol) at 0° C. The resulting mixture was stirred at 0° C. for 3 hours. The mixture was then partitioned between saturated aqueous sodium bicarbonate and dichloromethane. The organic layer was concentrated to dryness to give crude [(R)-5-(3'-methanesulfinyl-biphenyl-4-sulfonylamino)-5,6,7,8-tetrahydro-naphthalen-1-yloxy]-acetic acid tert-butyl ester, which was used in the next step without further purification. MS calcd. for $C_{29}H_{33}NO_6S_2$ 555, obsd. (ESI$^+$) [(M+H)$^+$] 556.

147

[(R)-5-(3'-Methanesulfinyl-biphenyl-4-sulfonylamino)-5,6,7,8-tetrahydro-naphthalen-1-yloxy]-acetic acid

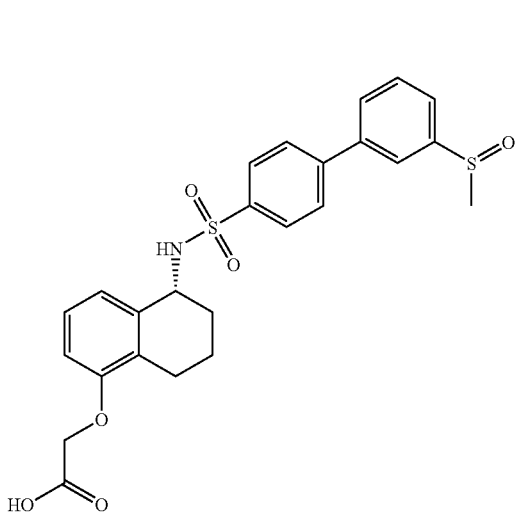

Starting with [(R)-5-(3'-methanesulfinyl-biphenyl-4-sulfonylamino)-5,6,7,8-tetrahydro-naphthalen-1-yloxy]-acetic acid tert-butyl ester, using the method analogous to the one for example 3-2, method F, [(R)-5-(3'-methanesulfinyl-biphenyl-4-sulfonylamino)-5,6,7,8-tetrahydro-naphthalen-1-yloxy]-acetic acid (9 mg, 32% over two steps) was obtained. $^1$H NMR (400 MHz, DMSO-$d_6$) δ ppm 13.12 (br. s, 1H), 8.19 (d, J=8.5 Hz, 1H), 8.04-8.07 (m, 1H), 7.97-8.03 (m, 4H), 7.95 (dt, J=7.5, 1.7 Hz, 1H), 7.77 (dt, J=7.5, 1.5 Hz, 1H), 7.73 (t, J=7.5 Hz, 1H), 7.04 (t, J=8.1 Hz, 1H), 6.74 (d, J=8.1 Hz, 1H), 6.66 (d, J=8.1 Hz, 1H), 4.62 (s, 2H), 4.32-4.47 (m, 1H), 2.84 (s, 3H), 2.39-2.63 (m, 2H), 1.69-1.94 (m, 1H), 1.50-1.67 (m, 3H); MS cald. for $C_{25}H_{25}NO_6S_2$ 499, obsd. 500 (ESI$^+$) [(M+H)$^+$].

Example 5-1

[(R)-5-(3'-Methanesulfonyl-biphenyl-4-sulfonylamino)-5,6,7,8-tetrahydro-naphthalen-1-yloxy]-acetic acid

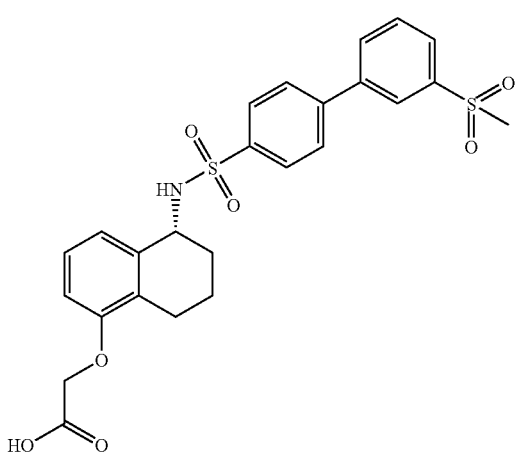

148

[(R)-5-(3'-Methanesulfonyl-biphenyl-4-sulfonylamino)-5,6,7,8-tetrahydro-naphthalen-1-yloxy]-acetic acid tert-butyl ester

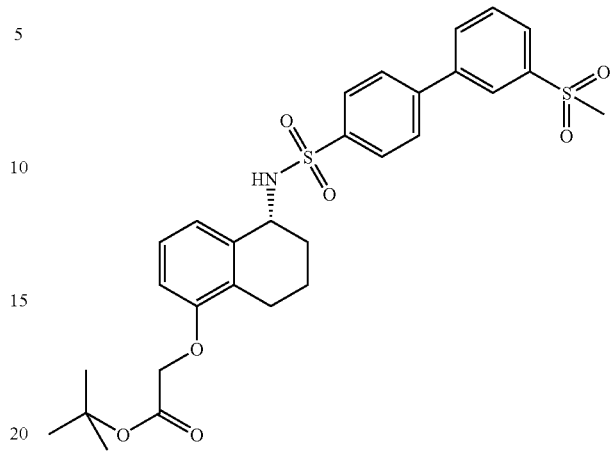

To a solution of (R)-5-(3'-methylsulfanyl-biphenyl-4-sulfonylamino)-5,6,7,8-tetrahydro-naphthalen-1-yloxy]-acetic acid tert-butyl ester (example 3-44) (30 mg, 0.055 mmol) in methanol (4 mL) were added OXONE (136 mg, 0.22 mmol) and alumina (70 mg). The resulting mixture was heated at reflux for 2 hours, and then was filtered. The filtrate was concentrated to dryness under reduced pressure to give crude [(R)-5-(3'-methanesulfonyl-biphenyl-4-sulfonylamino)-5,6,7,8-tetrahydro-naphthalen-1-yloxy]-acetic acid tert-butyl ester, which was used in the next step without purification. MS cald. for $C_{29}H_{33}NO_7S_2$ 571, obsd. 572 (ESI$^+$) [(M+H)$^+$].

[(R)-5-(3'-Methanesulfonyl-biphenyl-4-sulfonylamino)-5,6,7,8-tetrahydro-naphthalen-1-yloxy]-acetic acid

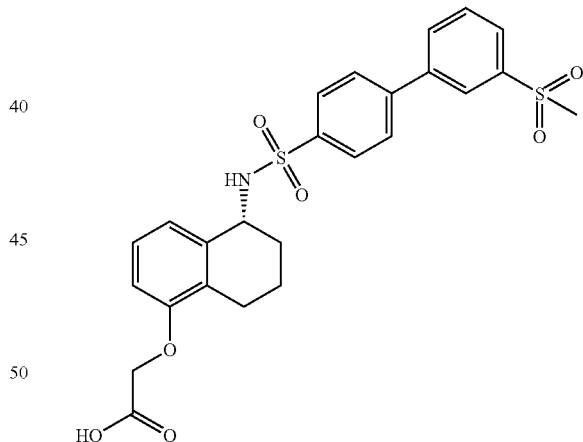

Starting with [(R)-5-(3'-methanesulfonyl-biphenyl-4-sulfonylamino)-5,6,7,8-tetrahydro-naphthalen-1-yloxy]-acetic acid tert-butyl ester, using the method analogous to the one for example 3-2, method F, 3$^{rd}$ step, (R)-[5-(3'-methanesulfonyl-biphenyl-4-sulfonylamino)-5,6,7,8-tetrahydro-naphthalen-1-yloxy]-acetic acid (22 mg, 78% over two steps) was obtained. $^1$H NMR (400 MHz, DMSO-$d_6$) δ ppm 12.94 (br. s, 1H), 8.28 (t, J=1.6 Hz, 1H), 8.21 (d, J=8.5 Hz, 1H), 8.15 (dt, J=7.9, 1.6 Hz, 1H), 8.02-8.07 (m, 2H), 7.99-8.02 (m, 2H), 7.98-8.01 (m, 1H), 7.81 (t, J=7.9 Hz, 1H), 7.05 (t, J=8.1 Hz, 1H), 6.76 (d, J=8.1 Hz, 1H), 6.68 (d, J=8.1 Hz, 1H), 4.65 (s, 2H), 4.35-4.46 (m, 1H), 3.33 (s, 3H), 2.48-2.62 (m, 2H), 1.66-1.89 (m, 1H), 1.45-1.68 (m, 3H); MS cald. for $C_{25}H_{25}NO_7S_2$ 515, obsd. 516 (ESI$^+$) [(M+H)$^+$].

Example 6-1

((R)-5-{[3-Chloro-4-(4-chloro-phenoxy)-benzene-sulfonyl]-methyl-amino}-5,6,7,8-tetrahydro-naphthalen-1-yloxy)-acetic acid tert-butyl ester

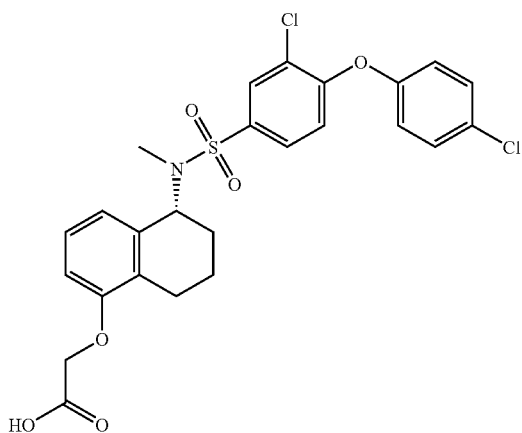

{(R)-5-[(3-Chloro-4-fluoro-benzenesulfonyl)-methyl-amino]-5,6,7,8-tetrahydro-naphthalen-1-yloxy}-acetic acid tert-butyl ester

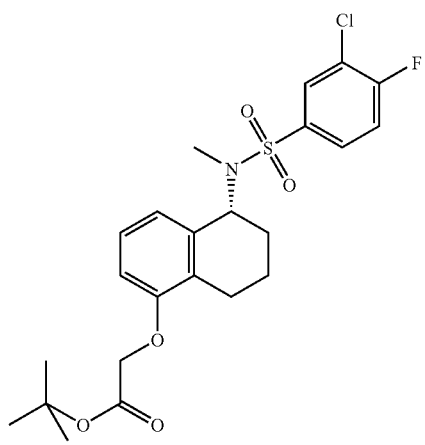

To a solution of [(R)-5-(3-chloro-4-fluoro-benzenesulfonylamino)-5,6,7,8-tetrahydro-naphthalen-1-yloxy]-acetic acid tert-butyl ester (example 2-2, method D, 2$^{nd}$ step) (400 mg, 0.85 mmol) in acetonitrile (15 mL) was added methyl iodide (182 mg, 1.28 mmol) and potassium carbonate (350 mg, 2.53 mmol). The reaction mixture was stirred at 70° C. for 5 hours, then cooled to room temperature and filtered through a glass funnel. The filtrate was concentrated in vacuo, and the residue was purified by column chromatography (gradient elution, 0-10% methanol in dichloromethane) to afford {(R)-5-[(3-chloro-4-fluoro-benzenesulfonyl)-methyl-amino]-5,6,7,8-tetrahydro-naphthalen-1-yloxy}-acetic acid tert-butyl ester (365 mg, 89%) as a yellow oil. MS cald. for $C_{23}H_{27}ClFNO_5S$ 483, obsd. 484 (ESI$^+$) [(M+H)$^+$].

((R)-5-{[3-Chloro-4-(4-chloro-phenoxy)-benzene-sulfonyl]-methyl-amino}-5,6,7,8-tetrahydro-naphthalen-1-yloxy)-acetic acid tert-butyl ester

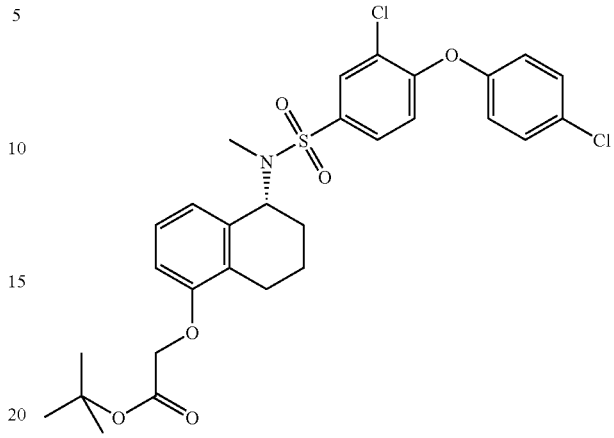

Starting with {(R)-5-[(3-chloro-4-fluoro-benzenesulfonyl)-methyl-amino]-5,6,7,8-tetrahydro-naphthalen-1-yloxy}-acetic acid tert-butyl ester (100 mg, 0.207 mmol) and 4-chlorophenol (315 mg, 2.45 mmol), using the method analogous to the one described for example 2-2, method D, 2$^{nd}$ step, ((R)-5-{[3-chloro-4-(4-chlorophenoxy)-benzenesulfonyl]-methyl-amino}-5,6,7,8-tetrahydro-naphthalen-1-yloxy)-acetic acid tert-butyl ester (92 mg, 75%) was obtained as a white powder. MS cald. For $C_{29}H_{31}Cl_2NO_6S$ 591, obsd. 592 (ESI$^+$) [(M+H)$^+$].

((R)-5-{[3-Chloro-4-(4-chloro-phenoxy)-benzene-sulfonyl]-methyl-amino}-5,6,7,8-tetrahydro-naphthalen-1-yloxy)-acetic acid

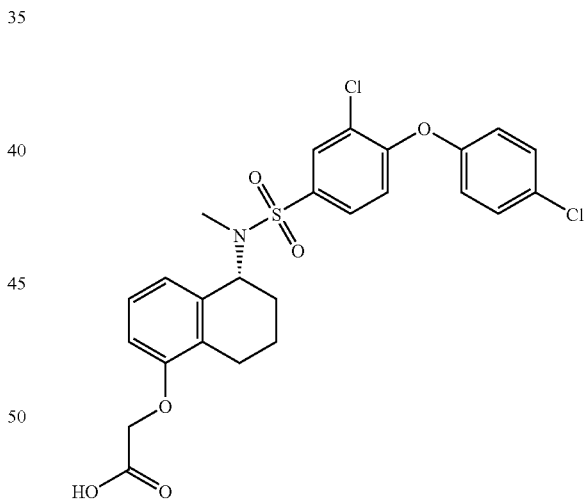

Starting with ((R)-5-{[3-chloro-4-(4-chloro-phenoxy)-benzenesulfonyl]-methyl-amino}-5,6,7,8-tetrahydro-naphthalen-1-yloxy)-acetic acid tert-butyl ester (80 mg, 0.135 mmol), using the method analogous to the one described for example 2-2, method D, 4$^{th}$ step, ((R)-5-{[3-chloro-4-(4-chloro-phenoxy)-benzenesulfonyl]-methyl-amino}-5,6,7,8-tetrahydro-naphthalen-1-yloxy)-acetic acid (55 mg, 76%) was obtained as a white powder. $^1$H NMR (400 MHz, DMSO-d$_6$) δ ppm 8.09 (d, J=2.27 Hz, 1H), 7.85 (dd, J=8.84, 2.27 Hz, 1H), 7.53 (d, J=4.55 Hz, 2H), 7.20 (d, J=5.81 Hz, 2H), 7.11 (t, J=7.96 Hz, 1H), 6.69 (t, J=7.83 Hz, 2H), 5.07-5.16 (m, 1H), 4.60-4.68 (m, 2H), 2.66-2.79 (m, 1H), 2.52 (s, 3H), 2.30-2.47 (m, 1H), 1.81-1.91 (m, 1H), 1.53-1.70 (m, 3H). MS cald. for $C_{25}H_{23}Cl_2NO_6S$ 535, obsd. 536 (ESI$^+$) [(M+H)$^+$].

Examples 6-2 to 6-3

The following examples 6-2 to 6-3 were prepared in the analogous manner to example 6-1.

| Example No | Systematic Name | $^1$H NMR (400 MHz, DMSO-$d_6$) δ ppm | MS (M + H$^+$) | Structure |
|---|---|---|---|---|
| 6-2 | ((R)-5-{[3-Chloro-4-(2-chloro-phenoxy)-benzenesulfonyl]-methyl-amino}-5,6,7,8-tetrahydro-naphthalen-1-yloxy)-acetic acid | 8.10 (d, J = 2.02 Hz, 1 H), 7.83 (dd, J = 8.84, 2.27 Hz, 1 H), 7.69 (dd, J = 8.08, 1.52 Hz, 1 H), 7.45-7.51 (m, 1 H), 7.33 (s, 1 H), 7.33-7.39 (m, J = 9.06, 6.16, 3.85, 3.66 Hz, 2 H), 7.09 (t, J = 7.96 Hz, 1 H), 6.95 (d, J = 8.84 Hz, 1 H), 6.68 (dd, J = 23.49, 8.08 Hz, 2 H), 5.03-5.13 (m, 1 H), 4.66 (s, 2 H), 2.71 (m, 1 H), 2.51 (s, 3 H), 2.45 (d, J = 4.55 Hz, 1 H), 1.79-1.91 (m, 1 H), 1.55 (br. s, 3 H) | 536 | 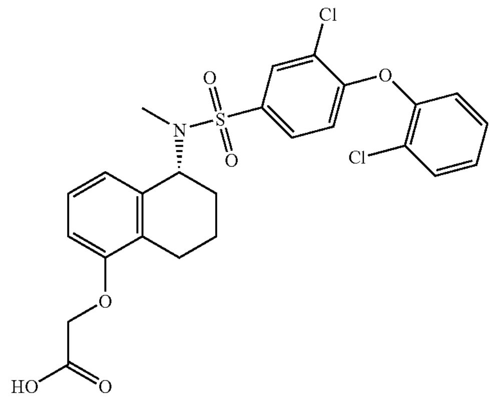 |
| 6-3 | ((R)-5-{[3-Chloro-4-(4-fluoro-phenoxy)-benzenesulfonyl]-methyl-amino}-5,6,7,8-tetrahydro-naphthalen-1-yloxy)-acetic acid | 8.07 (d, J = 2.02 Hz, 1 H), 7.83 (dd, J = 8.72, 2.15 Hz, 1 H), 7.33 (t, J = 8.72 Hz, 2 H), 7.22-7.27 (m, 2 H), 7.08 (d, J = 8.84 Hz, 1 H), 6.67-6.72 (m, 1 H), 5.08-5.13 (m, 1 H), 4.60-4.67 (m, 2 H), 2.65-2.77 (m, 2 H), 2.49 (s, 3 H), 1.84-1.91 (m, 1 H), 1.53-1.69 (m, 3 H) | 520 | 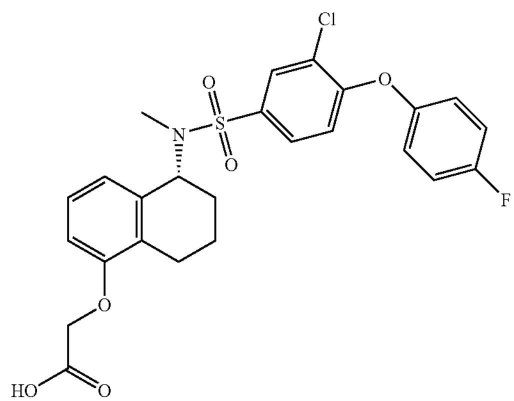 |

Example 7-1

((R)-5-{[5-(3-isopropyl-phenyl)-pyridine-2-sulfonyl]-methyl-amino}-5,6,7,8-tetrahydro-naphthalen-1-yloxy)-acetic acid

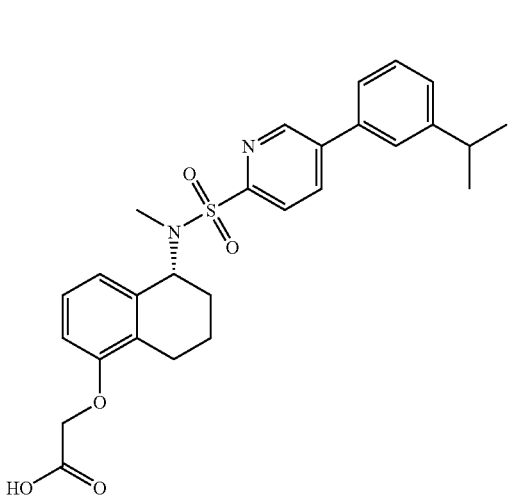

[(R)-5-[(5-Bromo-pyridine-2-sulfonylamino)-5,6,7,8,-tetrahydro-naphthalen-1-yloxy]-acetic acid tert-butyl ester

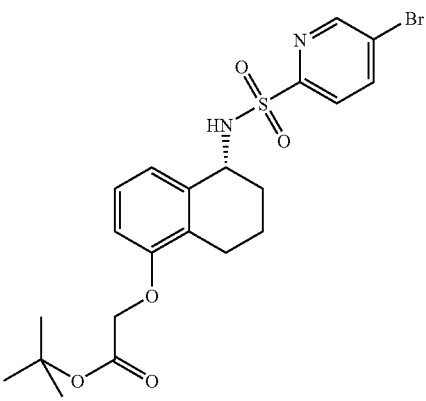

Starting with R-(5-amino-5,6,7,8-tetrahydro-naphthalen-1-yloxy)-acetic acid tert-butyl ester hydrochloride salt and 5-bromo-pyridine-2-sulfonyl chloride, using the method analogous to the one described for example 1-1, method A, 4$^{th}$ step, [(R)-5-[(5-bromo-pyridine-2-sulfonylamino)-5,6,78,-tetrahydro-naphthalen-1-yloxy]-acetic acid tert-butyl ester was obtained. MS cald. for $C_{21}H_{25}BrN_2O_5S$ 496, obsd. (ESI$^+$) [(M+H)$^+$] 497.

{(R)-5-[(5-Bromo-pyridine-2-sulfonyl)-methyl-amino]-5,6,7,8,-tetrahydro-naphthalen-1-yloxy}-acetic acid tert-butyl ester

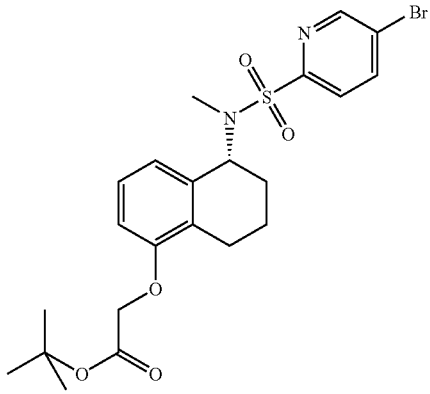

Starting with [(R)-5-[(5-bromo-pyridine-2-sulfonylamino)-5,6,78,-tetrahydro-naphthalen-1-yloxy]-acetic acid tert-butyl ester and methyl iodide, using the method analogous to the one described for example 6-1, 1$^{st}$ step, {(R)-5-[(5-bromo-pyridine-2-sulfonyl)-methyl-amino]-5,6,78,-tetrahydro-naphthalen-1-yloxy}-acetic acid tert-butyl ester was obtained. MS cald. for $C_{22}H_{27}BrN_2O_5S$ 510, obsd. (ESI$^+$) [(M+H)$^+$] 511.

((R)-5-{[5-(3-isopropyl-phenyl)-pyridine-2-sulfonyl]-methyl-amino}-5,6,7,8,-tetrahydro-naphthalen-1-yloxy)-acetic acid tert-butyl ester

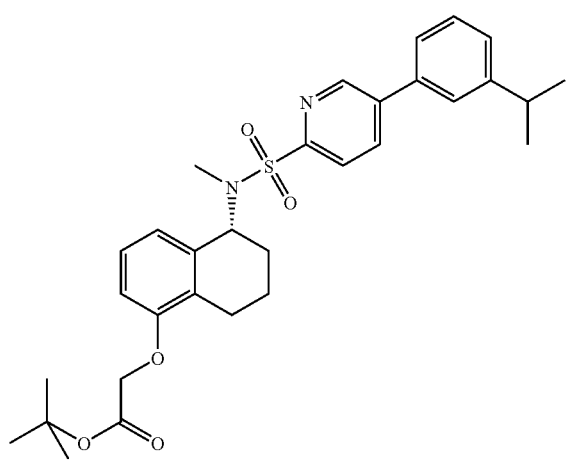

Starting with {(R)-5-[(5-bromo-pyridine-2-sulfonyl)-methyl-amino]-5,6,78,-tetrahydro-naphthalen-1-yloxy}-acetic acid tert-butyl ester and 3-isopropylphenylboronic acid, using the method analogous to the one described for example 3-2, method F, 2$^{nd}$ step, ((R)-5-{[5-(3-isopropyl-phenyl)-pyridine-2-sulfonyl]-methyl-amino}-5,6,7,8,-tetrahydro-naphthalen-1-yloxy)-acetic acid tert-butyl ester was obtained. MS cald. for $C_{31}H_{38}N_2O_5S$ 550, obsd. 551 (ESI$^+$) [(M+H)$^+$].

((R)-5-{[5-(3-isopropyl-phenyl)-pyridine-2-sulfonyl]-methyl-amino}-5,6,7,8,-tetrahydro-naphthalen-1-yloxy)-acetic acid

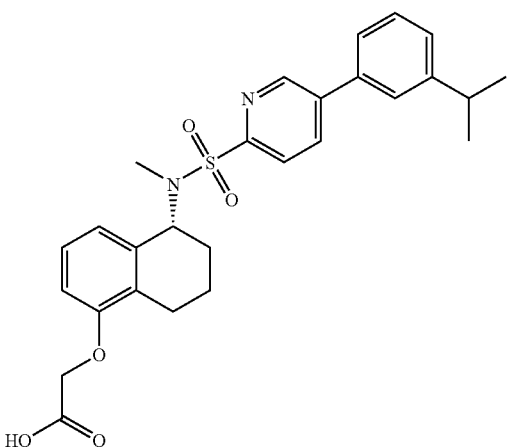

Starting with ((R)-5-{[5-(3-isopropyl-phenyl)-pyridine-2-sulfonyl]-methyl-amino}-5,6,7,8,-tetrahydro-naphthalen-1-yloxy)-acetic acid tert-butyl ester, using the method analogous to the one described for example 3-2, method F, 3$^{rd}$ step, ((R)-5-{[5-(3-isopropyl-phenyl)-pyridine-2-sulfonyl]-methyl-amino}-5,6,7,8,-tetrahydro-naphthalen-1-yloxy)-acetic acid was obtained. MS cald. for $C_{27}H_{30}N_2O_5S$ 494, obsd. 495 (ESI$^+$) [(M+H)$^+$].

Examples 7-2 to 7-4

The following examples 7-2 to 7-4 were prepared using methods analogous to those described for example 7-1, starting with (R)-(5-amino-5,6,7,8-tetrahydro-naphthalen-1-yloxy)-acetic acid tert-butyl ester hydrochloride salt and 5-bromo-pyridine-2-sulfonyl chloride, methyl iodide, and the appropriate commercially available aryl boronic acids

| Example No. | Systematic Name | ¹H NMR (400 MHz, DMSO-d₆) δ ppm | MS (ESI+, M + H⁺) | Structure |
|---|---|---|---|---|
| 7-2 | {(R)-5-[Methyl-(5-m-tolyl-pyridine-2-sulfonyl)-amino]-5,6,7,8-tetrahydro-naphthalen-1-yloxy}-acetic acid | 13.02 (br. s, 1 H), 9.13 (d, J = 1.7 Hz, 1 H), 8.39 (dd, J = 8.3, 2.3 Hz, 1 H), 8.08 (d, J = 8.3 Hz, 1 H), 7.69 (s, 1 H), 7.65 (d, J = 8.3 Hz, 1 H), 7.45 (t, J = 7.7 Hz, 1 H), 7.32 (d, J = 7.7 Hz, 1 H), 7.13 (t, J = 7.9 Hz, 1 H), 6.85 (d, J = 7.9 Hz, 1 H), 6.71 (d, J = 8.3 Hz, 1 H), 5.09-5.16 (m, 1 H), 4.66 (s, 2 H), 2.70-2.83 (m, 1 H), 2.63 (s, 3 H), 2.42 (s, 3 H), 2.37-2.48 (m, 1 H), 1.82-1.94 (m, 1 H), 1.71 (br. s, 3 H) | 467 | 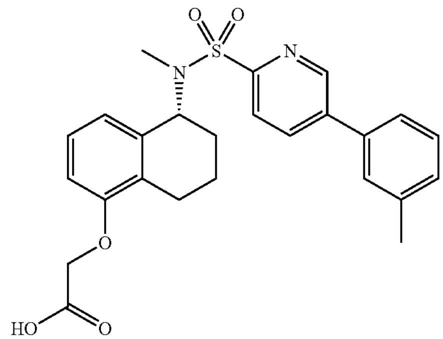 |
| 7-3 | ((R)-5-{[5-(2,3-Dimethyl-phenyl)-pyridine-2-sulfonyl]-methyl-amino}-5,6,7,8-tetrahydro-naphthalen-1-yloxy)-acetic acid | 13.01 (br. s, 1 H), 8.76 (dd, J = 2.1, 1.1 Hz, 1 H), 8.02-8.12 (m, 2 H), 7.30 (d, J = 7.0 Hz, 1 H), 7.24 (t, J = 7.6 Hz, 1 H), 7.13-7.18 (m, 1 H), 7.10 (t, J = 8.0 Hz, 1 H), 6.74 (d, J = 8.0 Hz, 1 H), 6.71 (d, J = 8.0 Hz, 1 H), 5.12 (dd, J = 9.0, 6.6 Hz, 1 H), 4.66 (s, 2 H), 2.70-2.80 (m, 1 H), 2.65 (s, 3 H), 2.39-2.48 (m, 1 H), 2.33 (s, 3 H), 2.14 (s, 3 H), 1.85-1.96 (m, 1 H), 1.71 (br. s, 3 H) | 481 | 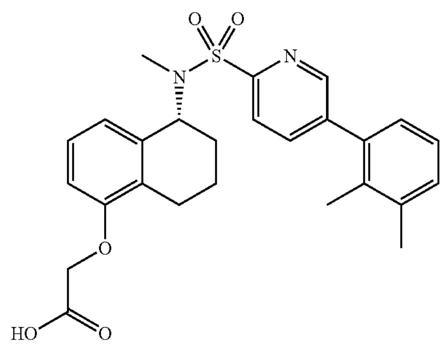 |
| 7-4 | ((R)-5-{[5-(3-tert-Butyl-5-methyl-phenyl)-pyridine-2-sulfonyl]-methyl-amino}-5,6,7,8-tetrahydro-naphthalen-1-yloxy)-acetic acid | 13.03 (br. s, 1 H), 9.12 (d, J = 2.0 Hz, 1 H), 8.39 (dd, J = 8.1, 2.0 Hz, 1 H), 8.07 (d, J = 8.1 Hz, 1 H), 7.61 (s, 1 H), 7.48 (s, 1 H), 7.35 (s, 1 H), 7.14 (t, J = 8.1 Hz, 1 H), 6.87 (d, J = 8.1 Hz, 1 H), 6.71 (d, J = 8.1 Hz, 1 H), 5.13 (t, J = 7.6 Hz, 1 H), 4.66 (s, 2 H), 2.70-2.81 (m, 1 H), 2.63 (s, 3 H), 2.42-2.47 (m, 1 H), 2.41 (s, 3 H), 1.82-1.97 (m, 1 H), 1.53-1.79 (m, 3 H), 1.35 (s, 9 H) | 523 | 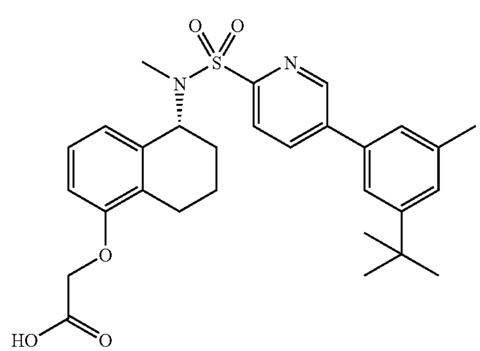 |

Example 8-1

((R)-5-{[3-(4-Chloro-benzenesulfonyl)-5-trifluoromethyl-benzenesulfonyl]-methyl-amino}-5,6,7,8-tetrahydro-naphthalen-1-yloxy)-acetic acid

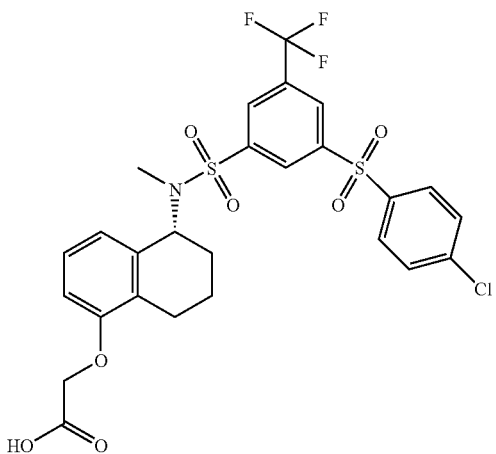

[(R)-5-(3-Fluoro-5-trifluoromethyl-benzenesulfonylamino)-5,6,7,8-tetrahydro-naphthalen-1-yloxy]-acetic acid tert-butyl ester

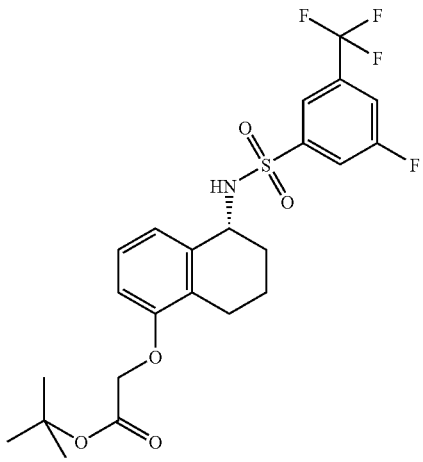

Starting with (R)-(5-amino-5,6,7,8-tetrahydro-naphthalen-1-yloxy)-acetic acid tert-butyl ester hydrochloride salt (1 g, 3.18 mmol) and 3-fluoro-5-trifluoromethyl-benzenesulfonyl chloride (1.09 g, 4.8 mmol), and using the method described for example 1-2, method B, 1$^{st}$ step, [(R)-5-(3-fluoro-5-trifluoromethyl-benzenesulfonylamino)-5,6,7,8-tetrahydro-naphthalen-1-yloxy]-acetic acid tert-butyl ester (1.3 g, 81.2%) was prepared as a white solid. MS cald. for $C_{18}H_{19}F_4N_3O_4S$ 503, obsd. 504 (ESI$^+$) [(M+H)$^+$].

{(R)-5-[(3-Fluoro-5-trifluoromethyl-benzenesulfonyl)-methyl-amino]-5,6,7,8-tetrahydro-naphthalen-1-yloxy}-acetic acid tert-butyl ester

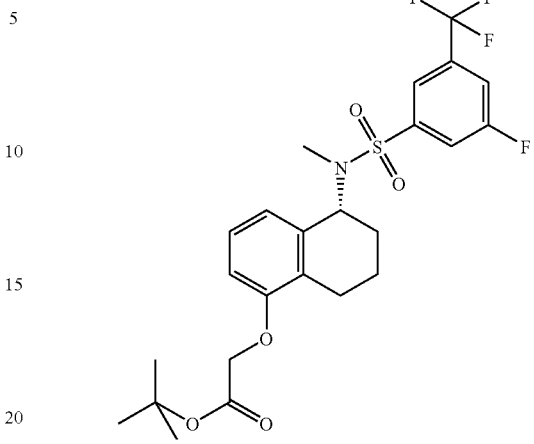

Starting with [(R)-5-(3-fluoro-5-trifluoromethyl-benzenesulfonylamino)-5,6,7,8-tetrahydro-naphthalen-1-yloxy]-acetic acid tert-butyl ester (1 g, 2 mmol) and methyl iodide (423 mg, 3 mmol), and using the method described for example 6-1, 1st step, {(R)-5-[(3-fluoro-5-trifluoromethyl-benzenesulfonyl)-methyl-amino]-5,6,7,8-tetrahydro-naphthalen-1-yloxy}-acetic acid tert-butyl ester (972 mg, 94%) was prepared as a white solid. MS cald. for $C_{24}H_{27}F_4NO_5S$ 517, obsd. 518 (ESI$^+$) [(M+H)$^+$].

((R)-5-{[3-(4-Chloro-phenylsulfanyl)-5-trifluoromethyl-benzenesulfonyl]-methyl-amino}-5,6,7,8-tetrahydro-naphthalen-1-yloxy)-acetic acid tert-butyl ester

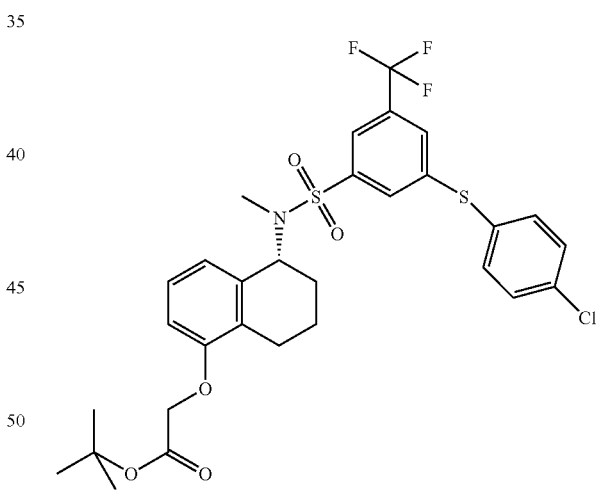

A mixture of {(R)-5-[(3-fluoro-5-trifluoromethyl-benzenesulfonyl)-methyl-amino]-5,6,7,8-tetrahydro-naphthalen-1-yloxy}-acetic acid tert-butyl ester (80.0 mg, 0.15 mmol), 4-chloro-benzenethiol (50 µL), and potassium carbonate (55.0 mg, 0.40 mmol) in N,N-dimethylformamide (1.0 mL) was heated in a microwave oven at 150° C. for 30 minutes. The resulting mixture was neutralized with 1N hydrochloric acid and then extracted with ethyl acetate (20 mL×3). The combined organic layers were washed with brine (20 mL×3), dried over anhydrous sodium sulfate, and concentrated in vacuo to afford ((R)-5-{[3-(4-chloro-phenylsulfanyl)-5-trifluoromethyl-benzenesulfonyl]-methyl-amino}-5,6,7,8-tetrahydro-naphthalen-1-yloxy)-acetic acid tert-butyl ester (67.5 mg, 70.2%) as a viscous oil, which was used for the next step without any further purification. MS cald. for $C_{30}H_{31}ClF_3NO_5S_2$ 641, obsd. 642 (ESI$^+$) [(M+H)$^+$].

159

((R)-5-{[3-(4-Chloro-benzenesulfonyl)-5-trifluoromethyl-benzenesulfonyl]-m ethyl-amino}-5,6,7,8-tetrahydro-naphthalen-1-yloxy)-acetic acid tert-butyl ester

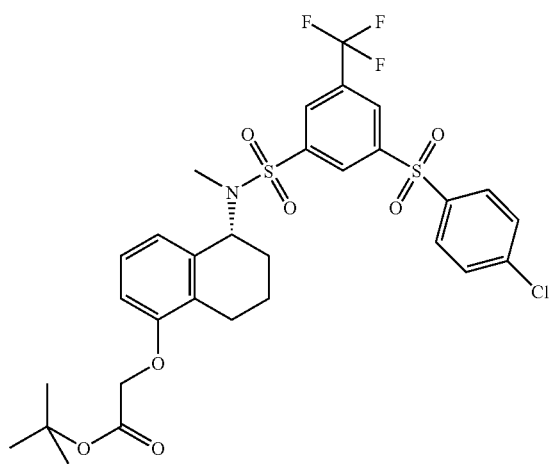

To a solution of ((R)-5-{[3-(4-chloro-phenylsulfanyl)-5-trifluoromethyl-benzenesulfonyl]-methyl-amino}-5,6,7,8-tetrahydro-naphthalen-1-yloxy)-acetic acid tert-butyl ester (45 mg, 0.07 mmol) in dichloromethane was added 3-chloroperoxybenzoic acid (m-CPBA, 85% active oxygen) (40.5 mg, 0.20 mmol) at 0° C. After being stirred at room temperature for 3 hours, the resulting mixture was concentrated under reduced pressure and purified by column chromatography (5% methanol in dichloromethane) to afford ((R)-5-{[3-(4-chloro-benzenesulfonyl)-5-trifluoromethyl-benzenesulfonyl]-methyl-amino}-5,6,7,8-tetrahydro-naphthalen-1-yloxy)-acetic acid tert-butyl ester (26.5 mg, 56%) as a semisolid. MS cald. for $C_{30}H_{31}ClF_3NO_7S_2$ 673, obsd. 674 (ESI$^+$) [(M+H)$^+$].

160

((R)-5-{[3-(4-Chloro-benzenesulfonyl)-5-trifluoromethyl-benzenesulfonyl]-m ethyl-amino}-5,6,7,8-tetrahydro-naphthalen-1-yloxy)-acetic acid

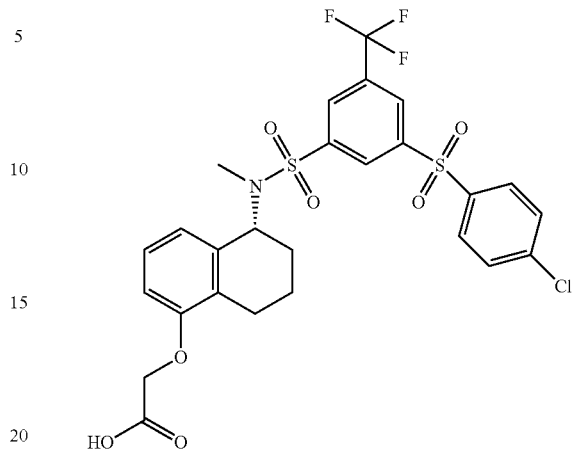

Starting from ((R)-5-{[3-(4-chloro-benzenesulfonyl)-5-trifluoromethyl benzenesulfonyl]-methyl-amino}-5,6,7,8-tetrahydro-naphthalen-1-yloxy)-acetic acid tert-butyl ester, and using the method described for example 2-2, method D, 4$^{th}$ step, ((R)-5-{[3-(4-chloro-benzenesulfonyl)-5-trifluoromethyl-benzenesulfonyl]-methyl-amino}-5,6,7,8-tetrahydro-naphthalen-1-yloxy)-acetic acid (10 mg, 44%) was obtained as a white solid. $^1$H NMR (400 MHz, methanol-d$_4$) δ ppm 8.56-8.60 (m, 2H), 8.42 (s, 1H), 8.07 (d, J=8.84 Hz, 2H), 7.64 (d, J=8.84 Hz, 2H), 6.94 (t, J=8.21 Hz, 1H), 6.67 (d, J=8.08 Hz, 1H) 6.53 (d, J=7.83 Hz, 1H), 5.19 (d, J=1.01 Hz, 1H), 4.66 (s, 2H), 2.86 (d, J=16.42 Hz, 1H), 2.56 (s, 3H), 2.44-2.54 (m, 1H), 1.82-1.90 (m, 1H), 1.55-1.69 (m, 1H), 1.46 (m, 3H); MS cald. for $C_{26}H_{23}ClF_3NO_7S_2$ 617, obsd. 618 (ESI$^+$) [(M+H)$^+$].

Example 8-2

The following example 8-2 was prepared by the method analogous to example 8-1, starting with (R)-(5-amino-5,6,7,8-tetrahydro-naphthalen-1-yloxy)-acetic acid tert-butyl ester hydrochloride salt and 3-fluoro-5-trifluoromethyl-benzenesulfonyl chloride, methyl iodide, and 4-chloro-benzenethiol.

| Example No | Systematic Name | $^1$H NMR (400 MHz, DMSO-d$_6$) δ ppm | MS (ESI+, M + H$^+$) | Structure |
|---|---|---|---|---|
| 8-2 | ((R)-5-{[3-(4-Fluoro-benzenesulfonyl)-5-trifluoromethyl-benzenesulfonyl]-methyl-amino}-5,6,7,8-tetrahydro-naphthalen-1-yloxy)-acetic acid | 8.53-8.61 (m, 2 H), 8.42 (s, 1 H), 8.16 (dd, J = 9.09, 5.05 Hz, 2 H), 7.37 (t, J = 8.72 Hz, 2 H), 6.92-7.02 (m, 1 H), 6.68 (d, J = 8.08 Hz, 1 H), 6.58 (d, J = 7.58 Hz, 1 H), 5.15-5.27 (m, 1 H), 4.67 (s, 2 H), 2.82-2.92 (m, 1 H), 2.56 (s, 3 H), 2.44-2.55 (m, 1 H), 1.82-1.94 (m, 1 H), 1.56-1.73 (m, 1 H), 1.42-1.55 (m, 3 H) | 618 | 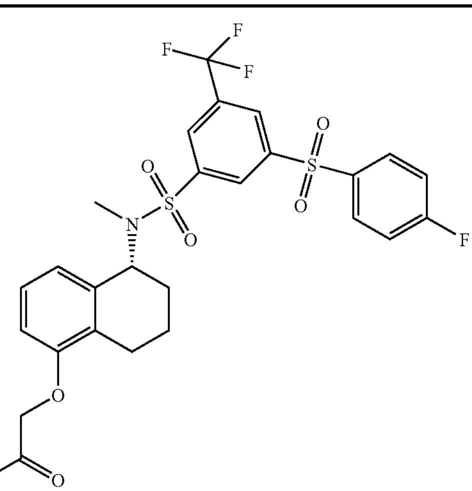 |

Activity and Use of the Compounds

The compounds of formula I possess valuable pharmacological properties. It has been found that said compounds are antagonists at the CRTH2 receptor and may be useful in treating diseases and disorders associated with that receptor such as asthma. The activity of the present compounds as CRTH2 receptor antagonists is demonstrated by the following biological assays.

Human CRTH2 Receptor Binding Assay

A whole cell receptor binding assay using [$^3$H]ramatroban as the competing radioactive ligand was employed to evaluate the compound binding activity to human CRTH2. The radioactive ligand [$^3$H]ramatroban was synthesized according to Sugimoto et. al. (*Eur. J. Pharmacol.* 524, 30-37, 2005) to a specific activity of 42 Ci/mmol.

A cell line stably expressing human CRTH2 was established by transfecting CHO-K1 cells with two mammalian expression vectors that harbored human CRTH2 and G-alpha16 cDNAs, respectively, using FuGene® 6 transfection reagent (from Roche). Stable clones expressing CRTH2 were selected by staining each clone with BM16 (BD Pharmingen™ from BD Biosciences, a division of Becton, Dickinson and Company), which is a rat monoclonal antibody to human CRTH2. The cells were maintained as monolayer cultures in Ham's F-12 medium containing 10% fetal bovine serum, 100 units/mL penicillin, 100 µg/mL streptomycin, 2 mM glutamine, 0.5 mg/mL G418 (geneticin) for CRTH2, and 0.2 mg/mL hygromycin-B (for G-alpha 16). For whole cell receptor binding assay, the monolayer cells were rinsed once with PBS (phosphate buffered saline), dissociated using ethylenediaminetetraacetate (Versene™ EDTA from the Lonza Inc.), and suspended in PBS containing 10 mM $MgCl_2$ and 0.06% BSA (bovine serum albumin) at $1.5 \times 10^6$ cells/mL.

The binding reactions (0.2 mL) were performed in 96-well plates at room temperature in PBS containing $1.5 \times 10^5$ cells, 10 mM $MgCl_2$, 0.06% BSA, 20 nM [$^3$H]ramatroban, and test compound at various concentrations. After 1 hour of binding reactions, the cells were harvested on GF™/B filter microplates (microtiter plates with embedded glass fiber from PerkinElmer, Inc.) and washed 5 times with PBS using a Filtermate™ Harvester (a cell harvester that harvests and washes cells from microplates from PerkinElmer, Inc.). The radioactivities bound to the cells were determined using a microplate scintillation counter (TopCount® NXT, from PerkinElmer, Inc.) after adding 50 µL of Microscint™ 20 scintillation fluid (from PerkinElmer, Inc.) to each well of the filter plates. The radioactivity from non-specific binding was determined by replacing compound with 10 µM of 15(R)-15-methyl $PGD_2$ (from Cayman Chemical Company) in the reaction mixtures. The radioactivity bound to the cells in the absence of compound (total binding) was determined by replacing compound with 0.25% of DMSO (dimethyl sulfoxide) in the reaction mixture. Specific binding data were obtained by subtracting the radioactivity of non-specific binding from each binding data.

The $IC_{50}$ value is defined as the concentration of the tested compound that is required for 50% inhibition of total specific binding. In order to calculate the $IC_{50}$ value, the percent inhibition data were determined for 7 concentrations for each compound. The percent inhibition for a compound at each concentration was calculated according to the following formula, [1-(specific binding in the presence of compound)/(total specific binding)]×100. The $IC_{50}$ value was then obtained by fitting the percent inhibition data to a sigmoidal dose-response (4 parameter logistic) model in the XLfit® software Excel add-in program [from ID Business Solutions Ltd., model 205, where $F(x)=(A+(B-A)/(1+((C/x)^\hat{}D)))$].

All the compounds of the foregoing examples were tested using the above Human CRTH2 Receptor Binding Assay (examples 1-1 to 8-2). The results of the assay showed that all of these compounds have binding activity exhibiting $IC_{50}$ values ranging from 0.0029 µM to 0.4061 µM. For instance, the following table shows the specific $IC_{50}$ values for some of these compounds:

| Example No. | Human CRTH2 Binding $IC_{50}$ (µM) |
|---|---|
| Example 1-2 | 0.0516 |
| Example 1-3 | 0.2000 |
| Example 1-6 | 0.1882 |
| Example 1-7 | 0.0526 |
| Example 1-8 | 0.0659 |
| Example 1-9 | 0.0841 |
| Example 1-10 | 0.0674 |
| Example 2-1 | 0.0764 |
| Example 2-2 | 0.0102 |
| Example 2-6 | 0.0603 |
| Example 2-9 | 0.0212 |
| Example 2-15 | 0.0752 |
| Example 2-17 | 0.1153 |
| Example 2-22 | 0.0317 |
| Example 2-42 | 0.0112 |
| Example 3-1 | 0.0551 |
| Example 3-3 | 0.2030 |
| Example 3-9 | 0.0749 |
| Example 3-16 | 0.0203 |
| Example 3-23 | 0.1241 |
| Example 3-30 | 0.0671 |
| Example 3-34 | 0.1570 |
| Example 3-41 | 0.0239 |
| Example 3-45 | 0.0059 |
| Example 3-48 | 0.0048 |
| Example 3-62 | 0.0707 |
| Example 4-1 | 0.0135 |
| Example 6-1 | 0.1465 |
| Example 8-1 | 0.0029 |

Calcium Flux Assay Using FLuorometric Imaging Plate Reader (FLIPR)

Cell Culture Conditions:

CHO-K1 cells previously transfected with G-alpha 16 were subsequently transfected with the human CRTH2 receptor and the neomycin resistance gene. Following selection in 800 µg/mL G418 (geneticin), individual clones were assayed for their receptor expression based on staining with an anti human CRTH2 IgG, followed by assaying for their response to 13,14-dihydro-15-keto Prostaglandin $D_2$ (DK-$PGD_2$) (ligand) in the $Ca^{2+}$ Flux assay. Positive clones were then cloned by limiting dilution cloning. The transfected cells were cultured in Ham's F-12 medium supplemented with 10% fetal bovine serum, 2 mM glutamine, 100 U/mL penicillin/100 µg/mL streptomycin, 200 µg/mL hygromycin B, and 800 µg/mL G418 (geneticin). Cells were harvested with trypsin-EDTA (trypsin-ethylenediaminetetraacetic acid) and counted using ViaCount® reagent (from Guava Technologies, Inc. which contains two DNA-binding dyes that enable the reagent user to distinguish between viable and non-viable cells). The cell suspension volume was adjusted to $2.5 \times 10^5$ cells/mL with complete growth media. Aliquots of 50 µL were dispensed into BD Falcon™ 384 well black/clear microplates (from BD Biosciences, a division of Becton, Dickinson and Company) and the microplates were placed in a 37° C. $CO_2$ incubator overnight. The following day, the microplates were used in the assay.

Dye Loading and Assay:

Loading Buffer containing dye (from the FLIPR® Calcium 3 Assay Kit from Molecular Devices, a division of MDS Analytical Technologies and MDS Inc.) was prepared by dissolving the contents of one bottle into 200 mL Hank's Balanced Salt Solution containing 20 mM HEPES (4-(2-hydroxyethyl)-1-piperazineethanesulfonic acid) and 2.5 mM probenecid. Growth media was removed from the cell plates and 25 μL of Hank's Balanced Salt Solution (HBSS) containing 20 mM HEPES, 0.05% BSA and 2.5 mM probenecid was added to each well followed by 25 μL of diluted dye using a Multidrop dispenser. The plates were then incubated for 1 hour at 37° C.

During the incubation, test compound plates were prepared by adding 90 μL of HBSS/20 mM HEPES/0.005% BSA buffer to the 2 μL of serial diluted compounds. To prepare serial diluted compounds, 20 mM stocks of compounds were dissolved in 100% DMSO. The compound dilution plate was set up as follows: well #1 received 5 μL of compound plus 10 μL of DMSO. Wells 2-10 received 10 μL of DMSO. 5 μL was mixed and transferred from well #1 into well #2.1:3 serial dilutions were continued out 10 steps. 2 μL of diluted compound was transferred into duplicate wells of a 384 well "assay plate" and then 90 μL of buffer was added.

After incubation, both the cell and "assay plate" plates were brought to the fluorometric imaging plate reader (FLIPR®) and 20 μL of the diluted compounds were transferred to the cell plates by the FLIPR®. Plates were then incubated for 1 hour at room temperature. After the 1 hour incubation, plates were returned to the FLIPR® and 20 μL of 4.5× concentrated ligand was added to the cell plates. During the assay, fluorescence readings were taken simultaneously from all 384 wells of the cell plate every 1.5 seconds. Five readings were taken to establish a stable baseline, then 20 μL of sample was rapidly (30 μL/sec) and simultaneously added to each well of the cell plate. The fluorescence was continuously monitored before, during and after sample addition for a total elapsed time of 100 seconds. Responses (increase in peak fluorescence) in each well following agonist addition were determined. The initial fluorescence reading from each well, prior to ligand stimulation, was used as a zero baseline value for the data from that well. The responses were expressed as % inhibition of the buffer control. The $IC_{50}$ value, defined as the concentration of a compound that was required for 50% inhibition of the buffer control, was calculated by fitting the percent inhibition data for 10 concentrations to a sigmoidal dose-response (4 parameter logistic) model using Genedata Screener® Condoseo software program [from Genedata AG, model 205, where $F(x)=(A+(B-A)/(1+((C/x)^D)))$].

Representative compounds tested in the binding assay were tested using the above FLIPR® assay. The results of the FLIPR® assay showed that all of the representative compounds tested in this assay have activity exhibiting $IC_{50}$ values ranging from 0.0001 μM to 12.37 μM.

DK-PGD$_2$-Induced IL-13 Production Assay in Th2 Cells

Inhibition of 13,14-dihydro-15-keto Prostaglandin $D_2$ (DK-PGD$_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by CD4$^+$ cell purification using a CD4$^+$ T Cell Isolation Kit II (from Miltenyi Biotec Inc.). The CD4$^+$ T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to phycoerythrin (PE).

To determine cellular inhibitory potency, compounds at various concentrations were incubated with $2.5 \times 10^4$ Th2 cells and 500 nM DK-PGD$_2$ for 4 hrs at 37° C. in 200 μL of X-VIVO 15® medium containing 10% human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and $IC_{50}$ calculations.

The percent inhibition of interleukin 13 (IL-13) production for a compound at various concentrations was calculated according to the following formula, [1-(IL-13 production in the presence of compound)/(IL-13 production in the presence of 0.15% DMSO)]×100. The $IC_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where $F(x)=(A+(B-A)/(1+((C/x)^D)))$].

Representative compounds tested in the binding assay were tested using the foregoing DK-PGD$_2$-induced IL-13 production assay. The results of the DK-PGD$_2$-induced IL-13 production assay showed that all of the representative compounds tested in this assay have activity in inhibiting IL-13 production, exhibiting $IC_{50}$ values ranging from 0.0046 μM to 3.6723 μM.

Thus, the compounds of the present are useful since the compounds tested show some activity in at least one of the above three assays (i.e., binding at the CRTH2 receptor), and therefore may be useful as antagonists in treating diseases and disorders associated with this receptor such as asthma.

In one embodiment, the present invention relates to a method for the treatment and/or prevention of diseases and disorders which are associated with the modulation of CRTH2 receptors, which method comprises administering a therapeutically effective amount of a compound of formula I to a human being or animal. A method for the treatment and/or prevention of an inflammatory or allergic disease or disorder is preferred. Such diseases or disorders may include (but are not limited to) asthma, chronic obstructive pulmonary disease (COPD), allergic rhinitis, allergic inflammation, and atopic dermatitis.

The present invention is also directed to the administration of a therapeutically effective amount of a compound of formula I in combination or association with other drugs or active agents for the treatment of inflammatory or allergic diseases and disorders. In one embodiment, the present invention relates to a method for the treatment and/or prevention of such diseases or disorders comprising administering to a human or animal simultaneously, sequentially, or separately, a therapeutically effective amount of a compound of formula I and another drug or active agent (such as another anti-inflammatory or anti-allergic drug or agent). These other drugs or active agents may have the same, similar, or a completely different mode of action. Suitable other drugs or active agents may include, but are not limited to: Beta2-adrenergic agonists such as albuterol or salmeterol; corticosteroids such as dexamethasone or fluticasone; antihistamines such as loratidine; leukotriene antagonists such as montelukast or zafirlukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and pimecrolimus; other antagonists of PGD2 acting at other receptors such as DP antagonists; inhibitors of phoshodiesterase type 4 such as cilomilast; drugs that modulate cytokine production such as inhibitors of TNF-alpha converting enzyme (TACE); drugs that modulate the activity of Th2 cytokines IL-4 and IL-5 such as blocking monoclonal antibodies and soluble receptors; PPAR-gamma agonists such as rosiglitazone; and 5-lipoxygenase inhibitors such as zileuton.

Unless stated to the contrary, all compounds in the examples were prepared and characterized as described. All patents and publications cited herein are hereby incorporated by reference in their entirety.

The invention claimed is:

1. A compound of formula I:

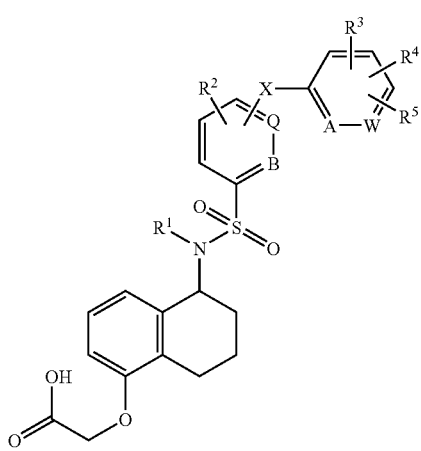

I or a pharmaceutically acceptable salt or ester thereof; wherein:

X is a direct bond, oxygen, or —S(O)$_2$—; and wherein X is bonded to the ring containing Q and B by substitution of a hydrogen atom of a ring carbon atom;

A, B, Q, and W, independently of each other, are carbon or nitrogen with the proviso that: (1) B and Q are not both nitrogen, (2) W and A are not both nitrogen, and (3) when A, B, Q or W is nitrogen the nitrogen is unsubstituted;

$R^1$ is hydrogen or methyl;

$R^2$ is selected from the group consisting of:
(1) hydrogen;
(2) halogen;
(3) lower alkyl optionally substituted by halogen; and
(4) lower cycloalkyl optionally substituted by lower alkyl;

$R^3$, $R^4$ and $R^5$ are bonded to the ring containing A and W by substitution of a hydrogen atom of a ring carbon atom; and $R^3$, $R^4$ and $R^5$, independently of each other, are selected from the group consisting of:
(1) hydrogen;
(2) hydroxyl;
(3) halogen;
(4) nitro;
(5) cyano;
(6) lower alkyl optionally substituted by halogen or hydroxyl;
(7) lower alkoxy optionally substituted by halogen;
(8) lower alkanoyl;
(9) carbamoyl, lower alkylaminocarbonyl, or lower dialkylaminocarbonyl;
(10) lower alkylcarbonylamino;
(11) lower alkylsulfinyl or lower cycloalkylsulfinyl;
(12) lower alkylsulfonyl or lower cycloalkylsulfonyl; and
(13) trimethylsilyl;

or alternatively, one of $R^3$, $R^4$ or $R^5$ is hydrogen and the remaining two of $R^3$, $R^4$ or $R^5$ are bound together with the carbon atom to which they are attached to form a ring of 5 or 6 carbon atoms.

2. A compound of claim 1 which is an (R)-enantiomer.

3. A compound of claim 1 wherein A, B, Q, and W are carbon.

4. A compound of claim 1 wherein A is nitrogen and B, Q, and W are carbon.

5. A compound of claim 1 wherein W is nitrogen and A, B, and Q are carbon.

6. A compound of claim 1 wherein B is nitrogen and A, Q, and W are carbon.

7. A compound of claim 1 wherein Q is nitrogen and A, B, and W are carbon.

8. A compound of claim 1 wherein A and B are nitrogen and Q and W are carbon.

9. A compound of claim 1 wherein A and Q are nitrogen and B and W are carbon.

10. A compound of claim 1 wherein W and B are nitrogen and A and Q are carbon.

11. A compound of claim 1 wherein W and Q are nitrogen and A and B are carbon.

12. A compound of claim 1 wherein X is a direct bond.

13. A compound of claim 1 wherein X is oxygen.

14. A compound of claim 1 wherein $R^1$ is hydrogen.

15. A compound of claim 1 wherein $R^1$ is methyl.

16. A compound of claim 1 wherein X is attached to the 3 or 4 position and $R^2$ is attached to the 5 position on the ring containing B and Q.

17. A compound of formula I according to claim 1 wherein at least one of $R^3$, $R^4$, and $R^5$ is hydrogen attached to position 10 and the two remaining R groups are attached to positions 9 and 11 on the ring containing A and W.

18. A compound of claim 1 wherein $R^2$ is selected from the group consisting of:
(1) hydrogen;
(2) bromo;
(3) chloro;
(4) methyl; and
(5) trifluoromethyl.

19. A compound of claim 1 wherein R³, R⁴ and R⁵, independently of each other, are selected from the group consisting of:
(1) hydrogen;
(2) halogen;
(3) nitro;
(4) lower alkyl optionally substituted by halogen or hydroxyl;
(5) lower alkoxy optionally substituted by halogen;
(6) lower alkanoyl; and
(7) carbamoyl, lower alkylaminocarbonyl, or lower dialkylaminocarbonyl; and
(8) lower alkylsulfonyl or lower cycloalkylsulfonyl.

20. A compound of claim 1 wherein R³, R⁴ and R⁵, independently of each other, are selected from the group consisting of:
(1) hydrogen;
(2) fluoro or chloro;
(3) nitro;
(4) isopropyl or tert-butyl;
(5) methoxy;
(6) acetyl;
(7) carbamoyl; and
(8) methylsulfonyl or ethylsulfonyl.

21. A compound of claim 1 selected from the group consisting of:
[(R)-5-(4'-Methyl-biphenyl-4-sulfonylamino)-5,6,7,8-tetrahydro-naphthalen-1-yloxy]-acetic acid;
[5-(3-Phenoxy-benzenesulfonylamino)-5,6,7,8-tetrahydro-naphthalen-1-yloxy]-acetic acid;
[5-(Biphenyl-3-sulfonylamino)-5,6,7,8-tetrahydro-naphthalen-1-yloxy]-acetic acid;
[5-(4-Phenoxy-benzenesulfonylamino)-5,6,7,8-tetrahydro-naphthalen-1-yloxy]-acetic acid;
[5-(6-Phenoxy-pyridine-3-sulfonylamino)-5,6,7,8-tetrahydro-naphthalen-1-yloxy]-acetic acid;
[(R)-5-(4'-Fluoro-biphenyl-4-sulfonylamino)-5,6,7,8-tetrahydro-naphthalen-1-yloxy]-acetic acid;
[(R)-5-(4'-Methoxy-biphenyl-4-sulfonylamino)-5,6,7,8-tetrahydro-naphthalen-1-yloxy]-acetic acid;
[(R)-5-(4'-Chloro-biphenyl-4-sulfonylamino)-5,6,7,8-tetrahydro-naphthalen-1-yloxy]-acetic acid;
[(R)-5-(4'-Acetyl-biphenyl-4-sulfonylamino)-5,6,7,8-tetrahydro-naphthalen-1-yloxy]-acetic acid;
[(R)-5-(4'-Methyl-biphenyl-3-sulfonylamino)-5,6,7,8-tetrahydro-naphthalen-1-yloxy]-acetic acid;
[(R)-5-(4-Phenoxy-benzenesulfonylamino)-5,6,7,8-tetrahydro-naphthalen-1-yloxy]-acetic acid;
{(R)-5-[4-(2-Chloro-phenoxy)-benzenesulfonylamino]-5,6,7,8-tetrahydro-naphthalen-1-yloxy}-acetic acid;
{5-[5-Bromo-6-(2-chloro-4-fluoro-phenoxy)-pyridine-3-sulfonylamino]-5,6,7,8-tetrahydro-naphthalen-1-yloxy}-acetic acid;
{(R)-5-[3-Chloro-4-(4-chloro-phenoxy)-benzenesulfonylamino]-5,6,7,8-tetrahydro-naphthalen-1-yloxy}-acetic acid;
{5-[5-Bromo-6-(2-fluoro-phenoxy)-pyridine-3-sulfonylamino]-5,6,7,8-tetrahydro-naphthalen-1-yloxy}-acetic acid;
{5-[5-Bromo-6-(2-chloro-phenoxy)-pyridine-3-sulfonylamino]-5,6,7,8-tetrahydro-naphthalen-1-yloxy}-acetic acid;
{5-[5-Bromo-6-(3-chloro-phenoxy)-pyridine-3-sulfonylamino]-5,6,7,8-tetrahydro-naphthalen-1-yloxy}-acetic acid;
{5-[5-Bromo-6-(3-cyano-phenoxy)-pyridine-3-sulfonylamino]-5,6,7,8-tetrahydro-naphthalen-1-yloxy}-acetic acid;
{5-[5-Bromo-6-(4-cyano-phenoxy)-pyridine-3-sulfonylamino]-5,6,7,8-tetrahydro-naphthalen-1-yloxy}-acetic acid;
{5-[5-Bromo-6-(4-fluoro-phenoxy)-pyridine-3-sulfonylamino]-5,6,7,8-tetrahydro-naphthalen-1-yloxy}-acetic acid;
{5-[5-Bromo-6-(3-isopropyl-phenoxy)-pyridine-3-sulfonylamino]-5,6,7,8-tetrahydro-naphthalen-1-yloxy}-acetic acid;
{5-[5-Bromo-6-(4-isopropyl-phenoxy)-pyridine-3-sulfonylamino]-5,6,7,8-tetrahydro-naphthalen-1-yloxy}-acetic acid;
{5-[5-Bromo-6-(4-methoxy-phenoxy)-pyridine-3-sulfonylamino]-5,6,7,8-tetrahydro-naphthalen-1-yloxy}-acetic acid;
{5-[5-Bromo-6-(3,4-dimethyl-phenoxy)-pyridine-3-sulfonylamino]-5,6,7,8-tetrahydro-naphthalen-1-yloxy}-acetic acid;
{5-[5-Bromo-6-(4-chloro-2-methyl-phenoxy)-pyridine-3-sulfonylamino]-5,6,7,8-tetrahydro-naphthalen-1-yloxy}-acetic acid;
{5-[5-Bromo-6-(4-ethyl-phenoxy)-pyridine-3-sulfonylamino]-5,6,7,8-tetrahydro-naphthalen-1-yloxy}-acetic acid;
{5-[5-Bromo-6-(3,5-dimethyl-phenoxy)-pyridine-3-sulfonylamino]-5,6,7,8-tetrahydro-naphthalen-1-yloxy}-acetic acid;
[5-(5-Bromo-6-phenoxy-pyridine-3-sulfonylamino)-5,6,7,8-tetrahydro-naphthalen-1-yloxy]-acetic acid;
{5-[5-Bromo-6-(indan-5-yloxy)-pyridine-3-sulfonylamino]-5,6,7,8-tetrahydro-naphthalen-1-yloxy}-acetic acid;
[5-(5-Bromo-6-m-tolyloxy-pyridine-3-sulfonylamino)-5,6,7,8-tetrahydro-naphthalen-1-yloxy]-acetic acid;
[5-(5-Bromo-6-o-tolyloxy-pyridine-3-sulfonylamino)-5,6,7,8-tetrahydro-naphthalen-1-yloxy]-acetic acid;
[5-(5-Bromo-6-p-tolyloxy-pyridine-3-sulfonylamino)-5,6,7,8-tetrahydro-naphthalen-1-yloxy]-acetic acid;
{5-[5-Bromo-6-(4-chloro-phenoxy)-pyridine-3-sulfonylamino]-5,6,7,8-tetrahydro-naphthalen-1-yloxy}-acetic acid;
(5-{5-Bromo-6-[4-(2-hydroxy-ethyl)-phenoxy]-pyridine-3-sulfonylamino}-5,6,7,8-tetrahydro-naphthalen-1-yloxy)-acetic acid;
{(R)-5-[5-Chloro-6-(4-chloro-phenoxy)-pyridine-3-sulfonylamino]-5,6,7,8-tetrahydro-naphthalen-1-yloxy}-acetic acid;
{(R)-5-[5-Bromo-6-(4-fluoro-phenoxy)-pyridine-3-sulfonylamino]-5,6,7,8-tetrahydro-naphthalen-1-yloxy}-acetic acid;
{(R)-5-[5-Bromo-6-(4-chloro-phenoxy)-pyridine-3-sulfonylamino]-5,6,7,8-tetrahydro-naphthalen-1-yloxy}-acetic acid;
{(R)-5-[5-Bromo-6-(2-chloro-phenoxy)-pyridine-3-sulfonylamino]-5,6,7,8-tetrahydro-naphthalen-1-yloxy}-acetic acid;
{(R)-5-[5-Bromo-6-(3-chloro-phenoxy)-pyridine-3-sulfonylamino]-5,6,7,8-tetrahydro-naphthalen-1-yloxy}-acetic acid;
{(R)-5-[5-Bromo-6-(2-chloro-4-fluoro-phenoxy)-pyridine-3-sulfonylamino]-5,6,7,8-tetrahydro-naphthalen-1-yloxy}-acetic acid;
[(R)-5-(5-Bromo-6-phenoxy-pyridine-3-sulfonylamino)-5,6,7,8-tetrahydro-naphthalen-1-yloxy]-acetic acid;

{(R)-5-[3-Chloro-4-(3-chloro-phenoxy)-benzenesulfonylamino]-5,6,7,8-tetrahydro-naphthalen-1-yloxy}-acetic acid;
{(R)-5-[3-Chloro-4-(4-fluoro-phenoxy)-benzenesulfonylamino]-5,6,7,8-tetrahydro-naphthalen-1-yloxy}-acetic acid;
{(R)-5-[3-Chloro-4-(2-chloro-phenoxy)-benzenesulfonylamino]-5,6,7,8-tetrahydro-naphthalen-1-yloxy}-acetic acid;
{(R)-5-[3-Chloro-4-(4-chloro-2-fluoro-phenoxy)-benzenesulfonylamino]-5,6,7,8-tetrahydro-naphthalen-1-yloxy}-acetic acid;
{(R)-5-[3-Chloro-4-(2-chloro-4-fluoro-phenoxy)-benzenesulfonylamino]-5,6,7,8-tetrahydro-naphthalen-1-yloxy}-acetic acid;
[(R)-5-(3-Chloro-4-phenoxy-benzenesulfonylamino)-5,6,7,8-tetrahydro-naphthalen-1-yloxy]-acetic acid;
{(R)-5-[2-Chloro-4-(4-fluoro-phenoxy)-benzenesulfonylamino]-5,6,7,8-tetrahydro-naphthalen-1-yloxy}-acetic acid;
{(R)-5-[2-Chloro-4-(2-chloro-phenoxy)-benzenesulfonylamino]-5,6,7,8-tetrahydro-naphthalen-1-yloxy}-acetic acid;
{(R)-5-[2-Chloro-4-(2-chloro-4-fluoro-phenoxy)-benzenesulfonylamino]-5,6,7,8-tetrahydro-naphthalen-1-yloxy}-acetic acid;
[(R)-5-(2-Chloro-4-phenoxy-benzenesulfonylamino)-5,6,7,8-tetrahydro-naphthalen-1-yloxy]-acetic acid;
{(R)-5-[2-Chloro-4-(4-chloro-phenoxy)-benzenesulfonylamino]-5,6,7,8-tetrahydro-naphthalen-1-yloxy}-acetic acid;
{(R)-5-[2-Chloro-4-(3-chloro-phenoxy)-benzenesulfonylamino]-5,6,7,8-tetrahydro-naphthalen-1-yloxy}-acetic acid;
{(R)-5-[4-(4-Fluoro-phenoxy)-3-trifluoromethyl-benzenesulfonylamino]-5,6,7,8-tetrahydro-naphthalen-1-yloxy}-acetic acid;
{(R)-5-[4-(2-Chloro-phenoxy)-3-trifluoromethyl-benzenesulfonylamino]-5,6,7,8-tetrahydro-naphthalen-1-yloxy}-acetic acid;
{(R)-5-[4-(4-Chloro-2-fluoro-phenoxy)-3-trifluoromethyl-benzenesulfonylamino]-5,6,7,8-tetrahydro-naphthalen-1-yloxy}-acetic acid;
{(R)-5-[4-(2-Chloro-4-fluoro-phenoxy)-3-trifluoromethyl-benzenesulfonylamino]-5,6,7,8-tetrahydro-naphthalen-1-yloxy}-acetic acid;
[(R)-5-(4-Phenoxy-3-trifluoromethyl-benzenesulfonylamino)-5,6,7,8-tetrahydro-naphthalen-1-yloxy]-acetic acid;
{(R)-5-[4-(4-Chloro-phenoxy)-3-trifluoromethyl-benzenesulfonylamino]-5,6,7,8-tetrahydro-naphthalen-1-yloxy}-acetic acid;
{(R)-5-[4-(3-Chloro-phenoxy)-3-trifluoromethyl-benzenesulfonylamino]-5,6,7,8-tetrahydro-naphthalen-1-yloxy}-acetic acid;
{5-[4-(4-Fluoro-pyridin-2-yl)-benzenesulfonylamino]-5,6,7,8-tetrahydro-naphthalen-1-yloxy}-acetic acid;
[(R)-5-(2'-Chloro-biphenyl-4-sulfonylamino)-5,6,7,8-tetrahydro-naphthalen-1-yloxy]-acetic acid;
{5-[4-(2-Fluoro-pyridin-3-yl)-benzenesulfonylamino]-5,6,7,8-tetrahydro-naphthalen-1-yloxy}-acetic acid;
{5-[4-(6-Fluoro-pyridin-3-yl)-benzenesulfonylamino]-5,6,7,8-tetrahydro-naphthalen-1-yloxy}-acetic acid;
{5-[4-(5-Fluoro-pyridin-3-yl)-benzenesulfonylamino]-5,6,7,8-tetrahydro-naphthalen-1-yloxy}-acetic acid;
{5-[4-(6-Methyl-pyridin-3-yl)-benzenesulfonylamino]-5,6,7,8-tetrahydro-naphthalen-1-yloxy}-acetic acid;
{5-[4-(6-Methyl-pyridin-2-yl)-benzenesulfonylamino]-5,6,7,8-tetrahydro-naphthalen-1-yloxy}-acetic acid;
{5-[4-(3-Methyl-pyridin-2-yl)-benzenesulfonylamino]-5,6,7,8-tetrahydro-naphthalen-1-yloxy}-acetic acid;
{5-[4-(6-Methoxy-pyridin-2-yl)-benzenesulfonylamino]-5,6,7,8-tetrahydro-naphthalen-1-yloxy}-acetic acid;
{5-[4-(5-Methyl-pyridin-3-yl)-benzenesulfonylamino]-5,6,7,8-tetrahydro-naphthalen-1-yloxy}-acetic acid;
{5-[4-(6-Trifluoromethyl-pyridin-3-yl)-benzenesulfonylamino]-5,6,7,8-tetrahydro-naphthalen-1-yloxy}-acetic acid;
{5-[4-(2-Chloro-5-methyl-pyridin-3-yl)-benzenesulfonylamino]-5,6,7,8-tetrahydro-naphthalen-1-yloxy}-acetic acid;
{5-[4-(5-Methanesulfonyl-pyridin-3-yl)-benzenesulfonylamino]-5,6,7,8-tetrahydro-naphthalen-1-yloxy}-acetic acid;
{5-[4-(6-Fluoro-5-methyl-pyridin-3-yl)-benzenesulfonylamino]-5,6,7,8-tetrahydro-naphthalen-1-yloxy}-acetic acid;
{5-[4-(2-Methyl-pyridin-3-yl)-benzenesulfonylamino]-5,6,7,8-tetrahydro-naphthalen-1-yloxy}-acetic acid;
[5-(2'-Chloro-biphenyl-4-sulfonylamino)-5,6,7,8-tetrahydro-naphthalen-1-yloxy]-acetic acid;
[5-(3'-Chloro-biphenyl-4-sulfonylamino)-5,6,7,8-tetrahydro-naphthalen-1-yloxy]-acetic acid;
[5-(4'-Chloro-biphenyl-4-sulfonylamino)-5,6,7,8-tetrahydro-naphthalen-1-yloxy]-acetic acid;
[(R)-5-(4'-Hydroxy-biphenyl-4-sulfonylamino)-5,6,7,8-tetrahydro-naphthalen-1-yloxy]-acetic acid;
[(R)-5-(3'-Acetyl-biphenyl-4-sulfonylamino)-5,6,7,8-tetrahydro-naphthalen-1-yloxy]-acetic acid;
[(R)-5-(2',3'-Dichloro-biphenyl-4-sulfonylamino)-5,6,7,8-tetrahydro-naphthalen-1-yloxy]-acetic acid;
[(R)-5-(2',5'-Dimethoxy-biphenyl-4-sulfonylamino)-5,6,7,8-tetrahydro-naphthalen-1-yloxy]-acetic acid;
[(R)-5-(2',6'-Dimethoxy-biphenyl-4-sulfonylamino)-5,6,7,8-tetrahydro-naphthalen-1-yloxy]-acetic acid;
[(R)-5-(2',5'-Dichloro-biphenyl-4-sulfonylamino)-5,6,7,8-tetrahydro-naphthalen-1-yloxy]-acetic acid;
[(R)-5-(2',5'-Dimethyl-biphenyl-4-sulfonylamino)-5,6,7,8-tetrahydro-naphthalen-1-yloxy]-acetic acid;
[(R)-5-(4'-Dimethylcarbamoyl-biphenyl-4-sulfonylamino)-5,6,7,8-tetrahydro-naphthalen-1-yloxy]-acetic acid;
[(R)-5-(2',3'-Dimethoxy-biphenyl-4-sulfonylamino)-5,6,7,8-tetrahydro-naphthalen-1-yloxy]-acetic acid;
[(R)-5-(5'-Chloro-2'-methyl-biphenyl-4-sulfonylamino)-5,6,7,8-tetrahydro-naphthalen-1-yloxy]-acetic acid;
[(R)-5-(3'-Dimethylcarbamoyl-biphenyl-4-sulfonylamino)-5,6,7,8-tetrahydro-naphthalen-1-yloxy]-acetic acid;
[(R)-5-(2,4'-Dimethyl-biphenyl-4-sulfonylamino)-5,6,7,8-tetrahydro-naphthalen-1-yloxy]-acetic acid;
[(R)-5-(2,3'-Dimethyl-biphenyl-4-sulfonylamino)-5,6,7,8-tetrahydro-naphthalen-1-yloxy]-acetic acid;
[(R)-5-(2,2'-Dimethyl-biphenyl-4-sulfonylamino)-5,6,7,8-tetrahydro-naphthalen-1-yloxy]-acetic acid;
[(R)-5-(4'-Chloro-2-methyl-biphenyl-4-sulfonylamino)-5,6,7,8-tetrahydro-naphthalen-1-yloxy]-acetic acid;
[(R)-5-(4'-Ethoxy-2-methyl-biphenyl-4-sulfonylamino)-5,6,7,8-tetrahydro-naphthalen-1-yloxy]-acetic acid;
[(R)-5-(4'-Methoxy-2,3',5'-trimethyl-biphenyl-4-sulfonylamino)-5,6,7,8-tetrahydro-naphthalen-1-yloxy]-acetic acid;

[(R)-5-(3',4'-Dichloro-2-methyl-biphenyl-4-sulfonylamino)-5,6,7,8-tetrahydro-naphthalen-1-yloxy]-acetic acid;
[(R)-5-(3'-Nitro-biphenyl-4-sulfonylamino)-5,6,7,8-tetrahydro-naphthalen-1-yloxy]-acetic acid;
[(R)-5-(2',4'-Dichloro-biphenyl-4-sulfonylamino)-5,6,7,8-tetrahydro-naphthalen-1-yloxy]-acetic acid;
[(R)-5-(4'-Methyl-3'-nitro-biphenyl-4-sulfonylamino)-5,6,7,8-tetrahydro-naphthalen-1-yloxy]-acetic acid;
[(R)-5-(3'-Methylsulfanyl-biphenyl-4-sulfonylamino)-5,6,7,8-tetrahydro-naphthalen-1-yloxy]-acetic acid;
[(R)-5-(3'-tert-Butyl-5'-methyl-biphenyl-4-sulfonylamino)-5,6,7,8-tetrahydro-naphthalen-1-yloxy]-acetic acid;
[(R)-5-(3'-Trifluoromethyl-biphenyl-4-sulfonylamino)-5,6,7,8-tetrahydro-naphthalen-1-yloxy]-acetic acid;
[(R)-5-(3'-Isopropyl-biphenyl-4-sulfonylamino)-5,6,7,8-tetrahydro-naphthalen-1-yloxy]-acetic acid;
{(R)-5-[5-(3-tert-Butyl-5-methyl-phenyl)-pyridine-2-sulfonylamino]-5,6,7,8-tetrahydro-naphthalen-1-yloxy}-acetic acid;
[(R)-5-(5'-Fluoro-3'-methoxy-biphenyl-4-sulfonylamino)-5,6,7,8-tetrahydro-naphthalen-1-yloxy]-acetic acid;
{(R)-5-[5-(3-Isopropyl-phenyl)-pyridine-2-sulfonylamino]-5,6,7,8-tetrahydro-naphthalen-1-yloxy}-acetic acid;
[(R)-5-(3'-Isopropoxy-biphenyl-4-sulfonylamino)-5,6,7,8-tetrahydro-naphthalen-1-yloxy]-acetic acid;
{(R)-5-[4-(5-Methyl-pyridin-3-yl)-benzenesulfonylamino]-5,6,7,8-tetrahydro-naphthalen-1-yloxy}-acetic acid;
[(R)-5-(3'-Methyl-biphenyl-4-sulfonylamino)-5,6,7,8-tetrahydro-naphthalen-1-yloxy]-acetic acid;
[(R)-5-(3'-Chloro-biphenyl-4-sulfonylamino)-5,6,7,8-tetrahydro-naphthalen-1-yloxy]-acetic acid;
[(R)-5-(3'-Methyl-biphenyl-3-sulfonylamino)-5,6,7,8-tetrahydro-naphthalen-1-yloxy]-acetic acid;
[(R)-5-(3'-Isopropyl-biphenyl-3-sulfonylamino)-5,6,7,8-tetrahydro-naphthalen-1-yloxy]-acetic acid;
[(R)-5-(2',3'-Dimethyl-biphenyl-3-sulfonylamino)-5,6,7,8-tetrahydro-naphthalen-1-yloxy]-acetic acid;
[(R)-5-(4'-Methoxy-3',5'-dimethyl-biphenyl-3-sulfonylamino)-5,6,7,8-tetrahydro-naphthalen-1-yloxy]-acetic acid;
{5-[5-(3-Trifluoromethyl-phenyl)-pyridine-2-sulfonylamino]-5,6,7,8-tetrahydro-naphthalen-1-yloxy}-acetic acid;
(5-{5-[3-(2-Hydroxy-ethyl)-phenyl]-pyridine-2-sulfonylamino}-5,6,7,8-tetrahydro-naphthalen-1-yloxy)-acetic acid;
{5-[5-(3-Ethoxy-phenyl)-pyridine-2-sulfonylamino]-5,6,7,8-tetrahydro-naphthalen-1-yloxy}-acetic acid;
{5-[5-(4-Trifluoromethoxy-phenyl)-pyridine-2-sulfonylamino]-5,6,7,8-tetrahydro-naphthalen-1-yloxy}-acetic acid;
{5-[6-(2-Trifluoromethyl-phenyl)-pyridine-3-sulfonylamino]-5,6,7,8-tetrahydro-naphthalen-1-yloxy}-acetic acid;
{5-[6-(4-Trifluoromethoxy-phenyl)-pyridine-3-sulfonylamino]-5,6,7,8-tetrahydro-naphthalen-1-yloxy}-acetic acid;
{5-[4-(5-Methyl-pyridin-2-yl)-benzenesulfonylamino]-5,6,7,8-tetrahydro-naphthalen-1-yloxy}-acetic acid;
{5-[4-(5-Fluoro-6-methyl-pyridin-2-yl)-benzenesulfonylamino]-5,6,7,8-tetrahydro-naphthalen-1-yloxy}-acetic acid;
[5-([2,3']Bipyridinyl-5-sulfonylamino)-5,6,7,8-tetrahydro-naphthalen-1-yloxy]-acetic acid;
{5-[6-(3-Cyano-phenyl)-pyridine-3-sulfonylamino]-5,6,7,8-tetrahydro-naphthalen-1-yloxy}-acetic acid;
{5-4-[(4-Methyl-pyridin-2-yl)-benzenesulfonylamino]-5,6,7,8-tetrahydro-naphthalen-1-yloxy}-acetic acid;
{5-[5-(2-Chloro-phenyl)-pyridine-2-sulfonylamino]-5,6,7,8-tetrahydro-naphthalen-1-yloxy}-acetic acid;
{5-[5-(3-Methoxy-phenyl)-pyridine-2-sulfonylamino]-5,6,7,8-tetrahydro-naphthalen-1-yloxy}-acetic acid;
{5-[5-(4-Methoxy-phenyl)-pyridine-2-sulfonylamino]-5,6,7,8-tetrahydro-naphthalen-1-yloxy}-acetic acid;
{5-[5-(4-Chloro-phenyl)-pyridine-2-sulfonylamino]-5,6,7,8-tetrahydro-naphthalen-1-yloxy}-acetic acid;
{5-[6-(3-Ethoxy-phenyl)-pyridine-3-sulfonylamino]-5,6,7,8-tetrahydro-naphthalen-1-yloxy}-acetic acid;
{5-[6-(5-Fluoro-2-methoxy-phenyl)-pyridine-3-sulfonylamino]-5,6,7,8-tetrahydro-naphthalen-1-yloxy}-acetic acid;
{5-[6-(3-Methoxy-phenyl)-pyridine-3-sulfonylamino]-5,6,7,8-tetrahydro-naphthalen-1-yloxy}-acetic acid;
{5-[6-(2-Chloro-phenyl)-pyridine-3-sulfonylamino]-5,6,7,8-tetrahydro-naphthalen-1-yloxy}-acetic acid;
{5-[6-(3-Chloro-4-fluoro-phenyl)-pyridine-3-sulfonylamino]-5,6,7,8-tetrahydro-naphthalen-1-yloxy}-acetic acid;
{5-[6-(3-Fluoro-phenyl)-pyridine-3-sulfonylamino]-5,6,7,8-tetrahydro-naphthalen-1-yloxy}-acetic acid;
{5-[6-(4-Chloro-phenyl)-pyridine-3-sulfonylamino]-5,6,7,8-tetrahydro-naphthalen-1-yloxy}-acetic acid;
{5-[6-(4-Fluoro-phenyl)-pyridine-3-sulfonylamino]-5,6,7,8-tetrahydro-naphthalen-1-yloxy}-acetic acid;
{5-[6-(2-Fluoro-phenyl)-pyridine-3-sulfonylamino]-5,6,7,8-tetrahydro-naphthalen-1-yloxy}-acetic acid;
{5-[6-(4-Fluoro-3-methyl-phenyl)-pyridine-3-sulfonylamino]-5,6,7,8-tetrahydro-naphthalen-1-yloxy}-acetic acid;
{5-[6-(3-Trifluoromethyl-phenyl)-pyridine-3-sulfonylamino]-5,6,7,8-tetrahydro-naphthalen-1-yloxy}-acetic acid;
{5-[6-(4-Methoxy-phenyl)-pyridine-3-sulfonylamino]-5,6,7,8-tetrahydro-naphthalen-1-yloxy}-acetic acid;
(5-{6-[3-(2-Hydroxy-ethyl)-phenyl]-pyridine-3-sulfonylamino}-5,6,7,8-tetrahydro-naphthalen-1-yloxy)-acetic acid;
[5-(6-m-Tolyl-pyridine-3-sulfonylamino)-5,6,7,8-tetrahydro-naphthalen-1-yloxy]-acetic acid;
[(R)-5-(3'-Methanesulfinyl-biphenyl-4-sulfonylamino)-5,6,7,8-tetrahydro-naphthalen-1-yloxy]-acetic acid;
[(R)-5-(3'-Methanesulfonyl-biphenyl-4-sulfonylamino)-5,6,7,8-tetrahydro-naphthalen-1-yloxy]-acetic acid;
((R)-5-{[3-Chloro-4-(4-chloro-phenoxy)-benzenesulfonyl]-methyl-amino}-5,6,7,8-tetrahydro-naphthalen-1-yloxy)-acetic acid;
((R)-5-{[3-Chloro-4-(2-chloro-phenoxy)-benzenesulfonyl]-methyl-amino}-5,6,7,8-tetrahydro-naphthalen-1-yloxy)-acetic acid;
((R)-5-{[3-Chloro-4-(4-fluoro-phenoxy)-benzenesulfonyl]-methyl-amino}-5,6,7,8-tetrahydro-naphthalen-1-yloxy)-acetic acid;
((R)-5-{[5-(3-isopropyl-phenyl)-pyridine-2-sulfonyl]-methyl-amino}-5,6,7,8-tetrahydro-naphthalen-1-yloxy)-acetic acid;
{(R)-5-[Methyl-(5-m-tolyl-pyridine-2-sulfonyl)-amino]-5,6,7,8-tetrahydro-naphthalen-1-yloxy}-acetic acid;

((R)-5-{[5-(2,3-Dimethyl-phenyl)-pyridine-2-sulfonyl]-methyl-amino}-5,6,7,8-tetrahydro-naphthalen-1-yloxy)-acetic acid;

((R)-5-{[5-(3-tert-Butyl-5-methyl-phenyl)-pyridine-2-sulfonyl]-methyl-amino}-5,6,7,8-tetrahydro-naphthalen-1-yloxy)-acetic acid;

((R)-5-{[3-(4-Chloro-benzenesulfonyl)-5-trifluoromethyl-benzenesulfonyl]-methyl-amino}-5,6,7,8-tetrahydro-naphthalen-1-yloxy)-acetic acid; and ((R)-5-{[3-(4-Fluoro-benzenesulfonyl)-5-trifluoromethyl-benzenesulfonyl]-methyl-amino}-5,6,7,8-tetrahydro-naphthalen-1-yloxy)-acetic acid.

22. A compound selected from the group consisting of:

[5-(4-Pyridin-4-yl-benzenesulfonylamino)-5,6,7,8-tetrahydro-naphthalen-1-yloxy]-acetic acid;

{5-[4-(2-Methoxy-pyridin-4-yl)-benzenesulfonylamino]-5,6,7,8-tetrahydro-naphthalen-1-yloxy}-acetic acid;

{5-[4-(2-Fluoro-pyridin-4-yl)-benzenesulfonylamino]-5,6,7,8-tetrahydro-naphthalen-1-yloxy}-acetic acid;

{5-[4-(2-Methyl-pyridin-4-yl)-benzenesulfonylamino]-5,6,7,8-tetrahydro-naphthalen-1-yloxy}-acetic acid;

{5-[4-(2,6-Difluoro-pyridin-4-yl)-benzenesulfonylamino]-5,6,7,8-tetrahydro-naphthalen-1-yloxy}-acetic acid;

[5-(6-Thiophen-3-yl-pyridine-3-sulfonylamino)-5,6,7,8-tetrahydro-naphthalen-1-yloxy]-acetic acid; and any pharmaceutically acceptable salt or ester thereof.

23. A pharmaceutical composition comprising a therapeutically effective amount of a compound according to claim 1 and a pharmaceutically acceptable carrier.

24. A pharmaceutically acceptable salt of a compound of claim 21.

25. A pharmaceutically acceptable ester of a compound of claim 21.

* * * * *

UNITED STATES PATENT AND TRADEMARK OFFICE
CERTIFICATE OF CORRECTION

| | | |
|---|---|---|
| PATENT NO. | : 8,163,781 B2 | |
| APPLICATION NO. | : 12/540804 | |
| DATED | : April 24, 2012 | |
| INVENTOR(S) | : Blanc et al. | |

It is certified that error appears in the above-identified patent and that said Letters Patent is hereby corrected as shown below:

Title page, Item (73) Assignee, delete "Hoffman-La Roche Inc." and insert -- Hoffmann-La Roche Inc. --

Signed and Sealed this
Nineteenth Day of June, 2012

David J. Kappos
*Director of the United States Patent and Trademark Office*